US008691566B1

(12) United States Patent
Zhu et al.

(10) Patent No.: US 8,691,566 B1
(45) **Date of Patent: *Apr. 8, 2014**

(54) CELLS USEFUL FOR IMMUNO-BASED BOTULINUM TOXIN SEROTYPE A ACTIVITY ASSAYS

(76) Inventors: Hong Zhu, San Diego, CA (US); Joanne Wang, Irvine, CA (US); Birgitte P. S. Jacky, Long Beach, CA (US); D. Dianne Hodges, Tustin, CA (US); Fernandez-Salas Ester, Fullerton, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 13/339,264

(22) Filed: Dec. 28, 2011

Related U.S. Application Data

(62) Division of application No. 12/722,801, filed on Mar. 12, 2010, now Pat. No. 8,361,789.

(60) Provisional application No. 61/160,199, filed on Mar. 13, 2009.

(51) Int. Cl.
*C12N 15/85* (2006.01)
*C12Q 1/68* (2006.01)

(52) U.S. Cl.
USPC .......................................... 435/325; 435/6.1

(58) Field of Classification Search
None
See application file for complete search history.

(56) References Cited

U.S. PATENT DOCUMENTS

| | | | |
|---|---|---|---|
| 5,962,637 | A | 10/1999 | Shone et al. |
| 6,043,042 | A | 3/2000 | Shone et al. |
| 6,337,386 | B1 | 1/2002 | Shone et al. |
| 7,183,066 | B2 | 2/2007 | Fernandez-Salas et al. |
| 7,208,285 | B2 | 4/2007 | Steward |
| 7,332,567 | B2 | 2/2008 | Steward |
| 7,399,607 | B2 | 7/2008 | Williams |
| 7,598,027 | B2 | 10/2009 | Fernandez-Salas et al. |
| 7,645,570 | B2 | 1/2010 | Fernandez-Salas et al. |
| 7,846,722 | B2 | 12/2010 | Williams |
| 8,124,357 | B2 | 2/2012 | Fernandez-Salas et al. |
| 2010/0233741 | A1 | 9/2010 | Wang |
| 2012/0122128 | A1 | 5/2012 | Fernandez-Salas et al. |

FOREIGN PATENT DOCUMENTS

| | | |
|---|---|---|
| WO | WO 95/33850 | 12/1995 |
| WO | WO 2006/042149 | 4/2006 |

OTHER PUBLICATIONS

Williamson, L.C., et al., Clostridial Neurotoxins and Substrate Proteolysis in Intact Neurons, J. Biol. Chem. 271(13) : 7694-7699 (1996).
Shimazaki, Y., et al., Phosphorylation of 25-kDa Synaptosome-Associated Protein, J. Biol. Chem. 271(24): 14548-14533 (1996).
Schulte-Baukloh, H., et al., Persistence of the Synaptosomal-Associated Protein-25 Cleavage Product After Intradetrusor Botulinum Toxin A Injections in Patients with Myelomeningocele Showing an Inadequate Response to Treatment, BJU Int. 100(5):1075-1080 (2007).
Rasooly R. and Do, P.M., Development of an In Vitro Assay as an Alternative to the Mouse Bioassay for *Clostridium botulinum* Neurotoxin Type A, App. Environ. Microbiol. 74(14): 4309-4313 (2008).
Nabokina, S., et al., Intracellular Location of SNAP-25 in Human Neutrophils, Biochem Biophys. Res. Comm. 239: 592-597 (1997).
Marini, P., et al., SiMa, a New Neuroblastoma Cell Line Combining Poor Prognostic Cytogenetic Markers with High Adrenergic Differentiation, Cancer Genet. Cytogenet. 112: 161-164 (1999).
Marconi, S., et al., A protein-chip Membrane-Capture Assay for Botulinum Neurotoxin Activity, Toxicol. App. Pharmacol. 233: 439-446 (2008).
Hallis, B., et al., Development of Novel Assays for Botulinum Type A and B Neurotoxins Based on Their Endopeptidase Activities, J. Clin. Microbiol 34(8): 1934-1938 (1996).
Jones R.G.A., et al., Development of Improved SNAP-25 Endopeptidase Immunoassays for Botulinum Type A and E Toxins, J. Immunol. Methods 329: 92-101 (2008).
Garcia-Rodriguez, C., et al., Molecular Evolution of Antibody Cross-Reactivity for Two Subtypes of Type a Botulinum Neurotoxin, Nature Bioltech 25(1): 107-116 (2007).
Foran, P., et al., Botulinum Neurotoxin C1 Cleaves Both Syntaxin and SNAP-25 in Intact and Permeabilized Chromaffin Cells: Correlation With Its Blockade of Catecholamine Release, Biochemistry 35: 2630-2636 (1996).
Boyd, R.S., et al., The Effect of Botulinum Neurotoxins on the Release of Insulin from the Insulinoma Cell Lines HIT-5 and RINm5F, J. Biol. Chem. 270(31): 18216-18218 (1995).
Amersdorfer, P., et al., Molecular Characterization of Murine Humoral Immune Response to Botulinum Neurotoxin Type A Binding Domain as Assessed by Using Phage Antibody Libraries, Infect. Immun. 65(9): 3743-3752 (1997).
Shih et al (Oncology Reports: 13: 517-524, 2005).
Mocellin et al (Ann Surg 2005, vol. 241, pp. 16-26).
Masumto, N.; et al.: Involvement of SNAP-25 in TRH-induced Exocytosis in Pituitary GH4CI Cells, Journal of Endocrinology, vol. 153, No. 1, 1997, pp. R5-RI0.
Pellett, Sabine; et al.: A Neuronal Cell-Based Botulinum Neurotoxin Assay for Highly Sensitive and Specific Detection of Neutralizing Serum Antibodies., Febs Letters Oct. 16, 2007 LNKDPUBMED: 17889852, vol. 581, No. 25, pp. 4803-4808.
Yowler, Brian; et al.: Botulinum Neurotoxin A Activity is Dependent Upon the Presence of Specific Gangliosides in Neuroblastoma Cells Expressing Synaptotagmin 1., The Journal of Biological Chemistry Sep. 6, 2002, vol. 277, No. 36, pp. 32815-32819.

*Primary Examiner* — Celine Qian
(74) *Attorney, Agent, or Firm* — Kenton Abel; Debra Condino

(57) ABSTRACT

The present specification discloses clonal cell lines susceptible to BoNT/A intoxication, methods of producing such clonal cell lines, and methods of detecting Botulinum toxin serotype A activity using such clonal cell lines.

5 Claims, 9 Drawing Sheets

CELLS USEFUL FOR IMMUNO-BASED BOTULINUM TOXIN SEROTYPE A ACTIVITY ASSAYS

This application is a divisional and claims priority pursuant to 35 U.S.C. §120 to U.S. patent application Ser. No. 12/722,801, filed Mar. 12, 2010 now U.S. Pat. No. 8,361,789, which claims priority pursuant to 35 U.S.C. §119(e) to U.S. Provisional Patent Application Ser. No. 61/160,199 filed Mar. 13, 2009, both incorporated entirely by reference.

The sequences disclosed in the present specification are contained in the Sequence Listing submitted with the present specification which is hereby incorporated by reference in its entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, Cosmetic and Clinical Applications of Botulinum Toxin (Slack, Inc., 2004). Clostridial toxins commercially available as pharmaceutical compositions include, BoNT/A preparations, such as, e.g., BOTOX® (Allergan, Inc., Irvine, Calif.), DYSPORT®/RELOXIN®, (Ipsen Ltd., Slough, England), PURTOX® (Mentor Corp., Santa Barbara, Calif.), XEOMIN® (Merz Pharmaceuticals, GmbH., Frankfurt, Germany), NEURONOX® (Medy-Tox, Inc., Ochang-myeon, South Korea), BTX-A (Biogen-tech Ltd., University, Yantai, Shandong, China); and BoNT/B preparations, such as, e.g., MYOBLOC®/NEUROBLOC® (Solstice Neurosciences, Inc., South San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

At present the mouse $LD_{50}$ bioassay, a lethality test, remains the "gold standard" test used by all pharmaceutical manufacturers to express the potency of their preparations. S. S. Arnon et al., JAMA 285: 1059-1070 (2001). In fact, the units on the pharmaceutical preparations' labels are mouse $LD_{50}$ units and the number of animals needed to produce statistically useful $LD_{50}$ data is large. The advantage of the mouse $LD_{50}$ bioassay is that it measures all the steps necessary for botulinum toxin uptake (e.g., toxin binding to a cell surface receptor, internalization of the toxin-receptor complex, light chain translocation into the cytoplasm, light chain cleavage of substrate), instead of merely determining the activity for only part of this intoxication process, such as, e.g., in vitro assays that only measure light chain enzymatic activity. Unfortunately, the mouse $LD_{50}$ bioassay suffers from many drawbacks including high operational cost due to the large numbers of laboratory animals required, a lack of specificity since all BoNT serotypes will cause the same measurable end-point, and the potential for inaccuracy unless large animal groups are used. In addition, animal rights groups have exerted pressure on regulatory agencies in the United States (FDA/NICEATM/ICCVAM) and Europe (MHRA and EDQM), and on pharmaceutical companies manufacturing botulinum neurotoxin products to reduce animal testing and more importantly replace the mouse $LD_{50}$ bioassay for product release. The regulatory agencies are engaging pharmaceutical companies to apply the three "Rs" principle to the potency testing of botulinum neurotoxins: Reduce, Refine, Replace. D. Straughan, *Progress in Applying the Three Rs to the Potency Testing of Botulinum Toxin Type A*, Altern. Lab. Anim. 34(3): 305-313 (2006). In recent years, several steps have been already taken to reduce and refine the mouse $LD_{50}$ bioassay in order to standardize the protocol and produce more consistent data using fewer animals per assay.

Thus, a simple, reliable, validated and governmental agency acceptable botulinum toxin activity assay that can evaluate the integrity of all the steps necessary in botulinum toxin uptake would be of significant value because such a non-animal based assay would alleviate the need for animal testing and all the disadvantages, costs and ethical concerns associated with this type of animal-based assay. Companion patent application Ester Fernandez-Salas, et al., Immuno-Based Botulinum Toxin Serotype A Activity Assays, U.S. patent application Ser. No. 12/403,531, provides novel compositions, cells, and methods for assaying the activity of a BoNT/A useful for various industries, such as, e.g., the pharmaceutical and food industries. Such compositions, cells, and methods do not use live animals or tissues taken from live animals, but can evaluate all the steps necessary for neurotoxin action, namely, binding and cellular uptake of toxin, translocation into the cell cytosol, and protease activity.

One of the necessary components for the methods disclosed in U.S. patent application Ser. No. 12/403,531 is the use of cells from an established cell line that are susceptible to low levels of BoNT/A intoxication because the amount of BoNT/A contained within a commercially-available pharmaceutical composition is very low. For example, approximately 4-5 ng of a BoNT/A complex is contained in the pharmaceutical composition sold as BOTOX®. Thus, there is a need to identify and create established cell lines comprising cells that are susceptible to BoNT/A intoxication when only very low levels of the neurotoxin is present in the sample. The present specification provides novel cells and cell compositions. that are susceptible to BoNT/A intoxication when only very low amounts of BoNT/A is present and thus allow assaying of commercially-available pharmaceutical composition comprising BoNT/A.

BRIEF DESCRIPTION OF THE DRAWINGS

FIG. 1 shows a schematic of the current paradigm of neurotransmitter release and Clostridial toxin intoxication in a central and peripheral neuron.

FIG. 2 shows volcano plots of genes that are more than 4-fold ($\log_2(4)=2$) up or down regulated in BB10 and H1 cell lines as compared to the 2D6 cell line.

FIG. 3 shows normalized BIAcore SPR curves of 7.8 nM of the antibodies 2E2A6, 1D3B8, 3C1A5 and 2C9B10 and commercial MC-6050 and MC-6053.

DETAILED DESCRIPTION

Figure 1A:
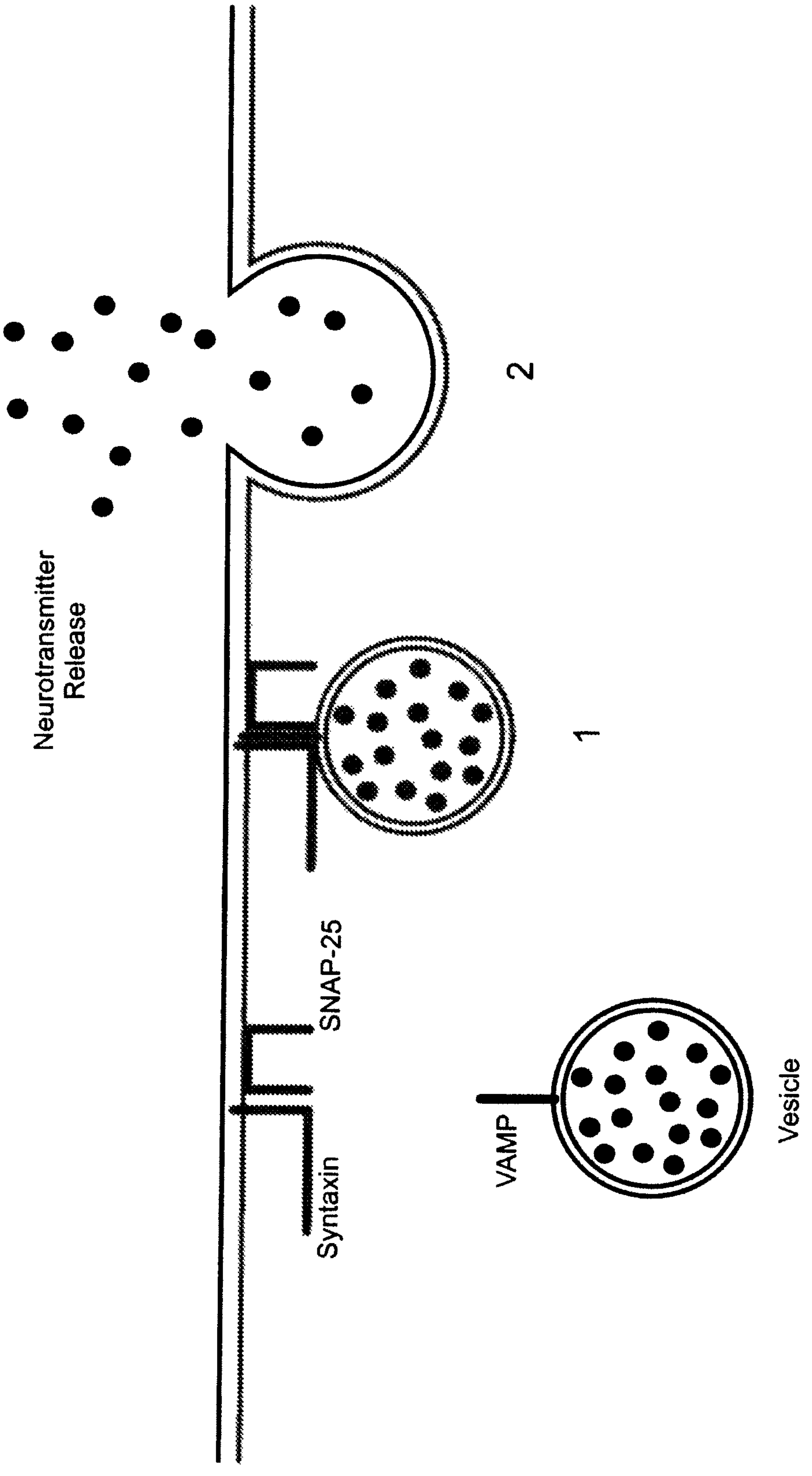
FIG. 1A shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed.

The present specification provides novel cells and cell compositions that are susceptible to BoNT/A intoxication to allow assaying of BoNT/A and BoNT/A compositions such as, e.g., commercially-available pharmaceutical composition comprising BoNT/A. The cell and cell compositions disclosed in the present specification are useful to conduct methods that can detect picomolar quantities of BoNT/A in a sample, such as the methods disclosed in, e.g., Ester Fernandez-Salas, et al., Immuno-Based Botulinum Toxin Serotype A Activity Assays, U.S. patent application Ser. No. 12/403,531, which is hereby incorporated by reference in its entirety. The cells and cell compositions, and their use in methods of detecting BoNT/A activity reduce the need for animal toxicity studies, yet serve to analyze the multiple steps of BoNT/A intoxication, namely, binding and cellular uptake of toxin, translocation into the cell cytosol, and protease activity. As discussed further below, the novel cells and cell compositions of the present specification can be used in assays that analyze crude and bulk samples as well as highly purified di-chain toxins and formulated toxin products and further are amenable to automated high throughput assay formats.

Thus, aspects of the present specification provide a cell composition comprising cells from a clonal cell line that are susceptible to BoNT/A intoxication.

Other aspects of the present specification provide a method of detecting BoNT/A activity using the clonal cell lines disclosed in the present specification.

Clostridia toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct serotypes of botulinum toxins (BoNTs), which have been identified by investigating botulism outbreaks in man (BoNT/A, BoNT/B, BoNT/E and BoNT/F), animals (BoNT/C1 and BoNT/D), or isolated from soil (BoNT/G). While all seven botulinum toxin serotypes have similar structure and biological properties, each also displays heterogeneous characteristics, such as, e.g., different pharmacological properties. In contrast, tetanus toxin (TeNT) is produced by a uniform group of *C. tetani*. Two other species of Clostridia, *C. baratii* and *C. butyricum*, also produce toxins similar to BoNT/F and BoNT/E, respectively.

Clostridial toxins are each translated as a single chain polypeptide of approximately 150 kDa that is subsequently cleaved by proteolytic scission within a disulfide loop by a naturally-occurring protease, such as, e.g., an endogenous Clostridial toxin protease or a naturally-occurring protease produced in the environment. This posttranslational processing yields a di-chain molecule comprising an approximately 50 kDa light chain (LC) and an approximately 100 kDa heavy chain (HC) held together by a single disulfide bond and non-covalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC ($H_N$) that facilitates release of the LC from intracellular vesicles into the cytoplasm of the target cell; and 3) a binding domain found within the carboxyl-terminal half of the HC ($H_C$) that determines the binding activity and binding specificity of the toxin to the receptor complex located at the surface of the target cell.

Figure 1B:
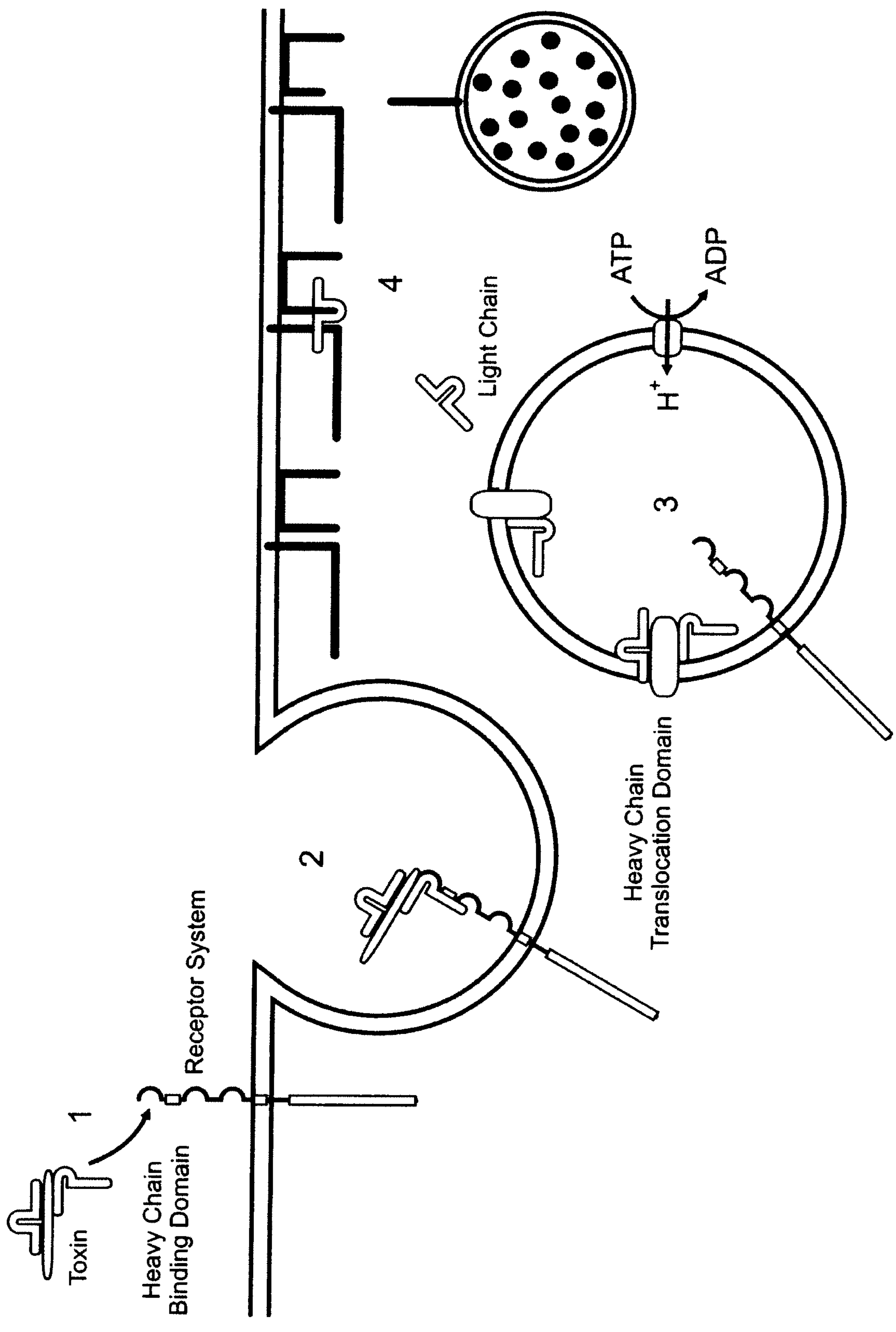
FIG. 1B shows a schematic of the intoxication mechanism for tetanus and botulinum toxin activity in a central and peripheral neuron. This intoxication process can be described as comprising four steps: 1) receptor binding, where Clostridial toxin binding to a Clostridial receptor complex and initiates the intoxication process; 2) complex internalization, where after toxin binding, a vesicle containing a toxin/receptor system complex is endocytosed into the cell; 3) light chain translocation, where multiple events are thought to occur, including changes in the internal pH of the vesicle, formation of a channel pore comprising the $H_N$ domain of Clostridial toxin heavy chain, separation of the Clostridial toxin light chain from the heavy chain, and release of the light chain and 4) enzymatic target modification, where the light chain of Clostridial toxin proteolytically cleaves its target SNARE substrates, such as, e.g., SNAP-25, VAMP or Syntaxin, thereby preventing vesicle docking and neurotransmitter release.
Figure 2A:
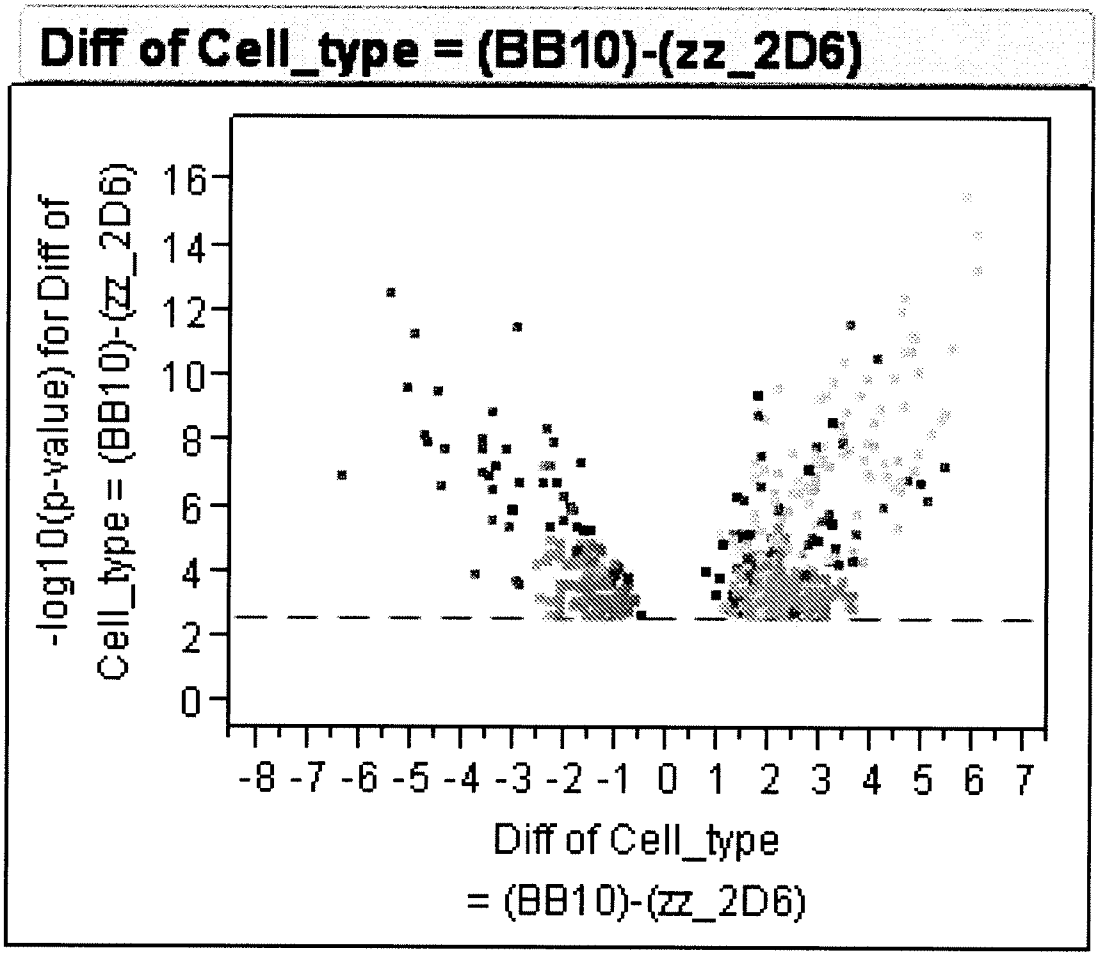
FIG. 2A shows the genes that are up regulated in the BB10 cell line as compared to the 2D6 cell line.
Figure 2B:
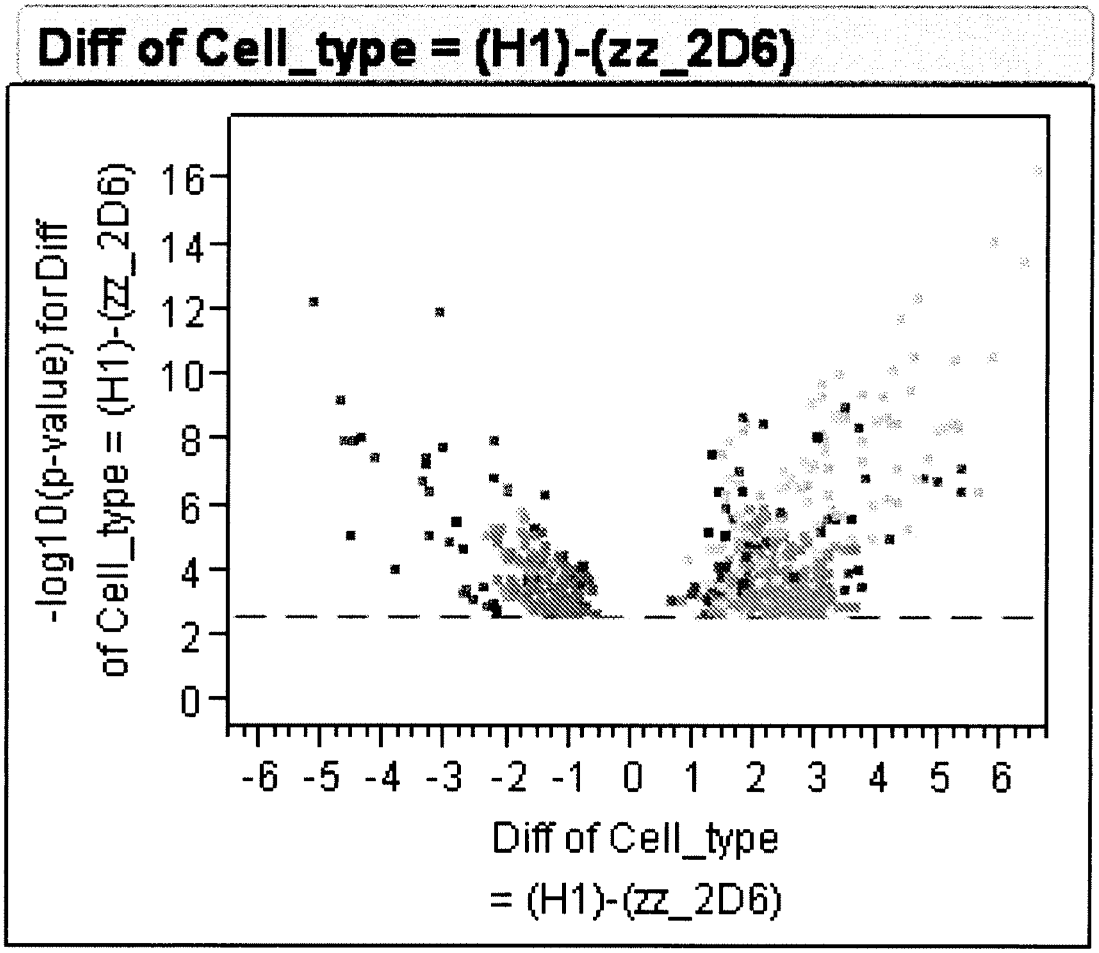
FIG. 2B shows the genes that are up regulated in the H1 cell line as compared to the 2D6 cell line.
Figure 2C:
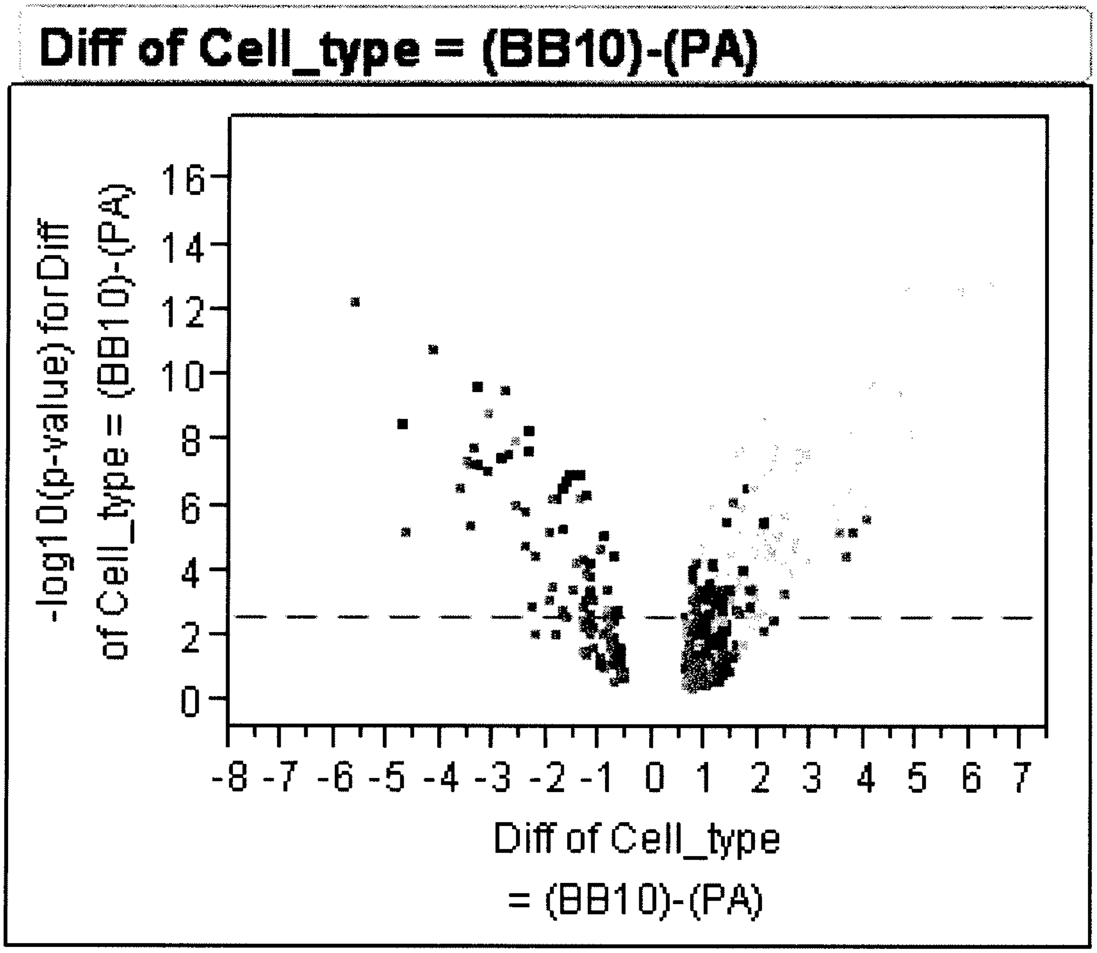
FIG. 2C shows the genes that are up regulated in the BB10 cell line as compared to the parental SiMa cell line (PA).
Figure 2D:
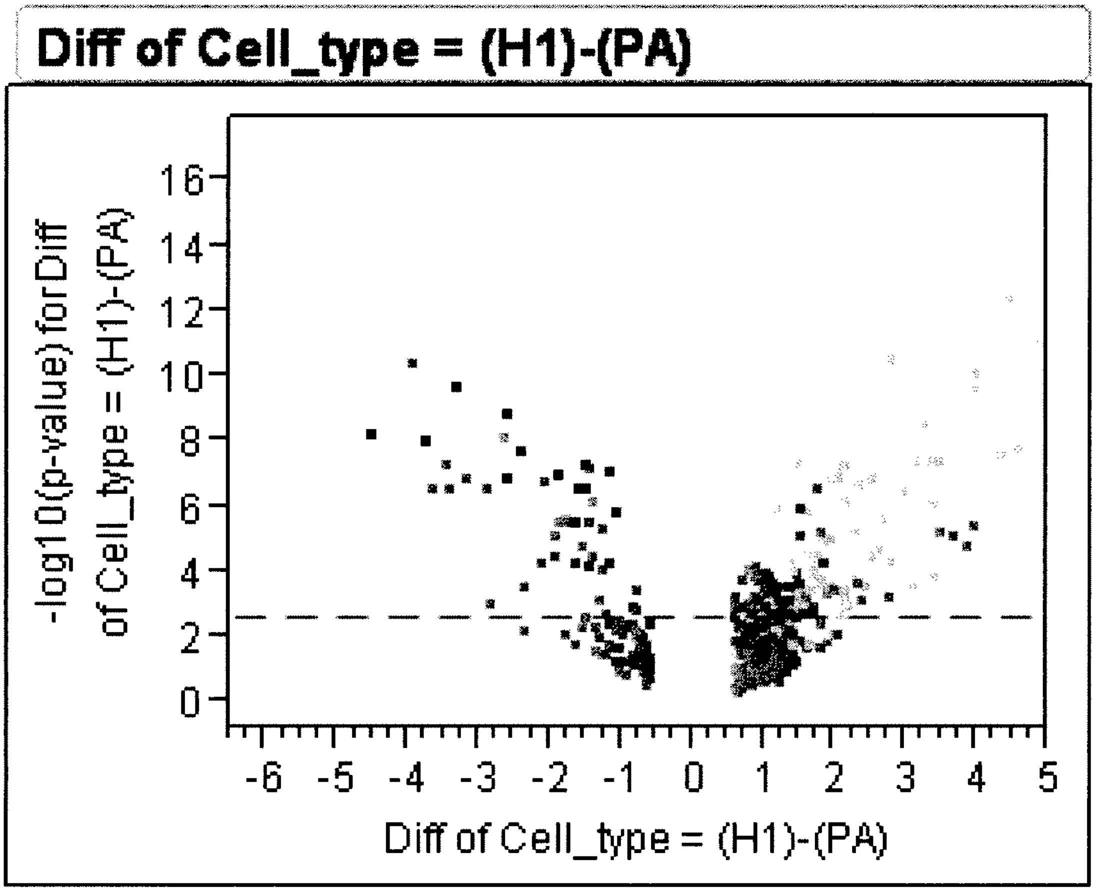
FIG. 2D shows the genes that are up regulated in the H1 cell line as compared to the parental SiMa cell line (PA).
Figure 2E:
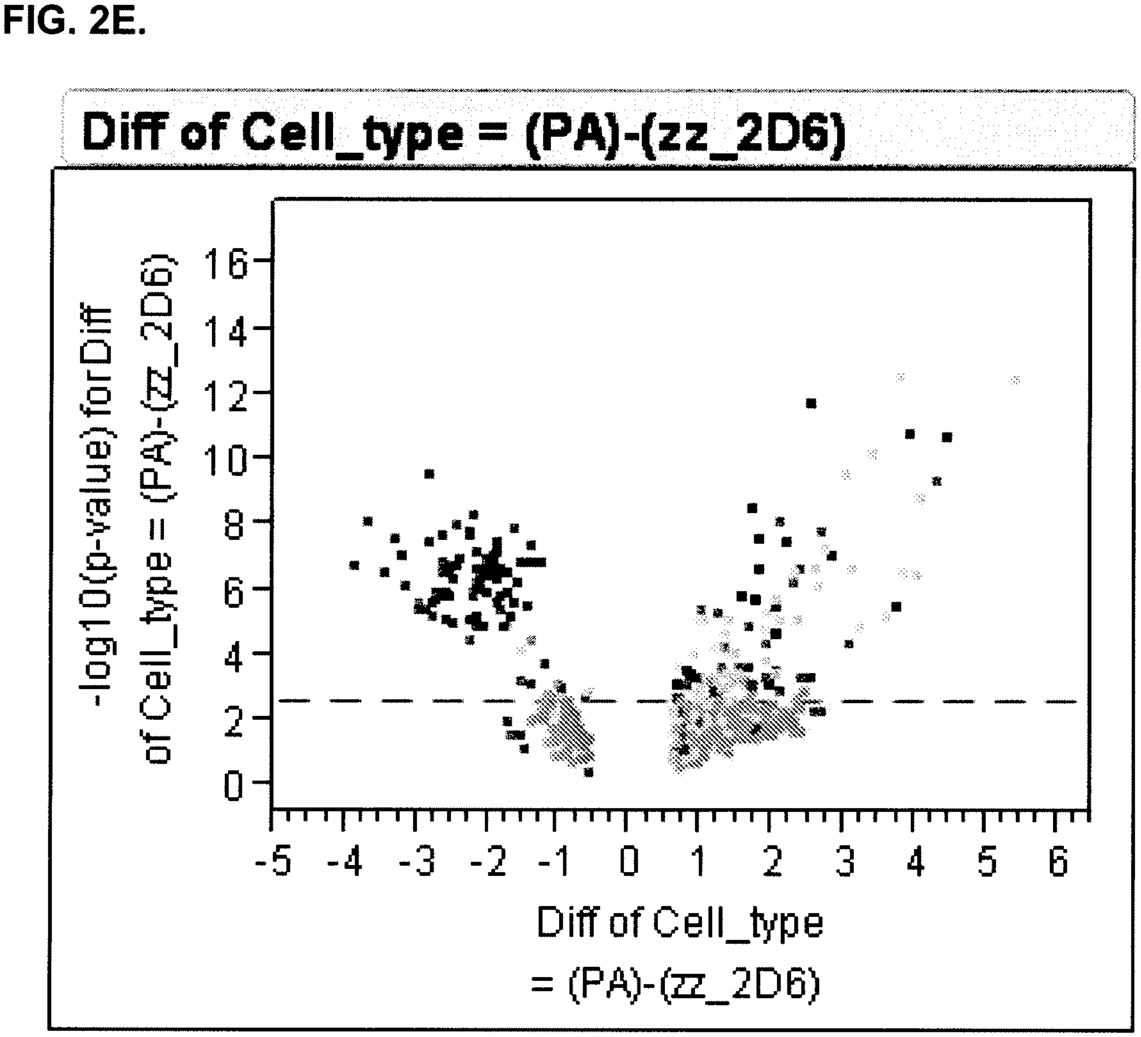
FIG. 2E shows the genes that are up regulated in the parental SiMa cell line (PA) as compared to the 2D6 cell line. Each dot represents a probe set. The dashed line marks the 95% confidence interval, $p \leq 0.05$. Most of the genes that are over expressed in BB10 and H1 compared to 2D6 (A and B) are also over or under-expressed in BB10 compared to PA (C), in H1 compared to PA (D), and in PA compared to 2D6 (E), however a number of them are less than 4-fold over-expressed and/or do not pass the 95% confidence interval.

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although the applicants have no wish to be limited by the following description, the intoxication mechanism can be described as comprising at least four steps: 1) receptor binding, 2) complex internalization, 3) light chain translocation, and 4) enzymatic target modification (FIG. 1). The process is initiated when the $H_C$ binding domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate important pH-dependent structural rearrangements that increase hydrophobicity, promote pore formation, and facilitate separation of the heavy and light chains of the toxin. Once separated, the light chain endopeptidase of the toxin is released from the intracellular vesicle into the cytosol where it appears to specifically target core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl terminal region, releasing a nine or twenty six amino acid fragment, respectively, and BoNT/C1 also cleaves SNAP-25 near the carboxyl terminus releasing an eight amino acid fragment. The botulinum serotypes BoNT/B, BoNT/D, BoNT/F and BoNT/G, and tetanus toxin, act on the conserved central portion of VAMP, and release the amino terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release,* 82(5) Biochimie. 427-446 (2000); Kathryn Turton et al., *Botulinum and Tetanus Neurotoxins: Structure, Function and Therapeutic Utility,* 27(11) Trends Biochem. Sci. 552-558. (2002); Giovanna Lalli et al., *The Journey of Tetanus and Botulinum Neurotoxins in Neurons,* 11(9) Trends Microbiol. 431-437, (2003).

Aspects of the present disclosure comprise, in part, a cell from an established cell line. As used herein, the term “cell” refers to any eukaryotic cell susceptible to BoNT/A intoxication by a BoNT/A or any eukaryotic cell that can uptake a BoNT/A. The term cell encompasses cells from a variety of organisms, such as, e.g., murine, rat, porcine, bovine, equine, primate and human cells; from a variety of cell types such as, e.g., neuronal and non-neuronal; and can be isolated from or part of a heterogeneous cell population, tissue or organism. As used herein, the term “established cell line” is synonymous with “immortal cell line,” or “transformed cell line” and refers to a cell culture of cells selected for indefinite propagation from a cell population derived from an organism, tissue, or organ source. By definition, an established cell line excludes a cell culture of primary cells. As used herein, the term “primary cells” are cells harvested directly from fresh tissues or organs and do not have the potential to propagate indefinitely. An established cell line can comprise a heterogeneous population of cells or a uniform population of cells. An established cell line derived from a single cell is referred to as a clonal cell line. An established cell line can be one whose cells endogenously express all component necessary for the cells to undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. Alternatively, an established cell line can be one whose cells have had introduced from an exogenous source at least one component necessary for the cells to undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. Also referred to as a genetically-engineered cell line, cells from such an established cell line may, e.g., express an exogenous FGFR2, an exogenous FGFR3, an exogenous SV2, an exogenous SNAP-25, or any combination thereof. As used herein, the term “established clonal cell line” or “clonal cell line” refers to a cell culture of cells selected from a heterogenous population of cell types comprising an established cell line, which can also be referred to as a parental cell line. Thus, as a non-limiting example, the cells from the A6, A7, A9, A10, A11, B5, B10, C5, C11, C12, D7, D11, E11, F10, H1, H3, H8, H10, 1E3, 2B9, 2E4, 3B8, 3D5, 3G10, 4B5, 4C8, 5F3, AC9, AF4, BB3, BB10, BE3, BF8, CC11, CD6, CE6, CG8, CG10, DC4, DD10, DE7, YF5, and H1 1.4 clonal cell lines were selected from the heterogenous population of cell types comprising the SiMa cell line (or parental SiMa cell line) DSMZ ACC 164.

Aspects of the present disclosure comprise, in part, a cell from an established clonal cell line susceptible to BoNT/A intoxication. As used herein, the terms “cell(s) susceptible to BoNT/A intoxication,” “cell(s) susceptible to BoNT/A intoxication by a BoNT/A,” or “cell(s) from an established clonal cell line susceptible to BoNT/A intoxication by a BoNT/A” refer to cell(s) that can undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. By definition, cell(s) susceptible to BoNT/A intoxication must express, or be engineered to express, at least one BoNT/A receptor and at least one SNAP-25 substrate. Non-limiting examples of a cell or cells from an established clonal cell line susceptible to BoNT/A intoxication, include A6, A7, A9, A10, A11, B5, B10, C5, C11, C12, D7, D11, E11, F10, H1, H3, H8, H10, 1E3, 2B9, 2D2, 2D6, 2E4, 3B8, 3D5, 3G10, 4B5, 4C8, 4D3, 5C10, 5F3, AC9, AF4, BB3, BB10, BE3, BF8, CC11, CD6, CE6, CG8, CG10, DC4, DD10, DE7, DF5, YB7, YF5, and H1 1.4 clonal cell lines. As used herein, the terms “cell(s) that can uptake BoNT/A” or “cell(s) comprising an established clonal cell line that can uptake BoNT/A” refer to cells that can undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. By definition, cell(s) that can uptake BoNT/A must express, or be engineered to express, at least one BoNT/A receptor and at least one SNAP-25 substrate. Non-limiting examples of a cell or cells from an established clonal cell line that can uptake BoNT/A, include A6, A7, A9, A10, A11, B5, B10, C5, C11, C12, D7, D11, E11, F10, H1, H3, H8, H10, 1E3, 2B9, 2D2, 2D6, 2E4, 3B8, 3D5, 3G10, 4B5, 4C8, 4D3, 5C10, 5F3, AC9, AF4, BB3, BB10, BE3, BF8, CC11, CD6, CE6, CG8, CG10, DC4, DD10, DE7, DF5, YB7, YF5, and H1 1.4 clonal cell lines. Cell lines comprising cell(s) from an established clonal cell line susceptible to BoNT/A intoxication or cell(s) that can uptake BoNT/A are referred to as a “responder cell line.”

Aspects of the present disclosure comprise, in part, cells from an established clonal cell line more susceptible to BoNT/A intoxication. As used herein, the terms “cell(s) more susceptible to BoNT/A intoxication,” “cell(s) more susceptible to BoNT/A intoxication by a BoNT/A,” or “cell(s) from an established clonal cell line more susceptible to BoNT/A intoxication by a BoNT/A” refer to cell(s) that undergo the overall cellular mechanism whereby a BoNT/A proteolytically cleaves a SNAP-25 substrate to a greater degree as compared to a cell(s) comprising a parental SiMa cell line, such as, e.g., parental SiMa cell line DSMZ ACC 164. Non-limiting examples of a cell or cells from an established clonal cell line more susceptible to BoNT/A intoxication, include a cell or cells from a A10, H1, 2E4, 3B8, 3D5, 5F3, AF4, BB3, BB10, DC4, or H1 1.4 clonal cell lines. As used herein, the terms “cell(s) that uptake BoNT/A more” or “cell(s) comprising an established clonal cell line that uptake BoNT/A more” refer to cells that undergo the overall cellular mechanism whereby a BoNT/A proteolytically cleaves a SNAP-25 substrate to a greater degree as compared to a cell(s) comprising a parental SiMa cell line, such as, e.g., parental SiMa cell line DSMZ ACC 164. Non-limiting examples of a cell or cells from an established clonal cell line that can uptake BoNT/A more, include a cell or cells from a A10, H1, 2E4, 3B8, 3D5, 5F3, AF4, BB3, BB10, DC4, or H1 1.4 clonal cell lines. Cell lines comprising cell(s) from an established clonal cell line more susceptible to BoNT/A intoxication or cell(s) that can uptake BoNT/A more are referred to as a "high responder cell line."

Aspects of the present disclosure comprise, in part, cells from an established clonal cell line less susceptible to BoNT/A intoxication. As used herein, the terms "cell(s) less susceptible to BoNT/A intoxication," "cell(s) less susceptible to BoNT/A intoxication by a BoNT/A," or "cell(s) from an established clonal cell line less susceptible to BoNT/A intoxication by a BoNT/A" refer to cell(s) that undergo the overall cellular mechanism whereby a BoNT/A proteolytically cleaves a SNAP-25 substrate to a lesser degree as compared to a cell(s) comprising a parental SiMa cell line, such as, e.g., parental SiMa cell line DSMZ ACC 164. Non-limiting examples of a cell or cells from an established clonal cell line less susceptible to BoNT/A intoxication, include A7, B10, D11, H10, 2D2, 2D6, 4D3, 5C10, DF5, and YB7 clonal cell lines. As used herein, the terms "cell(s) that uptake BoNT/A less" or "cell(s) comprising an established clonal cell line that uptake BoNT/A less" refer to cells that undergo the overall cellular mechanism whereby a BoNT/A proteolytically cleaves a SNAP-25 substrate to a lesser degree as compared to a cell(s) comprising a parental SiMa cell line, such as, e.g., parental SiMa cell line DSMZ ACC 164. Non-limiting examples of a cell or cells from an established clonal cell line that can uptake BoNT/A less, include A7, B10, D11, H10, 2D2, 2D6, 4D3, 5C10, DF5, and YB7 clonal cell lines. Cell lines comprising cell(s) from an established clonal cell line less susceptible to BoNT/A intoxication or cell(s) that can uptake BoNT/A less are referred to as a "low responder cell line."

Aspects of the present disclosure comprise, in part, a cell from an established clonal cell line not susceptible to BoNT/A intoxication. As used herein, the terms "cell(s) not susceptible to BoNT/A intoxication," "cell(s) not susceptible to BoNT/A intoxication by a BoNT/A," or "cell(s) from an established clonal cell line not susceptible to BoNT/A intoxication by a BoNT/A" refer to cell(s) that cannot undergo the overall cellular mechanism whereby a BoNT/A proteolytically cleaves a SNAP-25 substrate. As used herein, the terms "cell(s) that cannot uptake BoNT/A" or "cell(s) comprising an established clonal cell line that cannot uptake BoNT/A" refer to cells that cannot undergo the overall cellular mechanism whereby a BoNT/A proteolytically cleaves a SNAP-25 substrate. Cell lines comprising cell(s) from an established clonal cell line not susceptible to BoNT/A intoxication or cell(s) that cannot uptake BoNT/A are referred to as a "non-responder cell line."

Thus in an embodiment, cells from an established clonal cell line are susceptible to BoNT/A intoxication. In aspects of this embodiment, cells from an established clonal cell line are susceptible to BoNT/A intoxication by, e.g., about 500 pM or less, about 400 pM or less, about 300 pM or less, about 200 pM or less, or about 100 pM or less of a BoNT/A. In other aspects of this embodiment, cells from an established clonal cell line are susceptible to BoNT/A intoxication by, e.g., about 90 pM or less, about 80 pM or less, about 70 pM or less, about 60 pM or less, about 50 pM or less, about 40 pM or less, about 30 pM or less, about 20 pM or less, or about 10 pM or less of a BoNT/A. In still other aspects, cells from an established clonal cell line are susceptible to BoNT/A intoxication by, e.g., about 9 pM or less, about 8 pM or less, about 7 pM or less, about 6 pM or less, about 5 pM or less, about 4 pM or less, about 3 pM or less, about 2 pM or less, or about 1 pM or less of a BoNT/A. In yet other aspects, cells from an established clonal cell line are susceptible to BoNT/A intoxication by, e.g., about 0.9 pM or less, about 0.8 pM or less, about 0.7 pM or less, about 0.6 pM or less, about 0.5 pM or less, about 0.4 pM or less, about 0.3 pM or less, about 0.2 pM, or about 0.1 pM or less of a BoNT/A. As used herein, the term "about" when qualifying a value of a stated item, number, percentage, or term refers to a range of plus or minus ten percent of the value of the stated item, percentage, parameter, or term.

In another embodiment, cells comprising an established clonal cell line can uptake a BoNT/A. In aspects of this embodiment, cells comprising an established clonal cell line can uptake, e.g., about 500 pM or less, about 400 pM or less, about 300 pM or less, about 200 pM or less, or about 100 pM or less of a BoNT/A. In other aspects of this embodiment, cells comprising an established clonal cell line possess the ability to uptake about 90 pM or less, about 80 pM or less, about 70 pM or less, about 60 pM or less, about 50 pM or less, about 40 pM or less, about 30 pM or less, about 20 pM or less, or about 10 pM or less of a BoNT/A. In still other aspects, cells comprising an established clonal cell line possess the ability to uptake about 9 pM or less, about 8 pM or less, about 7 pM or less, about 6 pM or less, about 5 pM or less, about 4 pM or less, about 3 pM or less, about 2 pM or less, or about 1 pM or less of a BoNT/A. In yet other aspects, cells comprising an established clonal cell line possess the ability to uptake about 0.9 pM or less, about 0.8 pM or less, about 0.7 pM or less, about 0.6 pM or less, about 0.5 pM or less, about 0.4 pM or less, about 0.3 pM or less, about 0.2 pM or less, or about 0.1 pM or less of a BoNT/A. In other aspects, cells comprising an established clonal cell line can uptake BoNT/A from, e.g., about 0.01 pM to about 100 pM, about 0.01 pM to about 75 pM, about 0.01 pM to about 50 pM, about 0.01 pM to about 25 pM, about 0.01 pM to about 20 pM, about 0.01 pM to about 15 pM, about 0.01 pM to about 10 pM, about 0.01 pM to about 5 pM, about 0.001 pM to about 100 pM, about 0.001 pM to about 75 pM, about 0.001 pM to about 50 pM, about 0.001 pM to about 25 pM, about 0.001 pM to about 20 pM, about 0.001 pM to about 15 pM, about 0.001 pM to about 10 pM, or about 0.001 pM to about 5 pM of BoNT/A.

In another embodiment, cells from an established clonal cell line are not susceptible to BoNT/A intoxication. In aspects of this embodiment, cells from an established clonal cell line are not susceptible to BoNT/A intoxication by, e.g., about 500 pM or less, about 400 pM or less, about 300 pM or less, about 200 pM or less, or about 100 pM or less of a BoNT/A. In other aspects of this embodiment, cells from an established clonal cell line are susceptible to BoNT/A intoxication by, e.g., about 90 pM or less, about 80 pM or less, about 70 pM or less, about 60 pM or less, about 50 pM or less, about 40 pM or less, about 30 pM or less, about 20 pM or less A, or about 10 pM or less of a BoNT/A. In still other aspects, cells from an established clonal cell line are not susceptible to BoNT/A intoxication by, e.g., about 9 pM or less, about 8 pM or less, about 7 pM or less, about 6 pM or less, about 5 pM or less, about 4 pM or less, about 3 pM or less, about 2 pM or less, or about 1 pM or less of a BoNT/A. In yet other aspects, cells from an established clonal cell line are not susceptible to BoNT/A intoxication by, e.g., about 0.9 pM or less, about 0.8 pM or less, about 0.7 pM or less, about 0.6 pM or less, about 0.5 pM or less, about 0.4 pM or less, about 0.3 pM or less, about 0.2 pM, or about 0.1 pM or less of a BoNT/A. In other aspects, cells from an established clonal cell line are not susceptible to BoNT/A intoxication from, e.g., about 0.01 pM to about 100 pM, about 0.01 pM to about 75 pM, about 0.01 pM to about 50 pM, about 0.01 pM to about 25 pM, about 0.01 pM to about 20 pM, about 0.01 pM to about 15 pM, about 0.01 pM to about 10 pM, about 0.01 pM to about 5 pM, about 0.001 pM to about 100 pM, about 0.001 pM to about 75 pM, about 0.001 pM to about 50 pM, about 0.001 pM to about 25 pM, about 0.001 pM to about 20 pM, about 0.001 pM to about 15 pM, about 0.001 pM to about 10 pM, or about 0.001 pM to about 5 pM of BoNT/A.

Aspects of the present disclosure comprise, in part, cells from an established clonal cell line susceptible to BoNT/A intoxication that are more stable than cells from a parental SiMa cell line, such as, e.g., parental SiMa cell line DSMZ ACC 164. As used herein, the term "stable" refers to cells from an established clonal cell line for a particular passage number that exhibit a relative $EC_{50}$, sensitivity, efficacy, well-defined upper asymptote, and/or a well-defined dose-response curve for BoNT/A activity that is similar to the values for relative $EC_{50}$, sensitivity, efficacy, well-defined upper asymptote, and/or a well-defined dose-response curve exhibited by cells from a parental SiMa cell line, such as, e.g., parental SiMa cell line DSMZ ACC 164, at the same or similar passage number, where the same assay conditions and the same BoNT/A (or molecule) are used in both assays.

Thus in an embodiment, cells from an established clonal cell line are more stable as compared to a parental SiMa cell line. In an aspect of this embodiment, cells from an established clonal cell line are more stable as compared to the parental SiMa cell line DSMZ ACC 164. In other aspects of this embodiment, cells from an established clonal cell line are more stable for, e.g., at least 5 more passages, at least 10 more passages, at least 15 more passages, at least 20 more passages, at least 25 more passages, or at least 30 more passages, as compared to a parental SiMa cell line. In yet other aspects of this embodiment, cells from an established clonal cell line are more stable for, e.g., at least 5 more passages, at least 10 more passages, at least 15 more passages, at least 20 more passages, at least 25 more passages, or at least 30 more passages, as compared to a parental SiMa cell line DSMZ ACC 164.

Aspects of the present disclosure comprise, in part, cells from an established clonal cell line susceptible to BoNT/A intoxication that are stable over a plurality of cell passages. As used herein, the term "stable" refers to cells from an established clonal cell line for a particular passage number that exhibit a relative $EC_{50}$, sensitivity, efficacy, well-defined upper asymptote, and/or a well-defined dose-response curve for BoNT/A activity that is similar to the values for relative $EC_{50}$, sensitivity, efficacy, well-defined upper asymptote, and/or a well-defined dose-response curve exhibited by cells from the same established clonal cell line, but from a prior passage or passages, where the same assay conditions and the same BoNT/A (or molecule) are used in both assays.

Cells from an established cell line disclosed in the present specification can exhibit consistent sensitivity to BoNT/A activity over a plurality of cell passages. As used herein, the term "sensitivity to BoNT/A activity" refers to the lowest dose that an assay can measure consistently above the signal detected by a non-treatment control or background signal.

Thus, in an embodiment, cells from the established clonal cell line exhibit a sensitivity for BoNT/A activity for any given passages that is e.g., 100 pM or less, about 80 pM or less, about 70 pM or less, about 60 pM or less, about 50 pM or less, about 40 pM or less, about 30 pM or less, about 20 pM or less, about 10 pM or less, about 1 pM or less, about 0.9 pM or less, about 0.8 pM or less, about 0.7 pM or less, about 0.6 pM or less, about 0.5 pM or less, about 0.4 pM or less, about 0.3 pM or less, about 0.2 pM or less, or about 0.1 pM or less of a BoNT/A. In aspects of this embodiment, cells from the established clonal cell line exhibit a sensitivity for BoNT/A activity for any given passages that is, e.g., about 0.01 pM to about 100 pM, about 0.01 pM to about 75 pM, about 0.01 pM to about 50 pM, about 0.01 pM to about 25 pM, about 0.01 pM to about 20 pM, about 0.01 pM to about 15 pM, about 0.01 pM to about 10 pM, about 0.01 pM to about 5 pM, about 0.001 pM to about 100 pM, about 0.001 pM to about 75 pM, about 0.001 pM to about 50 pM, about 0.001 pM to about 25 pM, about 0.001 pM to about 20 pM, about 0.001 pM to about 15 pM, about 0.001 pM to about 10 pM, or about 0.001 pM to about 5 pM of BoNT/A.

In another embodiment, cells from the established clonal cell line exhibit a sensitivity for BoNT/A activity that is about 100 pM or less, about 75 pM or less, about 50 pM or less, about 25 pM or less, less about 20 pM or less, about 15 pM or less, about 10 pM or less, or about 1 pM or less for, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from the established clonal cell line exhibit a sensitivity for BoNT/A activity that is about 100 pM or less, about 75 pM or less, about 50 pM or less, about 25 pM or less, less about 20 pM or less, about 15 pM or less, about 10 pM or less, or about 1 pM or less for, e.g., about 15 to about 60 passages, about 20 to about 60 passages, about 25 to about 60 passages, about 30 to about 60 passages, about 35 to about 60 passages, about 40 to about 60 passages, about 45 to about 60 passages, about 50 to about 60 passages, about 15 to about 50 passages, about 20 to about 50 passages, about 25 to about 50 passages, about 30 to about 50 passages, about 35 to about 50 passages, about 40 to about 50 passages, about 15 to about 40 passages, about 20 to about 40 passages, about 25 to about 40 passages, or about 30 to about 40 passages.

Cells from an established cell line disclosed in the present specification can exhibit a consistent relative efficacy of BoNT/A uptake, BoNT/A activity, or BoNT/A intoxication over a plurality of cell passages. As used herein, the term "relative efficacy" refers to how well the upper asymptote for the BoNT/A activity detected in the current assay run compares to the upper asymptote for the BoNT/A activity detected in a reference standard, a reference molecule, or a reference passage number used on that assay. As used herein, the term "signal to noise ratio for the upper asymptote" refers to the signal detected in an assay at the upper limit of detection divided by the signal detected by a non-treatment control or background signal. The upper limit of detection is the highest dose that an assay can measure consistently before saturation of the signal occurs.

Thus, in an embodiment, cells from an established cell line disclosed in the present specification can exhibit a well defined upper asymptote over a plurality of cell passages and maintain a signal to noise ratio that is consistent and adequate for the assay. In aspects of this embodiment, cells from an established cell line disclosed in the present specification must have a signal to noise ratio for the upper asymptote for BoNT/A activity of, e.g., at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, at least 40:1, at least 45:1, at least 50:1, at least 60:1, at least 70:1, at least 80:1, at least 90:1, or at least 100:1, at least 150:1, at least 200:1, at least 250:1, at least 300:1, at least 350:1, at least 400:1, at least 450:1, at least 500:1, at least 550:1, or at least 600:1, over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from an established cell line disclosed in the present specification must have a signal to noise ratio for the upper asymptote for BoNT/A activity of, e.g., at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, at least 40:1, at least 45:1, at least 50:1, at least 60:1, at least 70:1, at least 80:1, at least 90:1, or at least 100:1, at least 150:1, at least 200:1, at least 250:1, at least 300:1, at least 350:1, at least 400:1, at least 450:1, at least 500:1, at least 550:1, or at least 600:1, over, e.g., about 15 to about 60 passages, about 20 to about 60 passages, about 25 to about 60 passages, about 30 to about 60 passages, about 35 to about 60 passages, about 40 to about 60 passages, about 45 to about 60 passages, about 50 to about 60 passages, about 15 to about 50 passages, about 20 to about 50 passages, about 25 to about 50 passages, about 30 to about 50 passages, about 35 to about 50 passages, about 40 to about 50 passages, about 15 to about 40 passages, about 20 to about 40 passages, about 25 to about 40 passages, or about 30 to about 40 passages.

Cells from an established cell line disclosed in the present specification can exhibit a well defined dose-response curve for BoNT/A activity over a plurality of cell passages. As used herein, the term "dose-response curve" refers to the how well the raw data fits the statistical model of choice for that assay. As a non-limiting example, a sigmoidal curve with a four parameter logistics fit is a dose-response curve for an enzymatic activity assay, such as, e.g., a potency assay. As another non-limiting example, a ligand binding with one site saturation fit is a dose-response curve for a ligand/antibody binding assay.

Thus, in an embodiment, cells from an established cell line disclosed in the present specification exhibit a well defined dose-response curve for BoNT/A activity over a plurality of cell passages. In aspects of this embodiment, cells from an established cell line disclosed in the present specification exhibit a well defined dose-response curve for BoNT/A activity over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from an established cell line disclosed in the present specification exhibit a well defined dose-response curve for BoNT/A activity over, e.g., about 15 to about 60 passages, about 20 to about 60 passages, about 25 to about 60 passages, about 30 to about 60 passages, about 35 to about 60 passages, about 40 to about 60 passages, about 45 to about 60 passages, about 50 to about 60 passages, about 15 to about 50 passages, about 20 to about 50 passages, about 25 to about 50 passages, about 30 to about 50 passages, about 35 to about 50 passages, about 40 to about 50 passages, about 15 to about 40 passages, about 20 to about 40 passages, about 25 to about 40 passages, or about 30 to about 40 passages.

Cells from an established cell line disclosed in the present specification can exhibit a consistent relative $EC_{50}$ value for BoNT/A activity over a plurality of cell passages. As used herein, the term "relative $EC_{50}$" or "relative $EC_{50}$ value" refers to an $EC_{50}$ value of BoNT/A activity that is normalized against the $EC_{50}$ calculated for a reference standard, a reference molecule, or a reference passage number used on that assay.

Thus, in an embodiment, cells from an established clonal cell line exhibit a consistent relative $EC_{50}$ for BoNT/A activity over a plurality of cell passages. In aspects of this embodiment, cells from an established clonal cell line exhibit a consistent relative $EC_{50}$ for BoNT/A activity that is, e.g., about ±10%, about ±20%, about ±30%, about ±40%, about ±50%, about 60%, about 70%, or about ±75%, the relative $EC_{50}$ for BoNT/A activity over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from an established clonal cell line exhibit a relative $EC_{50}$ for BoNT/A activity that is, e.g., about ±10% to about 75%, about ±10% to about 70%, about ±10% to about 60%, about ±10% to about 50%, about ±10% to about 40%, about ±10% to about 30%, or about ±10% to about 20% the relative $EC_{50}$ for BoNT/A activity over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages.

Aspects of the present disclosure comprise, in part, cells from an established clonal cell line susceptible to BoNT/A intoxication that exhibit at least a 1.5-fold difference in gene expression levels of one or more genes listed in Tables 5, 6, 7, or 8 as compared to the expression levels of these genes in cells from the 2D6 cell line. In other aspects of this embodiment, cells from an established clonal cell line susceptible to BoNT/A intoxication exhibit a difference in gene expression levels of one or more genes listed in Tables 5, 6, 7, or 8 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from the 2D6 cell line. In other aspects of this embodiment, cells from an established clonal cell line susceptible to BoNT/A intoxication exhibit a difference in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 5, 6, 7, or 8 as compared to the expression levels of these genes in cells from the 2D6 cell line. In yet other aspects, cells from an established clonal cell line susceptible to BoNT/A intoxication exhibit a difference in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 5, 6, 7, or 8 as compared to the expression levels of these genes in cells from the 2D6 cell line. The log ratio in Tables 5, 6, 7, and 8 represent $\log_2$ values where 0.585 is $\log_2(1.5)$ which is a 1.5-fold difference, 1 is $\log_2(2)$ which is a 2-fold difference, 1.584 is $\log_2(3)$ which is a 3-fold difference, 2 is $\log_2(4)$ which is a 4-fold difference, 2.321 is $\log_2(5)$ which is a 5-fold difference, 2.584 is $\log_2(6)$ which is a 6-fold difference, 2.807 is $\log_2(7)$ which is a 7-fold difference, 3 is $\log_2(8)$ which is a 8-fold difference, 3.169 is $\log_2(9)$ which is a 9-fold difference, and 3.321 is $\log_2(10)$ which is a 10-fold difference.

In an embodiment, cells from an established clonal cell line susceptible to BoNT/A intoxication exhibit at least a 1.5-fold increase in gene expression levels of one or more genes listed in Tables 5 or 7 as compared to the expression levels of these genes in cells from the 2D6 cell line. In aspects of this embodiment, cells from an established clonal cell line susceptible to BoNT/A intoxication exhibit an increase in gene expression levels of one or more genes listed in Tables 5 or 7 of, e.g., at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from the 2D6 cell line. In other aspects of this embodiment, cells from an established clonal cell line susceptible to BoNT/A intoxication exhibit an increase in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 5 or 7 as compared to the expression levels of these genes in cells from the 2D6 cell line. In yet other aspects, cells from an established clonal cell line susceptible to BoNT/A intoxication exhibit an increase in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 5 or 7 as compared to the expression levels of these genes in cells from the 2D6 cell line.

In an embodiment, cells from an established clonal cell line susceptible to BoNT/A intoxication exhibit at least a 1.5-fold increase in gene expression levels of one or more genes selected from A2BP1, ACO1, ACOT7, ACOT9, ACTL6A, ACTL6B, ADRBK2, AGPS, AIDA, AKAP13, ALCAM, ALDH7A1, AMOTL1, ANAPC7, ANKRD13A, ANKRD54, ANKS1B, ANLN, ANP32E, ANXA6, APAF1, APBB2, APOO, ARF3, ARHGAP11A, ARHGAP24, ARHGAP24, ARHGAP6, ARHGEF3, ARHGEF6, ARL13B, ARL6, ARL6IP1, ASCL1, ASF1A, ASF1B, ASXL3, ATAD2, ATP6V1A, AURKA, AURKB, BARD1, BASP1, BAX, BCL11A, BCR, BNC2, BOK, BRCA1, BRCA2, BRD4, BR13BP, BRIP1, BTBD3, BTG3, BUB1, BUB1B, BUB3, BVES, C10ORF58, C10ORF78, C11ORF75, C12ORF48, C12ORF49, C14ORF106, C14ORF143, C15ORF23, C15ORF42, C18ORF54, C1ORF112, C1ORF183, C1ORF43, C1QL1, C20ORF108, C20ORF20, C20ORF7, C20ORF72, C22ORF28, C22ORF29, C22ORF39, C3ORF14, C3ORF70, C4ORF46, C4ORF49, C5ORF32, C6ORF115, C9ORF100, CARHSP1, CBLB, CBWD1, CBX5, CCDC109B, CCDC117, CCDC15, CCDC21, CCDC3, CCDC34, CCDC52, CCDC86, CCDC99, CCNB1, CCNE2, CCNF, CCNYL1, CD24, CD47, CD9, CDC2, CDC25B, CDC42EP4, CDC45L, CDC5L, CDC6, CDCA2, CDCA4, CDCA5, CDCA7, CDCA8, CDH2, CDK2, CDK2AP1, CDK6, CDKAL1, CDKN2C, CDKN2D, CDO1, CDS2, CECR5, CELSR3, CENPF, CENPH), CENPI, CENPJ, CENPK, CENPL, CENPM, CENPN, CENPO, CEP135, CEP152, CEP55, CEP78, CEP97, CHAF1A, CHD6, CHEK1, CHEK2, CHMP4B, CHRNA3, CHRNA7, CHST15, CIT, CKAP2, CKAP2L, CKLF, CKS1B, CLDND1, CLSTN2, CMTM7, CNN3, CNOT4, CNP, CNTN1, CNTN4, COBLL1, COQ3, CPNE4, CPT1A, CPVL, CRISPLD1, CRTAC1, CRYBG3, CRYZ, CSE1L, CSRP2, CSRP2BP, CSTF1, CTDSPL2, CTNNBL1, CTSL2, CUGBP2, CXCR4, CYTSA, DACT1, DAZ1, DBF4B, DBH, DCLRE1B, DCPS, DDAH2, DDT, DEK, DENR, DEPDC1, DEPDC1B, DERA, DGCR14, DGKE, DHX15, DHX35, DIAPH1, DIAPH3, DKFZP434L187, DLEU2, DLGAP5, DLL3, DLX6, DNA2, DNM3, DNMT3B, DOCK10, DOK4, DOK5, DPF1, DPYD, DPYSL3, DRAM1, DRG1, DSCC1, DSN1, DTL, DTNBP1, DTYMK, DVL2, DYNLT3, DYRK4, E2F1, E2F2, E2F7, E2F8, EAF2, EBF1, ECT2, EFNA5, EFNB2, ELAVL4, ELOVL7, EME1, EMILIN2, EMILIN3, EML1, ENC1, EPB41L5, EPOR, ERCC6L, ESCO2, ESF1, ESPL1, ETS1, ETV1, EXO1, EXOC5, EXOSC6, EXPH5, EZH2, FAM101B, FAM105A, FAM110A, FAM114A1, FAM118A, FAM120C, FAM129B, FAM13A, FAM162B, FAM181B, FAM19A4, FAM19A5, FAM54A, FAM64A, FAM7A3, FAM83D, FANCG, FANCI, FANCL, FANCM, FARP1, FAT1, FBLN1, FBN1, FBP1, FBXO43, FBXO5, FEN1, FGFR2, FH, FIGNL1, FKBP5, FNDC5, FOXD1, FOXN3, FRMD6, FRZB, FSTL1, FZD2, FZD5, FZD8, G2E3, GABBR2, GAP43, GAP43, GAS2L3, GATM, GEMIN4, GFPT2, GFRA1, GFRA2, GGCX, GINS1, GINS3, GJC1, GLDC, GMNN, GNAI1, GNASAS, GNB4, GNG11, GNG12, GNG4, GPAM, GPN3, GPR125, GPR161, GPSM2, GPX3, GRP, GSG2, GSS, GSTCD, GTSE1, GTSF1, GXYLT1, H1F0, H2AFX, HAT1, HAUS6, HDAC8, HEG1, HES6, HGF, HIC2, HMG4L, HMGB1, HMGB2, HMGB3, HMGXB4, HMMR, HOOK3, HPS4, HRH3, HS3ST2, HS6ST2, HSPB11, HTATSF1, IDH2, IF127L1, IQGAP1, ITGA6, ITGAV, ITGB5, ITPRIP, JARID2, KCNG3, KCNJ8, KCNN1, KCTD12, KDELC2, KHDRBS3, KIAA0101, KIAA0406, KIAA1211, KIAA1524, KIF11, KIF14, KIF16B, KIF18A, KIF23, KIFC1, KLF7, KLHL13, KLHL5, KNTC1, KPNA2, LBH, LGR5, LHFPL2, LIFR, LIG3, LMF2, LMNB1, LOC100127983, LOC100128844, LOC100288551, LOC340109, LOC344595, LOC440288, LOC642597, LOC728052, LPAR1, LRFN2, LRRC1, LSM4, LUM, MAB21L1, MAB21L2, MAGEH1, MAN1A1, MAN2A1, MAOA, MAP3K13, MAPK11, MAPK12, MAPKAPK3, MASTL, MBD2, MCAM, MCM10, MCM3, MCM4, MCM5, MCM6, MCM7, MCM8, MDC1, MDM1, MED20, MEIS1, MEIS2, MELK, MEST, MFAP2, MGAT5B, MINA, MK167, MKL1, MLF11P, MMD, MNS1, MPHOSPH9, MPP5, MPPED2, MRC2, MRPL35, MRPL49, MRS2, MSN, MTF2, MTHFD1, MTUS1, MVK, MYBL1, MYBL2, MYD88, MYO1B, MYO6, MYST1, NAAA, NAGA, NANP, NARG1, NASP, NAT11, NAT13, NCAPD3, NCAPG, NCAPG2, NCAPH, NCAPH2, NDN, NEDD1, NEDD9, NEIL3, NELL2, NFIB, NOC4L, NOS1, NR3C1, NRG3, NRM, NRXN1, NSMCE4A, NTAN1, NUCKS1, NUDT1, NUF2, NUP107, NUP37, NUP43, NUP50, NUP93, NUSAP1, NXPH1, NXT2, ODZ3, ODZ4, OIP5, ORC1L, ORC6L, OSBPL3, PAICS, PANK2, PARP3, PASK, PBK, PCDH17, PCDH8, PCGF5, PCNA, PDCL, PDE5A, PDLIM5, PDRG1, PEG3, PELI2, PELO, PEX13, PEX26, PFKFB3, PGAM5, PGM2, PHF19, PHF20, PHF21B, PHF5A, PHLPP1, PHYHIPL, PI4KA, PIP4K2A, PIR, PKMYT1, PLCL2, PLD5, PLEKHF2, PLK2, PLK4, PLS3, PLXNA2, PLXNA4, PLXNB2, PM20D2, POLA1, POLA2, POLE, POLE2, POLQ, POSTN, PPAP2B, PPAT, PPIF, PPIL5, PPM1F, PPP1R13B, PPP1R3C, PPP2R2B, PPP3CB, PRIM1, PRIM2, PRLHR, PRPS1, PRSS12, PSMA7, PSMC31P, PSMD5, PSMD9, PSRC1, PTER, PTGES2, PTGFRN, PTGR1, PTPRE, PTPRG, PTPRK, PTPRM, PTTG1, PVRL3, PXMP4, PXN, RAB35, RAB3B, RAD18, RAD51, RAD51C, RALY, RAN, RANBP1, RANGAP1, RASEF, RBBP7, RBBP9, RBL1, RBPMS, RBX1, RECQL4, REEP1, RELB, RELL1, REXO2, RFC1, RFC2, RFC3, RFC4, RFC5, RGMA, RGS5, RILPL2, RIMBP2, RMI1, RNASEH2A, RNF182, RNF26, RNF34, RPA1, RPP30, RRM1, RRM2, RRP7A, RSRC1, S1PR3, SALL4, SAP30, SASS6, SBF2, SCD5, SCML1, SCML2, SDC1, SEC23A, SEC61A2, SELM, SEMA6A, SEMA6D, SESN3, SEZ6L, SF11, SFRP1, SGOL2, SH3D19, SHCBP1, SHMT1, SHOX2, SIM1, SIVA1, SKA1, SKA2, SKA3, SKP2, SLC25A10, SLC26A2, SLC2A4RG, SLC2A8, SLC43A3, SLC44A5, SLC7A2, SLC8A1, SLCO3A1, SLIT3, SLITRK5, SLK, SLMO2, SMC1A, SMC2, SMC4, SMC6, SMO, SMYD5, SNAI2, SNAP29, SNCAIP, SNRPD3, SNX18, SNX5, SORD, SOX4, SPAG6, SPARC, SPATS2L, SPC24, SPC25, SPOCK1, SPSB4, SRGAP1, SRRD, SRRM4, SSH2, ST8SIA1, ST8SIA2, ST8SIA4, STARD4, STIL, STK17A, STMN3, STOM, STON2, STRA6, SUSD5, SUV39H1, SVIP, SYN2, SYNE2, SYNM, SYT17, SYTL4, TBC1D1, TBX3, TCF19, TCF7L2, TCFL5, TDRKH, TEAD3, TESC, TFDP1, TFDP2, TFPI2, TH1L, THOC4, TIFA, TIMP3, TLE3, TLE4, TMCC3, TMEM107, TMEM132C, TMEM151B, TMEM170B, TMEM178, TMEM194A, TMEM38B, TMEM48, TMEM56, TMEM98, TMPO, TMSB15B, TNFAIP8, TOB2, TOMM34, TPBG, TPTE, TPX2, TRIM29, TRIM36, TRIM68, TRIM9, TRIP13, TROAP, TSHZ3, TSPAN14, TSPAN4, TSPAN5, TTC28, TTC9, TUBA1B, TUBB, TWIST1, TXNRD1, TYMS, TYRO3, UBE2C, UBE2L3, UBE2V1, UBE3B, UCK1, UCP2, UFD1L, UHRF1, UNC119B, UNG, UQCC, USP1, USP48, UTP18, VAPB, VAV3, VPS29, VSTM2L, WDHD1, WDR51A, WDR53, WDR62, WDR67, WEE1, WEE1, WHSC1, WRAP53, WWC3, XRCC4, XRCC6, ZAK, ZFHX4, ZFP82, ZGPAT, ZNF215, ZNF217, ZNF238, ZNF253, ZNF280B, ZNF367, ZNF43, ZNF443, ZNF503, ZNF521, ZNF560, ZNF608, ZNF626, ZNF681, ZNF71, ZNF823, ZNF85, ZNF92, ZNF93, and/or ZWINT, as compared to the expression levels of these genes in cells from the 2D6 cell line.

In an aspect of this embodiment, cells from an established clonal cell line susceptible to BoNT/A intoxication exhibit at least a 1.5-fold increase in gene expression levels of one or more genes selected from A2BP1, ACOT9, ALCAM, ANLN, ARHGAP24, ARHGAP6, ARHGEF3, ARHGEF6, ASCL1, ASF1B, ATAD2, AURKA, AURKB, BARD1, BASP1, BNC2, BRCA2, BRIP1, BTG3, BUB1, BUB1B, BVES, C11ORF75, C12ORF48, C14ORF106, C15ORF42, C18ORF54, C1ORF112, C3ORF70, C4ORF49, CCDC109B, CCDC3, CCNB1, CCNE2, CD9, CDC2, CDC25B, CDC45L, CDC6, CDCA2, CDCA5, CDCA8, CDK2, CDKN2D, CENPF, CENPI, CENPL, CENPN, CEP55, CHEK1, CHEK2, CHRNA7, CIT, CKAP2L, CLSTN2, CNTN1, CNTN4, CPVL, CRYBG3, CSRP2, CTSL2, CUGBP2, CXCR4, DAZ1, DEPDC1, DEPDC1B, DIAPH3, DLGAP5, DNA2, DOK5, DPYD, DPYSL3, DSCC1, DSN1, DTL, DYNLT3, E2F1, E2F2, E2F7, E2F8, ECT2, EFNB2, ELOVL7, EME1, EMILIN2, EMILIN3, EML1, ENC1, ERCC6L, ESCO2, ESPL1, ETV1, EXO1, EXPH5, FAM101B, FAM114A1, FAM54A, FAM64A, FAM7A3, FAM83D, FANCI, FAT1, FBLN1, FBP1, FBXO43, FGFR2, FNDC5, FOXD1, FRMD6, FRZB, FZD5, GAS2L3, GFRA2, GINS1, GINS3, GNAI1, GNB4, GNG11, GNG12, GPSM2, GRP, GTSE1, GTSF1, HGF, HMMR, HS3ST2, ITGA6, ITPRIP, KCNG3, KCTD12, KDELC2, KIAA0101, KIAA1524, KIF11, KIF14, KIF18A, KIF23, KIFC1, LOC340109, LOC642597, LOC728052, LOC728052, LPAR1, LUM, MAB21L1, MAB21L2, MAOA, MCM10, MCM5, MELK, MINA, MKI67, MLF11P, MPPED2, MRC2, MSN, MYBL1, MYBL2, MYO6, NCAPG, NCAPH, NDN, NEDD9, NEIL3, NR3C1, NRXN1, NUF2, NUSAP1, OIP5, ORC1L, OSBPL3, PBK, PCGF5, PDE5A, PEG3, PELO, PFKFB3, PHLPP1, PLD5, PLK2, PLK4, PLS3, POLA2, POLE2, POLQ, PPAP2B, PPP1R3c, PRLHR, PRSS12, PSRC1, PTGR1, PTPRE, PTPRK, PTPRM, PTTG1, PVRL3, RAD51, RBL1, RBPMS, RELL1, RFC5, RGMA, RGS5, RNF182, RRM2, S1PR3, SGOL2, SHCBP1, SHOX2, SIM1, SKA1, SLC43A3, SLC44A5, SLC7A2, SLITRK5, SMC2, SMC6, SPAG6, SPARC, SPC24, SPC25, ST8SIA4, STK17A, SUSD5, SYN2, SYNM, SYT17, TCF19, TESC, TFDP2, TFPI2, TIMP3, TLE3, TMEM132C, TMEM178, TNFAIP8, TPBG, TPTE, TPX2, TRIM29, TRIM36, TRIM68, TROAP, TWIST1, TYMS, UBE2C, UBE3B, UHRF1, WDHD1, WDR51A, WDR67, WEE1, ZFP82, ZNF367, ZNF521, and/or ZWINT, as compared to the expression levels of these genes in cells from the 2D6 cell line.

In another aspect of this embodiment, cells from an established clonal cell line susceptible to BoNT/A intoxication exhibit at least a 1.5-fold increase in gene expression levels of one or more genes selected from A2BP1, ALCAM, ANLN, ARHGAP24, ARHGAP6, ASCL1, ASF1B, ATAD2, AURKA, AURKB, BARD1, BASP1, BNC2, BRIP1, BUB1, BVES, C11ORF75, C12ORF48, C14ORF106, C18ORF54, C3ORF70, CCDC109B, CCDC3, CD9, CDC2, CDC45L, CDCA2, CDCA8, CDK2, CENPL, CEP55, CHEK2, CHRNA7, CKAP2L, CNTN1, CRYBG3, CUGBP2, CXCR4, DAZ1, DEPDC1, DIAPH3, DLGAP5, DOK5, DPYD, DTL, DYNLT3, E2F1, E2F7, E2F8, EFNB2, ELOVL7, EMILIN2, EML1, ENC1, ESPL1, ETV1, EXO1, EXPH5, FAM54A, FAM64A, FAM7A3, FAM83D, FANCI, FAT1, FBLN1, FBXO43, FGFR2, FZD5, GNAI1, GNB4, GNG11, GNG12, GPSM2, GRP, GTSE1, GTSF1, HGF, HMMR, ITGA6, ITPRIP, KCTD12, KDELC2, KIF11, KIF14, KIF18A, KIF23, KIFC1, LOC340109, LOC728052, LPAR1, LUM, MAB21L1, MAB21L2, MAOA, MCM10, MELK, MINA, MKI67, MSN, MYBL1, NCAPH, NDN, NEDD9, NEIL3, NRXN1, NUF2, NUSAP1, OIP5, ORC1L, OSBPL3, PBK, PCGF5, PEG3, PEG3, PHLPP1, PLD5, PLK2, PLK4, PLS3, POLE2, PPAP2B, PPP1R3c, PRLHR, PRSS12, PTPRE, PTPRK, PTPRM, RBPMS, RELL1, RGS5, RNF182, RRM2, S1PR3, SGOL2, SHCBP1, SHOX2, SIM1, SLC43A3, SLC44A5, SLC7A2, SLITRK5, SMC6, SPAG6, SPARC, SPC24, SPC25, ST8SIA4, STK17A, SYT17, TFPI2, TIMP3, TMEM132C, TMEM178, TPBG, TPTE, TPX2, TRIM36, TWIST1, UBE3B, and/or ZNF367, as compared to the expression levels of these genes in cells from the 2D6 cell line.

In yet another aspect of this embodiment, cells from an established clonal cell line susceptible to BoNT/A intoxication exhibit at least a 1.5-fold increase in gene expression levels of one or more genes selected from A2BP1, ARHGAP24, ARHGAP6, ASCL1, ASF1B, ATAD2, AURKA, BARD1, BASP1, BNC2, BUB1, BVES, C11ORF75, CCDC3, CHEK2, CHRNA7, CKAP2L, CNTN1, CRYBG3, CUGBP2, CUGBP2, CXCR4, DAZ1, DEPDC1, DIAPH3, DLGAP5, DOK5, DPYD, DTL, DYNLT3, E2F8, EFNB2, ELOVL7, ENC1, EXPH5, FAM7A3, FANCI, FAT1, FBLN1, FGFR2, GNAI1, GNB4, GNG11, GNG12, GRP, GTSE1, GTSF1, HMMR, ITGA6, ITPRIP, KCTD12, KDELC2, LOC728052, LPAR1, LUM, MAB21L1, MAB21L2, MAOA, MCM10, MELK, MINA, MKI67, MSN, MYBL1, NDN, NEDD9, NRXN1, OSBPL3, PEG3, PLK2, PLS3, PRLHR, PRSS12, PTPRK, PTPRM, RBPMS, RGS5, RNF182, RRM2, SGOL2, SIM1, SLC43A3, SLC44A5, SLC7A2, SMC6, SPAG6, SPARC, STK17A, TFPI2, TIMP3, TMEM132C, TMEM178, and/or TPTE, as compared to the expression levels of these genes in cells from the 2D6 cell line.

In another embodiment, cells from an established clonal cell line susceptible to BoNT/A intoxication exhibit at least a 1.5-fold increase in gene expression levels of one or more genes selected from ADAMTS9, ATAD2, C11ORF82, CDC45L, CNTN1, CNTN4, Cyclin A, Cyclin E, E2F1, E2F2, E2F7, ELOVL7, EME1, FGFR, FGFR2, KIAA1524, MELK, MYBL1, MYBL2, NDC80, NDN, ORC1L, PLS3, PRIMA1, RAD54L, RBL1, RBPMS, RRM2, S1PR3, SCLY, SLCIA3, SPC24, SPC25, ST8SIA4, TFDP1, TFP12, TK1, TMEM35, TTK, TWIST1, TYMS, TYK, and/or ZWINT, as compared to the expression levels of these genes in cells from the 2D6 cell line.

In yet another embodiment, cells from an established clonal cell line susceptible to BoNT/A intoxication exhibit at least a 1.5-fold increase in gene expression levels of one or more genes selected from AURKB, BIRC5, BRCA1, BRCA2, BRIP1, BUB1B, CD9, DLGAP3, DYNLT3, ENC1, FBLN1, FOXM1, Gβγ, GNAI1, GNG11, GNG12, GPSM2, GUCY1B3, HGF, ITGA6, JNK, KCNJ5, KIF18A, KITLG, MMD, MSN, MYRIP, NEK2, NR3C1, NXPH1, OSBPL3, PKMYT1, PTPRM, RAD51, RAD51AP1, SLC7A2, SLC43A3, SMC6, SNAI2, SNCAIP, SSH2, STK17A, SYNPO2, TOP2A, TPTE, TRAF4, TSPAN, TSPAN4, UBE3, UBE3B, and/or VAV3, as compared to the expression levels of these genes in cells from the 2D6 cell line. In still another embodiment, cells from an established clonal cell line susceptible to BoNT/A intoxication exhibit at least a 1.5-fold increase in gene expression levels of one or more genes selected from ALCAM, AURKA, CHEK, CIT, CSRP2, E2F, ECT2, EFNB2, ERK, ESPL1, GNAI, GPR161, HMMR, KIF4A, KIF14, KIF15, KIF22, KIF23, KIFC1, LPAR1, MK167, OIP5, PHLPP, PP1/PP2A, PPP1R3C, PRC1, PTTG1, RACGAP, RB, RGS5, SDC2, and/or TPX2, as compared to the expression levels of these genes in cells from the 2D6 cell line.

In another embodiment, cells from an established clonal cell line susceptible to BoNT/A intoxication exhibit at least a 1.5-fold increase in gene expression levels of one or more genes selected from ASCL1, HES6, MAPK, NMU, PEG3, PTPRK, PRLHR, PTPRK, SGOL2, SPARC, and/or ZNF217, as compared to the expression levels of these genes in cells from the 2D6 cell line. In yet another embodiment, cells from an established clonal cell line susceptible to BoNT/A intoxication exhibit at least a 1.5-fold increase in gene expression levels of one or more genes selected from ASF1B, BASP1, CHAF1A, NCAPH, PBK, PRAME, SMC2, UHRF1, and/or VRK1, as compared to the expression levels of these genes in cells from the 2D6 cell line. In still another embodiment, cells from an established clonal cell line susceptible to BoNT/A intoxication exhibit at least a 1.5-fold increase in gene expression levels of one or more genes selected from C14ORF106, CEP72, KIF20A, PCNA, PEX13, PFC5, POLQ, SPAG5, SYTL4, TROAP, and/or WDR51A, as compared to the expression levels of these genes in cells from the 2D6 cell line. In a further embodiment, cells from an established clonal cell line susceptible to BoNT/A intoxication exhibit at least a 1.5-fold increase in gene expression levels of one or more genes selected from ANLN, ARHGAP24, ASPM, BUB1, CCDC99, CEP55, CKAP2, DRAM, E2F8, PLXNA2, SLC16A10, UBE2C, UBE2S, and/or WDHD1, as compared to the expression levels of these genes in cells from the 2D6 cell line.

In another embodiment, cells from an established clonal cell line susceptible to BoNT/A intoxication exhibit at least a 1.5-fold increase in gene expression levels of one or more genes selected from ARHGEF3, CTSL2, DIAPH3, FBP1, KIF2C, KIF11, PFKFB3, and/or PLK4, as compared to the expression levels of these genes in cells from the 2D6 cell line. In yet another embodiment, cells from an established clonal cell line susceptible to BoNT/A intoxication exhibit at least a 1.5-fold increase in gene expression levels of one or more genes selected from ARHGEF3, CTSL2, DIAPH3, FBP1, KIF2C, KIF11, PFKFB3, and/or PLK4, as compared to the expression levels of these genes in cells from the 2D6 cell line. In still another embodiment, cells from an established clonal cell line susceptible to BoNT/A intoxication exhibit at least a 1.5-fold increase in gene expression levels of one or more genes selected from FNDC5, HSPC159, MAB21L2, SLITRK5, SYN2, and/or ZNF367, as compared to the expression levels of these genes in cells from the 2D6 cell line. In a further another embodiment, cells from an established clonal cell line susceptible to BoNT/A intoxication exhibit at least a 1.5-fold increase in gene expression levels of one or more genes selected from EXO1, KCTD12, MYO6, PHEBL1, SHCBP1, TPBG, and/or TUBB6, as compared to the expression levels of these genes in cells from the 2D6 cell line. In yet another embodiment, cells from an established clonal cell line susceptible to BoNT/A intoxication exhibit at least a 1.5-fold increase in gene expression levels of one or more genes selected from BTG3, GABRA5, TR1P10, and/or ZNF521, as compared to the expression levels of these genes in cells from the 2D6 cell line. In still another embodiment, cells from an established clonal cell line susceptible to BoNT/A intoxication exhibit at least a 1.5-fold increase in gene expression levels of one or more genes selected from BNC2, DPYD, EMILIN2, PPIL5, and/or TACC3, as compared to the expression levels of these genes in cells from the 2D6 cell line.

In another embodiment, cells from an established clonal cell line susceptible to BoNT/A intoxication exhibit at least a 1.5-fold difference in gene expression levels of one or more genes listed in Tables 14 or 16 as compared to the expression levels of these genes in cells from the 2D6 cell line. In an aspect of this embodiment, cells from an established clonal cell line susceptible to BoNT/A intoxication exhibit at least a 1.5-fold increase in gene expression levels of one or more genes selected from ACOT9, ADAMTS9, ARHGAP24, ARHGEF3, ASCL1, BARD1, BASP1, C3ORF70, C11ORF75, CCDC109B, CD9, CDCA7L, CDK2, CENPL, CLSTN2, CNTN1, CSRP2, CTSL2, CUGBP2, DEPDC1, DIAPH3, DOK5, DPYD, DYNLT3, EMILIN2, ETV1, FAM101B, FBLN1, FGFR2, FNDC5, GNAI1, GNB4, GNG11, GNG12, GPR177, GTSE1, HGF, KITLG, LPAR1, MAB21L2, MAOA, MCM10, MINA, MSN, MYO6, MYRIP, PAG1, PEG3, PLK2, POLA2, PPP1R3C, PRLHR, PRSS12, PTGR1, PTPRK, PVRL3, RAB32, RBPMS, SDC2, SGOL2, SLC43A3, SLC7A2, SMC2, SMC6, SPARC, SPC25, ST8SIA4, TCF7L1, TFPI2, TMEM35, TMEM178, TNFAIP8, TPTE, TRIP10, TWIST1, and/or ZNF521, as compared to the expression levels of these genes in cells from the 2D6 cell line. In another aspect of this embodiment, cells from an established clonal cell line susceptible to BoNT/A intoxication exhibit at least a 1.5-fold increase in gene expression levels of one or more genes selected from ADAMTS9, ARHGAP24, ASCL1, BARD1, BASP1, BVES, C11ORF75, CDCA7L, CNTN1, CUGBP2, DOK5, DPYD, DYNLT3, FBLN1, FGFR2, GNAI1, GNB4, GNG11, GNG12, GTSE1, GTSF1, ITPRIP, KDELC2, LOC728052, LPAR1, MAB21L2, MAOA, MINA, MSN, PEG3, PLK2, PRLHR, PRSS12, PTPRK, RBPMS, RNF182, SGOL2, SLC43A3, SLC44A5, SLC7A2, SMC6, SPARC, TFPI2, TMEM178, and/or TPTE, as compared to the expression levels of these genes in cells from the 2D6 cell line. In yet another aspect of this embodiment, cells from an established clonal cell line susceptible to BoNT/A intoxication exhibit at least a 1.5-fold increase in gene expression levels of one or more genes selected from ADAMTS9, ASCL1, BASP1, DOK5, DPYD, GNB4, GNG11, GTSF1, MAOA, MINA, MSN, PEG3, PLK2, PRSS12, RNF182, SLC44A5, SPARC, TFPI2, and/or TPTE, as compared to the expression levels of these genes in cells from the 2D6 cell line.

In yet another embodiment, cells from an established clonal cell line susceptible to BoNT/A intoxication exhibit at least a 1.5-fold increase in gene expression levels of one or more genes selected from ADAMTS9, ARHGAP24, ARHGEF3, ASCL1, BARD1, CD9, CDK2, CSRP2, CTSL2, DIAPH3, DOK5, DYNLT3, EMILIN2, ETV1, FBLN1, FGFR2, GNAI1, GNB4, GNG11, GNG12, HGF, KITLG, LPAR1, MCM10, MSN, PAG1, PEG3, PLK2, POLA2, PPP1R3C, PTPRK, RAB32, SDC2, SLC43A3, SLC7A2, SMC6, SPARC, SPC25, ST8SIA4, TCF7L1, TFPI2, TMEM35, TNFAIP8, TPTE, TRIP10, and/or TWIST1, as compared to the expression levels of these genes in cells from the 2D6 cell line. In an aspect of this embodiment, cells from an established clonal cell line susceptible to BoNT/A intoxication exhibit at least a 1.5-fold increase in gene expression levels of one or more genes selected from ADAMTS9, ARHGAP24, ASCL1, BARD1, DOK5, DYNLT3, FBLN1, FGFR2, GNAI1, GNB4, GNG11, GNG12, LPAR1, MSN, PEG3, PLK2, PTPRK, SLC43A3, SLC7A2, SMC6, SPARC, TFPI2, and/or TPTE, as compared to the expression levels of these genes in cells from the 2D6 cell line. In another aspect of this embodiment, cells from an established clonal cell line susceptible to BoNT/A intoxication exhibit at least a 1.5-fold increase in gene expression levels of one or more genes selected from ADAMTS9, ASCL1, DOK5, GNB4, GNG11, MSN, PEG3, PLK2, SPARC, TFPI2, and/or TPTE, as compared to the expression levels of these genes in cells from the 2D6 cell line.

In still another embodiment, cells from an established clonal cell line susceptible to BoNT/A intoxication exhibit at least a 1.5-fold increase in gene expression levels of one or more genes selected from ACOT9, BASP1, C11ORF75, CCDC109B, CDCA7L, CLSTN2, CNTN1, CUGBP2, DEPDC1, DPYD, FAM101B, FNDC5, GTSE1, MAOA, MINA, MYO6, MYRIP, PLK2, PRLHR, PVRL3, RBPMS, SGOL2, SMC2, TFP12, TMEM178, and/or ZNF521, as compared to the expression levels of these genes in cells from the 2D6 cell line. In an aspect of this embodiment, cells from an established clonal cell line susceptible to BoNT/A intoxication exhibit at least a 1.5-fold increase in gene expression levels of one or more genes selected from BASP1, C11ORF75, CDCA7L, CNTN1, CUGBP2, DPYD, GTSE1, MAOA, MINA, PLK2, PRLHR, RBPMS, SGOL2, TFPI2, and/or TMEM178, as compared to the expression levels of these genes in cells from the 2D6 cell line. In another aspect of this embodiment, cells from an established clonal cell line susceptible to BoNT/A intoxication exhibit at least a 1.5-fold increase in gene expression levels of one or more genes selected from BASP1, DPYD, MAOA, MINA, PLK2, and/or TFPI2, as compared to the expression levels of these genes in cells from the 2D6 cell line.

In a further embodiment, cells from an established clonal cell line susceptible to BoNT/A intoxication exhibit at least a 1.5-fold increase in gene expression levels of one or more genes selected from C3ORF70, MAB21L2, PRSS12, CENPL, GPR177, and/or PTGR1, as compared to the expression levels of these genes in cells from the 2D6 cell line. In an aspect of this embodiment, cells from an established clonal cell line susceptible to BoNT/A intoxication exhibit at least a 1.5-fold increase in gene expression levels of one or more genes selected from MAB21L2 and/or PRSS12, as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes listed in Tables 6 or 8 as compared to the expression levels of these genes in cells from a 2D6 cell line. In other aspects of this embodiment, cells from an established clonal cell line susceptible to BoNT/A intoxication exhibit a decrease in gene expression levels of one or more genes listed in Tables 6 or 8 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from a 2D6 cell line. In other aspects of this embodiment, cells from an established clonal cell line susceptible to BoNT/A intoxication exhibit a decrease in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 6 or 8 as compared to the expression levels of these genes in cells from the 2D6 cell line. In yet other aspects of this embodiment, cells from an established clonal cell line susceptible to BoNT/A intoxication exhibit an decrease in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 6 or 8 as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes selected from AATK, ABCA2, ABCC5, ABCC8, ABR, ABTB1, ACOT1, ACRBP, ACRV1, ACYP2, ADARB1, ADCY1, ADM, AFF1, AGAP4, AGPAT3, AGXT2L2, AHI1, AKAP9, AKIRIN1, AKT2, AMH, ANK2, ANK3, ANKHD1, ANKRD17, ANKRD50, ANKS1A, AQP1, ARF1, ARHGAP1, ARHGAP23, ARL17A, ASAM, ASPHD1, ATP2B3, ATP2B3, ATP6V0A1, ATP8B2, ATP9A, BACE1, BACH2, BLZF1, BPTF, BRUNOL4, BRUNOL5, BRWD1, BRWD2, BTBD18, BTN3A3, BZRAP1, C14ORF159, C15ORF24, C15ORF57, C16ORF52, C17ORF28, C1ORF21, C1ORF21, C1ORF50, C21ORF57, C21ORF59, C21ORF66, C2CD2, C2CD4A, C2ORF60, C2ORF68, C3ORF23, C4ORF41, C5ORF42, C6ORF154, C6ORF52, C7ORF28B, C7ORF54, C9ORF150, C9ORF68, CACNA1D, CALY, CAMK2B, CAMK2N2, CAP2, CAPN2, CARTPT, CBS, CCDC104, CCDC50, CCDC76, CD151, CD163L1, CD302, CDC42EP1, CDH10, CDH12, CDKN1C, CDKN2A, CDS1, CFC1, CHD5, CLCN3, CLDN12, CLIP4, CLMN, CNGA3, CNNM1, CNOT6L, COL6A1, COPA, CPNE8, CRKRS, CRTC1, CRYGS, CSTB, CTSK, CUL4A, CYGB, CYLD, CYP2E1, CYP3A5, CYTL1, D4S234E, DCLK1, DCTD, DEPDC6, DHX36, DIP2A, DIS3, DKFZP547G183, DNAJC22, DTNA, DTWD1, DUSP16, DUSP5, DVL3, EFNB3, EIF3C, ELFN2, ENOSF1, ERAP1, ERBB2, ERBB4, ERMAP, ETFDH, EXOSC6, FADS3, FAM120AOS, FAM150B, FAM165B, FAM184B, FAM30A, FAM46A, FAM66C, FAT4, FBRSL1, FBXW7, FGD5, FGF13, FLJ33630, FNBP1, FOXO6, FUBP3, GAL, GAL, GLT25D2, GNAS, GOLGA8A, GPR123, GPX7, GRIA2, GRIP2, GRM5, GUCY1A3, H2AFY, HCG 1776018, HCG 2022304, HCN4, HEATR1, HELQ, HERC4, HERPUD2, HEXDC, HGSNAT, H1ST1H2AC, H1ST1H2AE, HIST1H2BD, HIST1H2BK, HIST1H31, HIST2H2BE, HIVEP3, HNRNPM, HNRNPR, HPCAL1, HPCAL4, HSPD1, IER3, IL10RB, IL17B, INTU, JMY, KAT2B, KATNB1, KBTBD11, KCNMA1, KCNQ2, KCNS2, KCTD13, KHDC1, KIAA0125, KIAA1370, KIAA1598, KIF1A, KIF5C, KIF5C, KISS1R, KLHDC1, LCORL, LGALS3BP, LOC100130097, LOC100130360, LOC100130522, LOC100272228, LOC284408, LOC399491, LOC401320, LOC641298, LOC642852, LOC90110, LOC94431, LONRF2, LRP2BP, LRRC37A2, LRRFIP1, LTBP3, LYPLAL1, LYRM5, MAP3K5, MAP7, MAP9, MCM3AP, MCM3APAS, MCTP1, MEOX2, METTL3, MFSD4, MGAT4A, MLXIP, MRPL1, MRPS33, MST1, MUC20, MXD1, MZF1, NAMPT, NAP1L3, NBPF1, NBPF10, NCOA7, NCRNA00171, NCRNA00182, NDRG1, NDUFA4L2, NDUFV3, NEBL, NELF, NHEDC2, NHEG1, NIPAL2, NIPAL3, NLRX1, NOL3, NSMAF, NUDT19, NUP153, NUP54, OLFM3, OR7D2, OSBP, PABPC1L, PABPC4, PACRGL, PAM, PAPPA, PAQR6, PARP12, PCBD2, PCNXL2, PDCD6, PDE4C, PDE9A, PDGFRB, PDIA2, PGAP1, PHF17, PHKA1, PHKA2, PHLDA2, PIGH, PION, PKD1, PLA2G4C, PLCB4, PLEKHH1, PLP2, PLRG1, PLXNC1, PNCK, PNMA3, POFUT2, POGK, PPAPDC1A, PPAPDC1B, PPID, PPIE, PPM1K, PPP1R2, PPP2R2C, PPT1, PRKACB, PRPH, PSMB7, PTCD1, PTGER2, PTGS1, PTN, PTPRD, PTPRN, RAB11FIP3, RAB6B, RAF1, RGAG4, RGS11, RGS8, RHBDL1, RHOQ, RHOU, RLF, RNASET2, RNF13, RNF149, RNF165, RNF207, RNF41, RPL37, RSL1D1, RUNDC3A, S100A6, SCMH1, SCN2A, SERP1, SETX, SFRS18, SFXN3, SGK3, SH3BP5, SH3GL2, SH3YL1, SHC2, SHC4, SIGIRR, SIK1, SLC12A7, SLC1A2, SLC1A6, SLC22A17, SLC35F3, SLC38A5, SLCO1A2, SMAGP, SMAP2, SNCA, SOBP, SORCS1, SORL1, SPINT2, SPIRE2, SPOCK2, SRR, ST8SIA3, STAR, STEAP3, STOX2, STX3, SYNJ1, SYT13, SYT5, TAF10, TANC2, TCEA1, THBS2, THSD4, TIMP1, TM2D1, TMEM111, TMEM151A, TMEM184C, TMEM41B, TMEM43, TMEM5, TMEM59L, TMIE, TNFRSF25, TNFRSF25, TOX4, TP53BP1, TPM3, TRA2A, TRIM33, TRIM73, TRIM5, TRIT1, TSR1, TTC17, TTC3, TTC39C, TUSC3, TXLNB, U2AF1, UBE2D3, UBE2G2, UBN2, UBXN6, UCN, UGP2, UNC80, UNQ1887, USP36, USPL1, VN1R1, VPS13C, VPS53, VPS8, WDFY3, WDR27, WDR85, WSB1, YJEFN3, YLPM1, ZDHHC11, ZER1, ZG16B, ZNF275, ZNF440, ZNF573, ZNF641, ZNF662, ZNF785, and/or ZNF814, as compared to the expression levels of these genes in cells from the 2D6 cell line.

In an aspect of this embodiment, cells from an established clonal cell line susceptible to BoNT/A intoxication exhibit at least a 1.5-fold decrease in gene expression levels of one or more genes selected from ACOT1, ADARB1, ADM, ANK2, AQP1, ASAM, C2CD4A, C3ORF23, CACNA1D, CAMK2B, CAP2, CARTPT, CD163L1, CDC42EP1, CDH10, CDKN1C, CDKN2A, CFC1, CLMN, CPNE8, CYGB, CYP2E1, CYTL1, DNAJC22, DUSP5, ENOSF1, ERAP1, FGF13, FOXO6, GAL, GNAS, GPX7, GRIA2, GRM5, HCG 1776018, H1ST1H2AC, HIST1H2BD, HIST1H2BK, HIST2H2BE, IL17B, KIAA0125, KIAA1598, KISS1R, LRP2BP, MEOX2, NCRNA00182, NDRG1, NDUFA4L2, NIPAL2, NUDT19, PDE4C, PHKA2, PHLDA2, PTGER2, RGS11, S100A6, SCN2A, SHC4, SIGIRR, SLC1A2, SLC1A6, SLC35F3, SLC38A5, SORCS1, SYT13, SYT5, THBS2, TIMP1, and/or TMEM111, as compared to the expression levels of these genes in cells from the 2D6 cell line.

In another aspect of this embodiment, cells from an established clonal cell line susceptible to BoNT/A intoxication exhibit at least a 1.5-fold decrease in gene expression levels of one or more genes selected from ACOT1, ADARB1, ANK2, AQP1, C3ORF23, CAP2, CARTPT, CD163L1, CDC42EP1, CDKN2A, CFC1, CPNE8, CYGB, CYP2E1, CYTL1, FGF13, FOXO6, GNAS, GRIA2, GRM5, H1ST1H2AC, IL17B, KIAA0125, KIAA1598, KISS1R, MEOX2, NDRG1, NDUFA4L2, NIPAL2, PDE4C, PHKA2, RGS11, SCN2A, SLC1A2, SLC35F3, SLC38A5, SYT13, and/or THBS2, as compared to the expression levels of these genes in cells from the 2D6 cell line.

In yet another aspect of this embodiment, cells from an established clonal cell line susceptible to BoNT/A intoxication exhibit at least a 1.5-fold decrease in gene expression levels of one or more genes selected from AQP1, CAP2, CARTPT, CD163L1, CDC42EP1, CFC1, CPNE8, CYGB, CYP2E1, CYTL1, FGF13, GNAS, GRIA2, GRM5, H1ST1H2AC, IL17B, KIAA0125, MEOX2, NDUFA4L2, PDE4C, PHKA2, RGS11, SLC1A2, SLC35F3, SLC38A5, and/or SYT13, as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes selected from ANXA2, AQP1, ARHGAP9, CDH10, CDKN2A, CHPT1, CNTN2, ERAP1, and/or RGS11, as compared to the expression levels of these genes in cells from the 2D6 cell line. In yet another embodiment, cells from an established clonal cell line susceptible to BoNT/A intoxication exhibit at least a 1.5-fold decrease in gene expression levels of one or more genes selected from ABCC8, AELIM3, CAP2, IL17B, MEF2A, NEEBL, PHC, S100A6, SLC1A6, SMAD1, SMAD5, SMAD8, SYT13, and/or SYTL1, as compared to the expression levels of these genes in cells from the 2D6 cell line. In still another embodiment, cells from an established clonal cell line susceptible to BoNT/A intoxication exhibit at least a 1.5-fold decrease in gene expression levels of one or more genes selected from CSTB, GPCR, GRIM5, KISSR, SCN2A, SLC1A2, and/or THBS2, as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes selected from ADARB1, ADM, PTPPH, and/or SLCO1A2, as compared to the expression levels of these genes in cells from the 2D6 cell line. In yet another embodiment, cells from an established clonal cell line susceptible to BoNT/A intoxication exhibit at least a 1.5-fold decrease in gene expression levels of one or more genes selected from CNGA3, HIST1H3E, and/or PTGS1, as compared to the expression levels of these genes in cells from the 2D6 cell line. In still another embodiment, cells from an established clonal cell line susceptible to BoNT/A intoxication exhibit at least a 1.5-fold decrease in gene expression levels of one or more genes selected from HIST1H2BD and/or OSCAR as compared to the expression levels of these genes in cells from the 2D6 cell line. In a further embodiment, cells from an established clonal cell line susceptible to BoNT/A intoxication exhibit at least a 1.5-fold decrease in gene expression levels of one or more genes selected from CALY as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes selected from COL5A1 and/or MICAL2 as compared to the expression levels of these genes in cells from the 2D6 cell line. In yet another embodiment, cells from an established clonal cell line susceptible to BoNT/A intoxication exhibit at least a 1.5-fold decrease in gene expression levels of one or more genes selected from OLFML2A and/or SIGIRR as compared to the expression levels of these genes in cells from the 2D6 cell line. In still another embodiment, cells from an established clonal cell line susceptible to BoNT/A intoxication exhibit at least a 1.5-fold decrease in gene expression levels of one or more genes selected from HPCAL1 and/or LPAR5 as compared to the expression levels of these genes in cells from the 2D6 cell line. In a further embodiment, cells from an established clonal cell line susceptible to BoNT/A intoxication exhibit at least a 1.5-fold decrease in gene expression levels of one or more genes selected from HTR1E and/or SORCS1 as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes selected from ANK2, CPNE8, CREB5, IL17B, KIAA0125, LOC100289109, LOC144571, NPAS4, SLC1A2, SORCS1, THBS2, and/or ZNF814, as compared to the expression levels of these genes in cells from the 2D6 cell line.

Aspects of the present disclosure comprise, in part, cells from an established clonal cell line susceptible to BoNT/A intoxication that exhibit at least a 1.5-fold difference in gene expression levels of one or more genes listed in Tables 9, 10, 11, or 12 as compared to the expression levels of these genes in cells from a parental SiMa cell line. In aspects of this embodiment, cells from an established clonal cell line susceptible to BoNT/A intoxication exhibit at least a 1.5-fold difference in gene expression levels of one or more genes listed in Tables 9, 10, 11, or 12 as compared to the expression levels of these genes in cells from the parental SiMa cell line DSMZ ACC 164. In other aspects of this embodiment, cells from an established clonal cell line susceptible to BoNT/A intoxication exhibit a difference in gene expression levels of one or more genes listed in Tables 9, 10, 11, or 12 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from the parental SiMa cell line DSMZ ACC 164. In yet other aspects of this embodiment, cells from an established clonal cell line susceptible to BoNT/A intoxication exhibit a difference in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 9, 10, 11, or 12 as compared to the expression levels of these genes in cells from the parental SiMa cell line DSMZ ACC 164. In still other aspects of this embodiment, cells from an established clonal cell line susceptible to BoNT/A intoxication exhibit a difference in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 9, 10, 11, or 12 as compared to the expression levels of these genes in cells from the parental SiMa cell line DSMZ ACC 164. The log ratio in Tables 9, 10, 11, or 12 represent $\log_2$ values where 0.585 is $\log_2(1.5)$ which is a 1.5-fold difference, 1 is $\log_2(2)$ which is a 2-fold difference, 1.584 is $\log_2(3)$ which is a 3-fold difference, 2 is $\log_2(4)$ which is a 4-fold difference, 2.321 is $\log_2(5)$ which is a 5-fold difference, 2.584 is $\log_2(6)$ which is a 6-fold difference, 2.807 is $\log_2(7)$ which is a 7-fold difference, 3 is $\log_2(8)$ which is a 8-fold difference, 3.169 is $\log_2(9)$ which is a 9-fold difference, and 3.321 is $\log_2(10)$ which is a 10-fold difference.

In an embodiment, cells from an established clonal cell line susceptible to BoNT/A intoxication exhibit at least a 1.5-fold difference in gene expression levels of one or more genes selected from ACOT9, ADAMTS9, ARHGAP24, ARHGEF3, ASCL1, BARD1, BASP1, C3ORF70, C11ORF75, CCDC109B, CD9, CDCA7L, CDK2, CENPL, CLSTN2, CNTN1, CSRP2, CTSL2, CUGBP2, DEPDC1, DIAPH3, DOK5, DPYD, DYNLT3, EMILIN2, ETV1, FAM101B, FBLN1, FGFR2, FNDC5, GNAI1, GNB4, GNG11, GNG12, GPR177, GTSE1, HGF, KITLG, LPAR1, MAB21L2, MAOA, MCM10, MINA, MSN, MYO6, MYRIP, PAG1, PEG3, PLK2, POLA2, PPP1R3C, PRLHR, PRSS12, PTGR1, PTPRK, PVRL3, RAB32, RBPMS, SDC2, SGOL2, SLC43A3, SLC7A2, SMC2, SMC6, SPARC, SPC25, ST8SIA4, TCF7L1, TFPI2, TMEM35, TMEM178, TNFAIP8, TPTE, TRIP10, TWIST1, and/or ZNF521, as compared to the expression levels of these genes in cells from the parental SiMa cell line DSMZ ACC 164. In another aspect of this embodiment, cells from an established clonal cell line susceptible to BoNT/A intoxication exhibit at least a 1.5-fold difference in gene expression levels of one or more genes selected from ADAMTS9, ARHGAP24, ASCL1, BARD1, BASP1, BVES, C11ORF75, CDCA7L, CNTN1, CUGBP2, DOK5, DPYD, DYNLT3, FBLN1, FGFR2, GNAI1, GNB4, GNG11, GNG12, GTSE1, GTSF1, ITPRIP, KDELC2, LOC728052, LPAR1, MAB21L2, MAOA, MINA, MSN, PEG3, PLK2, PRLHR, PRSS12, PTPRK, RBPMS, RNF182, SGOL2, SLC43A3, SLC44A5, SLC7A2, SMC6, SPARC, TFPI2, TMEM178, and/or TPTE, as compared to the expression levels of these genes in cells from the parental SiMa cell line DSMZ ACC 164. In yet another aspect of this embodiment, cells from an established clonal cell line susceptible to BoNT/A intoxication exhibit at least a 1.5-fold difference in gene expression levels of one or more genes selected from ADAMTS9, ASCL1, BASP1, DOK5, DPYD, GNB4, GNG11, GTSF1, MAOA, MINA, MSN, PEG3, PLK2, PRSS12, RNF182, SLC44A5, SPARC, TFPI2, and/or TPTE, as compared to the expression levels of these genes in cells from the parental SiMa cell line DSMZ ACC 164.

In another embodiment, cells from an established clonal cell line susceptible to BoNT/A intoxication exhibit at least a 1.5-fold increase in gene expression levels of one or more genes listed in Tables 9 or 11 as compared to the expression levels of these genes in cells from a parental SiMa cell line DSMZ ACC 164. In other aspects of this embodiment, cells from an established clonal cell line susceptible to BoNT/A intoxication exhibit an increase in gene expression levels of one or more genes listed in Tables 9 or 11 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from a parental SiMa cell line DSMZ ACC 164. In other aspects of this embodiment, cells from an established clonal cell line susceptible to BoNT/A intoxication exhibit an increase in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 9 or 11 as compared to the expression levels of these genes in cells from the parental SiMa cell line DSMZ ACC 164. In yet other aspects of this embodiment, cells from an established clonal cell line susceptible to BoNT/A intoxication exhibit an increase in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 9 or 11 as compared to the expression levels of these genes in cells from the parental SiMa cell line DSMZ ACC 164.

In an embodiment, cells from an established clonal cell line susceptible to BoNT/A intoxication exhibit at least a 1.5-fold increase in gene expression levels of one or more genes selected from A2BP1, ADRM1, AFF4, AGAP4, ALCAM, ANAPC7, ANKRD13D, ANKRD28, API5, ARF1, ARHGAP6, ARHGEF10, ARHGEF6, ARL17A, ASCL1, ASXL1, ASXL3, ATF71P, B3GALNT2, BASP1, BLCAP, BNC2, C10ORF58, C12ORF49, C12ORF51, C1ORF43, C20ORF117, C20ORF7, CADM1, CADPS, CALCB, CAPN1, CAPRIN2, CBLB, CBLN2, CBWD1, CCDC150, CCDC3, CD9, CDC25B, CFDP1, CHRNA7, CIAPIN1, CLASP2, CNOT7, CPVL, CRYBG3, CSE1L, CTTNBP2NL, CUGBP2, CXCR4, DACT1, DAZ1, DBH, DCAF8, DENR, DHX35, DKFZP434L187, DLEU2, DLL1, DLL3, DYNC2H1, EAF2, EFNA5, EIF3B, EIF3C, ELOVL7, EML1, EML4, ENC1, EVL, EXOSC6, EXPH5, EZH2, FAM178A, FAM181B, FAM19A4, FAM7A3, FLJ10213, FUBP3, FUS, FZD5, GAP43, GFM1, GFRA2, GGA2, GNAI1, GNAS, GNB4, GNG11, GOLGA4, GPR125, GRM8, GRP, GSPT1, GSS, GSTCD, GULP1, HAUS2, HEG1, HNRNPL, HNRNPM, HOXA7, HOXD4, ID2, IDH3B, IL1A, INSM1, IREB2, ITGA6, ITGB5, KCTD12, KDELC2, KHDRBS3, KIAA0907, KIAA1267, KIF16B, KLC1, KLHL13, LBH, LMO4, LOC100128844, LOC340109, LOC641298, LOC647190, LOC728052, LOC728153, LRPPRC, LRRFIP2, LSM3, LUM, MAB21L1, MAB21L2, MAN2A1, MAOA, MARS, MDN1, MED13L, MED22, MGC24103, MINA, MKLN1, MLEC, MMD, MORF4L2, MPZL1, MSH6, MS12, MSN, MTMR9, MYO1B, MYO6, N4BP2, NAAA, NDUFS8, NEDD9, NFIB, NKTR, NLN, NOS1, NR2C1, NUFIP2, NUPL1, OSBPL3, PAPD4, PCBP2, PCDH9, PCGF5, PCNX, PDLIM5, PDZRN3, PELI2, PFKFB3, PGP, PHF20, PLK2, PLXNA2, PLXNA4, PM20D2, POLE, POLQ, PPP2R2A, PPP2R3C, PRDX2, PSMA7, PSME4, PTGFRN, PTK2, PTPN1, PTPRE, PTPRG, QKI, RAB12, RAB35, RAB3GAP2, RAD23B, RAF1, RALGAPA1, RAN, RASEF, RBL1, RDH11, RELL1, REPS1, RGS5, RIMBP2, RNF182, RNF34, RNPEP, ROBO2, RPAIN, RPL35A, RPRD1A, S1PR3, SALL4, SBNO1, SCARB2, SDHA, SEMA6A, SEZ6L, SF1, SFRS8, SIM1, SIRT2, SKIL, SLC20A1, SLC44A5, SLC7A2, SLCO3A1, SLITRK5, SMAD4, SMARCC2, SMC3, SNRPB2, SNRPN, SNX5, SOX2, SPAG6, SPAG9, SPATS2L, SPON1, SR140, SSBP2, ST8SIA1, STMN3, STRA6, SYNCRIP, SYTL3, TAF15, TCF7L2, TDG, TERT, TFPI2, TGFBR1, TH1L, THOC4, TIMP3, TLE3, TMEM132C, TMEM178, TMEM181, TNRC6A, TPBG, TRA2A, TRIM29, TRIM36, TSHZ3, TXNRD1, U2AF1, UBE2O, UBE2V1, UBE2Z, UBXN2A, UCHL1, USP25, USP32, USP34, VPS29, XPO1, XPO7, ZFAND6, ZFHX4, ZFYVE16, ZGPAT, ZNF217, ZNF451, ZNF503, and/or ZNF664, as compared to the expression levels of these genes in cells from the parental SiMa cell line DSMZ ACC 164.

In an aspect of this embodiment, cells from an established clonal cell line susceptible to BoNT/A intoxication exhibit at least a 1.5-fold increase in gene expression levels of one or more genes selected from ALCAM, ARHGAP6, ARHGEF6, ASCL1, BNC2, CBLN2, CCDC150, CCDC3, CHRNA7, CRYBG3, CUGBP2, CXCR4, DAZ1, DKFZP434L187, DLL1, EFNA5, ELOVL7, EML1, EML4, ENC1, EXPH5, FAM7A3, FZD5, GFRA2, GNAI1, GNB4, GNG11, GRP, ID2, ITGA6, KCTD12, LOC100128844, LOC340109, LOC728052, LUM, MAB21L1, MAB21L2, MAOA, MGC24103, MSN, NEDD9, NFIB, OSBPL3, PAPD4, PCDH9, PDZRN3, PLK2, POLQ, PTGFRN, PTPRE, PTPRG, RAD23B, RGS5, RNF182, ROBO2, SIM1, SLC20A1, SLC44A5, SLITRK5, SPAG6, SPAG9, SR140, TFPI2, TIMP3, TMEM132C, TPBG, TRIM29, TRIM36, and/or ZFAND6, as compared to the expression levels of these genes in cells from the parental SiMa cell line DSMZ ACC 164.

In another aspect of this embodiment, cells from an established clonal cell line susceptible to BoNT/A intoxication exhibit at least a 1.5-fold increase in gene expression levels of one or more genes selected from ALCAM, ARHGAP6, ARHGEF6, CBLN2, CCDC3, CHRNA7, CRYBG3, CUGBP2, CXCR4, DAZ1, ELOVL7, EML1, EXPH5, FAM7A3, GNB4, GNG11, GRP, ITGA6, KCTD12, LOC340109, LUM, MAB21L1, MAB21L2, MGC24103, PCDH9, PLK2, POLQ, PTPRE, RGS5, RNF182, ROBO2, SIM1, SLC44A5, SLITRK5, SPAG6, TIMP3, and/or TMEM132C, as compared to the expression levels of these genes in cells from the parental SiMa cell line DSMZ ACC 164.

In yet another aspect of this embodiment, cells from an established clonal cell line susceptible to BoNT/A intoxication exhibit at least a 1.5-fold increase in gene expression levels of one or more genes selected from CBLN2, CCDC3, CHRNA7, CRYBG3, CXCR4, DAZ1, EXPH5, FAM7A3, GNB4, GRP, KCTD12, LUM, MGC24103, PCDH9, PLK2, POLQ, PTPRE, RGS5, ROBO2, SIM1, SLITRK5, TIMP3, and/or TMEM132C, as compared to the expression levels of these genes in cells from the parental SiMa cell line DSMZ ACC 164.

In another embodiment, cells from an established clonal cell line susceptible to BoNT/A intoxication exhibit at least a 1.5-fold increase in gene expression levels of one or more genes listed in Tables 14 or 16 as compared to the expression levels of these genes in cells from the parental SiMa cell line DSMZ ACC 164. In aspects of this embodiment, cells from an established clonal cell line susceptible to BoNT/A intoxication exhibit at least a 1.5-fold increase in gene expression levels of one or more genes listed in Tables 14 or 16 as compared to the expression levels of these genes in cells from a parental SiMa cell line DSMZ ACC 164. In other aspects of this embodiment, cells from an established clonal cell line susceptible to BoNT/A intoxication exhibit an increase in gene expression levels of one or more genes listed in Tables 14 or 16 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from a parental SiMa cell line DSMZ ACC 164. In other aspects of this embodiment, cells from an established clonal cell line susceptible to BoNT/A intoxication exhibit an increase in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 14 or 16 as compared to the expression levels of these genes in cells from the parental SiMa cell line DSMZ ACC 164. In yet other aspects of this embodiment, cells from an established clonal cell line susceptible to BoNT/A intoxication exhibit an increase in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 14 or 16 as compared to the expression levels of these genes in cells from the parental SiMa cell line DSMZ ACC 164.

In aspects of this embodiment, cells from an established clonal cell line susceptible to BoNT/A intoxication exhibit at least a 1.5-fold increase in gene expression levels of one or more genes selected from ACOT9, ADAMTS9, ARHGAP24, ARHGEF3, ASCL1, BARD1, BASP1, C3ORF70, C11ORF75, CCDC109B, CD9, CDCA7L, CDK2, CENPL, CLSTN2, CNTN1, CSRP2, CTSL2, CUGBP2, DEPDC1, DIAPH3, DOK5, DPYD, DYNLT3, EMILIN2, ETV1, FAM101B, FBLN1, FGFR2, FNDC5, GNAI1, GNB4, GNG11, GNG12, GPR177, GTSE1, HGF, KITLG, LPAR1, MAB21L2, MAOA, MCM10, MINA, MSN, MYO6, MYRIP, PAG1, PEG3, PLK2, POLA2, PPP1R3C, PRLHR, PRSS12, PTGR1, PTPRK, PVRL3, RAB32, RBPMS, SDC2, SGOL2, SLC43A3, SLC7A2, SMC2, SMC6, SPARC, SPC25, ST8SIA4, TCF7L1, TFPI2, TMEM35, TMEM178, TNFAIP8, TPTE, TRIP10, TWIST1, and/or ZNF521, as compared to the expression levels of these genes in cells from the parental SiMa cell line DSMZ ACC 164. In another aspect of this embodiment, cells from an established clonal cell line susceptible to BoNT/A intoxication exhibit at least a 1.5-fold increase in gene expression levels of one or more genes selected from ADAMTS9, ARHGAP24, ASCL1, BARD1, BASP1, BVES, C11ORF75, CDCA7L, CNTN1, CUGBP2, DOK5, DPYD, DYNLT3, FBLN1, FGFR2, GNAI1, GNB4, GNG11, GNG12, GTSE1, GTSF1, ITPRIP, KDELC2, LOC728052, LPAR1, MAB21L2, MAOA, MINA, MSN, PEG3, PLK2, PRLHR, PRSS12, PTPRK, RBPMS, RNF182, SGOL2, SLC43A3, SLC44A5, SLC7A2, SMC6, SPARC, TFPI2, TMEM178, and/or TPTE, as compared to the expression levels of these genes in cells from the parental SiMa cell line DSMZ ACC 164. In yet another aspect of this embodiment, cells from an established clonal cell line susceptible to BoNT/A intoxication exhibit at least a 1.5-fold increase in gene expression levels of one or more genes selected from ADAMTS9, ASCL1, BASP1, DOK5, DPYD, GNB4, GNG11, GTSF1, MAOA, MINA, MSN, PEG3, PLK2, PRSS12, RNF182, SLC44A5, SPARC, TFPI2, and/or TPTE, as compared to the expression levels of these genes in cells from the parental SiMa cell line DSMZ ACC 164.

In yet another embodiment, cells from an established clonal cell line susceptible to BoNT/A intoxication exhibit at least a 1.5-fold increase in gene expression levels of one or more genes selected from ADAMTS9, ARHGAP24, ARHGEF3, ASCL1, BARD1, CD9, CDK2, CSRP2, CTSL2, DIAPH3, DOK5, DYNLT3, EMILIN2, ETV1, FBLN1, FGFR2, GNAI1, GNB4, GNG11, GNG12, HGF, KITLG, LPAR1, MCM10, MSN, PAG1, PEG3, PLK2, POLA2, PPP1R3C, PTPRK, RAB32, SDC2, SLC43A3, SLC7A2, SMC6, SPARC, SPC25, ST8SIA4, TCF7L1, TFPI2, TMEM35, TNFAIP8, TPTE, TRIP10, and/or TWIST1, as compared to the expression levels of these genes in cells from the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from ADAMTS9, ARHGAP24, ASCL1, BARD1, DOK5, DYNLT3, FBLN1, FGFR2, GNAI1, GNB4, GNG11, GNG12, LPAR1, MSN, PEG3, PLK2, PTPRK, SLC43A3, SLC7A2, SMC6, SPARC, TFPI2, and/or TPTE, as compared to the expression levels of these genes in cells from the parental SiMa cell line DSMZ ACC 164. In another aspect of this embodiment, cells from an established clonal cell line susceptible to BoNT/A intoxication exhibit at least a 1.5-fold increase in gene expression levels of one or more genes selected from ADAMTS9, ASCL1, DOK5, GNB4, GNG11, MSN, PEG3, PLK2, SPARC, TFPI2, and/or TPTE, as compared to the expression levels of these genes in cells from the parental SiMa cell line DSMZ ACC 164.

In still another embodiment, cells from an established clonal cell line susceptible to BoNT/A intoxication exhibit at least a 1.5-fold increase in gene expression levels of one or more genes selected from ACOT9, BASP1, C11ORF75, CCDC109B, CDCA7L, CLSTN2, CNTN1, CUGBP2, DEPDC1, DPYD, FAM101B, FNDC5, GTSE1, MAOA, MINA, MYO6, MYRIP, PLK2, PRLHR, PVRL3, RBPMS, SGOL2, SMC2, TFP12, TMEM178, and/or ZNF521, as compared to the expression level of these genes in cells from the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from BASP1, C11ORF75, CDCA7L, CNTN1, CUGBP2, DPYD, GTSE1, MAOA, MINA, PLK2, PRLHR, RBPMS, SGOL2, TFPI2, and/or TMEM178, as compared to the expression levels of these genes in cells from the parental SiMa cell line DSMZ ACC 164. In another aspect of this embodiment, cells from an established clonal cell line susceptible to BoNT/A intoxication exhibit at least a 1.5-fold increase in gene expression levels of one or more genes selected from BASP1, DPYD, MAOA, MINA, PLK2, and/or TFPI2, as compared to the expression levels of these genes in cells from the parental SiMa cell line DSMZ ACC 164.

In a further embodiment, cells from an established clonal cell line susceptible to BoNT/A intoxication exhibit at least a 1.5-fold increase in gene expression levels of one or more genes selected from C3ORF70, MAB21L2, PRSS12, CENPL, GPR177, and/or PTGR1, as compared to the expression levels of these genes in cells from the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from MAB21L2 and/or PRSS12, as compared to the expression levels of these genes in cells from the parental SiMa cell line DSMZ ACC 164.

In another embodiment, cells from an established clonal cell line susceptible to BoNT/A intoxication exhibit at least a 1.5-fold decrease in gene expression levels of one or more genes listed in Tables 10 or 12 as compared to the expression levels of these genes in cells from a parental SiMa cell line. In aspects of this embodiment, cells from an established clonal cell line susceptible to BoNT/A intoxication exhibit at least a 1.5-fold decrease in gene expression levels of one or more genes listed in Tables 10 or 12 as compared to the expression levels of these genes in cells from the parental SiMa cell line DSMZ ACC 164. In other aspects of this embodiment, cells from an established clonal cell line susceptible to BoNT/A intoxication exhibit a decrease in gene expression levels of one or more genes listed in Tables 10 or 12 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from the parental SiMa cell line DSMZ ACC 164. In other aspects cells from an established clonal cell line susceptible to BoNT/A intoxication exhibit a decrease in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 10 or 12 as compared to the expression levels of these genes in cells from the parental SiMa cell line DSMZ ACC 164. In yet other aspects cells from an established clonal cell line susceptible to BoNT/A intoxication exhibit an decrease in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 10 or 12 as compared to the expression levels of these genes in cells from the parental SiMa cell line DSMZ ACC 164.

In an embodiment, cells from an established clonal cell line susceptible to BoNT/A intoxication exhibit at least a 1.5-fold decrease in gene expression levels of one or more genes selected from 1-Mar, ABCG1, ABTB1, ACOT1, ACSL1, ACVR1, ACVR2A, ACYP2, ADAMTS1, ADAMTS3, ADAMTSL1, ADARB1, ADCY1, ADD2, ADO, AFF3, AKAP12, ALDH1A2, ALKBH1, ALLC, AMN1, ANKH, ANKRA2, ANKRD50, ANXA5, AP3B2, ARMC10, ARMCX5, ASAM, ASB13, ASPHD1, ATG5, ATL3, ATP2B3, ATP2C1, ATRNL1, B3GALTL, BACE1, BACE2, BBS10, BBS7, BCAP29, BCL2, BCORL1, BRUNOL4, BRUNOL6, BRWD1, BTN3A3, C10ORF10, C10ORF104, C11ORF57, C11ORF70, C14ORF167, C15ORF39, C16ORF52, C17ORF69, C18ORF18, C1GALT1C1, C1ORF21, C1ORF25, C1ORF97, C1RL, C21ORF57, C2CD2, C2CD4A, C2ORF67, C2ORF68, C3ORF23, C4ORF12, C4ORF39, C4ORF41, C5ORF42, C6ORF120, C9ORF150, CADM2, CAMK2D, CAMK2N1, CAMK2N2, CAP2, CAPN2, CARTPT, CCDC126, CCDC40, CCDC50, CCNY, CD248, CD302, CDC2L6, CDC37L1, CDC42EP3, CDH12, CDKN1C, CDKN2A, CDS1, CFC1, CHMP1B, CLCN3, CLDN12, CLMN, CLN8, CNGA3, CNNM1, CNOT6L, COL27A1, COL5A1, COL6A1, COL6A2, COL6A3, COX18, COX5B, CRYGD, CRYZL1, CTPS2, CTSC, CYB5R2, CYGB, CYLD, CYP2E1, CYP2U1, CYTL1, CYYR1, D4S234E, DAB1, DBT, DCAF10, DCLK1, DCTD, DDAH1, DHRSX, DISP1, DKFZP434I0714, DKK1, DNAJC12, DNAJC24, DNASE1L1, DNER, DOPEY2, DRAM2, DSCAM, DSCR3, DTX3L, DUSP16, DUSP22, ECEL1, ECHDC3, EEF1D, EEF2K, EFEMP2, EFNB3, EMID1, ENOX2, ERAP1, ERBB2, ERBB4, ETFDH, ETS2, EYA1, FAM13C, FAM162B, FAM165B, FAM172A, FAM175A, FAM190A, FAM26F, FAM46A, FAM49A, FAM71E1, FAM76A, FAM85A, FBXL5, FBXW7, FCRLB, FGD5, FGF1, FGF13, FGF19, FGF3, FGF7, FIP1L1, FKTN, FLJ10038, FLJ35220, FLJ35390, FLJ37798, FLJ39051, FOXO6, FSTL1, FUCA2, GAL, GART, GAS5, GDPD5, GLCE, GLI2, GLIS1, GLIS3, GLT25D2, GNA14, GNAS, GPR123, GPX7, GRM5, GTF2H5, GUCY1A3, H2AFJ, HCG 1776018, HDAC4, HEBP2, HELQ, HERPUD2, HHLA3, HIST1H2AC, HIST1H2BD, HIST1H2BK, HIST2H2BE, HMGCLL1, HNRNPR, HPCAL1, HPDL, HPS3, HSBP1L1, HSPA1A, HTATIP2, ICAM2, IFNAR1, IGFBP5, IGFBP7, IGSF5, IL10RB, IL13RA2, IL17D, IL20RA, IL7, IMMP2L, INSR, IRS1, ITGB1BP1, JMY, JRKL, KAT2B, KBTBD11, KCMF1, KCNMA1, KCNQ2, KCNQ5, KCTD18, KDM1A, KDSR, KHDC1, KIAA1109, KIAA1324, KIAA1598, KIAA1804, KIRREL3, KLHDC1, KRCC1, LGALS3, LGALS3BP, LIFR, LINGO1, LIPT1, LMAN2L, LMCD1, LOC100129195, LOC100129884, LOC100130522, LOC100130856, LOC100132167, LOC100216479, LOC100272217, LOC100287039, LOC151146, LOC153682, LOC220930, LOC254128, LOC255167, LOC283588, LOC285286, LOC285550, LOC285878, LOC286052, LOC339290, LOC401321, LOC645513, LOC80154, LOC90246, LOC93622, LOC94431, LPAR3, LPHN2, LRCH2, LRP2BP, LYRM1, LYRM5, MAGI2, MANSC1, MAP3K13, MAP3K5, MAP9, MAPKAP1, MBD5, MBLAC2, MBNL1, MCTP1, MED6, MEGF11, MEOX2, MET, METT5D1, MFSD4, MFSD6, MFSD9, MGAT4A, MORC3, MREG, MRPS18C, MRPS33, MST1, MTMR3, MTUS2, MXRA7, N4BP3, NAP1L3, NCAM1, NCAM2, NCOA7, NCRNA00081, NCRNA00117, NCRNA00171, NDUFA4L2, NDUFV3, NEAT1, NEBL, NEIL2, NETO1, NFATC4, NHEDC2, NIPAL3, NLRX1, NNAT, NOTCH4, NPW, NPY, NR1H3, NR2F1, NT5E, NUDT19, NUDT6, OGFRL1, OLFM3, OMA1, OPRM1, OPTN, P4HTM, PABPC4L, PABPC5, PAK1, PAM, PAPOLG, PAPPA, PBX1, PCDHB10, PCDHB16, PCNX, PCNXL2, PDCD2, PDE4DIP, PDGFRB, PEX12, PEX6, PHKA1, PHLDB3, PIBF1, PID1, PIGH, PIGP, PIK3CB, PIWIL2, PKNOX1, PKNOX2, PLA2G12A, PLCB1, PLEKHA2, PLEKHA3, PLIN2, PLRG1, POLR3GL, POU6F1, PPAPDC1A, PPDX, PPP1R14A, PPP2R5C, PPP3CA, PRAME, PRKACB, PRMT2, PRPH, PSD3, PSTK, PTGER2, PTGES, PTN, PTP4A3, PTPRD, PTPRN2, PTPRR, QPCT, RAB4A, RAB6B, RAC2, RAI2, RCAN1, RCC1, RDH13, RFPL1S, RG9MTD2, RGAG4, RHBDD1, RHBDF2, RHOU, RNF13, RNF41, RNLS, RPL31, RPL37, RPRD1A, RRN3, RSL1D1, RSPH3, SAP30, SAV1, SCG5, SCN5A, SERTAD4, SGMS1, SH3BGR, SH3GL2, SH3 KBP1, SH3YL1, SIAE, SIGIRR, SIK1, SIK3, SIX2, SLC12A7, SLC16A14, SLC22A17, SLC22A5, SLC25A12, SLC25A4, SLC35F3, SLC6A15, SLIT1, SMARCA2, SMEK2, SNAP91, SNCA, SOCS5, SORCS2, SPATA17, SPATA7, SPIN3, SPINT1, SPINT2, SPOCK2, SPRED1, SSPN, ST8SIA3, STAC2, STAR, STEAP3, STOX2, STX12, STXBP5L, SUCLG2, SYNJ1, SYNPR, SYT13, TAF12, TAF1B, TBC1D12, TBC1D15, TCEAL2, TEX264, THAP2, TM2D1, TMCC1, TMEM182, TMEM184C, TMEM196, TMEM45B, TMEM5, TMEM59L, TMEM65, TMIE, TNC, TNFRSF10D, TNFSF4, TOX, TRAPPC9, TRHDE, TRIM61, TRIM69, TSPAN7, TSPAN9, TTC23, TTC39C, TUSC3, TXLNB, UBE2D3, UBE2W, UCN, UNC5A, UTP23, VPS37A, VSTM2A, WASF3, WDFY3, WDTC1, XPR1, XYLT1, ZBTB41, ZC3H12B, ZNF148, ZNF185, ZNF22, ZNF23, ZNF25, ZNF250, ZNF280D, ZNF285A, ZNF295, ZNF346, ZNF528, ZNF585A, ZNF610, ZNF641, ZNF662, ZNF677, and/or ZNF862, as compared to the expression levels of these genes in cells from the parental SiMa cell line DSMZ ACC 164.

In an aspect of this embodiment, cells from an established clonal cell line susceptible to BoNT/A intoxication exhibit at least a 1.5-fold decrease in gene expression levels of one or more genes selected from ACOT1, ADARB1, ASAM, BACE2, C11ORF70, C2CD4A, C3ORF23, CADM2, CAP2, CARTPT, CDKN1C, CFC1, CNGA3, COL5A1, CYGB, CYP2E1, CYTL1, DSCAM, ECEL1, ECHDC3, FAM26F, FAM49A, FGF1, FGF13, FGF19, FLJ39051, FUCA2, GAL, GPX7, GRM5, HCG 1776018, HHLA3, HIST1H2AC, HIST1H2BD, HSPA1A, HTATIP2, ICAM2, IGFBP5, IGFBP7, IL13RA2, KCNMA1, KCNQ5, KIAA1598, KRCC1, LMCD1, LOC100216479, LOC254128, LOC339290, LPAR3, MEGF11, MEOX2, NCAM2, NDUFA4L2, NEAT1, NNAT, NPW, NPY, PABPC4L, PAPPA, PID1, PPAPDC1A, PRAME, PRKACB, PTGER2, PTN, PTP4A3, RAC2, SLC35F3, SYT13, TCEAL2, THAP2, TMIE, TNFRSF10D, TRHDE, TXLNB, and/or ZNF662, as compared to the expression levels of these genes in cells from the parental SiMa cell line DSMZ ACC 164.

In another aspect of this embodiment, cells from an established clonal cell line susceptible to BoNT/A intoxication exhibit at least a 1.5-fold decrease in gene expression levels of one or more genes selected from ACOT1, ASAM, BACE2, C11ORF70, C2CD4A, C3ORF23, CADM2, CAP2, CARTPT, CFC1, CNGA3, CYGB, CYP2E1, CYTL1, DSCAM, ECEL1, ECHDC3, FGF1, FGF13, FUCA2, GAL, GPX7, HSPA1A, HTATIP2, ICAM2, IGFBP5, IGFBP7, KIAA1598, KRCC1, LMCD1, LOC100216479, LOC254128, LOC339290, LPAR3, MEOX2, NDUFA4L2, NEAT1, NNAT, NPW, NPY, PAPPA, PID1, PPAPDC1A, PRAME, PTN, SLC35F3, SYT13, TCEAL2, TMIE, TNFRSF10D, TRHDE, and/or ZNF662, as compared to the expression levels of these genes in cells from the parental SiMa cell line DSMZ ACC 164.

In yet another aspect of this embodiment, cells from an established clonal cell line susceptible to BoNT/A intoxication exhibit at least a 1.5-fold decrease in gene expression levels of one or more genes selected from C11ORF70, CADM2, CAP2, CARTPT, CNGA3, CYGB, CYP2E1, CYTL1, DSCAM, FGF13, FUCA2, GAL, HSPA1A, HTATIP2, ICAM2, IGFBP5, IGFBP7, LMCD1, LOC100216479, MEOX2, NDUFA4L2, NEAT1, NNAT, NPW, PID1, PRAME, SLC35F3, SYT13, TCEAL2, TMIE, TNFRSF10D, and/or ZNF662, as compared to the expression levels of these genes in cells from the parental SiMa cell line DSMZ ACC 164.

In another embodiment, cells from an established clonal cell line susceptible to BoNT/A intoxication exhibit at least a 1.5-fold increase in gene expression levels of one or more genes listed in Tables 5 or 7 as compared to the expression levels of these genes in cells from the 2D6 cell line, and at least a 1.5-fold increase in gene expression levels of one or more genes listed in Tables 9 or 11 as compared to the expression levels of these genes in cells from a parental SiMa cell line. In aspects of this embodiment, cells from an established clonal cell line susceptible to BoNT/A intoxication exhibit at least a 1.5-fold increase in gene expression levels of one or more genes listed in Tables 5 or 7 as compared to the expression levels of these genes in cells from the 2D6 cell line, and at least a 1.5-fold increase in gene expression levels of one or more genes listed in Tables 9 or 11 as compared to the expression levels of these genes in cells from the parental SiMa cell line DSMZ ACC 164. In other aspects of this embodiment, cells from an established clonal cell line susceptible to BoNT/A intoxication exhibit an increase in gene expression levels of one or more genes listed in Tables 5 or 7 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least 7.0-fold, or at least 8.0-fold as compared to the expression levels of these genes in cells from the 2D6 cell line, and exhibit an increase in gene expression levels of one or more genes listed in Tables 9 or 11 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least 7.0-fold, or at least 8.0-fold as compared to the expression levels of these genes in cells from the parental SiMa cell line DSMZ ACC 164. In other aspects of this embodiment, cells from an established clonal cell line susceptible to BoNT/A intoxication exhibit an increase in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 5 or 7 as compared to the expression levels of these genes in cells from the 2D6 cell line, and listed in Tables 9 or 11 as compared to the expression levels of these genes in cells from the parental SiMa cell line DSMZ ACC 164. In yet other aspects cells from an established clonal cell line susceptible to BoNT/A intoxication exhibit an increase in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 5 or 7 as compared to the expression levels of these genes in cells from the 2D6 cell line, and listed in Tables 9 or 11 as compared to the expression levels of these genes in cells from the parental SiMa cell line DSMZ ACC 164.

In another embodiment, cells from an established clonal cell line susceptible to BoNT/A intoxication exhibit at least a 1.5-fold increase in gene expression levels of one or more genes selected from A2BP1, ALCAM, ANAPC7, ARF1, ARHGAP6, ARHGEF6, ARL17A, ASCL1, ASXL3, BASP1, BNC2, C10ORF58, C12ORF49, C1ORF43, C20ORF7, CBLB, CBWD1, CCDC3, CD9, CDC25B, CHRNA7, CPVL, CRYBG3, CSE1L, CUGBP2, CXCR4, DACT1, DAZ1, DBH, DHX35, DKFZP434L187, DLEU2, DLL3, EAF2, EFNA5, EIF3C, ELOVL7, EML1, ENC1, EXOSC6, EXPH5, EZH2, FAM181B, FAM19A4, FAM7A3, FUBP3, FZD5, GAP43, GFRA2, GNAI1, GNB4, GNG11, GPR125, GRP, GSS, ITGA6, ITGA6, ITGB5, KCTD12, KDELC2, KHDRBS3, KIF16B, KLHL13, LBH, LOC100128844, LOC340109, LOC641298, LOC728052, LUM, MAB21L1, MAN2A1, MAOA, MINA, MMD, MSN, MYO1B, MYO6, NAAA, NEDD9, NOS1, OSBPL3, PCGF5, PELI2, PFKFB3, PHF20, PLK2, PLS3, PLXNA2, PLXNA4, PM20D2, POLE, PSMA7, PTGFRN, PTPRE, PTPRG, RAB35, RAF1, RAN, RASEF, RBL1, RELL1, RGS5, RIMBP2, RNF182, RNF34, S1PR3, SALL4, SEMA6A, SEZ6L, SIM1, SLC44A5, SLC7A2, SLCO3A1, SLITRK5, SPAG6, SPATS2L, ST8SIA1, STMN3, STRA6, TCF7L2, TFPI2, TH1L, THOC4, TIMP3, TLE3, TMEM132C, TMEM178, TPBG, TRA2A, TRIM29, TRIM36, TSHZ3, TXNRD1, U2AF1, UBE2V1, VPS29, ZFHX4, ZGPAT, ZNF217, and/or ZNF503, as compared to the expression levels of these genes in cells from both the 2D6 cell line and the parental SiMa cell line DSMZ ACC 164.

In an aspect of this embodiment, cells from an established clonal cell line susceptible to BoNT/A intoxication exhibit at least a 1.5-fold increase in gene expression levels of one or more genes selected from ALCAM, ARHGAP6, ARHGEF6, ASCL1, BNC2, CCDC3, CHRNA7, CRYBG3, CUGBP2, CXCR4, DAZ1, EFNA5, ELOVL7, EML1, ENC1, EXPH5, FAM7A3, FZD5, GFRA2, GNAI1, GNB4, GNG11, GRP, ITGA6, KCTD12, LOC100128844, LOC340109, LOC728052, LUM, MAB21L1, MAB21L2, MAOA, MSN, NEDD9, OSBPL3, PLK2, PTGFRN, PTPRE, RGS5, RNF182, SIM1, SLC44A5, SLITRK5, SPAG6, TFPI2, TIMP3, TMEM132C, TPBG, TRIM29, and/or TRIM36, as compared to the expression levels of these genes in cells from both the 2D6 cell line and the parental SiMa cell line DSMZ ACC 164.

In another aspect of this embodiment, cells from an established clonal cell line susceptible to BoNT/A intoxication exhibit at least a 1.5-fold increase in gene expression levels of one or more genes selected from ALCAM, ARHGAP6, ARHGEF6, CCDC3, CHRNA7, CRYBG3, CUGBP2, CXCR4, DAZ1, ELOVL7, EML1, EXPH5, FAM7A3, GNB4, GNG11, GRP, ITGA6, KCTD12, LOC340109, LUM, MAB21L1, MAB21L2, PLK2, PTPRE, RGS5, RNF182, SIM1, SLC44A5, SLITRK5, SPAG6, TIMP3, and/or TMEM132C, as compared to the expression levels of these genes in cells from both the 2D6 cell line and the parental SiMa cell line DSMZ ACC 164.

In yet another aspect of this embodiment, cells from an established clonal cell line susceptible to BoNT/A intoxication exhibit at least a 1.5-fold increase in gene expression levels of one or more genes selected from CCDC3, CHRNA7, CRYBG3, CXCR4, DAZ1, EXPH5, FAM7A3, GNB4, GRP, KCTD12, LUM, PLK2, PTPRE, RGS5, SIM1, SLITRK5, TIMP3, and/or TMEM132C, as compared to the expression levels of these genes in cells from both the 2D6 cell line and the parental SiMa cell line DSMZ ACC 164.

In another embodiment, cells from an established clonal cell line susceptible to BoNT/A intoxication exhibit at least a 1.5-fold increase in gene expression levels of one or more genes selected from A2BP1, ALCAM, ARF1, ARL17A, ASCL1, BASP1, CD9, CUGBP2, EAF2, EIF3C, FAM181B, FUBP3, GNAI1, GNB4, GNG11, KDELC2, KHDRBS3, KLHL13, LOC641298, LOC728052, MAB21L2, MAOA, MINA, MSN, MYO6, PLK2, PLS3, RAF1, RELL1, RNF182, SEZ6L, SEZ6L, SIM1, SLC44A5, SLC7A2, SLCO3A1, SLITRK5, SPATS2L, TCF7L2, TFPI2, TMEM178, TRA2A, U2AF1, and/or ZNF217, as compared to the expression levels of these genes in cells from both the 2D6 cell line and the parental SiMa cell line DSMZ ACC 164.

In an aspect of this embodiment, cells from an established clonal cell line susceptible to BoNT/A intoxication exhibit at least a 1.5-fold increase in gene expression levels of one or more genes selected from A2BP1, ALCAM, ARF1, ASCL1, BASP1, CD9, CUGBP2, EIF3C, FUBP3, GNAI1, GNB4, GNG11, KDELC2, KHDRBS3, LOC641298, LOC728052, MAB21L2, MAOA, MINA, MSN, MYO6, PLK2, PLS3, RELL1, RNF182, SIM1, SLC44A5, SLC7A2, SLCO3A1, SLITRK5, TCF7L2, TFPI2, TMEM178, TRA2A, and/or ZNF217, as compared to the expression levels of these genes in cells from both the 2D6 cell line and the parental SiMa cell line DSMZ ACC 164.

In another aspect of this embodiment, cells from an established clonal cell line susceptible to BoNT/A intoxication exhibit at least a 1.5-fold increase in gene expression levels of one or more genes selected from ASCL1, CUGBP2, GNAI1, GNB4, GNG11, LOC728052, MAB21L2, MAOA, MSN, PLK2, RNF182, SIM1, SLC44A5, SLITRK5, and/or TFPI2, as compared to the expression levels of these genes in cells from both the 2D6 cell line and the parental SiMa cell line DSMZ ACC 164.

In yet another aspect of this embodiment, cells from an established clonal cell line susceptible to BoNT/A intoxication exhibit at least a 1.5-fold increase in gene expression levels of one or more genes selected from GNB4, GNG11, PLK2, RNF182, SIM1, SLC44A5, and/or SLITRK5, as compared to the expression levels of these genes in cells from both the 2D6 cell line and the parental SiMa cell line DSMZ ACC 164.

In still another aspect of this embodiment, cells from an established clonal cell line susceptible to BoNT/A intoxication exhibit at least a 1.5-fold increase in gene expression levels of one or more genes selected from GNB4, PLK2, SIM1, and/or SLITRK5, as compared to the expression levels of these genes in cells from both the 2D6 cell line and the parental SiMa cell line DSMZ ACC 164.

In another embodiment, cells from an established clonal cell line susceptible to BoNT/A intoxication exhibit at least a 1.5-fold decrease in gene expression levels of one or more genes listed in Tables 6 or 8 as compared to the expression levels of these genes in cells from the 2D6 cell line, and at least a 1.5-fold decrease in gene expression levels of one or more genes listed in Tables 10 or 12 as compared to the expression levels of these genes in cells from a parental SiMa cell line. In aspects of this embodiment, cells from an established clonal cell line susceptible to BoNT/A intoxication exhibit at least a 1.5-fold decrease in gene expression levels of one or more genes listed in Tables 6 or 8 as compared to the expression levels of these genes in cells from the 2D6 cell line, and at least a 1.5-fold decrease in gene expression levels of one or more genes listed in Tables 10 or 12 as compared to the expression levels of these genes in cells from the parental SiMa cell line DSMZ ACC 164. In other aspects of this embodiment, cells from an established clonal cell line susceptible to BoNT/A intoxication exhibit a decrease in gene expression levels of one or more genes listed in Tables 6 or 8 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least 7.0-fold, or at least 8.0- fold as compared to the expression levels of these genes in cells from the 2D6 cell line, and a decrease in gene expression levels of one or more genes listed in Tables 10 or 12 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least 7.0-fold, or at least 8.0-fold as compared to the expression levels of these genes in cells from the parental SiMa cell line DSMZ ACC 164. In other aspects of this embodiment, cells from an established clonal cell line susceptible to BoNT/A intoxication exhibit a decrease in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 6 or 8 as compared to the expression levels of these genes in cells from the 2D6 cell line, and listed in Tables 10 or 12 as compared to the expression levels of these genes in cells from the parental SiMa cell line DSMZ ACC 164. In yet other aspects cells from an established clonal cell line susceptible to BoNT/A intoxication exhibit a decrease in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 6 or 8 as compared to the expression levels of these genes in cells from the 2D6 cell line, and listed in Tables 10 or 12 as compared to the expression levels of these genes in cells from the parental SiMa cell line DSMZ ACC 164.

In an embodiment, cells from an established clonal cell line susceptible to BoNT/A intoxication exhibit at least a 1.5-fold decrease in gene expression levels of one or more genes selected from ABTB1, ACOT1, ACYP2, ADARB1, ADCY1, ANKRD50, ASAM, ASPHD1, ATP2B3, BACE1, BRUNOL4, BRWD1, BTN3A3, C16ORF52, C1ORF21, C21ORF57, C2CD2, C2CD4A, C3ORF23, C9ORF150, CAMK2N2, CAP2, CAPN2, CARTPT, CD302, CDH12, CDKN2A, CDS1, CFC1, CLCN3, CLDN12, CLMN, CNGA3, CNNM1, CNOT6L, COL6A1, CYGB, CYLD, CYP2E1, CYTL1, D4S234E, DCLK1, DCTD, DUSP16, EFNB3, ERAP1, ERBB2, ERBB4, ETFDH, FAM162B, FAM165B, FAM46A, FBXW7, FGD5, FGF13, FOXO6, FSTL1, GAL, GLT25D2, GNAS, GPR123, GPX7, GRM5, GUCY1A3, HCG 1776018, HELQ, HERPUD2, HIST1H2AC, HIST1H2BD, HIST1H2BK, HIST2H2BE, HNRNPR, HPCAL1, IL10RB, JMY, KAT2B, KBTBD11, KCNMA1, KCNQ2, KHDC1, KIAA1598, KLHDC1, LGALS3BP, LIFR, LOC100130522, LOC94431, LRP2BP, LYRM5, MAP3K5, MAP9, MCTP1, MEOX2, MFSD4, MGAT4A, MRPS33, MST1, NAP1L3, NCOA7, NCRNA00171, NDUFA4L2, NDUFV3, NEBL, NHEDC2, NIPAL3, NLRX1, NUDT19, OLFM3, PAM, PAPPA, PCNXL2, PDGFRB, PHKA1, PIGH, PLRG1, PLRG1, PPAPDC1A, PRKACB, PRPH, PTGER2, PTN, PTPRD, RAB6B, RGAG4, RHOU, RNF13, RNF41, RSL1D1, SH3GL2, SH3YL1, SIGIRR, SIK1, SLC12A7, SLC22A17, SLC35F3, SNCA, SPINT2, SPOCK2, ST8SIA3, STAR, STEAP3, STOX2, SYNJ1, SYT13, TM2D1, TMEM184C, TMEM5, TMEM59L, TMIE, TTC39C, TUSC3, TXLNB, UCN, WDFY3, WDFY3, ZNF641, and/or ZNF662, as compared to the expression levels of these genes in cells from both the 2D6 cell line and the parental SiMa cell line DSMZ ACC 164.

In an aspect of this embodiment, cells from an established clonal cell line susceptible to BoNT/A intoxication exhibit at least a 1.5-fold decrease in gene expression levels of one or more genes selected from ACOT1, ADARB1, ASAM, C2CD4A, C3ORF23, CAP2, CARTPT, CFC1, CNGA3, CYGB, CYP2E1, CYTL1, FGF13, GAL, GPX7, GRM5, HCG 1776018, HIST1H2AC, HIST1H2BD, KCNMA1, KIAA1598, MEOX2, NDUFA4L2, PPAPDC1A, PRKACB, PTGER2, PTN, SLC35F3, SYT13, TMIE, TXLNB, and/or ZNF662, as compared to the expression levels of these genes in cells from both the 2D6 cell line and the parental SiMa cell line DSMZ ACC 164.

In another aspect of this embodiment, cells from an established clonal cell line susceptible to BoNT/A intoxication exhibit at least a 1.5-fold decrease in gene expression levels of one or more genes selected from ACOT1, ASAM, C2CD4A, C3ORF23, CAP2, CARTPT, CFC1, CNGA3, CYGB, CYP2E1, CYTL1, FGF13, GAL, GPX7, KIAA1598, MEOX2, NDUFA4L2, PPAPDC1A, PTN, SLC35F3, SYT13, TMIE, and/or ZNF662, as compared to the expression levels of these genes in cells from both the 2D6 cell line and the parental SiMa cell line DSMZ ACC 164.

In yet another aspect of this embodiment, cells from an established clonal cell line susceptible to BoNT/A intoxication exhibit at least a 1.5-fold decrease in gene expression levels of one or more genes selected from CAP2, CARTPT, CNGA3, CYGB, CYP2E1, CYTL1, FGF13, GAL, MEOX2, NDUFA4L2, SLC35F3, SYT13, TMIE, and/or ZNF662, as compared to the expression levels of these genes in cells from both the 2D6 cell line and the parental SiMa cell line DSMZ ACC 164.

In another embodiment, cells from an established clonal cell line susceptible to BoNT/A intoxication exhibit at least a 1.5-fold decrease in gene expression levels of one or more genes selected from CAP2, CDKN2A, CNGA3, FAM162B, FGF13, FOXO6, FSTL1, KCNMA1, KHDC1, LIFR, MCTP1, MEOX2, PPAPDC1A, PTN, SYT13, TMIE, and/or ZNF662, as compared to the expression levels of these genes in cells from both the 2D6 cell line and the parental SiMa cell line DSMZ ACC 164.

In an aspect of this embodiment, cells from an established clonal cell line susceptible to BoNT/A intoxication exhibit at least a 1.5-fold decrease in gene expression levels of one or more genes selected from CAP2, CDKN2A, CNGA3, FGF13, FOXO6, FSTL1, KCNMA1, KHDC1, MCTP1, MEOX2, PPAPDC1A, PTN, SYT13, TMIE, and/or ZNF662, as compared to the expression levels of these genes in cells from both the 2D6 cell line and the parental SiMa cell line DSMZ ACC 164.

In another aspect of this embodiment, cells from an established clonal cell line susceptible to BoNT/A intoxication exhibit at least a 1.5-fold decrease in gene expression levels of one or more genes selected from CNGA3, FGF13, KCNMA1, MEOX2, PPAPDC1A, PTN, SYT13, TMIE, and/or ZNF662, as compared to the expression levels of these genes in cells from both the 2D6 cell line and the parental SiMa cell line DSMZ ACC 164.

In yet another aspect of this embodiment, cells from an established clonal cell line susceptible to BoNT/A intoxication exhibit at least a 1.5-fold decrease in gene expression levels of one or more genes selected from CNGA3, FGF13, MEOX2, PPAPDC1A, PTN, SYT13, TMIE, and/or ZNF662, as compared to the expression levels of these genes in cells from both the 2D6 cell line and the parental SiMa cell line DSMZ ACC 164.

In still another aspect of this embodiment, cells from an established clonal cell line susceptible to BoNT/A intoxication exhibit at least a 1.5-fold decrease in gene expression levels of one or more genes selected from CNGA3, FGF13, MEOX2, SYT13, TMIE, and/or ZNF662, as compared to the expression levels of these genes in cells from both the 2D6 cell line and the parental SiMa cell line DSMZ ACC 164.

In another embodiment, cells from an established clonal cell line susceptible to BoNT/A intoxication exhibit at least a 1.5-fold difference in gene expression levels of one or more genes listed in Tables 14 or 16 as compared to the expression levels of these genes in cells from both the 2D6 cell line and the parental SiMa cell line DSMZ ACC 164. In aspects of this embodiment, cells from an established clonal cell line susceptible to BoNT/A intoxication exhibit at least a 1.5-fold difference in gene expression levels of one or more genes listed in Tables 14 or 16 as compared to the expression levels of these genes in cells from both the 2D6 cell line and the parental SiMa cell line DSMZ ACC 164. In other aspects of this embodiment, cells from an established clonal cell line susceptible to BoNT/A intoxication exhibit a difference in gene expression levels of one or more genes listed in Tables 14 or 16 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from both the 2D6 cell line and the parental SiMa cell line DSMZ ACC 164. In other aspects of this embodiment, cells from an established clonal cell line susceptible to BoNT/A intoxication exhibit an increase in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 14 or 16 as compared to the expression levels of these genes in cells from both the 2D6 cell line and the parental SiMa cell line DSMZ ACC 164. In yet other aspects cells from an established clonal cell line susceptible to BoNT/A intoxication exhibit an increase in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 14 or 16 as compared to the expression levels of these genes in cells from both the 2D6 cell line and the parental SiMa cell line DSMZ ACC 164.

In an embodiment, cells from an established clonal cell line susceptible to BoNT/A intoxication exhibit at least a 1.5-fold difference in gene expression levels of one or more genes selected from ACOT9, ADAMTS9, ARHGAP24, ARHGEF3, ASCL1, BARD1, BASP1, C3ORF70, C11ORF75, CCDC109B, CD9, CDCA7L, CDK2, CENPL, CLSTN2, CNTN1, CSRP2, CTSL2, CUGBP2, DEPDC1, DIAPH3, DOK5, DPYD, DYNLT3, EMILIN2, ETV1, FAM101B, FBLN1, FGFR2, FNDC5, GNAI1, GNB4, GNG11, GNG12, GPR177, GTSE1, HGF, KITLG, LPAR1, MAB21L2, MAOA, MCM10, MINA, MSN, MYO6, MYRIP, PAG1, PEG3, PLK2, POLA2, PPP1R3C, PRLHR, PRSS12, PTGR1, PTPRK, PVRL3, RAB32, RBPMS, SDC2, SGOL2, SLC43A3, SLC7A2, SMC2, SMC6, SPARC, SPC25, ST8SIA4, TCF7L1, TFPI2, TMEM35, TMEM178, TNFAIP8, TPTE, TRIP10, TWIST1, and/or ZNF521, as compared to the expression levels of these genes in cells from both the 2D6 cell line and the parental SiMa cell line DSMZ ACC 164. In another aspect of this embodiment, cells from an established clonal cell line susceptible to BoNT/A intoxication exhibit at least a 1.5-fold difference in gene expression levels of one or more genes selected from ADAMTS9, ARHGAP24, ASCL1, BARD1, BASP1, BVES, C11ORF75, CDCA7L, CNTN1, CUGBP2, DOK5, DPYD, DYNLT3, FBLN1, FGFR2, GNAI1, GNB4, GNG11, GNG12, GTSE1, GTSF1, ITPRIP, KDELC2, LOC728052, LPAR1, MAB21L2, MAOA, MINA, MSN, PEG3, PLK2, PRLHR, PRSS12, PTPRK, RBPMS, RNF182, SGOL2, SLC43A3, SLC44A5, SLC7A2, SMC6, SPARC, TFPI2, TMEM178, and/or TPTE, as compared to the expression levels of these genes in cells from both the 2D6 cell line and the parental SiMa cell line DSMZ ACC 164. In yet another aspect of this embodiment, cells from an established clonal cell line susceptible to BoNT/A intoxication exhibit at least a 1.5-fold difference in gene expression levels of one or more genes selected from ADAMTS9, ASCL1, BASP1, DOK5, DPYD, GNB4, GNG11, GTSF1, MAOA, MINA, MSN, PEG3, PLK2, PRSS12, RNF182, SLC44A5, SPARC, TFPI2, and/or TPTE, as compared to the expression levels of these genes in cells from both the 2D6 cell line and the parental SiMa cell line DSMZ ACC 164.

In another embodiment, cells from an established clonal cell line susceptible to BoNT/A intoxication exhibit at least a 1.5-fold increase in gene expression levels of one or more genes selected from ADAMTS9, ARHGAP24, ARHGEF3, ASCL1, BARD1, CD9, CDK2, CSRP2, CTSL2, DIAPH3, DOK5, DYNLT3, EMILIN2, ETV1, FBLN1, FGFR2, GNAI1, GNB4, GNG11, GNG12, HGF, KITLG, LPAR1, MCM10, MSN, PAG1, PEG3, PLK2, POLA2, PPP1R3C, PTPRK, RAB32, SDC2, SLC43A3, SLC7A2, SMC6, SPARC, SPC25, ST8SIA4, TCF7L1, TFPI2, TMEM35, TNFAIP8, TPTE, TRIP10, and/or TWIST1, as compared to the expression levels of these genes in cells from both the 2D6 cell line and the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from ADAMTS9, ARHGAP24, ASCL1, BARD1, DOK5, DYNLT3, FBLN1, FGFR2, GNAI1, GNB4, GNG11, GNG12, LPAR1, MSN, PEG3, PLK2, PTPRK, SLC43A3, SLC7A2, SMC6, SPARC, TFPI2, and/or TPTE, as compared to the expression levels of these genes in cells from both the 2D6 cell line and the parental SiMa cell line DSMZ ACC 164. In another aspect of this embodiment, cells from an established clonal cell line susceptible to BoNT/A intoxication exhibit at least a 1.5-fold increase in gene expression levels of one or more genes selected from ADAMTS9, ASCL1, DOK5, GNB4, GNG11, MSN, PEG3, PLK2, SPARC, TFPI2, and/or TPTE, as compared to the expression levels of these genes in cells from both the 2D6 cell line and the parental SiMa cell line DSMZ ACC 164.

In yet another embodiment, cells from an established clonal cell line susceptible to BoNT/A intoxication exhibit at least a 1.5-fold increase in gene expression levels of one or more genes selected from ACOT9, BASP1, C11ORF75, CCDC109B, CDCA7L, CLSTN2, CNTN1, CUGBP2, DEPDC1, DPYD, FAM101B, FNDC5, GTSE1, MAOA, MINA, MYO6, MYRIP, PLK2, PRLHR, PVRL3, RBPMS, SGOL2, SMC2, TFP12, TMEM178, and/or ZNF521, as compared to the expression levels of these genes in cells from both the 2D6 cell line and the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from BASP1, C11ORF75, CDCA7L, CNTN1, CUGBP2, DPYD, GTSE1, MAOA, MINA, PLK2, PRLHR, RBPMS, SGOL2, TFPI2, and/or TMEM178, as compared to the expression levels of these genes in cells from both the 2D6 cell line and the parental SiMa cell line DSMZ ACC 164. In another aspect of this embodiment, cells from an established clonal cell line susceptible to BoNT/A intoxication exhibit at least a 1.5-fold increase in gene expression levels of one or more genes selected from BASP1, DPYD, MAOA, MINA, PLK2, and/or TFPI2, as compared to the expression levels of these genes in cells from both the 2D6 cell line and the parental SiMa cell line DSMZ ACC 164.

In a still another embodiment, cells from an established clonal cell line susceptible to BoNT/A intoxication exhibit at least a 1.5-fold increase in gene expression levels of one or more genes selected from C3ORF70, MAB21L2, PRSS12, CENPL, GPR177, and/or PTGR1, as compared to the expression levels of these genes in cells from both the 2D6 cell line and the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from MAB21L2 and/or PRSS12, as compared to the expression levels of these genes in cells from both the 2D6 cell line and the parental SiMa cell line DSMZ ACC 164.

Aspects of the present disclosure comprise, in part, cells from an established clonal cell line susceptible to BoNT/A intoxication that exhibit an equivalent or lower $EC_{50}$ for BoNT/A activity relative to the $EC_{50}$ for BoNT/A activity of cells from a parental SiMa cell line. In an aspect of this embodiment, cells from an established clonal cell line susceptible to BoNT/A intoxication exhibit an equivalent or lower $EC_{50}$ for BoNT/A activity relative to the $EC_{50}$ for BoNT/A activity of cells from the parental SiMa cell line DSMZ ACC 164. In an aspect of this embodiment, cells from an established clonal cell line susceptible to BoNT/A intoxication exhibit an equivalent $EC_{50}$ for BoNT/A activity relative to the $EC_{50}$ for BoNT/A activity of cells from the parental SiMa cell line DSMZ ACC 164. In aspects of this embodiment, cells from an established clonal cell line susceptible to BoNT/A intoxication exhibit a lower $EC_{50}$ for BoNT/A activity of, e.g., at least 10%, at least 20%, at least 30%, at least 40%, at least 50%, at least 60%, at least 70%, at least 80%, at least 90%, or at least 100% relative to the $EC_{50}$ for BoNT/A activity of cells from the parental SiMa cell line DSMZ ACC 164. In other aspects of this embodiment, cells from an established clonal cell line susceptible to BoNT/A intoxication exhibit a lower $EC_{50}$ for BoNT/A activity of, e.g., at least 110%, at least 120%, at least 130%, at least 140%, at least 150%, at least 160%, at least 170%, at least 180%, at least 190%, or at least 200% relative to the $EC_{50}$ for BoNT/A activity of cells from the parental SiMa cell line DSMZ ACC 164. In yet other aspects of this embodiment, cells from an established clonal cell line susceptible to BoNT/A intoxication exhibit a lower $EC_{50}$ for BoNT/A activity of, e.g., at least 225%, at least 250%, at least 275%, at least 300%, at least 325%, at least 350%, at least 375%, at least 400%, at least 425%, at least 450%, at least 475%, or at least 500% relative to the $EC_{50}$ for BoNT/A activity of cells from the parental SiMa cell line DSMZ ACC 164. In still other aspects of this embodiment, cells from an established clonal cell line susceptible to BoNT/A intoxication exhibit an $EC_{50}$ for BoNT/A activity of, e.g., 10 pM or less, 9 pM or less, 8 pM or less, 7 pM or less, 6 pM or less, 5 pM or less, 4 pM or less, 3.0 pM or less, 2.9 pM or less, 2.8 pM or less, 2.7 pM or less, 2.6 pM or less, 2.5 pM or less, 2.4 pM or less, 2.3 pM or less, 2.2 pM or less, 2.1 pM or less, 2.0 pM or less, 1.9 pM or less, 1.8 pM or less, 1.7 pM or less, 1.6 pM or less, 1.5 pM or less, 1.4 pM or less, 1.3 pM or less, 1.2 pM or less, 1.1 pM or less, 1.0 pM or less, 0.9 pM or less, 0.8 pM or less, 0.7 pM or less, 0.6 pM or less, 0.5 pM or less, 0.4 pM or less, 0.3 pM or less, 0.2 pM or less, or 0.1 pM or less.

Aspects of the present disclosure comprise, in part, a BoNT/A. As used herein, the term "BoNT/A" is synonymous with "botulinum neurotoxin serotype A" or "botulinum neurotoxin type A" and refers to both a naturally-occurring BoNT/A or a non-naturally occurring BoNT/As thereof, and includes BoNT/A complex comprising the about 150 kDa BoNT/A neurotoxin and associated non-toxin associated proteins (NAPs), as well as the about 150 kDa BoNT/A neurotoxin alone. Non-limiting examples of BoNT/A complexes include, e.g., the 900-kDa BoNT/A complex, the 500-kDa BoNT/A complex, the 300-kDa BoNT/A complex. Non-limiting examples of the about 150 kDa BoNT/A neurotoxin include, e.g., SEQ ID NO: 1, SEQ ID NO: 2, SEQ ID NO: 3, SEQ ID NO: 4.

As used herein, the term "naturally occurring BoNT/A" refers to any BoNT/A produced by a naturally-occurring process, including, without limitation, BoNT/A isoforms produced from a post-translational modification, an alternatively-spliced transcript, or a spontaneous mutation, and BoNT/A subtypes, such as, e.g., a BoNT/A1 subtype, BoNT/A2 subtype, BoNT/A3 subtype, BoNT/A4 subtype, and BoNT/A5 subtype. A naturally occurring BoNT/A includes, without limitation, SEQ ID NO: 1, SEQ ID NO: 2, SEQ ID NO: 3, SEQ ID NO: 4, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 amino acids from SEQ ID NO: 1, SEQ ID NO: 2, SEQ ID NO: 3, or SEQ ID NO: 4. Commercially available pharmaceutical compositions of a naturally-occurring BoNT/A includes, without limitation, BOTOX® (Allergan, Inc., Irvine, Calif.), DYSPORT®/RELOXIN®, (Ipsen Ltd., Slough, England), PURTOX® (Mentor Corp., Santa Barbara, Calif.), XEOMIN® (Merz Pharmaceuticals, GmbH., Frankfurt, Germany), NEURONOX® (Medy-Tox, Inc., Ochang-myeon, South Korea), BTX-A.

As used herein, the term "non-naturally occurring BoNT/A" refers to any BoNT/A whose structure was modified with the aid of human manipulation, including, without limitation, a BoNT/A with an altered amino acid sequence produced by genetic engineering using random mutagenesis or rational design and a BoNT/A produced by in vitro chemical synthesis. Non-limiting examples of non-naturally occurring BoNT/As are described in, e.g., Steward, L. E. et al., Post-translational Modifications and Clostridial Neurotoxins, U.S. Pat. No. 7,223,577; Dolly, J. O. et al., Activatable Clostridial Toxins, U.S. Pat. No. 7,419,676; Steward, L. E. et al., Clostridial Neurotoxin Compositions and Modified Clostridial Neurotoxins, US 2004/0220386; Steward, L. E. et al., Modified Clostridial Toxins With Enhanced Targeting Capabilities For Endogenous Clostridial Toxin Receptor Systems, U.S. Patent Publication No. 2008/0096248; Steward, L. E. et al., Modified Clostridial Toxins With Altered Targeting Capabilities For Clostridial Toxin Target Cells, U.S. Patent Publication No. 2008/0161543; Steward, L. E. et al., Modified Clostridial Toxins With Enhanced Translocation Capabilities and Altered Targeting Activity For Clostridial Toxin Target Cells, U.S. Patent Publication No. 2008/0241881, each of which is hereby incorporated by reference in its entirety.

Thus in an embodiment, the BoNT/A activity being detected is from a naturally occurring BoNT/A. In aspects of this embodiment, the BoNT/A activity being detected is from a BoNT/A isoform or a BoNT/A subtype. In aspects of this embodiment, the BoNT/A activity being detected is from the BoNT/A of SEQ ID NO: 1, SEQ ID NO: 2, SEQ ID NO: 3, or SEQ ID NO: 4. In other aspects of this embodiment, the BoNT/A activity being detected is from a BoNT/A having, e.g., at least 70%, at least 75%, at least 80%, at least 85%, at least 90%, or at least 95% amino acid identity with SEQ ID NO: 1, SEQ ID NO: 2, SEQ ID NO: 3, or SEQ ID NO: 4. In other aspects of this embodiment, the BoNT/A activity being detected is from BOTOX®, DYSPORT®/RELOXIN®, PURTOX®, XEOMIN®, NEURONOX®, or BTX-A.

In another embodiment, the BoNT/A activity being detected is from a non-naturally occurring BoNT/A. In other aspects of this embodiment, the BoNT/A activity being detected is from a non-naturally occurring BoNT/A variant having, e.g., at least 70%, at least 75%, at least 80%, at least 85%, at least 90%, or at least 95% amino acid identity with SEQ ID NO: 1, SEQ ID NO: 2, SEQ ID NO: 3, or SEQ ID NO: 4. In other aspects of this embodiment, the BoNT/A activity being detected is from a non-naturally occurring BoNT/A variant having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 1, SEQ ID NO: 2, SEQ ID NO: 3, or SEQ ID NO: 4. In yet other aspects of this embodiment, the BoNT/A activity being detected is from a non-naturally occurring BoNT/A variant having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 1, SEQ ID NO: 2, SEQ ID NO: 3, or SEQ ID NO: 4.

Aspects of the present disclosure comprise, in part, a SNAP-25. As used herein, the term "SNAP-25" refers to a naturally-occurring SNAP-25 or a non-naturally occurring SNAP-25 which is preferentially cleaved by a BoNT/A. As used herein, the term "preferentially cleaved" refers to that the cleavage rate of a BoNT/A substrate by a BoNT/A that is at least one order of magnitude higher than the cleavage rate of any other substrate by BoNT/A. In aspects of this embodiment, the cleavage rate of a BoNT/A substrate by a BoNT/A that is at least two orders of magnitude higher, at least three orders of magnitude higher, at least four orders of magnitude higher, or at least five orders of magnitude higher than the cleavage rate of any other substrate by BoNT/A.

As used herein, the term "naturally occurring SNAP-25" refers to any SNAP-25 produced by a naturally-occurring process, including, without limitation, SNAP-25 isoforms produced from a post-translational modification, an alternatively-spliced transcript, or a spontaneous mutation, and SNAP-25 subtypes. A naturally occurring SNAP-25 includes, without limitation, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

As used herein, the term "non-naturally occurring SNAP-25" refers to any SNAP-25 whose structure was modified with the aid of human manipulation, including, without limitation, a SNAP-25 produced by genetic engineering using random mutagenesis or rational design and a SNAP-25 produced by in vitro chemical synthesis. Non-limiting examples of non-naturally occurring SNAP-25s are described in, e.g., Steward, L. E. et al., FRET Protease Assays for Clostridial Toxins, U.S. Pat. No. 7,332,567; Fernandez-Salas et al., Lipohilic Dye-based FRET Assays for Clostridial Toxin Activity, U.S. Patent Publication 2008/0160561, each of which is hereby incorporated by reference in its entirety. A non-naturally occurring SNAP-25 may substitute, delete or add, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

Thus in an embodiment, a SNAP-25 is a naturally occurring SNAP-25. In aspects of this embodiment, the SNAP-25 is a SNAP-25 isoform or a SNAP-25 subtype. In aspects of this embodiment, the naturally occurring SNAP-25 is the naturally occurring SNAP-25 of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In other aspects of this embodiment, the SNAP-25 is a naturally occurring SNAP-25 having, e.g., at least 70% amino acid identity, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

In another embodiment, a SNAP-25 is a non-naturally occurring SNAP-25. In other aspects of this embodiment, the SNAP-25 is a non-naturally occurring SNAP-25 having, e.g., at least 70%, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In other aspects of this embodiment, the SNAP-25 is a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet other aspects of this embodiment, the SNAP-25 is a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

A SNAP-25 can be an endogenous SNAP-25 or an exogenous SNAP-25. As used herein, the term "endogenous SNAP-25" refers to a SNAP-25 naturally present in the cell because it is naturally encoded within the cell's genome, such that the cell inherently expresses the SNAP-25 without the need of an external source of SNAP-25 or an external source of genetic material encoding a SNAP-25. The expression of an endogenous SNAP-25 may be with or without environmental stimulation such as, e.g., cell differentiation. By definition, an endogenous SNAP-25 can only be a naturally-occurring SNAP-25 or variants thereof. For example, the following established cell lines express an endogenous SNAP-25: BE(2)-M17, Kelly, LA1-55n, N1E-115, N4TG3, N18, Neuro-2a, NG108-15, PC12, SH-SY5Y, SiMa, and SK-N-BE(2)-C.

As used herein, the term "exogenous SNAP-25" refers to a SNAP-25 expressed in a cell through the introduction of an external source of SNAP-25 or an external source of genetic material encoding a SNAP-25 by human manipulation. The expression of an exogenous SNAP-25 may be with or without environmental stimulation such as, e.g., cell differentiation. As a non-limiting example, cells from an established clonal cell line can express an exogenous SNAP-25 by transient or stably transfection of a SNAP-25 coding sequence. As another non-limiting example, cells from an established clonal cell line can express an exogenous SNAP-25 by protein transfection of a SNAP-25. An exogenous SNAP-25 can be a naturally-occurring SNAP-25 or variants thereof, or a non-naturally occurring SNAP-25 or variants thereof.

Thus in an embodiment, cells from an established clonal cell line express an endogenous SNAP-25. In aspects of this embodiment, the endogenous SNAP-25 expressed by cells from an established clonal cell line is a naturally-occurring SNAP-25. In other aspects of this embodiment, the endogenous SNAP-25 expressed by cells from an established clonal cell line is SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet other aspects of this embodiment, the endogenous SNAP-25 expressed by cells from an established clonal cell line is a naturally occurring SNAP-25, such as, e.g., a SNAP-25 isoform or a SNAP-25 subtype. In other aspects of this embodiment, the endogenous SNAP-25 expressed by cells from an established clonal cell line is a naturally occurring SNAP-25 having, e.g., at least 70% amino acid identity, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

In another embodiment, cells from an established clonal cell line are transiently or stably engineered to express an exogenous SNAP-25. In an aspect of this embodiment, cells from an established clonal cell line are transiently or stably engineered to express a naturally-occurring SNAP-25. In other aspects of this embodiment, cells from an established clonal cell line are transiently or stably engineered to express the naturally-occurring SNAP-25 of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet other aspects of this embodiment, cells from an established clonal cell line are transiently or stably engineered to express a naturally occurring SNAP-25, such as, e.g., a SNAP-25 isoform or a SNAP-25 subtype. In still other aspects of this embodiment, cells from an established clonal cell line are transiently or stably engineered to express a naturally occurring SNAP-25 having, e.g., at least 70% amino acid identity, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

In another aspect of the embodiment, cells from an established clonal cell line are transiently or stably engineered to express a non-naturally occurring SNAP-25. In other aspects of this embodiment, cells from an established clonal cell line are transiently or stably engineered to express a non-naturally occurring SNAP-25 having, e.g., at least 70%, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In other aspects of this embodiment, cells from an established clonal cell line are transiently or stably engineered to express a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet other aspects of this embodiment, cells from an established clonal cell line are transiently or stably engineered to express a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 5, SEQ ID NO:

6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

Assays that detect the cleavage of a BoNT/A substrate after exposure to a BoNT/A can be used to assess whether a cell is expressing an endogenous or an exogenous SNAP-25. In these assays, generation of a SNAP-25 cleavage-product would be detected in cells expressing a SNAP-25 after BoNT/A treatment. Non-limiting examples of specific Western blot analysis, as well as well-characterized reagents, conditions and protocols are readily available from commercial vendors that include, without limitation, Amersham Biosciences, Piscataway, N.J.; Bio-Rad Laboratories, Hercules, Calif.; Pierce Biotechnology, Inc., Rockford, Ill.; Promega Corporation, Madison, Wis., and Stratagene, Inc., La Jolla, Calif. It is understood that these and similar assays for SNAP-25 cleavage can be useful in identifying cells expressing an endogenous or an exogenous SNAP-25.

As non-limiting examples, Western blot analysis using an antibody that recognizes BoNT/A SNAP-25-cleaved product or both the cleaved and uncleaved forms of SNAP-25 can be used to assay for uptake of BoNT/A. Examples of α-SNAP-25 antibodies useful for these assays include, without limitation, α-SNAP-25 mouse monoclonal antibody SMI-81 (Sternberger Monoclonals Inc., Lutherville, Md.), mouse α-SNAP-25 monoclonal antibody CI 71.1 (Synaptic Systems, Goettingen, Germany), α-SNAP-25 mouse monoclonal antibody CI 71.2 (Synaptic Systems, Goettingen, Germany), α-SNAP-25 mouse monoclonal antibody SP12 (Abcam, Cambridge, Mass.), α-SNAP-25 rabbit polyclonal antiserum (Synaptic Systems, Goettingen, Germany), α-SNAP-25 rabbit polyclonal antiserum (Abcam, Cambridge, Mass.), and α-SNAP-25 rabbit polyclonal antiserum S9684 (Sigma, St Louis, Mo.).

Aspects of the present disclosure comprise, in part, a BoNT/A receptor. As used herein, the term "BoNT/A receptor" refers to either a naturally-occurring BoNT/A receptor or a non-naturally occurring BoNT/A receptor which preferentially interacts with BoNT/A in a manner that elicits a BoNT/A intoxication response. As used herein, the term "preferentially interacts" refers to that the equilibrium dissociation constant (KD) of BoNT/A for a BoNT/A receptor is at least one order of magnitude less than that of BoNT/A for any other receptor. The equilibrium dissociation constant, a specific type of equilibrium constant that measures the propensity of an BoNT/A-BoNT/A receptor complex to separate (dissociate) reversibly into its component molecules, namely the BoNT/A and the BoNT/A receptor complex. The disassociation constant is defined as KD=[L][R]/[C], where [L] equals the molar concentration of BoNT/A, [R] is the molar concentration of a BoNT/A receptor, and [C] is the molar concentration of the BoNT/A-BoNT/A receptor complex, and where all concentrations are of such components when the system is at equilibrium. The smaller the dissociation constant, the more tightly bound the BoNT/A is to its receptor, or the higher the binding affinity between BoNT/A and BoNT/A receptor. In aspects of this embodiment, the disassociation constant of BoNT/A for a BoNT/A receptor is at least two orders of magnitude less, at least three orders of magnitude less, at least four orders of magnitude less, or at least five orders of magnitude less than that of BoNT/A for any other receptor. In other aspects of this embodiment, the binding affinity of a BoNT/A that preferentially interacts with a BoNT/A receptor can have an equilibrium disassociation constant of, e.g., of 500 nM or less, 400 nM or less, 300 nM or less, 200 nM, or less 100 nM or less. In other aspects of this embodiment, the binding affinity of a BoNT/A that preferentially interacts with a BoNT/A receptor can have an equilibrium disassociation constant of, e.g., of 90 nM or less, 80 nM or less, 70 nM or less, 60 nM or less, 50 nM or less, 40 nM or less, 30 nM or less, 20 nM, or less 10 nM or less. As used herein, the term "elicits a BoNT/A intoxication response" refers to the ability of a BoNT/A receptor to interact with a BoNT/A to form a neurotoxin/receptor complex and the subsequent internalization of that complex into the cell cytoplasm.

As used herein, the term "naturally occurring BoNT/A receptor" refers to any BoNT/A receptor produced by a naturally-occurring process, including, without limitation, BoNT/A receptor isoforms produced from a post-translational modification, an alternatively-spliced transcript, or a spontaneous mutation, and BoNT/A receptor subtypes. A naturally occurring BoNT/A receptor includes, without limitation, a fibroblast growth factor receptor 2 (FGFR2), a fibroblast growth factor receptor 3 (FGFR3), a synaptic vesicle glycoprotein 2 (SV2), and a complex ganglioside like GT1b, such as those described in Ester Fernandez-Salas, et al., Botulinum Toxin Screening Assays, U.S. Patent Publication 2008/0003240; Ester Fernandez-Salas, et al., Botulinum Toxin Screening Assays, U.S. Patent Publication 2008/0182799; Min Dong et al., *SV2 is the Protein Receptor for Botulinum Neurotoxin A*, Science (2006); S. Mahrhold et al, *The Synaptic Vesicle Protein 2C Mediates the Uptake of Botulinum Neurotoxin A into Phrenic Nerves,* 580(8) FEBS Lett. 2011-2014 (2006), each of which is hereby incorporated by reference in its entirety. A naturally occurring FGFR2 includes, without limitation, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70. A naturally occurring FGFR3 includes, without limitation, SEQ ID NO: 25, SEQ ID NO: 26, and SEQ ID NO: 27, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 25, SEQ ID NO: 26, and SEQ ID NO: 27. A naturally occurring SV2 includes, without limitation, SEQ ID NO: 28, SEQ ID NO: 29, SEQ ID NO: 30, and SEQ ID NO: 31, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 28, SEQ ID NO: 29, SEQ ID NO: 30, and SEQ ID NO: 31.

As used herein, the term "non-naturally occurring BoNT/A receptor variant" refers to any BoNT/A receptor produced with the aid of human manipulation or design, including, without limitation, a BoNT/A receptor produced by genetic engineering using random mutagenesis or rational design and a BoNT/A receptor produced by chemical synthesis. Non-limiting examples of non-naturally occurring BoNT/A variants include, e.g., conservative BoNT/A receptor variants, non-conservative BoNT/A receptor variants, BoNT/A receptor chimeric variants and active BoNT/A receptor fragments.

As used herein, the term "non-naturally occurring BoNT/A receptor" refers to any BoNT/A receptor whose structure was modified with the aid of human manipulation, including, without limitation, a BoNT/A receptor produced by genetic engineering using random mutagenesis or rational design and a BoNT/A receptor produced by in vitro chemical synthesis. Non-limiting examples of non-naturally occurring BoNT/A receptors are described in, e.g., Ester Fernandez-Salas, et al., Botulinum Toxin Screening Assays, U.S. Patent Publication 2008/0003240; Ester Fernandez-Salas, et al., Botulinum Toxin Screening Assays, U.S. Patent Publication 2008/0182799, each of which is hereby incorporated by reference in its entirety. A non-naturally occurring BoNT/A receptor may substitute, delete or add, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

Thus in an embodiment, a BoNT/A receptor is a naturally occurring BoNT/A receptor such as, e.g., FGFR2, FGFR3 or SV2. In aspects of this embodiment, the BoNT/A receptor is a BoNT/A receptor isoform or a BoNT/A receptor subtype. In aspects of this embodiment, the naturally occurring BoNT/A receptor is the naturally occurring BoNT/A receptor of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In other aspects of this embodiment, the BoNT/A receptor is a naturally occurring BoNT/A receptor having, e.g., at least 70% amino acid identity, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

In another embodiment, a BoNT/A receptor is a non-naturally occurring BoNT/A receptor, such as, e.g., a genetically-engineered FGFR2, a genetically-engineered FGFR3, or a genetically-engineered SV2. In other aspects of this embodiment, the BoNT/A receptor is a non-naturally occurring BoNT/A receptor having, e.g., at least 70%, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In other aspects of this embodiment, the BoNT/A receptor is a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet other aspects of this embodiment, the BoNT/A receptor is a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

A BoNT/A receptor can be an endogenous BoNT/A receptor or an exogenous BoNT/A receptor. As used herein, the term "endogenous BoNT/A receptor" refers to a BoNT/A receptor naturally present in the cell because it is naturally encoded within the cell's genome, such that the cell inherently expresses the BoNT/A receptor without the need an external source of BoNT/A receptor or an external source of genetic material encoding a BoNT/A receptor. Expression of an endogenous BoNT/A receptor may be with or without environmental stimulation such as e.g., cell differentiation or promoter activation. For example, the following established clonal cell lines express at least one endogenous BoNT/A receptor: BE(2)-M17, Kelly, LA1-55n, N1E-115, N4TG3, N18, Neuro-2a, NG108-15, PC12, SH-SY5Y, SiMa, and SK-N-BE(2)-C. An endogenous BoNT/A receptor can only be a naturally-occurring BoNT/A receptor or naturally-occurring variants thereof.

As used herein, the term "exogenous BoNT/A receptor" refers to a BoNT/A receptor expressed in a cell through the introduction of an external source of BoNT/A receptor or an external source of genetic material encoding a BoNT/A receptor by human manipulation. The expression of an exogenous BoNT/A receptor may be with or without environmental stimulation such as, e.g., cell differentiation or promoter activation. As a non-limiting example, cells from an established clonal cell line can express one or more exogenous BoNT/A receptors by transient or stably transfection of a polynucleotide molecule encoding a BoNT/A receptor, such as, e.g., a FGFR2, a FGFR3, or a SV2. As another non-limiting example, cells from an established clonal cell line can express one or more exogenous BoNT/A receptors by protein transfection of the BoNT/A receptors, such as, e.g., a FGFR2, a FGFR3, or a SV2. An exogenous BoNT/A receptor can be a naturally-occurring BoNT/A receptor or naturally occurring variants thereof, or non-naturally occurring BoNT/A receptor or non-naturally occurring variants thereof.

Thus in an embodiment, cells from an established clonal cell line express an endogenous BoNT/A receptor. In aspects of this embodiment, the endogenous BoNT/A receptor expressed by cells from an established clonal cell line is a naturally-occurring BoNT/A receptor. In other aspects of this embodiment, the endogenous BoNT/A receptor expressed by cells from an established clonal cell line is SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet aspects of this embodiment, the endogenous BoNT/A receptor expressed by cells from an established clonal cell line is a naturally occurring BoNT/A receptor, such as, e.g., a BoNT/A receptor isoform or a BoNT/A receptor subtype. In other aspects of this embodiment, the endogenous BoNT/A receptor expressed by cells from an established clonal cell line is a naturally occurring BoNT/A receptor having, e.g., at least 70% amino acid identity, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

In another embodiment, cells from an established clonal cell line are transiently or stably engineered to express an exogenous BoNT/A receptor. In an aspect of this embodiment, cells from an established clonal cell line are transiently or stably engineered to express a naturally-occurring BoNT/A receptor. In other aspects of this embodiment, cells from an established clonal cell line are transiently or stably engineered to express the naturally-occurring BoNT/A receptor of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet other aspects of this embodiment, cells from an established clonal cell line are transiently or stably engineered to express a naturally occurring BoNT/A receptor, such as, e.g., a BoNT/A receptor isoform or a BoNT/A receptor subtype. In still other aspects of this embodiment, cells from an established clonal cell line are transiently or stably engineered to express a naturally occurring BoNT/A receptor having, e.g., at least 70% amino acid identity, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

In another aspect of the embodiment, cells from an established clonal cell line are transiently or stably engineered to express a non-naturally occurring BoNT/A receptor. In other aspects of this embodiment, cells from an established clonal cell line are transiently or stably engineered to express a non-naturally occurring BoNT/A receptor having, e.g., at least 70%, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In other aspects of this embodiment, cells from an established clonal cell line are transiently or stably engineered to express a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet other aspects of this embodiment, cells from an established clonal cell line are transiently or stably engineered to express a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70

In another embodiment, cells from an established clonal cell line are transiently or stably engineered to express an exogenous FGFR2, an exogenous FGFR3, an exogenous SV2, or any combination thereof. In aspects of this embodiment, cells from an established clonal cell line are transiently or stably engineered to express a naturally-occurring FGFR2, a naturally-occurring FGFR3, a naturally-occurring SV2, or any combination thereof. In yet other aspects of this embodiment, cells from an established clonal cell line are transiently or stably engineered to express a non-naturally-occurring FGFR2, a non-naturally-occurring FGFR3, a non-naturally-occurring SV2, or any combination thereof. In still other aspects of this embodiment, cells from an established clonal cell line are transiently or stably engineered to express either a naturally-occurring FGFR2 or a non-naturally-occurring FGFR2, a naturally-occurring FGFR3 or a non-naturally-occurring FGFR3, a naturally-occurring SV2 or a non-naturally-occurring SV2, or any combination thereof.

Cells that express one or more endogenous or exogenous BoNT/A receptors can be identified by routine methods including direct and indirect assays for toxin uptake. Assays that determine BoNT/A binding or uptake properties can be used to assess whether a cell is expressing a BoNT/A receptor. Such assays include, without limitation, cross-linking assays using labeled BoNT/A, such as, e.g., [$^{125}$I] BoNT/A, see, e.g., Noriko Yokosawa et al., *Binding of Clostridium botulinum type C neurotoxin to different neuroblastoma cell lines,* 57(1) Infect. Immun. 272-277 (1989); Noriko Yokosawa et al., *Binding of botulinum type Cl, D and E neurotoxins to neuronal cell lines and synaptosomes,* 29(2) Toxicon 261-264 (1991); and Tei-ichi Nishiki et al., *Identification of protein receptor for Clostridium botulinum type B neurotoxin in rat brain synaptosomes,* 269(14) J. Biol. Chem. 10498-10503 (1994). Other non-limiting assays include immunocytochemical assays that detect BoNT/A binding using labeled or unlabeled antibodies, see, e.g., Atsushi Nishikawa et al., *The receptor and transporter for internalization of Clostridium botulinum type C progenitor toxin into HT-29 cells,* 319(2) Biochem. Biophys. Res. Commun. 327-333 (2004) and immunoprecipitation assays, see, e.g., Yukako Fujinaga et al., *Molecular characterization of binding subcomponents of Clostridium botulinum type C progenitor toxin for intestinal epithelial cells and erythrocytes,* 150(Pt 5) Microbiology 1529-1538 (2004), that detect bound toxin using labeled or unlabeled antibodies. Antibodies useful for these assays include, without limitation, antibodies selected against BoNT/A, antibodies selected against a BoNT/A receptor, such as, e.g., FGFR2, FGFR3, or SV2, and/or antibodies selected against a ganglioside, such as, e.g., GD1a, GD1b, GD3, GQ1b, or GT1b. If the antibody is labeled, the binding of the molecule can be detected by various means, including Western blot analysis, direct microscopic observation of the cellular location of the antibody, measurement of cell or substrate-bound antibody following a wash step, flow cytometry, electrophoresis or capillary electrophoresis, employing techniques well-known to those of skill in the art. If the antibody is unlabeled, one may employ a labeled secondary antibody for indirect detection of the bound molecule, and detection can proceed as for a labeled antibody. It is understood that these and similar assays that determine BoNT/A uptake properties or characteristics can be useful in identifying cells expressing endogenous or exogenous BoNT/A receptors.

Assays that monitor the release of a molecule after exposure to BoNT/A can also be used to assess whether a cell is expressing one or more endogenous or exogenous BoNT/A receptors. In these assays, inhibition of the molecule's release would occur in cells expressing a BoNT/A receptor after BoNT/A treatment. Well known assays include methods that measure inhibition of radio-labeled catecholamine release from neurons, such as, e.g., [3H] noradrenaline or [3H] dopamine release, see e.g., A Fassio et al., *Evidence for calcium-dependent vesicular transmitter release insensitive to tetanus toxin and botulinum toxin type F,* 90(3) Neuroscience 893-902 (1999); and Sara Stigliani et al., *The sensitivity of catecholamine release to botulinum toxin C1 and E suggests selective targeting of vesicles set into the readily releasable pool,* 85(2) J. Neurochem. 409-421 (2003), or measures catecholamine release using a fluorometric procedure, see, e.g., Anton de Paiva et al., *A role for the interchain disulfide or its participating thiols in the internalization of botulinum neurotoxin A revealed by a toxin derivative that binds to ecto-acceptors and inhibits transmitter release intracellularly,* 268(28) J. Biol. Chem. 20838-20844 (1993); Gary W. Lawrence et al., *Distinct exocytotic responses of intact and permeabilised chromaffin cells after cleavage of the 25-kDa synaptosomal-associated protein (SNAP-25) or synaptobrevin by botulinum toxin A or B,* 236(3) Eur. J. Biochem. 877-886 (1996); and Patrick Foran et al., *Botulinum neurotoxin C1 cleaves both syntaxin and SNAP-25 in intact and permeabilized chromaffin cells: correlation with its blockade of catecholamine release,* 35(8) Biochemistry 2630-2636 (1996). Other non-limiting examples include assays that measure inhibition of hormone release from endocrine cells, such as, e.g., anterior pituitary cells or ovarian cells. It is understood that these and similar assays for molecule release can be useful in identifying cells expressing endogenous or exogenous or BoNT/A receptors.

Assays that detect the cleavage of a BoNT/A substrate after exposure to a BoNT/A can also be used to assess whether a cell is expressing one or more endogenous or exogenous BoNT/A receptors. In these assays, generation of a BoNT/A substrate cleavage-product, or disappearance of the intact BoNT/A substrate, would be detected in cells expressing a BoNT/A receptor after BoNT/A treatment. Non-limiting examples of specific Western blot analysis, as well as well-characterized reagents, conditions and protocols are readily available from commercial vendors that include, without limitation, Amersham Biosciences, Piscataway, N.J.; Bio-Rad Laboratories, Hercules, Calif.; Pierce Biotechnology, Inc., Rockford, Ill.; Promega Corporation, Madison, Wis., and Stratagene, Inc., La Jolla, Calif. It is understood that these and similar assays for BoNT/A substrate cleavage can be useful in identifying cells expressing endogenous or exogenous BoNT/A receptors.

As non-limiting examples, Western blot analysis using an antibody that recognizes BoNT/A SNAP-25-cleaved product or both the cleaved and uncleaved forms of SNAP-25 can be used to assay for uptake of BoNT/A. Examples of α-SNAP-25 antibodies useful for these assays include, without limitation, SMI-81 α-SNAP-25 mouse monoclonal antibody (Sternberger Monoclonals Inc., Lutherville, Md.), CI 71.1 mouse α-SNAP-25 monoclonal antibody (Synaptic Systems, Goettingen, Germany), CI 71.2 α-SNAP-25 mouse monoclonal antibody (Synaptic Systems, Goettingen, Germany), SP12 α-SNAP-25 mouse monoclonal antibody (Abcam, Cambridge, Mass.), α-SNAP-25 rabbit polyclonal antiserum (Synaptic Systems, Goettingen, Germany), α-SNAP-25 rabbit polyclonal antiserum S9684 (Sigma, St. Louis, Mo.), and α-SNAP-25 rabbit polyclonal antiserum (Abcam, Cambridge, Mass.).

Aspects of the present disclosure provide cells that through genetic manipulation or recombinant engineering are made to express an exogenous SNAP-25 and/or one or more exogenous BoNT/A receptors. Cells useful to express an exogenous SNAP-25 and/or one or more exogenous BoNT/A receptors through genetic manipulation or recombinant engineering include neuronal cells and non-neuronal cells that may or may not express an endogenous SNAP-25 and/or one or more endogenous BoNT/A receptors. It is further understood that such genetically manipulated or recombinantly engineered cells may express an exogenous SNAP-25 and one or more exogenous BoNT/A receptors under control of a constitutive, tissue-specific, cell-specific or inducible promoter element, enhancer element or both. It is understood that any cell is useful as long as the cell can be genetically manipulated or recombinantly engineered to expresses an exogenous SNAP-25 and/or one or more exogenous BoNT/A receptors and is capable of undergoing BoNT/A intoxication.

Methods useful for introducing into a cell an exogenous polynucleotide molecule encoding a component necessary for the cells to undergo the overall cellular mechanism whereby a BoNT/A proteolytically cleaves a SNAP-25 substrate, such as, e.g., a SNAP-25, a FGFR2, a FGFR3, or a SV2, include, without limitation, chemical-mediated delivery methods, such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated delivery methods, such as, e.g., biolistic particle delivery, microinjection, protoplast fusion and electroporation; and viral-mediated delivery methods, such as, e.g., retroviral-mediated transfection, see e.g., *Introducing Cloned Genes into Cultured Mammalian Cells*, pp. 16.1-16.62 (Sambrook & Russell, eds., Molecular Cloning A Laboratory Manual, Vol. 3, $3^{rd}$ ed. 2001); Alessia Colosimo et al., *Transfer and Expression of Foreign Genes in Mammalian Cells,* 29(2) Biotechniques 314-318, 320-322, 324 (2000); Philip Washbourne & A. Kimberley McAllister, *Techniques for Gene Transfer into Neurons,* 12(5) Curr. Opin. Neurobiol. 566-573 (2002); and Current Protocols in Molecular Biology, John Wiley and Sons, pp 9.16.4-9.16.11 (2000), each of which is incorporated by reference in its entirety. One skilled in the art understands that selection of a specific method to introduce a polynucleotide molecule into a cell will depend, in part, on whether the cell will transiently or stably contain a component necessary for the cells to undergo the overall cellular mechanism whereby a BoNT/A proteolytically cleaves a SNAP-25 substrate. Non-limiting examples of polynucleotide molecule encoding a component necessary for the cells to undergo the overall cellular mechanism whereby a BoNT/A proteolytically cleaves a SNAP-25 substrate as follows: FGFR2 polynucleotide molecule of SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, or SEQ ID NO: 138; FGFR3 polynucleotide molecule of SEQ ID NO: 139, SEQ ID NO: 140, or SEQ ID NO: 141; SV2 polynucleotide molecule of SEQ ID NO: 142, SEQ ID NO: 143, or SEQ ID NO: 144; and SNAP-25 polynucleotide molecule of SEQ ID NO: 145, or SEQ ID NO: 146.

Chemical-mediated delivery methods are well-known to a person of ordinary skill in the art and are described in, e.g., Martin Jordan & Florian Worm, *Transfection of Adherent and Suspended Cells by Calcium Phosphate,* 33(2) Methods 136-143 (2004); Chun Zhang et al., *Polyethylenimine Strategies for Plasmid Delivery to Brain-Derived Cells,* 33(2) Methods 144-150 (2004), each of which is hereby incorporated by reference in its entirety. Such chemical-mediated delivery methods can be prepared by standard procedures and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

Physical-mediated delivery methods are well-known to a person of ordinary skill in the art and are described in, e.g., Jeike E. Biewenga et al., *Plasmid-Mediated Gene Transfer in Neurons using the Biolistics Technique,* 71(1) J. Neurosci. Methods. 67-75 (1997); John O'Brien & Sarah C. R. Lummis, *Biolistic and Diolistic Transfection: Using the Gene Gun to Deliver DNA and Lipophilic Dyes into Mammalian Cells,* 33(2) Methods 121-125 (2004); M. Golzio et al., *In Vitro and In Vivo Electric Field-Mediated Permeabilization, Gene Transfer, and Expression,* 33(2) Methods 126-135 (2004); and Oliver Gresch et al., *New Non-Viral Method for Gene Transfer into Primary Cells,* 33(2) Methods 151-163 (2004), each of which is hereby incorporated by reference in its entirety.

Viral-mediated delivery methods are well-known to a person of ordinary skill in the art and are described in, e.g., Chooi M. Lai et al., *Adenovirus and Adeno-Associated Virus Vectors,* 21(12) DNA Cell Biol. 895-913 (2002); Ilya Frolov et al., *Alphavirus-Based Expression Vectors: Strategies and Applications,* 93(21) Proc. Natl. Acad. Sci. U.S.A. 11371-11377 (1996); Roland Wolkowicz et al., *Lentiviral Vectors for the Delivery of DNA into Mammalian Cells,* 246 Methods Mol. Biol. 391-411 (2004); A. Huser & C. Hofmann, *Baculovirus Vectors: Novel Mammalian Cell Gene-Delivery Vehicles and Their Applications,* 3(1) Am. J. Pharmacogenomics 53-63 (2003); Tiziana Tonini et al., *Transient Production of Retroviral- and Lentiviral-Based Vectors for the Transduction of Mammalian Cells,* 285 Methods Mol. Biol. 141-148 (2004); Manfred Gossen & Hermann Bujard, Tight Control of Gene Expression in Eukaryotic Cells by Tetracycline-Responsive Promoters, U.S. Pat. No. 5,464,758; Hermann Bujard & Manfred Gossen, Methods for Regulating Gene Expression, U.S. Pat. No. 5,814,618; David S. Hogness, Polynucleotides Encoding Insect Steroid Hormone Receptor Polypeptides and Cells Transformed With Same, U.S. Pat. No. 5,514,578; David S. Hogness, Polynucleotide Encoding Insect Ecdysone Receptor, U.S. Pat. No. 6,245,531; Elisabetta Vegeto et al., Progesterone Receptor Having C. Terminal Hormone Binding Domain Truncations, U.S. Pat. No. 5,364,791; Elisabetta Vegeto et al., Mutated Steroid Hormone Receptors, Methods for Their Use and Molecular Switch for Gene Therapy, U.S. Pat. No. 5,874,534, each of which is hereby incorporated by reference in its entirety. Such viral-mediated delivery methods can be prepared by standard procedures and are commercially available, see, e.g., VIRAPOWER™ Adenoviral Expression System (Invitrogen, Inc., Carlsbad, Calif.) and VIRAPOWER™ Adenoviral Expression System Instruction Manual 25-0543 version A, Invitrogen, Inc., (Jul. 15, 2002); and ADEASY™ Adenoviral Vector System (Stratagene, Inc., La Jolla, Calif.) and ADEASY™ Adenoviral Vector System Instruction Manual 064004f, Stratagene, Inc. Furthermore, such viral delivery systems can be prepared by standard methods and are commercially available, see, e.g., BD™ Tet-Off and Tet-On Gene Expression Systems (BD Biosciences-Clonetech, Palo Alto, Calif.) and BD™ Tet-Off and Tet-On Gene Expression Systems User Manual, PT3001-1, BD Biosciences Clonetech, (Mar. 14, 2003), GeneSwitch™ System (Invitrogen, Inc., Carlsbad, Calif.) and GENESWITCH™ System A Mifepristone-Regulated Expression System for Mammalian Cells version D, 25-0313, Invitrogen, Inc., (Nov. 4, 2002); VIRAPOWER™ Lentiviral Expression System (Invitrogen, Inc., Carlsbad, Calif.) and VIRAPOWER™ Lentiviral Expression System Instruction Manual 25-0501 version E, Invitrogen, Inc., (Dec. 8, 2003); and COMPLETE CONTROL® Retroviral Inducible Mammalian Expression System (Stratagene, La Jolla, Calif.) and COMPLETE CONTROL® Retroviral Inducible Mammalian Expression System Instruction Manual, 064005e.

As mentioned above, an exogenous component necessary for the cells to undergo the overall cellular mechanism whereby a BoNT/A proteolytically cleaves a SNAP-25 substrate, such as, e.g., a SNAP-25, a FGFR2, a FGFR3, or a SV2 disclosed in the present specification can be introduced into a cell. Any and all methods useful for introducing such an exogenous component with a delivery agent into a cell population can be useful with the proviso that this method introduce the exogenous component disclosed in the present specification in at least 50% of the cells within a given cell population. Thus, aspects of this embodiment can include a cell population in which, e.g., at least 50%, at least 60%, at least 70%, at least 80%, or at least 90% of the given cell population contains an exogenous component necessary for the cells to undergo the overall cellular mechanism whereby a BoNT/A proteolytically cleaves a SNAP-25 substrate, such as, e.g., a SNAP-25, a FGFR2, a FGFR3, or a SV2 disclosed in the present specification. As used herein, the term "delivery agent" refers to any molecule that enables or enhances internalization of a covalently-linked, non-covalently-linked or in any other manner associated with a polypeptide into a cell. Thus, the term "delivery agent" encompasses, without limitation, proteins, peptides, peptidomimetics, small molecules, polynucleotide molecules, liposomes, lipids, viruses, retroviruses and cells that, without limitation, transport a covalently or non-covalently linked molecule to the cell membrane, cell cytoplasm or nucleus. It further is understood that the term "delivery agent" encompasses molecules that are internalized by any mechanism, including delivery agents which function via receptor mediated endocytosis and those which are independent of receptor mediated endocytosis.

A delivery agent can also be an agent that enables or enhances cellular uptake of a covalently linked component, like FGFR2, FGFR3, SV2, or SNAP-25, such as, e.g., by chemical conjugation or by genetically produced fusion proteins. Methods that covalently link delivery agents and methods of using such agents are described in, e.g., Steven F. Dowdy, Protein Transduction System and Methods of Use Thereof, International Publication No WO 00/34308; Gérard Chassaing & Alain Prochiantz, Peptides which can be Used as Vectors for the Intracellular Addressing of Active Molecules, U.S. Pat. No. 6,080,724; Alan Frankel et al., Fusion Protein Comprising TAT-derived Transport Moiert, U.S. Pat. No. 5,674,980; Alan Frankel et al., TAT-derived Transport Polypeptide Conjugates, U.S. Pat. No. 5,747,641; Alan Frankel et al., TAT-derived Transport Polypeptides and Fusion Proteins, U.S. Pat. No. 5,804,604; Peter F. J. O'Hare et al., Use of Transport Proteins, U.S. Pat. No. 6,734,167; Yao- Zhong Lin & Jack J. Hawiger, Method for Importing Biologically Active Molecules into Cells, U.S. Pat. No. 5,807,746; Yao-Zhong Lin & Jack J. Hawiger, Method for Importing Biologically Active Molecules into Cells, U.S. Pat. No. 6,043,339; Yao-Zhong Lin et al., Sequence and Method for Genetic Engineering of Proteins with Cell Membrane Translocating Activity, U.S. Pat. No. 6,248,558; Yao-Zhong Lin et al., Sequence and Method for Genetic Engineering of Proteins with Cell Membrane Translocating Activity, U.S. Pat. No. 6,432,680; Jack J. Hawiger et al., Method for Importing Biologically Active Molecules into Cells, U.S. Pat. No. 6,495,518; Yao-Zhong Lin et al., Sequence and Method for Genetic Engineering of Proteins with Cell Membrane Translocating Activity, U.S. Pat. No. 6,780,843; Jonathan B. Rothbard & Paul A Wender, Method and Composition for Enhancing Transport Across Biological Membranes, U.S. Pat. No. 6,306,993; Jonathan B. Rothbard & Paul A Wender, Method and Composition for Enhancing Transport Across Biological Membranes, U.S. Pat. No. 6,495,663; and Pamela B. Davis et al., Fusion Proteins for Protein Delivery, U.S. Pat. No. 6,287,817, each of which is incorporated by reference in its entirety.

A delivery agent can also be an agent that enables or enhances cellular uptake of a non-covalently associated component, like FGFR2, FGFR3, SV2c, or SNAP-25. Methods that function in the absence of covalent linkage and methods of using such agents are described in, e.g., Gilles Divita et al, Peptide-Mediated Transfection Agents and Methods of Use, U.S. Pat. No. 6,841,535; Philip L Feigner and Olivier Zelphati, Intracellular Protein Delivery Compositions and Methods of Use, U.S. Patent Publication No. 2003/0008813; and Michael Karas, Intracellular Delivery of Small Molecules, Proteins and Nucleic Acids, U.S. Patent Publication 2004/0209797, each of which is incorporated by reference in its entirety. Such peptide delivery agents can be prepared and used by standard methods and are commercially available, see, e.g. the CHARIOT™ Reagent (Active Motif, Carlsbad, Calif.); BIO-PORTER® Reagent (Gene Therapy Systems, Inc., San Diego, Calif.), BIO TREK™ Protein Delivery Reagent (Stratagene, La Jolla, Calif.), and PRO-JECT™ Protein Transfection Reagent (Pierce Biotechnology Inc., Rockford, Ill.).

Aspects of the present disclosure can also be described as follows:

1. An established clonal cell line comprising a cell susceptible to intoxication by BoNT/A.
2. The established clonal cell line of 1, wherein the clonal cell line is selected from a parental SiMa cell line.
3. The established clonal cell line of 1 or 2, wherein the cell is susceptible to BoNT/A intoxication by about 100 pM or less, by about 50 pM or less, by about 10 pM or less, by about 5 pM or less, by about 1 pM or less, by about 0.5 pM or less, or by about 0.1 pM or less of a BoNT/A.
4. The established clonal cell line of 1 or 2, wherein susceptibility to BoNT/A intoxication is measured before differentiation of the cell.
5. The established clonal cell line of 2, wherein in the undifferentiated state, the cell exhibits at least a 1.5-fold increase in gene expression of one or more genes relative to the expression of the one or more genes in a cell from a 2D6 cell line, the genes being taken from Table 5, or wherein the cell exhibits at least a 1.5-fold decrease in gene expression of one or more genes relative to the expression of the one or more genes in a cell from a 2D6 cell line, the genes being taken from Table 6.
6. The established clonal cell line of 2, wherein in the differentiated state, the cell exhibits at least a 1.5-fold increase in gene expression of one or more genes relative to the expression of the one or more genes in a cell from a 2D6 cell line, the genes being taken from Table 9, or wherein the cell exhibits at least a 1.5-fold decrease in gene expression of one or more genes relative to the expression of the one or more genes in a cell from a 2D6 cell line, the genes being taken from Table 10.
7. The established clonal cell line of 2, wherein in the undifferentiated state, the cell exhibits at least a 1.5-fold increase in gene expression of one or more genes relative to the expression of the one or more genes in a cell from a parental SiMa cell line, the genes being taken from Table 7, or wherein the cell exhibits at least a 1.5-fold decrease in gene expression of one or more genes relative to the expression of the one or more genes in a cell from a parental SiMa cell line, the genes being taken from Table 8.
8. The established clonal cell line of 2, wherein in the differentiated state, the cell exhibits at least a 1.5-fold increase in gene expression of one or more genes relative to the expression of the one or more genes in a cell from a parental SiMa cell line, the genes being taken from Table 11, or wherein the cell exhibits at least a 1.5-fold decrease in gene expression of one or more genes relative to the expression of the one or more genes in a cell from a parental SiMa cell line, the genes being taken from Table 12.
9. The established clonal cell line of 1 or 2, wherein the cell exhibits a sensitivity for BoNT/A activity that is 100 pM or less or about 25 pM for about 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passage, or 60 or more cell passage.
10. The established clonal cell line of 1 or 2, wherein the cell from an established clonal cell line exhibits a well defined signal to noise ratio for the upper asymptote for BoNT/A activity of at least 3:1, at least 4:1, at least 5:1, at least 6:1, at least 7:1, at least 8:1, at least 9:1, at least 10:1, over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passage, or 60 or more cell passage.
11. An established clonal cell line comprising a cell susceptible to intoxication by BoNT/A produced from a parental SiMa cell line, wherein the cell is susceptible to BoNT/A intoxication by about 100 pM or less, by about 50 pM or less, by about 10 pM or less, by about 5 pM or less, by about 1 pM or less, by about 0.5 pM or less, or by about 0.1 pM or less of a BoNT/A.
12. An established clonal cell line comprising cells susceptible to intoxication by BoNT/A,
    wherein the clonal cell line is selected from a parental SiMa cell line; and
    wherein the clonal cell line comprises cells susceptible to BoNT/A intoxication by about 100 pM or less of a BoNT/A.
13. The established clonal cell line of 12, wherein the parental SiMa cell line is the parental SiMa cell line DSMZ ACC 164.
14. The established clonal cell line of 12, wherein the cell exhibits a sensitivity for BoNT/A activity that is 100 pM or less or about 25 pM for about 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passage, or 60 or more cell passage.

15. The established clonal cell line of 12, wherein the cell from an established clonal cell line exhibits a well defined signal to noise ratio for the upper asymptote for BoNT/A activity of at least 3:1, at least 4:1, at least 5:1, at least 6:1, at least 7:1, at least 8:1, at least 9:1, at least 10:1, over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passage, or 60 or more cell passage.

16. The established clonal cell line of 12, wherein susceptibility to BoNT/A intoxication is measured before differentiation of the cell or after differentiation of the cell.

17. An established clonal cell line comprising cells susceptible to intoxication by BoNT/A, wherein the cells exhibits at least a 1.5-fold difference in gene expression levels of three or more genes as compared to the expression levels of these genes in cells from the 2D6 cell line;

wherein the gene expression levels are selected from the group ADAMTS9, ASCL1, BASP1, DOK5, DPYD, GNB4, GNG11, GTSF1, MAOA, MINA, MSN, PEG3, PLK2, PRSS12, RNF182, SLC44A5, SPARC, TFPI2, and TPTE; and wherein the clonal cell line comprises cells susceptible to BoNT/A intoxication by about 100 pM or less of a BoNT/A.

18. The established clonal cell line of 17, wherein the cells exhibits at least a 2.0-fold difference in gene expression levels of one or more genes as compared to the expression levels of these genes in cells from the 2D6 cell line, at least a 3.0-fold difference in gene expression levels of one or more genes as compared to the expression levels of these genes in cells from the 2D6 cell line, or at least a 4.0-fold difference in gene expression levels of one or more genes as compared to the expression levels of these genes in cells from the 2D6 cell line.

19. The established clonal cell line of 17, wherein the gene expression levels are measured before differentiation of the cell or after differentiation of the cell.

20. The established clonal cell line of 17, wherein the cell exhibits a sensitivity for BoNT/A activity that is 100 pM or less or about 25 pM for about 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passage, or 60 or more cell passage.

21. The established clonal cell line of 17, wherein the cell from an established clonal cell line exhibits a well defined signal to noise ratio for the upper asymptote for BoNT/A activity of at least 3:1, at least 4:1, at least 5:1, at least 6:1, at least 7:1, at least 8:1, at least 9:1, at least 10:1, over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passage, or 60 or more cell passage.

EXAMPLES

Example I

Screening for Cell Lines Comprising Cells Susceptible to BoNT/A Intoxication The following example illustrates how to identify clonal cells from a parental established cell line that are susceptible to BoNT/A intoxication or have neurotoxin uptake capacity.

1. Isolation of Clonal Cell Lines.

Companion patent application Ester Fernandez-Salas, et al., Immuno-Based Botulinum Toxin Serotype A Activity Assays, U.S. patent application Ser. No. 12/403,531 identified several established cell lines useful for conducting the disclosed immuno-based methods of detecting BoNT/A activity, including, e.g., LA1-55n (ECACC 06041203), N18 (ECACC 88112301), Neuro-2a (ATCC CCL-131), PC12 (ATCC CRL-1721), SH-SY5Y (ATCC CRL-2266), and SiMa (DSMZ ACC 164). During characterization of the SiMa cell line, it was discovered that the cells comprising this established cell line comprised at least five different cellular phenotypes. To determine whether any one of these phenotypically-distinct cell types was responsible for the susceptibility of this cell line to BoNT/A intoxication, two different limited-dilution screens were conducted to obtain single colony isolates for each phenotypically-distinct cell type.

In both screens, a suitable density of cells from a SiMa stock were grown in RPMI 1640 medium, having 10% fetal bovine serum, 1% Penicillin-Streptomycin, 2 mM L-Glutamine, contained in a T175 Collagen IV coated flask. After the second passage, the cells were trypsin-treated to produce a cell suspension and the cell concentration was determined. About $4.0\times10^6$ cells from this cell suspension was transferred into a 50 mL tube and the cells were dissociated into single cells by repeated vigorous expulsion through an 18.5 gauge needle using a 10 mL syringe. Cells from this disassociated single-cell suspension were then diluted to a concentration of $0.2\times10^6$ cells/mL by adding 15 mL of fresh growth medium, and 2.5 μL of this dilution was added to 50 mL of fresh growth medium to obtain a concentration of 10 cells/mL. From this final dilution stock, 100 μL of growth medium was added to each well of a 96-well Collagen IV coated plates (final average density of one cell/well), and the cells were grown undisturbed in a 37° C. incubator under 5% carbon dioxide for four weeks. A total of nineteen 96-well plates were setup for analysis. Plates were microscopically examined periodically to assess colony growth. After four weeks, each well was microscopically examined to identify growing colonies, and for each growing colony identified, 100 μL of fresh growth medium was added to each well and the cells were grown undisturbed in a 37° C. incubator under 5% carbon dioxide for two weeks. After two additional weeks of growth, the growing single colonies were trypsin-treated and transferred to a new 96-well plate for continued growth. Once colonies grew to about 1,000 cells, based on visual inspection, the cells were trypsin-treated and each cell-suspension was transferred into a new well from a 24-well Collagen IV-coated plate. The cells were grown in a 37° C. incubator under 5% carbon dioxide with fresh growth medium being replenished every 2-3 days, if needed. The cells were grown until the culture reached approximately 60% confluence or greater, at which point the cells were trypsin-treated and each cell-suspension was transferred into a 25 $cm^2$ Collagen IV-coated flask. The cells were grown in a 37° C. incubator under 5% carbon dioxide with fresh growth medium being replenished every 2-3 days, if needed. Once the cells in the flask reached 70-80% confluence, they were frozen and stored in liquid nitrogen until the clonal cell lines were tested to determine their susceptibility to BoNT/A intoxication. Of the 1,824 colony isolates initially setup from both screens, 130 clonal cell lines were selected based on viability and growth criteria and expanded for subsequent screening procedures.

2. Primary Screen for BoNT/A Intoxication Susceptibility of Cells from a Clonal Cell Line Using a BoNT/A Complex.

One way to determine whether cells from a clonal cell line were susceptible to BoNT/A intoxication was to conduct a primary screen using a CELLTITER-GLO® luminescent cell viability assay (Promega, Madison, Wis.) for normalizing the cell number in each well and an immuno-based method for determining BoNT/A activity as described in Ester Fernandez-Salas, et al., Immuno-Based Botulinum Toxin Serotype A Activity Assays, U.S. patent application Ser. No. 12/403,531, which is hereby incorporated by reference in its entirety. Two separate 96-well plates were set up, one for the BoNT/A activity assay and the other for the cell viability assay.

To conduct the BoNT/A activity assay, a lysate was prepared from cells treated with BoNT/A by plating cells from each isolated clonal cell line into a well from a poly-D-lysine 96-well plate (BD Biosciences, Bedford, Mass.). The wells contained 0.1 mL of a serum-free medium comprising Minimum Essential Medium, 2 mM GlutaMAX™ I with Earle's salts, 1×B27 supplement, 1×N2 supplement, 0.1 mM Non-Essential Amino Acids, 10 mM HEPES and 25 μg/mL GT1b (302-011-M005, Alexis Biochemicals, San Diego, Calif.). These cells were incubated in a 37° C. incubator under 5% carbon dioxide until the cells differentiated, as assessed by standard and routine morphological criteria, such as growth arrest and neurite extension (approximately 3 days). The media from the differentiated cells was aspirated from each well and replaced with fresh media containing 1 nM of a BoNT/A complex. After a 24 hrs incubation, the cells were washed by aspirating the growth media and rinsing each well with 200 μL of 1×PBS. To harvest the cells, 1×PBS was aspirated, the cells lysed by adding 30 μl of Lysis Buffer comprising 20 mM Tris-HCl (pH 7.5), 150 mM NaCl, 1 mM EDTA, 1 mM EGTA, 1% Triton X-100 to each well, and the plate incubated on a shaker rotating at 500 rpm for 30 minutes at 4° C. The plate was centrifuged at 4000 rpm for 20 minutes at 4° C. to pellet cellular debris and the supernatant was transferred to a capture antibody coated 96-well plate to perform the detection step.

To prepare an α-SNAP-25 capture antibody solution, the α-SNAP-25 mouse monoclonal antibody contained in the ascites from hybridoma cell line 2E2A6 (Example VII) was purified using a standard Protein A purification protocol.

To prepare an α-SNAP-25 detection antibody solution, α-SNAP-25 rabbit polyclonal antibody S9684 (Sigma, St. Louis, Mo.) was conjugated to Ruthenium(II)-tris-bipyridine-(4-methysulfonate) NHS ester labeling reagent (Meso Scale Discovery, Gaithersburg, Md.) according to the manufacturer's instructions (Meso Scale Discovery, Gaithersburg, Md.). The conjugation reaction was performed by adding 30 μL of distilled water reconstituted MSD SULFO-TAG™ stock solution to 200 μL of 2 mg/mL α-SNAP-25 polyclonal antibodies and incubating the reaction at room temperature for 2 hours in the dark. The labeled antibodies were purified using a standard spin column protocol and the protein concentration determined using a standard colorimetric protein assay. The absorbance of the α-SNAP-25 antibody/MSD SULFO-TAG™ conjugate was measured at 455 nm using a spectrophotometer to determine the concentration in moles per liter. The detection antibody solution was stored at 4° C. until needed.

To prepare an α-SNAP-25 solid phase support comprising an α-SNAP-25 capture antibody, approximately 5 μL of the appropriate α-SNAP-25 monoclonal antibody solution (20 μg/mL in 1×PBS) is added to each well of a 96-well MSD High Bind plate and the solution is allowed to air dry in a biological safety cabinet for 2-3 hours in order to liquid evaporate the solution. The capture antibody-bound wells were sealed and stored at 4° C. until needed.

To detect the presence of a cleaved SNAP-25 product by ECL sandwich ELISA, the wells from an α-SNAP-25 solid phase support were then blocked by adding 150 μL of Blocking Buffer comprising 2% Amersham Blocking Reagent (GE Life Sciences, Piscataway, N.J.) and 10% goat serum (VWR, West Chester, Pa.) at room temperature for 2 hours. The Blocking Buffer was aspirated, 25 μL of a lysate from cells treated with BoNT/A was added to each well and the plates were incubated at 4° C. for overnight. Plate wells were washed three times by aspirating the cell lysate and rinsing each well three times with 200 μL 1×PBS, 0.1% TWEEN-20® (polyoxyethylene (20) sorbitan monolaureate). After washing, 25 μl of 5 μg/mL α-SNAP-25 detection antibody solution comprising 2% Amersham Blocking Reagent in 1×PBS, 0.1% TWEEN-20® (polyoxyethylene (20) sorbitan monolaureate) was added to each well, sealed, and incubated at room temperature for 1 hour with shaking. After α-SNAP-25 detection antibody incubation, the wells were washed three times with 200 μL 1×PBS, 0.1% TWEEN-20® (polyoxyethylene (20) sorbitan monolaureate). After washing 150 μL of 1× Read Buffer (Meso Scale Discovery, Gaithersburg, Md.) was added to each well and the plates were read using a SECTOR™ Imager 6000 Image Reader (Meso Scale Discovery, Gaithersburg, Md.). The raw data was collected using the ECL imager.

To conduct the luminescent cell viability assay, cells from each isolated clonal cell line were plated and differentiated as described above. The media from the differentiated cells was aspirated from each well and replaced with 100 μl of the reagent mixture comprising the CELLTITER-GLO® substrate and CELLTITER-GLO® buffer according to the manufacturer's instructions. The plate was then protected from light and mixed for two minutes on an orbital shaker. The solution from the 96-well cell plate with clear bottom was transferred to a white luminometer plate and after 10 minutes incubation was read on the luminometer.

These results indicated that the cell viability readings ranged from 9,838 to 10,423,188 and BoNT/A activity signals ranged from 84 to 27,242 (Table 1). In addition, a ratio of BoNT/A activity over cell viability was calculated to normalize the data, although there was not always a 1:1 ratio of viability and activity. Seven clonal cell lines exhibited activity/viability ratios of about $0.2\times10^{-2}$ or greater: H1, A7, A11, F10, A9, A10, and C11 (Table 1). Nine clonal cell lines exhibited activity/viability ratios of about $0.125\times10^{-2}$ to about $0.150\times10^{-2}$: H3, H8, E11, H10, A6, C5, C12, D11, and B5 (Table 1). Two cell lines exhibited activity/viability ratios of about $0.100\times10^{-2}$: D7 and B10 (Table 1). Based on these activity/viability ratios in conjunction with the cell viability and BoNT/A activity signal measurements, these 18 clonal cell lines were selected for further testing by conducting a secondary screen using a BoNT/A activity assay in order to generate a dose-response curve to BoNT/A.

TABLE 1

Primary Screen for Clonal Cell Lines Susceptible to BoNT/A Intoxication Using Viability and Activity Signals

| Well | Cell Viability Reading (RLU) | BoNT/A Activity Signal (RLU) | Activity/Viability Ratio | Well | Cell Viability Reading (RLU) | BoNT/A Activity Signal (RLU) | Activity/Viability Ratio |
|---|---|---|---|---|---|---|---|
| A1 | 2634417 | 2425 | 0.092 x $10^{-2}$ | A7 | 10132753 | 27242 | 0.269 x $10^{-2}$ |
| B1 | 731808 | 198 | 0.027 x $10^{-2}$ | B7 | 2977371 | 1642 | 0.055 x $10^{-2}$ |
| C1 | 4258160 | 1641 | 0.039 x $10^{-2}$ | C7 | 5746577 | 4878 | 0.085 x $10^{-2}$ |
| D1 | 6554606 | 4885 | 0.075 x $10^{-2}$ | D7 | 5861338 | 6044 | 0.103 x $10^{-2}$ |
| E1 | 2374483 | 897 | 0.038 x $10^{-2}$ | E7 | 2819910 | 1399 | 0.050 x $10^{-2}$ |
| F1 | 2801444 | 1842 | 0.066 x $10^{-2}$ | F7 | 23523 | 84 | 0.357 x $10^{-2}$ |
| G1 | 5094510 | 4579 | 0.090 x $10^{-2}$ | G7 | 6232344 | 4031 | 0.065 x $10^{-2}$ |
| H1 | 3808699 | 10861 | 0.285 x $10^{-2}$ | H7 | 4916756 | 2759 | 0.056 x $10^{-2}$ |
| A2 | 9593106 | 7090 | 0.074 x $10^{-2}$ | A8 | 5945833 | 5611 | 0.094 x $10^{-2}$ |
| B2 | 5374966 | 5673 | 0.106 x $10^{-2}$ | B8 | 4591002 | 2128 | 0.046 x $10^{-2}$ |
| C2 | 4170158 | 2972 | 0.071 x $10^{-2}$ | C8 | 5648241 | 8758 | 0.155 x $10^{-2}$ |
| D2 | 31283 | 88 | 0.281 x $10^{-2}$ | D8 | 4207887 | 3360 | 0.080 x $10^{-2}$ |
| E2 | 5706902 | 3743 | 0.066 x $10^{-2}$ | E8 | 5894699 | 3844 | 0.065 x $10^{-2}$ |
| F2 | 4884798 | 4568 | 0.094 x $10^{-2}$ | F8 | 5585487 | 4651 | 0.083 x $10^{-2}$ |
| G2 | 3552045 | 2190 | 0.062 x $10^{-2}$ | G8 | 4758800 | 4545 | 0.096 x $10^{-2}$ |
| H2 | 3743690 | 3421 | 0.091 x $10^{-2}$ | H8 | 5439137 | 8017 | 0.147 x $10^{-2}$ |
| A3 | 15372 | 89 | 0.579 x $10^{-2}$ | A9 | 10423188 | 20706 | 0.199 x $10^{-2}$ |
| B3 | 5381672 | 1551 | 0.029 x $10^{-2}$ | B9 | 6493893 | 4444 | 0.068 x $10^{-2}$ |
| C3 | 4270534 | 3959 | 0.093 x $10^{-2}$ | C9 | 5742047 | 5788 | 0.101 x $10^{-2}$ |
| D3 | 48702 | 97 | 0.199 x $10^{-2}$ | D9 | 3424405 | 1848 | 0.054 x $10^{-2}$ |
| E3 | 4707349 | 2671 | 0.057 x $10^{-2}$ | E9 | 5771943 | 8064 | 0.140 x $10^{-2}$ |
| F3 | 3053132 | 1539 | 0.050 x $10^{-2}$ | F9 | 24524 | 88 | 0.359 x $10^{-2}$ |
| G3 | 5518292 | 4195 | 0.076 x $10^{-2}$ | G9 | 7291510 | 6674 | 0.092 x $10^{-2}$ |
| H3 | 4156632 | 6339 | 0.153 x $10^{-2}$ | H9 | 4169883 | 6048 | 0.145 x $10^{-2}$ |
| A4 | 19793 | 89 | 0.450 x $10^{-2}$ | A10 | 9050811 | 17617 | 0.195 x $10^{-2}$ |
| B4 | 6224766 | 4299 | 0.069 x $10^{-2}$ | B10 | 5590113 | 5175 | 0.093 x $10^{-2}$ |
| C4 | 3212859 | 3202 | 0.100 x $10^{-2}$ | C10 | 2325807 | 1713 | 0.074 x $10^{-2}$ |
| D4 | 4376180 | 2367 | 0.054 x $10^{-2}$ | D10 | 2644116 | 2589 | 0.098 x $10^{-2}$ |
| E4 | 3931793 | 3975 | 0.101 x $10^{-2}$ | E10 | 4210945 | 2666 | 0.063 x $10^{-2}$ |
| F4 | 1150134 | 526 | 0.046 x $10^{-2}$ | F10 | 2932749 | 6390 | 0.218 x $10^{-2}$ |
| G4 | 19023 | 94 | 0.494 x $10^{-2}$ | G10 | 3980127 | 3114 | 0.078 x $10^{-2}$ |
| H4 | 3368425 | 2645 | 0.079 x $10^{-2}$ | H10 | 4519035 | 6187 | 0.137 x $10^{-2}$ |
| AS | 8231689 | 7809 | 0.095 x $10^{-2}$ | A11 | 9870025 | 24690 | 0.250 x $10^{-2}$ |
| B5 | 5332004 | 6545 | 0.123 x $10^{-2}$ | B11 | 4973892 | 2235 | 0.045 x $10^{-2}$ |
| C5 | 3869441 | 5042 | 0.130 x $10^{-2}$ | C11 | 3326448 | 6405 | 0.193 x $10^{-2}$ |
| D5 | 2554300 | 1161 | 0.045 x $10^{-2}$ | D11 | 5747961 | 7169 | 0.125 x $10^{-2}$ |
| E5 | 3781403 | 764 | 0.020 x $10^{-2}$ | E11 | 5831546 | 8432 | 0.145 x $10^{-2}$ |
| F5 | 4608801 | 3720 | 0.081 x $10^{-2}$ | F11 | 5291803 | 4317 | 0.082 x $10^{-2}$ |
| G5 | 7105403 | 7330 | 0.103 x $10^{-2}$ | G11 | 3499587 | 2790 | 0.080 x $10^{-2}$ |
| H5 | 5585607 | 7544 | 0.135 x $10^{-2}$ | H11 | 3225750 | 4518 | 0.140 x $10^{-2}$ |
| A6 | 7698708 | 10152 | 0.132 x $10^{-2}$ | A12 | 9838 | 89 | 0.905 x $10^{-2}$ |
| B6 | 4706560 | 3196 | 0.068 x $10^{-2}$ | B12 | 3728293 | 2016 | 0.054 x $10^{-2}$ |
| C6 | 5866251 | 6145 | 0.105 x $10^{-2}$ | C12 | 4086862 | 5308 | 0.130 x $10^{-2}$ |
| D6 | 2285787 | 768 | 0.034 x $10^{-2}$ | D12 | 5044526 | 3860 | 0.077 x $10^{-2}$ |
| E6 | 2471979 | 1038 | 0.042 x $10^{-2}$ | E12 | 4787913 | 2719 | 0.057 x $10^{-2}$ |
| F6 | 10958 | 91 | 0.830 x $10^{-2}$ | F12 | 5101695 | 2585 | 0.051 x $10^{-2}$ |
| G6 | 19590 | 91 | 0.465 x $10^{-2}$ | G12 | 2887390 | 1622 | 0.056 x $10^{-2}$ |
| H6 | 2057687 | 2564 | 0.125 x $10^{-2}$ | H12 | 2829307 | 5105 | 0.180 x $10^{-2}$ |

To conduct BoNT/A activity assay in order to generate a dose-response curve to BoNT/A, cells from each isolated clonal cell line were seeded in a poly-D-lysine 96-well plate and differentiated as described above. Of the top 18 clonal cell lines selected for further testing, only 8 remained viable, the remaining 10 clonal cell lines failed to regrow and were lost. The media from the differentiated cells was aspirated from each well and replaced with fresh media containing either 0 (untreated sample), 0.03 pM, 0.1 pM, 0.3 pM, 0.9 pM, 2.8 pM, 8.3 pM, and 25 pM of a BoNT/A complex. After a 24 hrs treatment, the cells were washed, incubated for an additional two days in serum-free medium without toxin to allow for the cleavage of the SNAP-25 substrate, and harvested as described above. The supernatant was transferred to a capture antibody coated 96-well plate to perform the detection step.

The α-SNAP-25 capture antibody solution, the α-SNAP-25 detection antibody solution, and the α-SNAP-25 solid phase support were prepared as described above. Detection of the presence of cleaved SNAP-25 product by ECL sandwich ELISA analysis was performed as described above. The raw data obtained from the ECL imager was then transferred to SigmaPlot v. 9.0 and a 4-parameter logistics fit was used to define the dose-response curves. There were no constraints used for the 4-parameter logistic function when plotting the data. Graphical reports were generated using the following analysis: R2 (correlation coefficient), a (Max for data set), b (hillslope), and X0±SE ($EC_{50}$ value±standard error).

These results indicate that of the 8 clonal cell lines tested, only two were more susceptible to BoNT/A intoxication when compared to cells comprising the parental SiMa cell line (Table 2). For example, cells comprising the parental SiMa cell line exhibited an $EC_{50}$ activity for BoNT/A of 2.20 pM, whereas cells comprising the H1 and A10 cell lines exhibited an $EC_{50}$ activity for BoNT/A of 1.76 pM or less.

Conversely, cells comprising the H10 and D11 cell line exhibited an $EC_{50}$ activity for BoNT/A that was higher than that observed for cells comprising the parental SiMa cell line, but less than 5.0 pM. It should be noted that any clonal cell line exhibiting an $EC_{50}$ activity for BoNT/A that is 5.0 pM or less (100 U/mL or less) is useful for an immuno-based method for determining BoNT/A activity described in Ester Fernandez-Salas, et al., Immuno-Based Botulinum Toxin Serotype A Activity Assays, U.S. patent application Ser. No. 12/403,531.

TABLE 2

Secondary Screen for Clonal Cell Lines Susceptible to BoNT/A Intoxication

| | BoNT/A Activity | | |
|---|---|---|---|
| Clone | $EC_{50}$ (pM) | $Signal_{MIN}$ (RLU) | $Signal_{MAX}$ (RLU) |
| SiMa | 2.20 | 123 | 47,611 |
| H1 | 0.77 | 193 | 125,252 |
| H3 | ND | ND | ND |
| B5 | >25.0 | 115 | 22,277 |
| C5 | ND | ND | ND |
| A6 | ND | ND | ND |
| A7 | 5.59 | 153 | 100,412 |
| D7 | ND | ND | ND |
| H8 | ND | ND | ND |
| A9 | ND | ND | ND |
| A10 | 1.76 | 207 | 113,029 |
| B10 | 6.35 | 147 | 101,935 |
| F10 | >25.0 | 111 | 32,663 |
| H10 | 2.80 | 171 | 120,975 |
| A11 | ND | ND | ND |
| C11 | ND | ND | ND |
| D11 | 4.4 | 1.84 | 105,527 |
| E11 | ND | ND | ND |
| C12 | ND | ND | ND |

ND = Not determined.

3. Primary Screen for BoNT/A Intoxication Susceptibility of Cells from a Clonal Cell Line Using a Formulated BoNT/A Pharmaceutical Product.

Another way to determine whether cells from a clonal cell line were susceptibility to BoNT/A intoxication was to conduct a primary screen by generating a dose-response curve to BoNT/A and calculate the $EC_{50}$ value using an immuno-based method for determining BoNT/A activity as described in Ester Fernandez-Salas, et al., Immuno-Based Botulinum Toxin Serotype A Activity Assays, U.S. patent application Ser. No. 12/403,531, which is hereby incorporated by reference in its entirety.

Initially six of 35 clonal cell line isolates were examined using a full dose response to BoNT/A. To prepare a lysate from cells treated with BoNT/A, cells from six clonal cell line were seeded in a poly-D-lysine 96-well plate and differentiated as described above in Section 2 except that the serum-free medium comprised 60 μg/mL GT1b. The clonal cell lines used were 3D8, YB8, 1D4, 2D6, 1E11, 2F5. The H1 and H10 clonal cell lines identified above, along with the parental SiMa cell line, were used as references to identify cell lines highly susceptible to BoNT/A intoxication. The media from the differentiated cells was aspirated from each well and replaced with fresh media containing either 0 (untreated sample), 0.98 U/mL, 1.9 U/mL, 3.91 U/mL, 7.81 U/mL, 15.6 U/mL, 31.3 U/mL, 62.5 U/mL, 125 U/mL, 250 U/mL, or 500 U/mL of a formulated BoNT/A pharmaceutical product. After a 24 hrs treatment, the cells were washed, incubated for an additional two days in serum-free medium without toxin to allow for the cleavage of the SNAP-25 substrate. To harvest the cells, 1×PBS was aspirated, the cells lysed by adding 30 μl of Lysis Buffer comprising 20 mM Tris-HCl (pH 7.5), 150 mM NaCl, 1 mM EDTA, 1 mM EGTA, 1% Triton X-100 to each well, and the plate incubated on a shaker rotating at 500 rpm for 30 minutes at 4° C. The plate was centrifuged at 4000 rpm for 20 minutes at 4° C. to pellet cellular debris. The protein concentration was determined using standard methods. The supernatant was transferred to a capture antibody coated 96-well plate to perform the detection step of the immuno-based method.

The α-SNAP-25 capture antibody solution, the α-SNAP-25 detection antibody solution, and the α-SNAP-25 solid phase support were prepared as described above in Section 2. Detection of the presence of SNAP-25 cleavage product by ECL sandwich ELISA analysis was performed, collected data was analyzed and the $EC_{50}$ calculated as described above in Section 2, except that SigmaPlot v. 10 was used.

These results show that clonal cell line H1 comprises cells that are more susceptible to BoNT/A than the parental SIMa cell line (Table 3). In addition, results indicate that although clonal cell lines H10, 1D4, 1E11, 2D6, 2F5, 3D8, and YB8 all comprise cells that are less susceptible to BoNT/A than the parental SiMa cell line, all have an $EC_{50}$ of BoNT/A activity that is below 30 U/mL (Table 3). It should be noted that any clonal cell line exhibiting an $EC_{50}$ activity for BoNT/A that is 100 U/mL or less (5.0 pM or less) is useful for an immuno-based method for determining BoNT/A activity described in Ester Fernandez-Salas, et al., Immuno-Based Botulinum Toxin Serotype A Activity Assays, U.S. patent application Ser. No. 12/403,531.

TABLE 3

Primary Screen for Clonal Cell Lines Susceptible to BoNT/A Intoxication

| | BoNT/A Activity | | |
|---|---|---|---|
| Clone | $EC_{50}$ (U/mL) | $Signal_{MIN}$ (RLU) | $Signal_{MAX}$ (RLU) |
| SiMa | 10.8 ± 1.0 | 10,519 | 253,484 |
| H1 | 10.2 ± 0.6 | 13,996 | 276,982 |
| H10 | 22.2 ± 2.0 | 5,379 | 296,168 |
| 1D4 | 22.4 ± 0.8 | 6,064 | 239,096 |
| 1E11 | 14.2 ± 1.7 | 8,698 | 276,323 |
| 2D6 | 27.3 ± 1.8 | 3,347 | 179,454 |
| 2F5 | 15.8 ± 0.9 | 7,007 | 265,461 |
| 3D8 | 13.4 ± 0.6 | 11,658 | 266,279 |
| YB8 | 19.7 ± 1.3 | 8,477 | 293,559 |

This initial primary screen using a dose-response curve with the 10 different BoNT/A concentrations identified three concentrations that were useful for a shortened assay using 3 different BoNT/A concentrations, with one concentration being slightly higher than the lower asymptote (8 U/mL), one concentration near the $EC_{50}$ (25 U/mL), and one concentration representing about 80% of the upper asymptote (80 U/mL). In these subsequent primary screens the remaining 29 clonal cell line isolates were tested as described above except that the cells were treated with either 0 (untreated sample), 8 U/mL, 25 U/mL, or 80 U/mL of a formulated BoNT/A pharmaceutical product. The clonal cell lines tested were 1E3, 2B9, 2D2, 2E4, 3B8, 3D5, 3G10, 4B5, 4C8, 4D3, 5C10, 5F3, AC9, AF4, BB3, BB10, BE3, BF8, CC11, CD6, CE6, CG8, CG10, DC4, DD10, DE7, DF5, YB7, and YF5. In addition, the parental SiMa was used as positive control.

These results show that clonal cell lines 2E4, 3B8, 3D5, 5F3, AF4, BB3, BB10, and DC4 all comprise cells that are more susceptible to BoNT/A than the parental SiMa cell line (Table 4). In addition, these results indicate that clonal cell lines 1E3, 2B9, 3G10, 4B5, 4C8, AC9, BE3, BF8, CC11, CD6, CE6, CG8, CG10, DD10, DE7, and YF5 all comprise cells that are of similar susceptibility to BoNT/A to that of the parental SiMa cell line (Table 4). Lastly, these results reveal that clonal cell lines 2D2, 4D3, 5C10, DF5, and YB7 all comprise cells that are less susceptible to BoNT/A than the parental SiMa cell line (Table 4).

susceptible at all, then as this cell type became the dominant one in the cell line the $EC_{50}$ for BoNT/A activity in this overtaken SiMa cell line would decrease. Thus, because the established clonal cell lines were derived from only one of these cell types, then it follows that the clonal cell line would exhibit greater stability in terms of maintaining an $EC_{50}$ for BoNT/A activity that was routinely under 5.0 pM.

TABLE 4

Primary Screen for Clonal Cell Lines Susceptible to BoNT/A Intoxication

| Clone | 8 U/mL BoNT/A Activity Signal (RLU) | 8 U/mL BoNT/A Fold Difference | 25 U/mL BoNT/A Activity Signal (RLU) | 25 U/mL BoNT/A Fold Difference | 80 U/mL BoNT/A Activity Signal (RLU) | 80 U/mL BoNT/A Fold Difference |
|---|---|---|---|---|---|---|
| SiMa | 75811/80562* | — | 138952/175685* | — | 173979/225768* | — |
| 1E3 | 71040 | 0.9 | 128771 | 0.9 | 155107 | 0.9 |
| 2B9 | 66962 | 0.9 | 135006 | 1.0 | 166871 | 1.0 |
| 2D2 | 60224* | 0.8 | 136947* | 0.8 | 199786* | 0.9 |
| 2E4 | 103680 | 1.4 | 217980 | 1.6 | 270463 | 1.6 |
| 3B8 | 123521 | 1.6 | 227367 | 1.6 | 249218 | 1.4 |
| 3D5 | 113532 | 1.5 | 201683 | 1.5 | 270578 | 1.6 |
| 3G10 | 83049 | 1.1 | 130930 | 0.9 | 175540 | 1.0 |
| 4B5 | 74344 | 1.0 | 137604 | 1.0 | 177363 | 1.0 |
| 4C8 | 87047 | 1.1 | 144395 | 1.0 | 185115 | 1.1 |
| 4D3 | 38063 | 0.5 | 80180 | 0.6 | 101724 | 0.6 |
| 5C10 | 16024* | 0.2 | 49030 | 0.3 | 116396* | 0.6 |
| 5F3 | 98263* | 1.7 | 182902* | 1.4 | 212275* | 1.5 |
| AC9 | 60016* | 1.0 | 127030* | 1.0 | 180384* | 1.4 |
| AF4 | 115460 | 1.5 | 179901 | 1.3 | 190867 | 1.1 |
| BB3 | 74668 | 1.3 | 120966 | 1.4 | 170177 | 1.4 |
| BB10 | 152748 | 2.0 | 232406 | 1.7 | 266555 | 1.5 |
| BE3 | 100849 | 1.0 | 199487 | 0.9 | 236415 | 1.0 |
| BF8 | 55763* | 1.0 | 111746* | 1.0 | 153074* | 1.3 |
| CC11 | 54421* | 1.0 | 123576* | 1.0 | 155337* | 1.2 |
| CD6 | 74970 | 1.0 | 151862 | 1.1 | 183377 | 1.1 |
| CE6 | 70019 | 0.9 | 146292 | 1.1 | 208184 | 1.2 |
| CG8 | 81790* | 1.0 | 159098* | 1.0 | 189209* | 1.3 |
| CG10 | 69503 | 0.9 | 141079 | 1.0 | 185801 | 1.1 |
| DC4 | 112085 | 1.5 | 163319 | 1.2 | 169352 | 1.0 |
| DD10 | 116325 | 1.5 | 205445 | 1.5 | 223473 | 1.3 |
| DE7 | 60994* | 0.9 | 131237* | 0.9 | 174487* | 0.9 |
| DF5 | 34,165* | 0.5 | 104,696* | 0.7 | 179,314* | 0.9 |
| YB7 | 50433 | 0.7 | 103707 | 0.7 | 143423 | 0.8 |
| YF5 | 65848 | 0.9 | 122487 | 0.9 | 146263 | 0.4 |

*Two separate screens were done. In the first, the signal detected for the SiMa cell line was 75811 RLU and this value was used to determine the fold difference for clonal cell lines tested in this screen (numbers with no asterisk). For the second screen, the signal detected for the SiMa cell line was 80562 RLU and this value was used to determine the fold difference for clonal cell lines tested in this screen (numbers with asterisk).

Example II

Stability Analysis of Clonal Cell Lines

The following example illustrates how to characterize the stability of cells from an established clonal cell line that are susceptible to BoNT/A intoxication or have neurotoxin uptake capacity.

During characterization of the SiMa cell line, it was determined that the parental SiMa cell line became unstable in terms of a significant loss of sensitivity to BoNT/A. For example, prior to passage 13, cells comprising the parental SiMa cell line routinely exhibited an $EC_{50}$ for BoNT/A activity that was under 5.0 pM. However, after passages about 14 to about 20 passages, cells comprising the parental SiMa cell exhibited an $EC_{50}$ for BoNT/A activity that was routinely over 25.0 pM. One reason for this dramatic reduction in the $EC_{50}$ value may be because the SiMa cell line is heterogeneous in nature since it comprises at least five different cell types. Over time, one of these cell types could overtake the culture to the exclusion of the other four. If the overtaking cell type was less susceptible to BoNT/A intoxication, or not To determine whether the cells from the established clonal cell lines showed increased stability relative to the cells comprising the parental SIMa cell line, the $EC_{50}$ for BoNT/A activity was determined for clonal cell lines BB10, H1, H10, and the parental SiMa cell line at different passage numbers using an immuno-based method for determining BoNT/A activity. The media from the differentiated cells was aspirated from each well and replaced with fresh media containing either 0 (untreated sample), 0.98 U/mL, 1.9 U/mL, 3.91 U/mL, 7.81 U/mL, 15.6 U/mL, 31.3 U/mL, 62.5 U/mL, 125 U/mL, 250 U/mL, or 500 U/mL of a formulated BoNT/A pharmaceutical product. After a 24 hrs treatment, the cells were washed, incubated for an additional two days in serum-free medium without toxin to allow for the cleavage of the SNAP-25 substrate, and harvested as described above. The supernatant was transferred to a capture antibody coated 96-well plate to perform the detection step.

Similarly, the preparation of the α-SNAP-25 capture antibody solution, α-SNAP-25 detection antibody solution, and the solid phase support comprising an α-SNAP-25 capture antibody were as described in Section 3. Lastly, detection of the presence of SNAP-25 cleavage product by ECL sandwich ELISA was performed, collected data was analyzed, and the $EC_{50}$ calculated as described above in Section 2, except that PLA v. 2 was used for the 4-parameter logistics fit.

The results from this stability experiments indicated that BB10, H1 and H10 cell lines all exhibited increase stability as compared to the parental SiMa cell line. For example, where cells from the parental SiMa cell line exhibited an $EC_{50}$ for BoNT/A activity that was over 500 U/mL (or 25 pM) after passages about 14 to about 20 passages, cells comprising the BB10, H1 and H10 cell lines all exhibited an $EC_{50}$ for BoNT/A activity that was below 10 U/mL (or 0.5 pM) after passage about 30.

Example III

Gene Expression Profile of Cell Lines Comprising Cells Susceptible to BoNT/A Intoxication The following example illustrates how to characterize cells from an established clonal cell line that are susceptible to BoNT/A intoxication or have neurotoxin uptake capacity by gene expression profiling.

To determine the changes in genome-wide gene transcription levels in cells susceptible to BoNT/A intoxication, gene expression analysis was performed on cells from H1, BB10, 2D6 and the parental SiMa cell line, in both differentiated and undifferentiated states using GENECHIP® U133 Plus 2 microarray technology (Affymetrix, Inc., Santa Clara, Calif.) according to the manufacturer's instructions, see, e.g., *GENECHIP® Expression Analysis Technical Manual,* 702232, Rev. 2 (2006) which is hereby incorporated by reference in its entirety.

To prepare differentiated cells for these cell lines, a suitable density of cells from the H1, BB10, 2D6, and SiMa cell lines were seeded in separate T175 tissue culture flasks containing 50 mL of a serum-free medium comprising Enhanced Minimum Essential Medium, 10 mM HEPES, 1 mM sodium pyruvate, 0.1 mM Non-Essential Amino Acids, 1×B27 supplement, 1×N2 supplement, and 60 μg/mL GT1b (302-011-M005, Alexis Biochemicals, San Diego, Calif.). These cells were incubated in a 37° C. incubator under 5% carbon dioxide until the cells differentiated, as assessed by standard and routine morphological criteria, such as growth arrest and neurite extension, and attained 80% confluence (approximately 3 days). The cells were then washed with 50 mL of 1×PBS, trypsin-treated for 5 min at room temperature, and then 15 mL of growth medium was added to the flask to inactivate the trypsin. The cell suspension was transferred to a 50 mL tube and centrifuge at 200 RCF for 5 min at room temperature to pellet the cells. The cell pellet was washed once in 50 mL of 1×PBS, centrifuge at 200 RCF for 5 min at room temperature to pellet the cells, and the supernatant was removed. The cell pellet was quick frozen on dry ice and stored at −80° C. until needed.

To prepare undifferentiated cells for these cell lines, a suitable density of cells from the H1, BB10, 2D6, and SiMa cell lines were seeded in separate T175 tissue culture flasks containing 50 mL of growth medium comprising RPMI 1640, 10% fetal bovine serum, 10 mM HEPES, 1 mM sodium pyruvate, 0.1 mM Non-Essential Amino Acids, and 60 μg/mL GT1b. These cells were incubated in a 37° C. incubator under 5% carbon dioxide until the cells attained 80% confluence (approximately 3 days). The cells were then processed as described above and the cell pellet was quick frozen on dry ice and stored at −80° C. until needed.

To prepare total RNA, cells for each cell line were lysed and total RNA isolated and purified using a RNA isolation kit (QIAGEN, Valencia, Calif.) according to the manufacturer's protocols. DNA was digested using an on-column DNase I procedure (QIAGEN, Valencia, Calif.). RNA was quantified photospectrometrically at 260 nm and purity assessed by the A260A280 ratio using a spectrophotometer. RNA integrity was assessed using a Bioanalyser 2100 (Agilent Technologies, Inc., Santa Clara, Calif.). Extracted total RNA aliquots were snap-frozen in liquid nitrogen and stored at −80° C.

To prepare cDNA probes for the gene microarray chips, about 1-15 μg was reversed transcribed using a T7-Oligo(dT) promoter primer in the first strand cDNA synthesis reaction. Following RNase H-mediated second strand cDNA synthesis, the double-stranded cDNA was purified and served as a template for subsequent in vitro transcription reaction. The in vitro transcription reaction was carried out in the presence of T7 RNA polymerase and a biotinylated nucleotide analog/ribonucleotide mix for complementary RNA (cRNA) amplification and biotin labeling. The biotinylated cRNA targets were then cleaned up, fragmented, and hybridized to microchip expression arrays for 17 hours at 65° C. according to the manufacturer's instructions, see, e.g., *GENECHIP® Expression Analysis Technical Manual,* 702232, Rev. 2 (2006) which is hereby incorporated by reference in its entirety. To identify substantial treatment-related up- or down-regulated gene expression differences compared to control cell lines, greater than 1.5-fold differences ($log_2$ 0.58) were considered significant, and only those genes that displayed consistent changes in expression in the triplicate analysis were considered (Tables 5-12).

Expression profiling for cell lines H1, BB10 and 2D6 analyzed in the undifferentiated state revealed that 1,323 genes were identified as having their expression levels increase by 1.5-fold ($log_2$ 0.58) or more in the H1 and BB10 cell lines as compared to the gene expression levels obtained from the 2D6 cell line (Table 5). Of these, 686 genes exhibited an increase in expression levels in the H1 and BB10 cell lines by 2-fold ($log_2$ 1.0) or more as compared to the expression level for these genes determined from the 2D6 cell line; and 231 genes exhibited an increase in expression levels in the H1 and BB10 cell lines by 4-fold ($log_2$ 2.0) or more as compared to the expression level for these genes determined from the 2D6 cell line. With respect to decreased expression, 1,438 genes were identified as having their expression levels decreased by 1.5-fold ($log_2$ 0.58) or more in the H1 and BB10 cell lines as compared to the gene expression levels obtained from the 2D6 cell line (Table 6). Of these, 668 genes exhibited a decrease in expression levels in the H1 and BB10 cell lines by 2-fold ($log_2$ 1.0) or more as compared to the expression level for these genes determined from the 2D6 cell line; and 107 genes exhibited a decrease in expression levels in the H1 and BB10 cell lines by 4-fold ($log_2$ 2.0) or more as compared to the expression level for these genes determined from the 2D6 cell line.

Expression profiling for cell lines H1, BB10 and 2D6 analyzed in the differentiated state revealed that 2,556 genes were identified as having their expression levels increased by 1.5-fold ($log_2$ 0.58) or more in the H1 and BB10 cell lines as compared to the gene expression levels obtained from the 2D6 cell line (Table 7). Of these, 1,634 genes exhibited an increase in expression levels in the H1 and BB10 cell lines by 2-fold ($log_2$ 1.0) or more as compared to the expression level for these genes determined from the 2D6 cell line; and 696 genes exhibited an increase in expression levels in the H1 and BB10 cell lines by 4-fold ($log_2$ 2.0) or more as compared to the expression level for these genes determined from the 2D6 cell line. With respect to decreased expression, 2,087 genes were identified as having their expression levels decreased by 1.5-fold ($log_2$ 0.58) or more in the H1 and BB10 cell lines as compared to the gene expression levels obtained from the 2D6 cell line (Table 8). Of these, 1,215 genes exhibited a decrease in expression levels in the H1 and BB10 cell lines by 2-fold ($log_2$ 1.0) or more as compared to the expression level for these genes determined from the 2D6 cell line; and 280 genes exhibited a decrease in expression levels in the H1 and BB10 cell lines by 4-fold ($log_2$ 2.0) or more as compared to the expression level for these genes determined from the 2D6 cell line.

Expression profiling for cell lines H1, BB10 and SiMa analyzed in the undifferentiated state revealed that 1,232 genes were identified as having their expression levels increase by 1.5-fold ($log_2$ 0.58) or more in the H1 and BB10 cell lines as compared to the gene expression levels obtained from the SiMa parental cell line (Table 9). Of these, 764 genes exhibited an increase in expression levels in the H1 and BB10 cell lines by 2-fold ($log_2$ 1.0) or more as compared to the expression level for these genes determined from the SiMa parental cell line; and 228 genes exhibited an increase in expression levels in H1 and BB10 cell lines by 4-fold ($log_2$ 2.0) or more as compared to the expression level for these genes determined from the SiMa parental cell line. With respect to decreased expression, 1,265 genes were identified as having their expression levels decreased by 1.5-fold ($log_2$ 0.58) or more in the H1 and BB10 cell lines as compared to the gene expression levels obtained from the SiMa parental cell line (Table 10). Of these, 648 genes exhibited a decrease in expression levels in the H1 and BB10 cell lines by 2-fold ($log_2$ 1.0) or more as compared to the expression level for these genes determined from the SiMa parental cell line; and 189 genes exhibited a decrease in expression levels in H1 and BB10 cell lines by 4-fold ($log_2$ 2.0) or more as compared to the expression level for these genes determined from the SiMa parental cell line.

Expression profiling for cell lines H1, BB10 and SiMa analyzed in the differentiated state revealed that 756 genes were identified as having their expression levels increase by 1.5-fold ($log_2$ 0.58) or more in the H1 and BB10 cell lines as compared to the gene expression levels obtained from the SiMa parental cell line (Table 11). Of these, 472 genes exhibited an increase in expression levels in the H1 and BB10 cell lines by 2-fold ($log_2$ 1.0) or more as compared to the expression level for these genes determined from the SiMa parental cell line; and 150 genes exhibited an increase in expression levels in H1 and BB10 cell lines by 4-fold ($log_2$ 2.0) or more as compared to the expression level for these genes determined from the SiMa parental cell line. With respect to decreased expression, 912 genes were identified as having their expression levels decreased by 1.5-fold ($log_2$ 0.58) or more in the H1 and BB10 cell lines as compared to the gene expression levels obtained from the SiMa parental cell line (Table 12). Of these, 411 genes exhibited a decrease in expression levels in the H1 and BB10 cell lines by 2-fold ($log_2$ 1.0) or more as compared to the expression level for these genes determined from the SiMa parental cell line; and 108 genes exhibited a decrease in expression levels in H1 and BB10 cell lines by 4-fold ($log_2$ 2.0) or more as compared to the expression level for these genes determined from the SiMa parental cell line.

Example IV

Pathway Analysis of Gene Expression Profiles from Clonal Cell Lines

The following example illustrates how to characterize gene expression profiles from clonal cells from an established clonal cell line that are susceptible to BoNT/A intoxication or have neurotoxin uptake capacity in order to identify biological networks or pathways associated with BoNT/A intoxication.

An Ingenuity Pathway Analysis (IPA) Core Analysis (Ingenuity Systems Inc., Redwood City, Calif.) was performed to characterize the RNA expression phenotype of two independently derived BoNT/A very sensitive single clone cell lines, BB10 and H1, compared to a related but much less BoNT/A sensitive single clone cell line, 2D6. The analysis was done to identify the specific gene expression phenotype of a BoNT/A sensitive cell line. The result can also be used to predict and potentially identify proteins that function to enhance BoNT/A uptake.

An Ingenuity Pathway Analysis (IPA) Core Analysis was performed that identified biologically relevant networks to BoNT/A intoxication based on connectivity among the genes from an IPA library and the genes exhibiting significant changes as determined from the expression profiling discussed above. For this analysis, all genes that exhibited an increased or decrease in expression levels in the H1 and BB10 cell lines by 4-fold ($log_2$ 2.0) or more as compared to the expression level for these genes determined from the 2D6 cell line were used, in conjunction with, selected genes with known or suspected relevance to BoNT/A intoxication, hereafter referred to as the Profile genes. The significance of the association to a given network was measured and ranked by the ratio of the number of Profile genes that mapped to the specific network divided by the total number of genes that map to that network. Fisher's exact test was used to calculate p-scores, which represent the association between the Profile genes and the network, and based on the p-scores the genes from the Profile genes were used to rank the networks. The p-scores were derived from p-values. If there are n genes in the network and f of them are Profile genes, then the p-value is the probability of finding f or more Profile genes in a set of n genes randomly selected from the Global Molecular Network. Since significant p-values are quite low (e.g., $1\times10^{-8}$), a p-score was defined as the component of the p-value; p-score=−log 10 (p-value). The identified networks were overlaid with differentially expressed genes which had more than 1.5-fold differential expression and a p-value≤0.001 either before or after differentiation.

Using IPA Core Analysis the differentially expressed Profile genes were connected to 26 Networks. Nineteen of these included 10 or more Profile genes (Table 13). Among these nineteen networks three overall networks groups, named A, B and C were identified (Table 13). Within the networks in these three groups there were overlapping genes and the expression for more than three genes was increased after differentiation. Group A genes include the FGFR2 receptor which has been shown to function in the BoNT/A intoxication process as a receptor for BoNT/A and are as follows: genes exhibiting a 1.5-fold or more decrease in expression levels in the H1 and BB10 cell lines as compared to their expression in cells from the 2D6 cell line, ANXA2, AQP1, ARHGAP9, CDH10, CDKN2A, CHPT1, CNTN2, ERAP1, and RGS11; genes exhibiting a 1.5-fold or more increase in expression levels in the H1 and BB10 cell lines as compared to their expression in cells from the 2D6 cell line, ADAMTS9, ATAD2, C11ORF82, CDC45L, CNTN1, CNTN4, Cyclin A, Cyclin E, E2F1, E2F2, E2F7, ELOVL7, EME1, FGFR, FGFR2, KIAA1524, MELK, MYBL1, MYBL2, NDC80, NDN, ORC1L, PLS3, PRIMA1, RAD54L, RBL1, RBPMS, RRM2, S1PR3, SCLY, SLCIA3, SPC24, SPC25, ST8SIA4, TFDP1, TFP12, TK1, TMEM35, TTK, TWIST1, TYMS, TYK, and ZWINT.

Group B genes include the EGFR, a receptor which is regulated by NGF, which has been shown to increase BoNT/A uptake in cell culture experiments and are as follows: genes exhibiting a 1.5-fold or more decrease in expression levels in the H1 and BB10 cell lines as compared to their expression in cells from the 2D6 cell line, ABCC8, AELIM3, CAP2, IL17B, MEF2A, NEEBL, PHC, S100A6, SLC1A6, SMAD1, SMAD5, SMAD8, SYT13, and SYTL1; genes exhibiting a 1.5-fold or more increase in expression levels in the H1 and BB10 cell lines as compared to their expression in cells from the 2D6 cell line, AURKB, BIRC5, BRCA1, BRCA2, BRIP1, BUB1B, CD9, DLGAP3, DYNLT3, ENC1, FBLN1, FOXM1, Gβγ, GNAI1, GNG11, GNG12, GPSM2, GUCY1B3, HGF, ITGA6, JNK, KCNJ5, KIF18A, KITLG, MMD, MSN, MYRIP, NEK2, NR3C1, NXPH1, OSBPL3, PKMYT1, PTPRM, RAD51, RAD51AP1, SLC7A2, SLC43A3, SMC6, SNAI2, SNCAIP, SSH2, STK17A, SYNPO2, TOP2A, TPTE, TRAF4, TSPAN, TSPAN4, UBE3, UBE3B, and VAV3.

Group C genes include a number of microtubule motor proteins of the kinesin family that may function in the intracellular trafficking of BoNT/A and are as follows: genes exhibiting a 1.5-fold or more decrease in expression levels in the H1 and BB10 cell lines as compared to their expression in cells from the 2D6 cell line, CSTB, GPCR, GRIM5, KISSR, SCN2A, SLC1A2, and THBS2; genes exhibiting a 1.5-fold or more increase in expression levels in the H1 and BB10 cell lines as compared to their expression in cells from the 2D6 cell line, ALCAM, AURKA, CHEK, CIT, CSRP2, E2F, ECT2, EFNB2, ERK, ESPL1, GNAI, GPR161, HMMR, KIF4A, KIF14, KIF15, KIF22, KIF23, KIFC1, LPAR1, MK167, OIP5, PHLPP, PP1/PP2A, PPP1R3C, PRC1, PTTG1, RACGAP, RB, RGS5, SDC2, and TPX2.

The remaining networks identified did not share common genes between any other network. For Network 3, genes exhibiting a 1.5-fold or more decrease in expression levels in the H1 and BB10 cell lines as compared to their expression in cells from the 2D6 cell line, ADARB1, ADM, PTPPH, and SLCO1A2; genes exhibiting a 1.5-fold or more increase in expression levels in the H1 and BB10 cell lines as compared to their expression in cells from the 2D6 cell line, ASCL1, HES6, MAPK, NMU, PEG3, PTPRK, PRLHR, PTPRK, SGOL2, SPARC, and ZNF217. For Network 6, genes exhibiting a 1.5-fold or more decrease in expression levels in the H1 and BB10 cell lines as compared to their expression in cells from the 2D6 cell line, CNGA3, HIST1H3E and PTGS1; genes exhibiting a 1.5-fold or more increase in expression levels in the H1 and BB10 cell lines as compared to their expression in cells from the 2D6 cell line, ASF1B, BASP1, CHAF1A, NCAPH, PBK, PRAME, SMC2, UHRF1, and VRK1. For Network 9, genes exhibiting a 1.5-fold or more decrease in expression levels in the H1 and BB10 cell lines as compared to their expression in cells from the 2D6 cell line, HIST1H2BD and OSCAR; genes exhibiting a 1.5-fold or more increase in expression levels in the H1 and BB10 cell lines as compared to their expression in cells from the 2D6 cell line, C14ORF106, CEP72, KIF20A, PCNA, PEX13, PFC5, POLQ, SPAG5, SYTL4, TROAP, and WDR51A. For Network 12, genes exhibiting a 1.5-fold or more increase in expression levels in the H1 and BB10 cell lines as compared to their expression in cells from the 2D6 cell line, ANLN, ARHGAP24, ASPM, BUB1, CCDC99, CEP55, CKAP2, DRAM, E2F8, PLXNA2, SLC16A10, UBE2C, UBE2S, and WDHD1. For Network 13, genes exhibiting a 1.5-fold or more decrease in expression levels in the H1 and BB10 cell lines as compared to their expression in cells from the 2D6 cell line, CALY; genes exhibiting a 1.5-fold or more increase in expression levels in the H1 and BB10 cell lines as compared to their expression in cells from the 2D6 cell line, ARHGEF3, CTSL2, DIAPH3, FBP1, KIF2C, KIF11, PFKFB3, and PLK4. For Network 14, genes exhibiting a 1.5-fold or more decrease in expression levels in the H1 and BB10 cell lines as compared to their expression in cells from the 2D6 cell line, COL5A1 and MICAL2; genes exhibiting a 1.5-fold or more increase in expression levels in the H1 and BB10 cell lines as compared to their expression in cells from the 2D6 cell line, FNDC5, HSPC159, MAB21L2, SLITRK5, SYN2, and ZNF367. For Network 15, genes exhibiting a 1.5-fold or more decrease in expression levels in the H1 and BB10 cell lines as compared to their expression in cells from the 2D6 cell line, OLFML2A and SIGIRR; genes exhibiting a 1.5-fold or more increase in expression levels in the H1 and BB10 cell lines as compared to their expression in cells from the 2D6 cell line, EXO1, KCTD12, MYO6, PHEBL1, SHCBP1, TPBG, and TUBB6. For Network 17, genes exhibiting a 1.5-fold or more decrease in expression levels in the H1 and BB10 cell lines as compared to their expression in cells from the 2D6 cell line, HPCAL1 and LPAR5; genes exhibiting a 1.5-fold or more increase in expression levels in the H1 and BB10 cell lines as compared to their expression in cells from the 2D6 cell line, BTG3, GABRA5, TR1P10, and ZNF521. For Network 19, genes exhibiting a 1.5-fold or more decrease in expression levels in the H1 and BB10 cell lines as compared to their expression in cells from the 2D6 cell line, HTR1E and SORCS1; genes exhibiting a 1.5-fold or more increase in expression levels in the H1 and BB10 cell lines as compared to their expression in cells from the 2D6 cell line, BNC2, DPYD, EMILIN2, PPIL5, and TACC3.

TABLE 13

IPA Core Analysis of Profile Genes

| | | | | | Expression Undifferentiated State | | Expression Differentiated State | |
|---|---|---|---|---|---|---|---|---|
| Group | Network | Proteins in Network | pvalue | Profile Gene Number | Decreased | Increased | Decreased | Increased |
| A | 1 | ADAMTS9, ATAD2, CDC45L, CDKN2A, CNTN1, CNTN2, Cyclin A, Cyclin E, DIRAS3, E2F1, E2F2, E2F7, FGFR2, HDAC, | 51 | 30 | CDKN2A, | ADAMTS9, CNTN1, HDAC, NDN, PLS3, S1PR3,TFPI2 | CDKN2A CNTN2, | ADAMTS9, ATAD2, CDC45L, CNTN1, Cyclin A, Cyclin E, E2F1, E2F2, E2F7, FGFR2, MYBL1, |

TABLE 13-continued

IPA Core Analysis of Profile Genes

| Group | Network | Proteins in Network | pvalue | Profile Gene Number | Expression Undifferentiated State Decreased | Expression Undifferentiated State Increased | Expression Differentiated State Decreased | Expression Differentiated State Increased |
|---|---|---|---|---|---|---|---|---|
| | | MYBL1, MYBL2, NDC80, NDN, NFkB, ORC1L, PLS3, RAD54L, RBL1, RRM2, S1PR3, SPC24, SPC25, TFDP1, TFPI2, TK1, TNFRSF10D, TTK, TYMS, TYK, ZWINT | | | | | | MYBL2, NDC80, NDN, ORC1L, PLS3, RAD54L, RBL1, RRM2, S1PR3, SPC24, SPC25, TFDP1, TFPI2, TK1, TTK, TYMS, TYK, ZWINT |
| C | 2 | ALCAM, ANK2, ANK3, AURKA, DOK5, E2F, ERK, ESPL1, GDF15, GFRA2, HMMR, ITGA9, KIF15, KIF22, KISS1R, KPNA, KPNB, LGI1, MAFB, MAP2K1, MAP2K2, MKI67, NRG3, 0IP5, PHKA2, PHLPP, POSTN, PP1/PP2A, PP2A, PPP1R3C, PPP2R2B, PPP2R2C, PTTG1, RAF1, RB, SCN2A, TPX2 | 46 | 28 | ANK2, ANK3, PHKA2, PPP2R2C, SCN2A | ALCAM, DOK5, ERK, GFRA2, PP1/PP2A, PP2A, PPP1R3C, PPP2R2B | KISSR, SCN2A | ALCAM, AURKA, E2F, ERK, ESPL1, HMMR, KIF15, KIF22, MKI67, OIP5, PHLPP, PP1/PP2A, PPP1R3C, PTTG1, RB, TPX2 |
| — | 3 | ADARB1, ADM, AKAP12, ALP, ASCL1, BHLHB2, CRH, DLL1, FRZB, FSH, GRIA2, GRIP2, hCG, HES6, HTATIP2, IL13RA2, MAPK, NMU, PDGF BB, PDLIM3, PEG3, PLAT, PPFIA4, PRLHR, PTPRH, PTPRK, SGOL2, SLCO1A2, SMAD6, SPARC, STC1, TEAD4, TGFB, VEGF, ZNF217 | 46 | 28 | ADARB1, GRIP2, SLCO1A2, | ASCL1, DLL1, FRZB, MAPK, PEG3, PLAT, PRLHR, SMAD6, SPARC, ZNF217 | ADARB1, ADM, PTPPH, SLCO1A2 | ASCL1, HES6, MAPK, NMU, PEG3, PRLHR, PTPRK, SGOL2 SPARC, ZNF217 |
| C | 4 | AKT, ACTN1, ACTN2, ACTN3, ATF5, ATM/ATR, BDKRB2, CHEK1, CHEK2, CIT, CSRP2, CSTB, | 43 | 27 | CSTB, GPCR, GRIM5, SLC1A2, | GNAI, GPR161, LPAR1, RGS5 | CSTB, GPCR, GRIM5, SLC1A2 THBS2 | CIT, CSRP2, ECT2, EFNB2, CHEK, GNAI, GPR161, KIF4A, KIF14, KIF23, |

TABLE 13-continued

IPA Core Analysis of Profile Genes

| Group | Network | Proteins in Network | pvalue | Profile Gene Number | Expression Undifferentiated State Decreased | Expression Undifferentiated State Increased | Expression Differentiated State Decreased | Expression Differentiated State Increased |
|---|---|---|---|---|---|---|---|---|
| | | CTSH, ECT2, EFNB2, ELMO1, GNAI, GABBR2, GPCR, GPR161, GRM5, ICAM2, KIF4A, KIF14, KIF23, KIFC1, LPAR1, MMP, PDGFA PDGFB, PRC1, RAC, RAC2, RACGAP1, RGS5, SDC2, SLC1A2, THBS2 | | | | | | KIFC1, LPAR1 PRC1, RACGAP, RGS5, SDC2, |
| B | 5 | ABLIM3, F-ACTF, G-ACT, CD9, CXCR4, DTNA, ENC1, FNBP1, Gβy, GNAI1, GNG11, GNG12, GPSM2, ITG, ITA5, ITGA6, JNK, KCNJ4, MLC, MSN, MYRIP, NOX, NET1, NRXN1, NXPH1, PI3K, RHO, S100A6, STK17A, SYT13, SYTL1, TRAF4, TSPAN, TSPAN3, TSPAN4, VAV3 | 38 | 25 | SYT13, S100A6 | CD9, CXCR4, ENC1, Gβy, GNAI1, GNG11, GNG12, ITGA6, JNK, MSN, MYRIP, STK17A | AELIM3, S100A6, SYT13, SYTL1 | CD9, ENC1, Gβy, GNAI1, GNG11, GNG12, GPSM2, ITGA6, JNK, KCNJ4, MSN, MYRIP, NXPH1, STK17A, TRAF4, TSPAN, TSPAN4, VAV3 |
| — | 6 | ADCY, ADCY1, API, ASF1B, ATP2B4, BASP1, BCL11B, CAM, CAMK2B, CHAF1A, CNGA3, CYP2E1, DACH1, HIST1H3E, HISH3, HRH3, HSP90, IL1, IL12, INS, INFA, ISG20, KCNN2, LDL, MMP14, NCAPH, PBK, PDGF, PIAS1, PRAME, PTGS1, SEC31A, SMC2, UHRF1, VRK1 | 36 | 24 | CAMK2B | BASP1, HRH3 | CNGA3, HIST1H3E, PTGS1 | ASF1B, BASP1, CHAF1A, NCAPH, PBK, PRAME, SMC2, UHRF1, VRK1 |
| B | 7 | BARD1, BRCA1, BRCA2, BRIP1, BUB1B, CNA, CAP2, CK2, DLGAP5, FAT, GUCY1B3, | 32 | 24 | CAP2, CNA, PHLDA2, PKC(s), CAP2, | NR3C1, SMC6, SNCAIP, TCF7L2 | CAP2, MEF2A, PKC(s), SLC1A6 | BRCA1, BRCA2, BRIP1, BUB1B, DLGAP3, GUCY1B3, NEK2, KITLG, |

TABLE 13-continued

IPA Core Analysis of Profile Genes

| Group | Network | Proteins in Network | pvalue | Profile Gene Number | Expression Undifferentiated State Decreased | Expression Undifferentiated State Increased | Expression Differentiated State Decreased | Expression Differentiated State Increased |
|---|---|---|---|---|---|---|---|---|
| | | HSP70, KITLG, MEF2A, NEK2, NFAT, NR3C1, NF1, PHLDA2, PKC(s), RAD51, RAD51AP1, TOP2, SAMD4A, SLC1A6, SMC6, SNAI2, SNCAIP, STAT5a, STAT5b, TCF7L2, UBE3, UBE3B, UBN, XPO1 | | | | | | NR3C1, RAD51, RAD51AP1, SMC6, SNAI2, SNCAIP, UBE3, UBE3B |
| B | 8 | CBP, AURKB, BIRC5, CACNA1D, CBP/p300, CD3, CREB, CREB5, DBH, EGR1, ERK1, ERK2, FBLN1, FBN1, FOXM1, HGF, INCENP, KCNMA1, LGALS1, MAOA, MEK, NDRG1, NID1, P38 MAPK, PKA, PKMYT1, PRKAC, PRKACB, RAF, RAP1, RAS, RGMA, RSK, SMAD1, SMAD5, SMAD8, SYNPO2, TOP2A | 30 | 21 | KCNMA1, NDRG1, RAS | ERK1, ERK2, MAOA, P38 MAPK, RGMA | NDRG1, SMAD1, SMAD5, SMAD8 | AURKB, BIRC5, ERK1, ERK2, FBLN1, FOXM1, HGF, MAOA, P38 MAPK, PKMYT1, SYNPO2, TOP2A |
| — | 9 | C14ORF106, CDKN1A, CEP72, DHX8, FKBPL, HIST1H2BD HNF4A, KIF20A, KRT18, MTHFS, OSCAR, PCGF5, PCNA, PELO, PEX13, PFC5, POLD4, POLK, POLL, POLM, POLQ, POLS, R3HDM1, RASL12, RFC5, SLC33A1, SPAG5, STAT4, SULT1A1, SULT1C2, SYTL4, TCEAL3, TROAP, VEZT, WDR51A, ZBTB16 | 19 | 15 | — | PCGF5 | HIST1H2BD, OSCAR | C14ORF106, CEP72, KIF20A, PCNA, PEX13, PFC5, POLQ, SPAG5, SYTL4, TROAP, WDR51A |

TABLE 13-continued

IPA Core Analysis of Profile Genes

| Group | Network | Proteins in Network | pvalue | Profile Gene Number | Expression Undifferentiated State Decreased | Expression Undifferentiated State Increased | Expression Differentiated State Decreased | Expression Differentiated State Increased |
|---|---|---|---|---|---|---|---|---|
| A | 10 | ARHGAP9, CDH10, CDS1, CDS2, CHPT1, CNTN4, ELOVL7, EME1, FGFR, GAS6, HAND1, IFI202B, ISL1, KIAA1524, KRT74, MIRN31, MUS81, MYF6, MYOD1, NFYB, OTX1, PRIMAL, QKI, RBM9, RBPMS, RORA, SHOX2, SLC39A8, SOX2, SOX15, ST8SIA4, STAT3, TWIST1, VPS39, ZFHX3 | 18 | 15 | CHPT1 | CNTN4, ELOVL7, HAND1, ODS2, SOX2, TWIST1 | ARHGAP9, CDH10 | CNTN4, ELOVL7, EME1, FGFR, KIAA1524, PRIMA1, RBPMS, ST8SIA4, TWIST1 |
| B | 11 | ALDH3A2, B3GALT2, BAMBI, CNN2, CTNNAL1, CTNNB1, CTSC, CUGBP2, DYNLT3, IL13, KIF18A, LIN7C, MFI2, MPP5, MRC2, NDST1, PDGF-CC, PHLDA2, PLAU, PPM1J, PPP1CA, PTPN14, PTPRM, SLC16A3, SLC26A2, SLC43A3, SLC7A2, SSH2, STK17A, TAXI BP3, TCF7L1, TGFB1, TPTE, TSPAN8 | 18 | 15 | PHLDA2 | BAMBI, CUGBP2, DYNLT3, SLC7A2, SLC43A3, STK17A, TPTE | — | DYNLT3, KIF18A, PTPRM, SLC7A2, SLC43A3, SSH2, STK17A, TPTE |
| — | 12 | AHR, AHRR, ANLN, APH1B, ARHGAP24, ASPM, BUB1, CCDC99, CEP55, CKAP2, DRAM, E2F8, HS3ST1, JPH1, MIRN124-1, NMT2, PDZRN3, PLXNA2, PMM1, PPP1R13L, PVRL3, RFFL, S100A2, SLC16A10, TP53, UBE2A, | 17 | 15 | HS3ST1 | PDZRN3, PVRL3 | — | ANLN, ARHGAP24, ASPM, BUB1, CCDC99, CEP55, CKAP2, DRAM, E2F8, PLXNA2, SLC16A10, UBE2C, UBE2S, WDHD1 |

TABLE 13-continued

IPA Core Analysis of Profile Genes

| Group | Network | Proteins in Network | pvalue | Profile Gene Number | Expression Undifferentiated State Decreased | Expression Undifferentiated State Increased | Expression Differentiated State Decreased | Expression Differentiated State Increased |
|---|---|---|---|---|---|---|---|---|
| | | UBE2C, UBE2D2, UBE2S, UBE2V1, UBE2V2, UBL3, VPS37C, WDHD1 | | | | | | |
| — | 13 | ARHGEF3, CALY, CSH2, CTSL2, DIAPH3, ECEL1, FBP1, FFAR2, FRAT2, GSK3B, HSD17B4, IL6 IL19, KIF11, KIF2C, KNG1, LARGE, LEFTY2, LGR5, LIF, LPAR3, MPZ, MSLN, ORM2, PFKFB3, PLK4, PMP22, PRPH, PRSS8, PTGER3, SCN7A, SCNN1B, SLC4A11, TAL1 | 17 | 14 | CALY | ARHGEF3, GSK3B, RMP22 | CALY | ARHGEF3, CTSL2, DIAPH3, FBP1, KIF2C, KIF11, PFKFB3, PLK4 |
| — | 14 | AGT, AGTRAP, Beta ARK, CADPS, CD160, COL5A1, CPNE8, FNDC5, HSPC159, INA, ITGA7, LIMA1, LPP, MAB21L2, MAPK1, MERTK, MICAL2, MIRN294, MIRN185, MIRN352, NTN1, PLCG1, PLCG2, PTGFR, RASGEF1B, RBM4B, RSU1, SKAP1, SLITRK5, SPRED1, ST8SIA2, SYN2, TGFB3, TNS1, ZNF367 | 15 | 13 | CPNE3 | CADPS, FNDC5, MAB21L2, SLITRK5, ST8SIA2 | COL5A1, MICAL2 | FNDC5, HSPC159, MAB21L2, SLITRK5, SYN2, ZNF367 |
| — | 15 | ACT1, BAG5, CPVL, EXO1, GIPC1, GJC1, GPR37, HSPA5, HSPA1A, HSPBP1, IkBKB, KCTD12, MAP3K3, MAP3K14, MEKK3/NIK, | 15 | 13 | — | KCTD12, TPBG | OLFML2A, SIGIRR | EXO1, KCTD12, MYO6, PHEBL1, SHCBP1, TPBG, TUBB6 |

TABLE 13-continued

IPA Core Analysis of Profile Genes

| Group | Network | Proteins in Network | pvalue | Profile Gene Number | Expression Undifferentiated State Decreased | Expression Undifferentiated State Increased | Expression Differentiated State Decreased | Expression Differentiated State Increased |
|---|---|---|---|---|---|---|---|---|
| | | MIRN30B, MYO6, OLFML2A, PELI3, RHEBL1, RNF126, RPL10A, RPN1, SEC16A, SHC1, SHCBP1, SIGIRR, TJP3, TPBG, TRAF6, TRAF2-TRAF5, TRAF2-TRAF5, TRAF6, TUBB6, TUBB2B | | | | | | |
| B | 16 | ABCC8, BACE2, CLASP1, COLEC12, CXCR7, DACT1, ENTPD5, FGD6, FMO1, GSTT1, IL17B, KRT34, KYNU, LAMP3, LMCD1, MIRN101B, MMD, NEBL, NFRKB, OSBPL3, PCDH8, PEMT, RASAL2, SAMD4A, ST3GAL3, SYNGR3, SYNPO2, TNF, TNNC1, TXN2, YWHAG, ZNF267, ZYX | 15 | 13 | IL17B | DACT1, PCDH8 | ABCC8, IL17B, NEEBL | MMD, OSBPL3, SYNPO2 |
| — | 17 | ARPP-19, BTG3, CBFA2T2, CBLN1, CNGA2, EBF1, EGF, EGFR, GABA, GABRA5, GABRB3, GABRD, GABRR1, HDAC9, HPCAL1, HTT, IDS, INSL3, LPAR5, OPRL1, PCDH9, PDE10A, PDE11A, PDE1A, PDE1B, PDE2A, PDE4C, PDE6H, PPAP2B, PPP1R1B, ROBO2, SH3D2C1, | 14 | 13 | HPCAL1 | PPAP2B | HPCAL1, LPAR5 | BTG3, GABRA5, TRIP10, ZNF521 |

TABLE 13-continued

IPA Core Analysis of Profile Genes

| Group | Network | Proteins in Network | pvalue | Profile Gene Number | Expression Undifferentiated State Decreased | Expression Undifferentiated State Increased | Expression Differentiated State Decreased | Expression Differentiated State Increased |
|---|---|---|---|---|---|---|---|---|
| | | TRIP10, ZNF521 | | | | | | |
| A | 18 | ANXA2, AQP1, C11ORF82, CCNI, CDKN2A, DEFB104A, DEFB4, EGLN3, ERAP1, FAM129A, GNAO1, IFNG, IL1B, IL1F7, INCA, LOC729687 MELK, MINA, MIRN210, MPA2L, MYC, NNAT, PDE5A, RGS11, RNASE7, RT1-B, SCLY, SCUBE1, SLC11A1, SLC14A1, SLC1A3, ST18, TSH, TMEM35, TREM3 | 14 | 12 | AQP1, CDKN2A | MINA, PDE5A | ANXA2, CDKN2A, ERAP1, RGS11 | C11ORF82, MELK, MINA, PDE5A SCLY, SLC1A3, TMEM35 |
| — | 19 | BIRC8, BNC2, CASP5, CASP10, CASP14, CASP, CBLN2, DEDD2, DNASE1L1, DPYD, DSG3, EIF4E, EMILIN2, HTR1D, HTR1E, HTR1F, HTR3A, IFT57, KHDC1, MIRN20A, MTCH1, NGFR, PLXNA4, PPIL5, RB1 , RP11-257K9.7, SEMA6D, SERPINA3K, SORCS1, STK25, SYT5, TACC3, TERT | 10 | 10 | — | EMILIN2, PLXNA4 | HTR1E, SORCS1 | BNC2, DPYD, EMILIN2, PPIL5, TACC3 |
| — | 20 | EGFL7, GFI1B | 2 | 1 | — | — | — | — |
| — | 21 | AGRN, PRSS12 | 2 | 1 | — | — | — | — |
| — | 22 | KCNB1, KCNG3 | 2 | 1 | — | — | — | — |
| — | 23 | NUP37, NUP43 | 2 | 1 | — | — | — | — |
| — | 24 | HS6ST1, HS6ST2 | 2 | 1 | — | — | — | — |
| — | 25 | FUCA1, FUCA2 | 2 | 1 | — | — | — | — |
| — | 26 | IQGAP, IQGAP3, MIRN339 | 2 | 1 | — | — | — | — |

Example V

Pathway Analysis of Gene Expression Profiles from Clonal Cell Lines

The following example illustrates how to characterize gene expression profiles from clonal cells from an established clonal cell line that are susceptible to BoNT/A intoxication or have neurotoxin uptake capacity in order to identify biological networks or pathways associated with BoNT/A intoxication.

Computer analysis was performed to characterize the RNA expression phenotype of two independently derived single clone cell lines, BB10 and H1, very sensitive to BoNT/A activity and a single clone cell line, 2D6, that was less sensitive BoNT/A activity. The results are useful in identifying clonal cell lines selected from the SiMa parental cell line that are useful to practice the methods disclosed in the present specification.

To identify the specific gene expression phenotype associated with a BoNT/A sensitive cell line, the data was analyzed using JMP Genomic (SAS Institute Inc., Cary, N.C.). To perform a JMP Genomics analysis, the RNA expression data was imported to JMP Genomics by creating two SAS files, designated "data" and "Experiment design." A basic expression workflow was performed, including a variance analysis and one-way analysis of variance (one-way ANOVA) to identify differences in mean expression values. The variance analysis was used to identify differences between the cell lines and the differentiation state of each cell line (differentiated or non-differentiated). The expression values of all four cell lines were compared pair wise, independent of differentiation and genes that were 4-fold over-expressed in the H1 cell line as compared to the 2D6 cell line, in the BB10 cell line as compared to the 2D6 cell line, and in SiMa parental cell line (PA) compared to the 2D6 cell line. The variance analysis treats all factors in the study as random effects, to find out what their contribution is to the proportion of variance explained (total variance=100%). About half of the variance, 46.9% was assigned to differences among the different cell types, while 26% was assigned to differences before and after differentiation. Only 4.6% of the variance was assigned to differences among differentiated or non-differentiated cells types, meaning that the genes that were differentially expressed after differentiation were similar for all cell types examined, suggesting that the difference in BoNT/A sensitivity among the cell lines is independent of differentiation state. As such, the focus was placed on genes that are different among the different cells types irrespective of differentiation.

Based on the results from the variance analysis, the expression values of all cell lines were compared pair wise, independent of differentiation (FIG. 2). Only gene probes that were 4-fold over-expressed in the H1 cell line as compared to the 2D6 cell line, and in the BB10 cell line as compared to the 2D6 cell line are shown. The gene probes were plotted as expression value ($Log_2$) on the x-axis and p-value ($-log_{10}$(p-value)) on the y-axis. The red dashed line marks the 95% confidence interval. The genes probes that were 4-fold over-expressed in the H1 cell line as compared to the 2D6 cell line (FIG. 2A), and the BB10 cell line as compared to the 2D6 cell line (FIG. 2B), were also to a large extend among the genes that were over-expressed in the BB10 cell line as compared to the SiMa parental cell line (PA, FIG. 2C), in the H1 cell line as compared to the SiMa parental cell line (FIG. 2D), and in the SiMa parental cell line as compared to the 2D6 cell line (FIG. 2E). These data suggest that BoNT/A sensitivity was related to a gradual increase in expression of these genes. Based on this finding, the number of gene probes was further narrowed down to 119 by including only gene probes that were also over-expressed in the SiMa parental cell line compared to the 2D6 cell line, rationalizing that gene probes that were differential expressed across one more cell line would be even more likely to be important for BoNT/A sensitivity. As such, the JMP Genomic analysis resulted in the identification of 119 gene probes, designated the JMP probe set.

The JMP probe set was exported to Ingenuity Pathway Analysis (IPA) Core Analysis (Ingenuity Systems Inc., Redwood City, Calif.) to further characterize the JMP probe set. Using this analysis, biologically relevant networks to BoNT/A intoxication were identified based on connectivity among the genes from an IPA library and the gene probes contained in the JMP probe set. The significance of the association to a given network was measured and ranked by the ratio of the number of gene probes from the JMP probe set that mapped to the specific network divided by the total number of genes that map to that network. Fisher's exact test was used to calculate p-scores, and based on the p-scores the genes from the JMP probe set were used to rank the networks. The p-scores were derived from p-values. If there are n genes in the network and f of them are gene probes from the JMP probe set, then the p-value is the probability of finding f or more gene probes from the JMP probe set in a set of n genes randomly selected from the Global Molecular Network. Since significant p-values are quite low (e.g., $1\times10^{-8}$), a p-score was defined as the component of the p-value; p-score=−log 10 (p-value). The identified networks were overlaid with differentially expressed genes which had more than 1.5-fold differential expression and a p-value≤0.001 either before or after differentiation. Using IPA Core Analysis, 111 of the 119 gene probes from the JMP probe set were mapped to networks. The eight unmapped probes most likely represent either a probe with an outdated nomenclature or one representing a gene without a known gene product. The 111 gene probes corresponded to 79 genes that were greater than 4.0-fold differentially expressed in the H1 and BB10 cell lines when compared to the 2D6 cell line and that were also greater than 4.0-fold differentially expressed in the SiMa parental cell lines when compared to the 2D6 cell line, when the p-value cut off was set to 0.05 (Table 14).

TABLE 14

Genes Identified using IPA Core Analysis

| Gene Name | Gene Symbol | Probe ID. No. | Location | Type | Log Ratio |
|---|---|---|---|---|---|
| Achaete-scute complex homolog 1 | ASCL1 | 209985_s_at | Nucleus | Transcription regular | 4.469 |
| Achaete-scute complex homolog 1 | ASCL1 | 209988_s_at | Nucleus | Transcription regulator | 2.774 |
| Achaete-scute complex homolog 1 | ASCL1 | 213768_s_at | Nucleus | Transcription regulator | 2.955 |

TABLE 14-continued

Genes Identified using IPA Core Analysis

| Gene Name | Gene Symbol | Probe ID. No. | Location | Type | Log Ratio |
|---|---|---|---|---|---|
| Acyl-CoA thioesterase 9 | ACOT9 | 221641_s_at | Cytoplasm | Enzyme | 2.251 |
| ADAM metallopeptidase with thrombospondin type 1 motif, 9 | ADAMTS9 | 226814_ at | Extracellular Space | Peptidase | 4.034 |
| Ankyrin 2, neuronal | ANK2 | 216195_at | Plasma Membrane | Other | −2.673 |
| Ankyrin 2, neuronal | ANK2 | 232606_at | Plasma Membrane | Other | −2.621 |
| Blood vessel epicardial substance | BVES | 228783_at | Plasma Membrane | Other | 3.174 |
| Brain abundant, membrane attached signal protein 1 | BASP1 | 202391_at | Plasma Membrane | Other | 4.549 |
| BRCA1 associated RING domain 1 | BARD1 | 205345_at | Nucleus | Transcription regulator | 3.44 |
| Calsyntenin 2 | CLSTN2 | 219414_at | Plasma Membrane | Transporter | 2.024 |
| cAMP responsive element binding protein 5 | CREB5 | 232555_at | Nucleus | Transcription | −2.67 |
| Cathepsin L2 | CTSL2 | 210074_at | Cytoplasm | Peptidase | 2.119 |
| CD9 molecule | CD9 | 201005_at | Plasma Membrane | Other | 2.887 |
| Cell division cycle associated 7-like | CDCA7L | 225081_s_at | Nucleus | Other | 3.737 |
| Centromere protein L | CENPL | 1554271_a_at | Unknown | Other | 2.582 |
| Chromosome 11 open reading frame 75 | C11ORF75 | 219806_s_at | Unknown | Other | 3.914 |
| Chromosome 3 open reading frame 70 | C3ORF70 | 242447_at | Unknown | Other | 2.705 |
| Coiled-coil domain containing 109B | CCDC109B | 218802_at | Unknown | Other | 2.881 |
| Contactin 1 | CNTN1 | 211203_s_at | Plasma Membrane | Enzyme | 3.684 |
| Contactin 1 | CNTN1 | 227202_at | Plasma Membrane | Enzyme | 3.184 |
| Contactin 1 | CNTN1 | 227209_at | Plasma Membrane | Enzyme | 3.188 |
| Copine VIII | CPNE8 | 228365_at | Unknown | Other | −3.355 |
| Copine VIII | CPNE8 | 241706_at | Unknown | Other | −2.736 |
| CUG triplet repeat, RNA binding protein 2 | CUGBP2 | 202157_s_at | Nucleus | Other | 3.588 |
| Cyclin-dependent kinase 2 | CDK2 | 204252_at | Nucleus | Kinase | 2.744 |
| Cysteine and glycine-rich protein 2 | CSRP2 | 207030_s_at | Nucleus | Other | 2.487 |
| Cysteine and glycine-rich protein 2 | CSRP2 | 211126_s_at | Nucleus | Other | 2.109 |
| DEP domain containing 1 | DEPDC1 | 220295_x_at | Unknown | Other | 2.795 |
| Diaphanous homolog 3 | DIAPH3 | 232596_at | Cytoplasm | Enzyme | 2.434 |
| Dihydropyrimidine dehydrogenase | DPYD | 204646 _at | Cytoplasm | Enzyme | 4.248 |
| Docking protein 5 | DOK5 | 214844_s_at | Plasma Membrane | Other | 4.56 |
| Dynein, light chain, Tctex-type 3 | DYNLT3 | 203303_at | Cytoplasm | Other | 3.449 |
| Elastin microfibril interfacer 2 | EMILIN2 | 224374_s_at | Extracellular Space | Other | 2.603 |
| Ets variant 1 | ETV1 | 206501_x_at | Nucleus | Transcription regulator | 2.578 |
| Ets variant 1 | ETV1 | 217053_x_at | Nucleus | Transcription regulator | 2.499 |
| Ets variant 1 | ETV1 | 217061_s_at | Nucleus | Transcription regulator | 2.557 |
| Family with sequence similarity 101, member B | FAM101B | 226876_at | Unknown | Other | 2.399 |
| Fibroblast growth factor receptor 2 | FGFR2 | 203638_s_at | Plasma Membrane | Kinase | 2.306 |
| Fibroblast growth factor receptor 2 | FGFR2 | 203639_s_at | Plasma Membrane | Kinase | 3.239 |
| Fibroblast growth factor receptor 2 | FGFR2 | 208228_s_at | Plasma Membrane | Kinase | 2.151 |
| Fibronectin type III domain containing 5 | FNDC5 | 226096_at | Unknown | Other | 2.054 |
| Fibulin 1 | FBLN1 | 201787_at | Extracellular Space | Other | 2.801 |
| Fibulin 1 | FBLN1 | 202994_s_at | Extracellular Space | Other | 2.378 |
| Fibulin 1 | FBLN1 | 202995_s_at | Extracellular Space | Other | 3.733 |

TABLE 14-continued

Genes Identified using IPA Core Analysis

| Gene Name | Gene Symbol | Probe ID. No. | Location | Type | Log Ratio |
|---|---|---|---|---|---|
| G protein-coupled receptor 177 | GPR177 | 221958_s_at | Unknown | Other | 2.389 |
| G protein-coupled receptor 177 | GPR177 | 228950_s_at | Unknown | Other | 2.622 |
| G-2 and S-phase expressed 1 | GTSE1 | 204317_at | Cytoplasm | Other | 3.334 |
| Gametocyte specific factor 1 | GTSF1 | 227711_at | Unknown | Other | 6.407 |
| Guanine nucleotide binding protein (G protein), alpha inhibiting activity polypeptide 1 | GNAI1 | 227692_at | Plasma Membrane | Enzyme | 3.123 |
| Guanine nucleotide binding protein (G protein), beta polypeptide 4 | GNB4 | 225710_at | Plasma Membrane | Enzyme | 6.066 |
| Guanine nucleotide binding protein (G protein), gamma 11 | GNG11 | 204115_at | Plasma Membrane | Enzyme | 4.251 |
| Guanine nucleotide binding protein (G protein), gamma 12 | GNG12 | 212294_at | Plasma Membrane | Enzyme | 2.315 |
| Guanine nucleotide binding protein (G protein), gamma 12 | GNG12 | 222834_s_at | Plasma Membrane | Enzyme | 3.403 |
| Hepatocyte growth factor (hepapoietin A) | HGF | 209960_at | Extracellular Space | Growth factor | 2.939 |
| Hypothetical protein LOC100289109 | LOC100289109 | 216189_at | Unknown | Other | −3.256 |
| Hypothetical protein LOC144571 | LOC144571 | 1564139_at | Unknown | Other | −2.394 |
| Inositol 1,4,5-triphosphate receptor interacting protein | ITPRIP | 225582_at | Unknown | Other | 3.522 |
| Interleukin 17B | IL17B | 220273_at | Extracellular Space | Cytokine | −4.735 |
| KDEL (Lys-Asp-Glu-Leu) containing 2 | KDELC2 | 225128_at | Unknown | Other | 3.003 |
| KIAA0125 | KIAA0125 | 206478_at | Unknown | Other | −8.436 |
| KIT ligand | KITLG | 226534_at | Extracellular Space | Growth factor | 2.59 |
| LY6/PLAUR domain containing 6 | LYPD6 | 227764_at | Extracellular Space | Other | 2.64 |
| Lysophosphatidic acid receptor 1 | LPAR1 | 204036_at | Plasma Membrane | Receptor | 3.151 |
| MAB-21-like 2 | MAB21L2 | 210303_at | Unknown | Other | 3.817 |
| Minichromosome maintenance complex component 10 | MCM10 | 223570_at | Nucleus | Other | 2.249 |
| Moesin | MSN | 200600_at | Plasma Membrane | Other | 5.842 |
| Monoamine oxidase A | MAOA | 204388_s_at | Cytoplasm | Enzyme | 4.029 |
| Monoamine oxidase A | MAOA | 204389_at | Cytoplasm | Enzyme | 3.355 |
| Monoamine oxidase A | MAOA | 212741_at | Cytoplasm | Enzyme | 4.157 |
| MYC induced nuclear antigen | MINA | 213188_s_at | Nucleus | Other | 4.019 |
| MYC induced nuclear antigen | MINA | 213189_at | Nucleus | Other | 4.636 |
| Myosin VI | MYO6 | 203216_s_at | Cytoplasm | Other | 2.406 |
| Myosin VITA and Rab interacting protein | MYRIP | 214156_at | Cytoplasm | Other | 2.805 |
| Neuronal PAS domain protein 4 | NPAS4 | 1554299_at | Nucleus | Transcription regulator | −2.515 |
| Paternally expressed 3 | PEG3 | 209242_at | Nucleus | Kinase | 5.896 |
| Paternally expressed 3 | PEG3 | 209243_s_at | Nucleus | Kinase | 4.556 |
| Phosphoprotein associated with glycosphingolipid microdomains 1 | PAG1 | 225626_at | Plasma Membrane | Other | 2.193 |
| Poliovirus receptor-related 3 | PVRL3 | 213325_at | Plasma Membrane | Other | 2.325 |
| Polo-like kinase 2 | PLK2 | 201939_at | Nucleus | Kinase | 4.93 |
| Polymerase (DNA directed), alpha 2 (70 kD subunit) | POLA2 | 204441_s_at | Nucleus | Enzyme | 2.198 |
| Prolactin releasing hormone receptor | PRLHR | 231805_at | Plasma Membrane | Receptor | 3.19 |
| Prostaglandin reductase 1 | PTGR1 | 228824_s_at | Cytoplasm | Enzyme | 2.398 |
| Prostaglandin reductase 1 | PTGR1 | 231897_at | Cytoplasm | Enzyme | 2.33 |
| Protease, serine, 12 (neurotrypsin, motopsin) | PRSS12 | 205515_at | Extracellular Space | Peptidase | 5.146 |
| Protein phosphatase 1, regulatory (inhibitor) subunit 3C | PPP1R3C | 204284_at | Cytoplasm | Phosphatase | 2.827 |
| Protein tyrosine phosphatase, receptor type, K | PTPRK | 203038_at | Plasma Membrane | Phosphatase | 3.451 |
| RAB32, member RAS oncogene family | RAB32 | 204214_s_at | Cytoplasm | Other | 2.192 |
| RELT-like 1 | RELL1 | 226430_at | Unknown | Other | 2.88 |
| Rho GTPase activating protein 24 | ARHGAP24 | 223422_s_at | Cytoplasm | Other | 3.043 |
| Rho guanine nucleotide exchange factor (GEF) 3 | ARHGEF3 | 218501_at | Cytoplasm | Other | 2.473 |

TABLE 14-continued

Genes Identified using IPA Core Analysis

| Gene Name | Gene Symbol | Probe ID. No. | Location | Type | Log Ratio |
|---|---|---|---|---|---|
| Ring finger protein 182 | RNF182 | 230720_at | Unknown | Other | 4.746 |
| RNA binding protein with multiple splicing | RBPMS | 209487_at | Unknown | Other | 2.329 |
| RNA binding protein with multiple splicing | RBPMS | 209488_s_at | Unknown | Other | 3.292 |
| Secreted protein, acidic, cysteine-rich (osteonectin) | SPARC | 200665_s_at | Extracellular Space | Other | 4.919 |
| Secreted protein, acidic, cysteine-rich (osteonectin) | SPARC | 212667 _at | Extracellular Space | Other | 4.58 |
| Shugoshin-like 2 | SGOL2 | 230165_at | Nucleus | Other | 3.108 |
| Similar to hCG2031213 | LOC728052 | 1558795_at | Unknown | Other | 3.402 |
| Solute carrier family 1 (glial high affinity glutamate transporter), member 2 | SLC1A2 | 225491_at | Plasma Membrane | Transporter | −4.354 |
| Solute carrier family 43, member 3 | SLC43A3 | 210692_s_at | Extracellular Space | Other | 3.126 |
| Solute carrier family 43, member 3 | SLC43A3 | 213113_s_at | Extracellular Space | Other | 2.804 |
| Solute carrier family 44, member 5 | SLC44A5 | 1569112_at | Unknown | Other | 3.923 |
| Solute carrier family 44, member 5 | SLC44A5 | 235763_at | Unknown | Other | 4.439 |
| Solute carrier family 7 (cationic amino acid transporter, y + system), member 2 | SLC7A2 | 225516_at | Plasma Membrane | Transporter | 3.23 |
| Sortilin-related VPS10 domain containing receptor 1 | SORCS1 | 1556891_at | Plasma Membrane | Transporter | −2.424 |
| SPC25, NDC80 kinetochore complex component, homolog | SPC25 | 209891_at | Unknown | Other | 2.634 |
| ST8 alpha-N-acetyl-neuraminide alpha-2,8-sialyltransferase 4 | ST8SIA4 | 230836_at | Cytoplasm | Enzyme | 2.705 |
| Structural maintenance of chromosomes 2 | SMC2 | 204240_s_at | Nucleus | Transporter | 2.442 |
| Structural maintenance of chromosomes 6 | SMC6 | 218781_at | Nucleus | Other | 3.327 |
| Structural maintenance of chromosomes 6 | SMC6 | 236535_at | Nucleus | Other | 3.44 |
| Syndecan 2 | SDC2 | 212154_at | Plasma Membrane | Other | 2.367 |
| Syndecan 2 | SDC2 | 212158_at | Plasma Membrane | Other | 2.098 |
| Thrombospondin 2 | THBS2 | 203083_at | Extracellular Space | Other | −2.81 |
| Thyroid hormone receptor interactor 10 | TRIP10 | 202734_at | Cytoplasm | Other | 2.663 |
| Tissue factor pathway inhibitor 2 | TFPI2 | 209278_s_at | Extracellular Space | Other | 4.666 |
| Transcription factor 7-like 1 (T-cell specific, HMG-box) | TCF7L1 | 221016_s_at | Nucleus | Transcription regulator | 2.835 |
| Transmembrane phosphatase with tensin homology | TPTE | 220205_at | Plasma Membrane | Phosphatase | 6.04 |
| Transmembrane protein 178 | TMEM178 | 229302_at | Unknown | Other | 3.194 |
| Transmembrane protein 35 | TMEM35 | 219685_at | Unknown | Other | 2.879 |
| Tumor necrosis factor, alpha-induced protein 8 | TNFAIP8 | 210260_s_at | Cytoplasm | Other | 2.389 |
| Twist homolog 1 | TWIST1 | 213943_at | Nucleus | Transcription regulator | 2.573 |
| Zinc finger protein 521 | ZNF521 | 226676_at | Nucleus | Other | 2.382 |
| Zinc finger protein 521 | ZNF521 | 226677_at | Nucleus | Other | 2.943 |
| Zinc finger protein 814 | ZNF814 | 1556204_a_at | Unknown | Other | −2.505 |

The log ratio represent $\log_2$ values where 0.585 is $\log_2(1.5)$ which is a 1.5-fold difference, 1 is $\log_2(2)$ which is a 2-fold difference, 1.584 is $\log_2(3)$ which is a 3-fold difference, 2 is $\log_2(4)$ which is a 4-fold difference, 2.321 is $\log_2(5)$ which is a 5-fold difference, 2.584 is $\log_2(6)$ which is a 6-fold difference, 2.807 is $\log_2(7)$ which is a 7-fold difference, 3 is $\log_2(8)$ which is a 8-fold difference, 3.169 is $\log_2(9)$ which is a 9-fold difference, and 3.321 is $\log_2(10)$ which is a 10-fold difference.

Using IPA Core Analysis, 73 of the 79 genes were mapped to 5 different protein networks (Table 15). Based on overlapping gene mapping, 73 of the 79 genes that were up-regulated could be associated with two major protein network groups, named A and B (Table 15). Networks 1, 2 and 5 belong to Group A, and Networks 3 and 4 belong to Group B. Similarly, all down-regulated genes were all associated with one network, named C (Table 15).

Group A genes include the FGFR2 receptor which has been shown to function in the BoNT/A intoxication process as a receptor for BoNT/A and are as follows: genes exhibiting a 1.5-fold or more increase in expression levels in the H1 and BB10 cell lines as compared to their expression in cells from the 2D6 cell line, ADAMTS9, ARHGAP24, ARHGEF3, ASCL1, BARD1, CD9, CDK2, CSRP2, CTSL2, DIAPH3, DOK5, DYNLT3, EMILIN2, ETV1, FBLN1, FGFR2, GNAI1, GNB4, GNG11, GNG12, HGF, KITLG, LPAR1, MCM10, MSN, PAG1, PEG3, PLK2, POLA2, PPP1R3C, PTPRK, RAB32, SDC2, SLC43A3, SLC7A2, SMC6, SPARC, SPC25, ST8SIA4, TCF7L1, TFPI2, TMEM35, TNFAIP8, TPTE, TRIP10, and TWIST1.

Group B genes are as follows: genes exhibiting a 1.5-fold or more increase in expression levels in the H1 and BB10 cell lines as compared to their expression in cells from the 2D6 cell line, ACOT9, BASP1, C11ORF75, CCDC109B, CDCA7L, CLSTN2, CNTN1, CUGBP2, DEPDC1, DPYD, FAM101B, FNDC5, GTSE1, MAOA, MINA, MYO6, MYRIP, PLK2, PRLHR, PVRL3, RBPMS, SGOL2, SMC2, TFP12, TMEM178, and ZNF521.

Group C genes are as follows: genes exhibiting a 1.5-fold or more decrease in expression levels in the H1 and BB10 cell lines as compared to their expression in cells from the 2D6 cell line, ANK2, CPNE8, CREB5, IL17B, KIAA0125, LOC100289109, LOC144571, NPAS4, SLC1A2, SORCS1, THBS2, and/or ZNF814.

The remaining networks identified did not share common genes between any other network. Individually, however, genes exhibiting a 1.5-fold or more increase in expression levels in the H1 and BB10 cell lines as compared to their expression in cells from the 2D6 cell line were as follows: C3ORF70 (Network 6), MAB21L2 (Network 7), PRSS12 (Network 8), CENPL (Network 9), GPR177 (Network 10), and PTGR1 (Network 11).

TABLE 15

IPA Core Analysis of Genes

| Network | Group | Proteins in Network | pvalue | JMP Gene Number | Expression Profile Increased | Expression Profile Decreased |
|---|---|---|---|---|---|---|
| 1 | A | ADAMTS9, AKT, ASCL1, CDK2, CSRP2, CTSL2, DOK5, E2F, FBLN1, FSH, GNAI1, GNG11, hCG, HGF, KITLG, LPAR1, MAPK, MCM10, MEK, MSN, NF$_{K}$B, P38, MAPK, PAG1, PDGF BB, PEG3, PLK2, RAC, RAS, SDC2, SPARC, TFPI2, TGFβ, TNFAIP8, TRIP10, VEGF | 48 | 22 | ADAMTS9, ASCL1, CDK2, CSRP2, CTSL2, DOK5, FBLN1, GNAI1, GNG11, HGF, KITLG, LPAR1, MCM10, MSN, PAG1, PEG3, PLK2, SDC2, SPARC, TFPI2, TNFAIP8, TRIP10 | — |
| 2 | A | CASP3, Caspase 3/7, CCL6, DIAPH3, DYNLT3, EMILIN2, EPM2A, ETV1, EYA2, FAM3B, FASTK, GNAI1, GNB4, GNG10, GNG11, GNG12, GSTM2, HK1' IGFBP3, IL13, PLCE1, POLA2, PPP1 R3C, PTPRK, PTPRZ1, RAB32, SLC43A3, SLC7A2, SRC, ST8SIA4, TNF, TPTE, TWIST1 | 35 | 17 | DIAPH3, DYNLT3, EMILIN2, ETV1, GNAI1, GNB4, GNG11, GNG12, POLA2, PPP1R3C, PTPRK, RAB32, SLC43A3, SLC7A2, ST8SIA4, TPTE, TWIST1 | — |
| 3 | B | ACOT9, AR, ATXN7, BASP1, CCNE2, CCNK, CLSTN2, CNTN1, CUGBP2, DGKA, FNDC5, GTSE1, IL4, MAOA, MSH2, NOVA1, NF1, PICK1, PLK2, PNRC1, POM121, PRLHR, PTP4A1, PTP4A2, PVRL1, PVRL3, PVRL4, RBPMS, SERPINB5, SMARCA4, SPN, TFP12, TP53, ZNF521 | 26 | 14 | ACOT9, BASP1, CLSTN2, CNTN1, CUGBP2, FNDC5, GTSE1, MAOA, PLK2, PRLHR, PVRL3, RBPMS, TFP12, ZNF521 | — |
| 4 | B | ARHGAP17, AXL, C11ORF75, CAPN6, CCDC109B, CDCA7L, DEPDC1, DPYD, EIF4E, FAM101B, GRB2, HNRNPF, HTATIP2, MAOA, MINA, MIR124, MIRLET7A1, MYC' MY06, MYRIP, NCAPD3, NF2, PPP2R5A, PPP2R5D, PPP2R5E, RPS16, RPS23, SGOL2, SLC25Al2, SMC2, SMC4, TMEM178, TUSC2, TXNIP, ZBTB16 | 24 | 13 | C11ORF75, CCDC109B, CDCA7L, DEPDC1, DPYD, FAM101B, MAOA, MINA, MYO6, MYRIP, SGOL2, SMC2, TMEM178 | — |
| 5 | A | ARHGAP24, ARHGEF, ARHGEF3, BARD1, CD9, CD53, CTNNB1, DUSP3, ERK, ERM, FGF9, FGF18, FGF21, FGF23, FGFR2, IL1, IL6, IL17RD, Integrina6131, KLB, LEF/TCF, LPAR1, MIRN297-2, P13K, RAS | 17 | 10 | ARHGAP24, ARHGEF3, BARD1, CD9, FGFR2, LPAR1, SMC6, SPC25, TCF7L1, TMEM35 | — |

TABLE 15-continued

| IPA Core Analysis of Genes | | | | | | |
|---|---|---|---|---|---|---|
| | | | | JMP Gene | Expression Profile | |
| Network | Group | Proteins in Network | pvalue | Number | Increased | Decreased |
| | | homolog, RNAPOLII, SLC26A2, SMC6, SPC25, SREBF1, TACC1, TCF7L1, TMEM35, TPT1, WISP1 | | | | |
| 6 | — | C3ORF70, MIR31 | 2 | 1 | C3ORF70 | — |
| 7 | — | MAB21L2, MIRN294 | 2 | 1 | MAB21L2 | — |
| 8 | — | AGPN, PRSS12 | 2 | 1 | PRSS12 | — |
| 9 | — | CENPL, MIRN340 | 2 | 1 | CENPL | — |
| 10 | — | GPR177, MIRN324 | 2 | 1 | GPR177 | — |
| 11 | — | ADH, PTGR1 | 2 | 1 | PTGR1 | — |
| 12 | C | ANK2, ATP2A2, BDNF, CEBPG, CPNE8, CREB5, GRM3, GRM5, IGFBP2, IL17B, ITPR, ITPR1, K+, L1CAM, MIRN330, Neurotrophin, NFE2L1, NGFR, NME1, NPAS4, Pro-inflammatory Cytokine, PSEN1, SCN2A, SCN3A, SCNN1B, SLC1A2, SLC8A1, SORCS1, SORT1, TGFA, THBS2, TNF, TNFAIP6 | 22 | 8 | — | ANK2, CPNE8, CREB5, IL17B, KIAA0125, LOC100289109, LOC144571, NPAS4, SLC1A2, SORCS1, THBS2, ZNF814 |

Computer analysis was performed as in Example V, except that the list of probes reflects genes that were greater than 1.5-fold differential expressed in the H1 and the BB10 cell lines when compared to both the 2D6 and SiMa parental cell lines. When the p-value cut off was set to 0.05, this analysis identified 439 gene probes that could be classified to 369 genes (Table 16).

TABLE 16

| Genes Identified using IPA Core Analysis | | | | | |
|---|---|---|---|---|---|
| Gene Name | Gene Symbol | Probe ID. No. | Location | Type | Log Ratio |
| 6-phosphofructo-2-kinase/fructose-2,6-biphosphatase 3 | PFKFB3 | 202464_s_at | Cytoplasm | kinase | 1.811 |
| achaete-scute complex homolog 1 | ASCL1 | 209985_s_at | Nucleus | transcription regulator | 2.429 |
| achaete-scute complex homolog 1 | ASCL1 | 209987_s_at | Nucleus | transcription regulator | 2.097 |
| achaete-scute complex homolog 1 | ASCL1 | 209988_s_at | Nucleus | transcription regulator | 1.446 |
| achaete-scute complex homolog 1 | ASCL1 | 213768_s_at | Nucleus | transcription regulator | 1.578 |
| activated leukocyte cell adhesion molecule | ALCAM | 1569362_at | Plasma Membrane | other | 2.612 |
| activated leukocyte cell adhesion molecule | ALCAM | 201951_at | Plasma Membrane | other | 1.774 |
| activated leukocyte cell adhesion molecule | ALCAM | 201952_at | Plasma Membrane | other | 1.521 |
| acyl-CoA thioesterase 1 | ACOT1 | 202982_s_at | Cytoplasm | enzyme | −2.875 |
| acylphosphatase 2, muscle type | ACYP2 | 206833_s_at | unknown | enzyme | −1.15 |
| additional sex combs like 3 | ASXL3 | 233536_at | unknown | other | 1.572 |
| adenosine deaminase, RNA-specific, B1 | ADARB1 | 203865_s_at | Nucleus | enzyme | −2.474 |
| adenylate cyclase 1 | ADCY1 | 213245_at | Plasma Membrane | enzyme | −1.935 |
| adipocyte-specific adhesion molecule | ASAM | 228082_at | Plasma Membrane | other | −2.802 |
| ADP-ribosylation factor 1 | ARF1 | 1565651_at | Cytoplasm | enzyme | 1.063 |
| ADP-ribosylation factor-like 17A | ARL17A | 243899_at | unknown | other | 0.741 |
| anaphase promoting complex subunit 7 | ANAPC7 | 225554_s_at | unknown | other | 0.679 |
| ankyrin repeat and BTB (POZ) domain containing 1 | ABTB1 | 229164_s_at | Cytoplasm | translation regulator | −0.656 |
| ankyrin repeat domain 50 | ANKRD50 | 225731_at | unknown | other | −0.654 |

TABLE 16-continued

| Genes Identified using IPA Core Analysis | | | | | |
|---|---|---|---|---|---|
| Gene Name | Gene Symbol | Probe ID. No. | Location | Type | Log Ratio |
| ankyrin repeat domain 50 | ANKRD50 | 225735_at | unknown | other | −1.114 |
| aspartate beta-hydroxylase domain containing 1 | ASPHD1 | 214993 at | unknown | other | −0.763 |
| ataxin 2-binding protein 1 | A2BP1 | 1553422_s_at | Cytoplasm | other | 1.453 |
| ataxin 2-binding protein 1 | A2BP1 | 221217_s_at | Cytoplasm | other | 1.497 |
| ATPase, Ca++ transporting, plasma membrane 3 | ATP2B3 | 207026_s_at | Plasma Membrane | transporter | −1.248 |
| ATPase, Ca++ transporting, plasma membrane 3 | ATP2B3 | 242036_x_at | Plasma Membrane | transporter | −1.777 |
| basonuclin 2 | BNC2 | 220272_at | Nucleus | other | 2.466 |
| basonuclin 2 | BNC2 | 230722_at | Nucleus | other | 1.641 |
| βycrystallin domain containing | 3CRYBG3 | 214030_at | unknown | other | 4.74 |
| β-site APP-cleaving enzyme 1 | BACE1 | 217904_s_at | Cytoplasm | peptidase | −1.57 |
| brain abundant, membrane attached signal protein 1 | BASP1 | 202391_at | Plasma Membrane | other | 1.146 |
| bromodomain and WD repeat domain containing 1 | BRWD1 | 225446_at | Nucleus | transcription regulator | −1.018 |
| bruno-like 4, RNA binding protein | BRUNOL4 | 238966_at | Nucleus | translation regulator | −0.81 |
| butyrophilin, subfamily 3, member A3 | BTN3A3 | 38241_at | unknown | other | −1.108 |
| C2 calcium dependent domain containing 2 | C2CD2 | 212875 s at | unknown | other | −1.27 |
| C2 calcium dependent domain containing 4A | C2CD4A | 241031_at | unknown | other | −2.615 |
| 2cadherin 12, type 2 (N-cadherin) | CDH12 | 207149_at | Plasma Membrane | other | −1.408 |
| calcium/calmodulin-dependent protein kinase II inhibitor 2 | CAMK2N2 | 230706_s_at | Nucleus | other | −0.692 |
| calmin (calponin-like, transmembrane) | CLMN | 213839_at | Cytoplasm | other | −1.911 |
| calpain 2, (m/II) large subunit | CAPN2 | 208683_at | Cytoplasm | peptidase | −1.429 |
| CAP, adenylate cyclase-associated protein, 2 | CAP2 | 212551_at | Plasma Membrane | other | -1.974 |
| CAP, adenylate cyclase associated protein, 2 | CAP2 | 212554_at | Plasma Membrane | other | −3.68 |
| carboxypeptidase, vitellogenic-like | CPVL | 208146 s_at | unknown | peptidase | 1.708 |
| CART prepropeptide | CARTPT | 206339_at | Extracellular Space | other | −4.676 |
| Cas-Br-M (murine) ecotropic retroviral transforming sequence b | CBLB | 209682_at | Nucleus | other | 1.032 |
| CCR4-NOT transcription complex, subunit 6-like | CNOT6L | 227119_at | Cytoplasm | other | −0.785 |
| CD302 molecule | CD302 | 203799_at | Plasma Membrane | receptor | −1.518 |
| CD9 molecule | CD9 | 201005_at | Plasma Membrane | other | 1.415 |
| CDP-diacylglycerol synthase (phosphatidate cytidylyltransferase) 1 | CDS1 | 226185_at | Cytoplasm | enzyme | −1.74 |
| cell division cycle 25 homolog B (S. pombe) | CDC25B | 201853_s_at | Nucleus | phosphatase | 1.453 |
| chemokine (C-X-C motif) receptor 4 | CXCR4 | 209201_x_at | Plasma Membrane | receptor | 4.135 |
| chemokine (C-X-C motif) receptor 4 | CXCR4 | 211919_s_at | Plasma Membrane | receptor | 3.957 |
| chemokine (C-X-C motif) receptor 4 | CXCR4 | 217028_at | Plasma Membrane | receptor | 3.176 |
| chloride channel 3 | CLCN3 | 201733 at | Plasma Membrane | ion channel | −0.908 |
| chloride channel 3 | CLCN3 | 201734_at | Plasma Membrane | ion channel | −0.987 |
| cholinergic receptor, nicotinic, alpha 7 | CHRNA7 | 210123_s_at | Plasma Membrane | receptor | 3.098 |
| chromosome 1 open reading frame 21 | C1ORF21 | 221272_s_at | unknown | other | −0.74 |
| chromosome 1 open reading frame 21 | C1ORF21 | 223127_s_at | unknown | other | −0.748 |
| chromosome 1 open reading frame 43 | C1ORF43 | 1555225_at | unknown | other | 1.604 |
| chromosome 10 open reading frame 58 | C10ORF58 | 224435_at | Extracellular Space | other | 0.918 |

TABLE 16-continued

| Genes Identified using IPA Core Analysis | | | | | |
|---|---|---|---|---|---|
| Gene Name | Gene Symbol | Probe ID. No. | Location | Type | Log Ratio |
| chromosome 12 open reading frame 49 | C120RF49 | 218867_s_at | unknown | other | 0.692 |
| chromosome 16 open reading frame 52 | C160RF52 | 230721_at | unknown | other | −0.87 |
| chromosome 20 open reading frame 7 | C200RF7 | 227160 sat | unknown | other | 0.624 |
| chromosome 21 open reading frame 57 | C210RF57 | 227421 at | unknown | other | −1.086 |
| chromosome 21 open reading frame 57 | C210RF57 | 239208 sat | unknown | other | −0.657 |
| chromosome 3 open reading frame 23 | C3ORF23 | 1555905_a_at | Cytoplasm | other | −2.797 |
| chromosome 3 open reading frame 23 | C3ORF23 | 1555906_s_at | Cytoplasm | other | −1.502 |
| chromosome 3 open reading frame 23 | C3ORF23 | 241666_at | Cytoplasm | other | −1.017 |
| chromosome 9 open reading frame 150 | C9ORF150 | 227443_at | unknown | other | −1.773 |
| claudin 12 | CLDN12 | 223249_at | Plasma Membrane | other | −0.766 |
| COBW domain containing 1 | CBWD1 | 226193_x_at | unknown | other | 0.849 |
| coiled-coil domain containing 3 | CCDC3 | 223316_at | Cytoplasm | other | 3.357 |
| collagen, type VI, alpha 1 | COL6A1 | 213428_s_at | Extracellular Space | other | −1.638 |
| cripto, FRL-1, cryptic family 1 | CFC1 | 223753_s_at | Extracellular Space | other | −2.834 |
| cripto, FRL-1, cryptic family 1 | CFC1 | 236724_at | Extracellular Space | other | −1.636 |
| CSE1 chromosome segregation 1-like | CSE1L | 210765_at | Nucleus | transporter | 1.581 |
| CUG triplet repeat, RNA binding protein 2 | CUGBP2 | 202156_s_at | Nucleus | other | 1.318 |
| CUG triplet repeat, RNA binding protein 2 | CUGBP2 | 202157_s_at | Nucleus | other | 2.156 |
| CUG triplet repeat, RNA binding protein 2 | CUGBP2 | 202158_s_at | Nucleus | other | 2.539 |
| cyclic nucleotide gated channel alpha 3 | CNGA3 | 207261_at | Plasma Membrane | ion channel | −3.182 |
| cyclin M1 | CNNM1 | 220166_at | Plasma Membrane | other | −1.214 |
| cyclin-dependent kinase inhibitor 2A (melanoma, p16, inhibits CDK4) | CDKN2A | 209644_x_at | Nucleus | transcription regulator | −1.277 |
| cylindromatosis (turban tumor syndrome) | CYLD | 213295_at | Nucleus | transcription regulator | −0.815 |
| cytochrome P450, family 2, subfamily E, polypeptide 1 | CYP2E1 | 1431_at | Cytoplasm | enzyme | −4.466 |
| cytochrome P450, family 2, subfamily E, polypeptide 1 | CYP2E1 | 209975_at | Cytoplasm | enzyme | −3.946 |
| cytochrome P450, family 2, subfamily E, polypeptide 1 | CYP2E1 | 209976_s_at | Cytoplasm | enzyme | −3.429 |
| cytoglobin | CYGB | 1553572_a_at | Cytoplasm | transporter | −4.921 |
| cytokine-like 1 | CYTL1 | 219837_s_at | Extracellular Space | cytokine | −6.33 |
| dapper, antagonist of beta-catenin, homolog 1 | DACT1 | 219179_at | Cytoplasm | other | 1.682 |
| dCMP deaminase | DCTD | 201572_x_at | unknown | enzyme | −0.649 |
| DEAN (Asp-Glu-Ala-His) box polypeptide 35 | DHX35 | 218579_s_at | unknown | enzyme | 0.735 |
| deleted in azoospermia 1 | DAZ1 | 207909_x_at | Nucleus | translation regulator | 6.92 |
| deleted in azoospermia 1 | DAZ1 | 207912_s_at | Nucleus | translation regulator | 5.558 |
| deleted in azoospermia 1 | DAZ1 | 208281 x at | Nucleus | translation regulator | 5.258 |
| deleted in azoospermia 1 | DAZ1 | 208282 x at | Nucleus | translation regulator | 7.008 |
| deleted in azoospermia 1 | DAZ1 | 216351 x at | Nucleus | translation regulator | 3.596 |
| deleted in azoospermia 1 | DAZ1 | 216922 x at | Nucleus | translation regulator | 5.185 |
| deleted in lymphocytic leukemia 2 (non-protein coding) | DLEU2 | 216870_x_at | unknown | other | 1.233 |
| delta-like 3 (Drosophila) | DLL3 | 219537 x at | other | Extracellular Space | 0.779 |

TABLE 16-continued

Genes Identified using IPA Core Analysis

| Gene Name | Gene Symbol | Probe ID. No. | Location | Type | Log Ratio |
|---|---|---|---|---|---|
| DNA segment on chromosome 4 (unique) 234 expressed sequence | D4S234E | 209569_x_at | Cytoplasm | other | −1.247 |
| DNA segment on chromosome 4 (unique) 234 expressed sequence | D4S234E | 209570_s_at | Cytoplasm | other | −1.488 |
| DNA segment on chromosome 4 (unique) 234 expressed sequence | D4S234E | 213533_at | Cytoplasm | other | −1.507 |
| dopamine beta-hydroxylase (dopamine beta-monooxygenase) | DBH | 206450_at | Cytoplasm | enzyme | 1.311 |
| doublecortin-like kinase 1 | DCLK1 | 215303_at | Cytoplasm | kinase | −1.62 |
| dual specificity phosphatase 16 | DUSP16 | 224832_at | Nucleus | phosphatase | −0.918 |
| echinoderm microtubule associated protein like 1 | EML1 | 204797_s_at | Cytoplasm | other | 2.668 |
| ectodermal-neural cortex (with BTB-like domain) | ENC1 | 201340_s_at | Nucleus | peptidase | 2.445 |
| ectodermal-neural cortex (with BTB-like domain) | ENC1 | 201341_at | Nucleus | peptidase | 1.91 |
| electron-transferring-flavoprotein dehydrogenase | ETFDH | 33494_at | Cytoplasm | enzyme | −0.807 |
| ELL associated factor 2 | EAF2 | 219551 _at | Nucleus | transcription regulator | 0.693 |
| ELOVL family member 7, elongation of long chain fatty acids | ELOVL7 | 227180_at | unknown | other | 2.644 |
| endoplasmic reticulum aminopeptidase 1 | ERAP1 | 214012_at | Extracellular Space | peptidase | −1.885 |
| enhancer of zeste homolog 2 | EZH2 | 203358_s_at | Nucleus | transcription regulator | 0.94 |
| ephrin-A5 | EFNAS | 214036_at | Plasma Membrane | kinase | 2.041 |
| ephrin-A5 | EFNAS | 227955_s_at | Plasma Membrane | kinase | 1.84 |
| ephrin-A5 | EFNAS | 233814_at | Plasma Membrane | kinase | 1.805 |
| ephrin-B3 | EFNB3 | 205031_at | Plasma Membrane | kinase | −0.816 |
| eukaryotic translation initiation factor 3, subunit C | EIF3C | 236700_at | Cytoplasm | translation regulator | 1.378 |
| exophilin 5 | EXPH5 | 214734_at | unknown | other | 3.973 |
| exosome component 6 | EXOSC6 | 231916_at | Nucleus | other | 1.057 |
| family with sequence similarity 162, member B | FAM162B | 228875_at | unknown | other | −0.743 |
| family with sequence similarity 165, member B | FAM165B | 228239_at | Plasma Membrane | other | −0.822 |
| family with sequence similarity 181, member B | FAM181B | 231430 at | unknown | other | 0.794 |
| family with sequence similarity 19 (chemokine (C-C motif)-like), member A4 | FAM19A4 | 242348_at | Extracellular Space | other | 1.282 |
| family with sequence similarity 46, member A | FAM46A | 224973 at | unknown | other | −1.509 |
| family with sequence similarity 7, member A3 | FAM7A3 | 243356 at | unknown | other | 3.495 |
| far upstream element (FUSE) binding protein 3 | FUBP3 | 239193_at | Nucleus | transcription regulator | 1.192 |
| F-box and WD repeat domain containing 7 | FBXW7 | 229419_at | transcription regulator | Nucleus | −0.921 |
| fibroblast growth factor 13 | FGF13 | 205110_s_at | Extracellular Space | growth factor | −3.522 |
| follistatin-like 1 | FSTL1 | 208782 at | Extracellular Space | other | −1.275 |
| forkhead box O6 | FOXO6 | 239657_x_at | Nucleus | other | −1.512 |
| frizzled homolog 5 | FZD5 | 221245_s_at | Plasma Membrane | receptor | 2.347 |
| FYVE, RhoGEF and PH domain containing 5 | FGD5 | 226985_at | Cytoplasm | other | −1.952 |
| G protein-coupled receptor 123 | GPR123 | 239221_at | Plasma Membrane | receptor | −1.302 |
| G protein-coupled receptor 125 | GPR125 | 210473_s_at | Plasma Membrane | receptor | 0.714 |
| galanin prepropeptide | GAL | 207466_at | Extracellular Space | other | −1.434 |

TABLE 16-continued

Genes Identified using IPA Core Analysis

| Gene Name | Gene Symbol | Probe ID. No. | Location | Type | Log Ratio |
|---|---|---|---|---|---|
| galanin prepropeptide | GAL | 214240_at | Extracellular Space | other | −3.128 |
| gastrin-releasing peptide | GRP | 206326_at | Extracellular Space | growth factor | 4.698 |
| GDNF family receptor alpha | 2GFRA2 | 205721_at | Plasma Membrane | receptor | 1.847 |
| GDNF family receptor alpha | 2GFRA2 | 205722_s_at | Plasma Membrane | receptor | 2.265 |
| glutamate receptor, metabotropic 5 | GRM5 | 214217_at | Plasma Membrane | receptor | −2.231 |
| glutathione peroxidase 7 | GPX7 | 213170_at | Cytoplasm | enzyme | −2.692 |
| glutathione synthetase | GSS | 211630_s_at | Cytoplasm | enzyme | 0.599 |
| glycosyltransferase 25 domain containing 2 | GLT25D2 | 209883_at | unknown | other | −1.223 |
| GNAS complex locus | GNAS | 214157_at | Plasma Membrane | enzyme | −1.794 |
| growth associated protein 43 | GAP43 | 204471_at | Plasma Membrane | other | 0.869 |
| growth associated protein 43 | GAP43 | 216963_s_at | Plasma Membrane | other | 1.151 |
| guanine nucleotide binding protein (G protein), alpha inhibiting activity polypeptide 1 | GNAI1 | 209576_at | Plasma Membrane | enzyme | 2.225 |
| guanine nucleotide binding protein (G protein), alpha inhibiting activity polypeptide 1 | GNAI1 | 227692_at | Plasma Membrane | enzyme | 2.111 |
| guanine nucleotide binding protein (G protein), beta polypeptide 4 | GNB4 | 225710_at | Plasma Membrane | enzyme | 4.695 |
| guanine nucleotide binding protein (G protein), gamma 11 | GNG11 | 204115 at | Plasma Membrane | enzyme | 2.587 |
| guanylate cyclase 1, soluble, alpha 3 | GUCY 1A3 | 221942_s_at | Cytoplasm | enzyme | −1.522 |
| guanylate cyclase 1, soluble, alpha 3 | GUCY 1A3 | 229530_at | Cytoplasm | enzyme | −1.696 |
| helicase, POLQ-like | HELQ | 228736_at | Nucleus | enzyme | −1.28 |
| HERPUD family member 2 | HERPUD 2 | 236170_x_at | unknown | other | −0.897 |
| heterogeneous nuclear ribonucleoprotein R | HNRNPR | 208765_s_at | Nucleus | other | −0.64 |
| hippocalcin-like 1 | HPCAL 1 | 205462_s_at | Cytoplasm | other | −1.551 |
| hippocalcin-like 1 | HPCAL 1 | 212552_at | Cytoplasm | other | −1.387 |
| histone cluster 1, H2ac | HIS T1H2A C | 215071 s at | Nucleus | other | −2.462 |
| histone cluster 1, H2bd | HIST1H2BD | 209911_x_at | Nucleus | other | −2.036 |
| histone cluster 1, H2bk | HIST1H2B K | 209806_at | Nucleus | other | −1.575 |
| histone cluster 2, H2be | HISTE H2B E | 202708_s_at | Nucleus | other | −1.735 |
| hypothetical LOC100130522 | LOC10013 0522 | 230477_at | unknown | other | −0.928 |
| hypothetical LOC26082 | DKFZP434 L187 | 230861_at | unknown | other | 0.968 |
| hypothetical protein LOCI 00128844 | LOC10012 8844 | 229110_at | unknown | other | 2.106 |
| hypothetical protein LOC643401 | LOC340109 | 1557765_at | unknown | other | 2.848 |
| integrin, alpha 6 | ITGA6 | 201656_at | Plasma Membrane | other | 2.822 |
| integrin, alpha 6 | ITGA6 | 215177_s_at | Plasma Membrane | other | 2.024 |
| integrin, beta 5 | ITGB5 | 201125_s_at | Plasma Membrane | other | 0.913 |
| interleukin 10 receptor, beta | IL1ORB | 209575_at | Plasma Membrane | transmembr ane receptor | −1.444 |
| junction mediating and regulatory protein, p53 cofactor | JMY | 226352_at | Nucleus | transcription regulator | −0.744 |
| K(lysine) acetyltransferase 2B | KAT2B | 203845_at | Nucleus | transcription regulator | −0.731 |
| KDEL (Lys-Asp-Glu-Leu) containing 2 | KDELC2 | 225128_at | unknown | other | 1.085 |
| kelch domain containing 1 | KLHDC1 | 1552733_at | unknown | other | −0.952 |
| kelch repeat and BTB (POZ) domain containing 11 | KBTBD11 | 204301_at | unknown | other | −0.733 |
| kelch-like 13 (Drosophila) | KLHL13 | 227875_at | unknown | other | 0.902 |
| KH domain containing, RNA binding, signal transduction associated 3 | KHDRBS3 | 209781_s_at | Nucleus | other | 1.082 |
| KH homology domain containing 1 | KHDC1 | 230055_at | unknown | other | −1.656 |
| KIAA1598 | KIAA1598 | 221802_s_at | unknown | other | −2.811 |

TABLE 16-continued

Genes Identified using IPA Core Analysis

| Gene Name | Gene Symbol | Probe ID. No. | Location | Type | Log Ratio |
|---|---|---|---|---|---|
| kinesin family member 16B | KIF16B | 232083_at | Cytoplasm | other | 1.688 |
| lectin, galactoside-binding, soluble, 3 binding protein | LGALS3BP | 200923_at | Plasma Membrane | transmembrane receptor | −1.417 |
| leukemia inhibitory factor receptor alpha | LIFR | 225575_at | Plasma Membrane | transmembrane receptor | −0.941 |
| limb bud and heart development homolog (mouse) | LBH | 221011_s_at | Nucleus | transcription regulator | 0.788 |
| LRP2 binding protein | LRP2BP | 207797_s_at | unknown | other | −1.365 |
| lumican | LUM | 201744_s_at | Extracellular Space | other | 5.638 |
| LYR motif containing 5 | LYRM5 | 225469_at | unknown | other | −0.93 |
| mab-21-like 1 | MAB21L1 | 206163_at | unknown | other | 2.722 |
| mab-21-like 2 | MAB21L2 | 210302_s_at | unknown | other | 2.871 |
| mab-21-like 2 | MAB21L2 | 210303_at | unknown | other | 2.204 |
| macrophage stimulating 1 (hepatocyte growth factor-like) | MST1 | 216320_x_at | Extracellular Space | growth factor | −1.012 |
| major facilitator superfamily domain containing 4 | MFSD4 | 229254_at | unknown | other | −1.752 |
| mannosidase, alpha, class 2A, member 1 | MAN2A1 | 226538_at | Cytoplasm | enzyme | 0.864 |
| mannosyl (alpha-l,3-)-glycoprotein beta-1,4-N-acetylglucosaminyltransferase, isozyme A | MGAT4A | 226039_at | unknown | enzyme | −0.904 |
| mesenchyme homeobox 2 | MEOX2 | 206201_s_at | Nucleus | transcription regulator | −4.213 |
| microtubule-associated protein 9 | MAP9 | 220145_at | unknown | other | −0.7 |
| microtubule-associated protein 9 | MAP9 | 228423_at | unknown | other | −1.108 |
| microtubule-associated protein 9 | MAP9 | 235550_at | unknown | other | −0.863 |
| mitochondrial ribosomal protein S33 | MRPS33 | 218654_s_at | Cytoplasm | other | −0.609 |
| mitogen activated protein kinase kinase kinase 5 | MAP3K5 | 203836_s_at | Cytoplasm | kinase | −1.159 |
| moesin | MSN | 200600_at | Plasma Membrane | other | 2.082 |
| monoamine oxidase A | MAOA | 204388_s_at | Cytoplasm | enzyme | 2.15 |
| monoamine oxidase A | MAOA | 204389_at | Cytoplasm | enzyme | 1.88 |
| monoamine oxidase A | MAOA | 212741_at | Cytoplasm | enzyme | 2.048 |
| monocyte to macrophage differentiation-associated | MMD | 244523_at | Plasma Membrane | other | 1.045 |
| multiple C2 domains, transmembrane 1 | MCTP1 | 220122_at | unknown | other | −1.597 |
| MYC induced nuclear antigen | MINA | 213188_s_at | Nucleus | other | 1.391 |
| MYC induced nuclear antigen | MINA | 213189_at | Nucleus | other | 1.641 |
| myosin IB | MYO1B | 212365_at | Cytoplasm | other | 0.71 |
| myosin VI | MYO6 | 203216_s_at | Cytoplasm | other | 1.104 |
| myosin VI | MYO6 | 210480_s_at | Cytoplasm | other | 1.41 |
| Na+/H+ exchanger domain containing 2 | NHEDC2 | 1564746_at | Plasma Membrane | other | −1.462 |
| N-acylethanolamine acid amidase | NAAA | 214765_s_at | Cytoplasm | enzyme | 0.911 |
| NADH dehydrogenase (ubiquinone) 1 alpha subcomplex, 4-like 2 | NDUFA4L2 | 218484 at | unknown | enzyme | −3.507 |
| NADH dehydrogenase (ubiquinone) flavoprotein 3, 10 kDa | NDUFV3 | 226616_s_at | Cytoplasm | enzyme | −0.875 |
| nebulette | NEBL | 203961_at | Cytoplasm | other | −1.359 |
| neural precursor cell expressed, developmentally down-regulated 9 | NEDD9 | 202150_s_at | Nucleus | other | 2.41 |
| NIPA-like domain containing 3 | NIPAL3 | 225876_at | unknown | other | −1.203 |
| nitric oxide synthase 1 (neuronal) | NOS1 | 239132_at | Cytoplasm | enzyme | 1.138 |
| nitric oxide synthase 1 (neuronal) | NOS1 | 240911_at | Cytoplasm | enzyme | 1.187 |
| NLR family member X1 | NLRX1 | 219680_at | unknown | other | −1.541 |
| non-protein coding RNA 171 | NCR A001 71 | 215985_at | unknown | other | −0.692 |
| nuclear receptor coactivator 7 | NCOA7 | 225344_at | Nucleus | other | −0.842 |
| nucleosome assembly protein 1-like 3 | NAP1L3 | 204749_at | Nucleus | other | −1.53 |
| nudix (nucleoside diphosphate linked moiety X)-type motif 19 | NUDT19 | 235384_at | Cytoplasm | other | −1.685 |
| olfactomedin 3 | OLFM3 | 1554524_a_at | Cytoplasm | other | −0.927 |

TABLE 16-continued

Genes Identified using IPA Core Analysis

| Gene Name | Gene Symbol | Probe ID. No. | Location | Type | Log Ratio |
|---|---|---|---|---|---|
| oxysterol binding protein-like 3 | OSBPL3 | 209626_s_at | Cytoplasm | other | 2.083 |
| pecanex-like 2 | PCNXL2 | 1554256_a_at | unknown | other | −0.728 |
| pellino homolog 2 | PELI2 | 219132_at | Cytoplasm | other | 0.732 |
| peptidase M20 domain containing 2 | PM20D2 | 22542_at | unknown | other | 1.6 |
| peptidylglycine alpha-amidating monooxygenase | PAM | 202336_s_at | Plasma Membrane | enzyme | −0.861 |
| peripherin | PRPH | 213847_at | Plasma Membrane | other | −1.417 |
| PHD finger protein 20 | PHF20 | 235389_at | Nucleus | other | 0.596 |
| phosphatidic acid phosphatase type 2 domain containing 1A | PPAPDC1 A | 236044_at | unknown | phosphatase | −2.621 |
| phosphatidylinositol glycan anchor biosynthesis, class H | PIGH | 209625_at | Cytoplasm | enzyme | −0.597 |
| phosphoinositide-interacting regulator of transient receptor potential channels | HCG 1776018 | 232887_at | unknown | other | −2.019 |
| phosphorylase kinase, alpha 1 (muscle) | PHKA1 | 229876_at | Cytoplasm | kinase | −1.2 |
| plastin 3 (T isoform) | PLS3 | 201215_at | Cytoplasm | other | 1.068 |
| platelet-derived growth factor receptor, beta polypeptide | PDGFRB | 202273_at | Plasma Membrane | kinase | −1.373 |
| pleiotrophin | PTN | 209466_x_at | Extracellular Space | growth factor | −1.426 |
| pleiotrophin | PTN | 211737_x_at | Extracellular Space | growth factor | −2.929 |
| pleiotropic regulator 1 | PLRG1 | 225194_at | Nucleus | transcription regulator | −0.701 |
| pleiotropic regulator 1 | PLRG1 | 227246 at | Nucleus | transcription regulator | −1.228 |
| plexin A2 | PLXNA2 | 213030_s_at | Plasma Membrane | other | 0.946 |
| plexin A4 | PLXNA4 | 232317_at | Plasma Membrane | receptor | 1.368 |
| polo-like kinase 2 | PLK2 | 201939 at | Nucleus | kinase | 3.606 |
| polycomb group ring finger 5 | PCGFS | 227935_s_at | unknown | other | 0.791 |
| polymerase (DNA directed), epsilon | POLE | 216026_s_at | Nucleus | enzyme | 1.053 |
| potassium channel tetramerisation domain containing 12 | KCTD12 | 212188_at | unknown | ion channel | 3.396 |
| potassium channel tetramerisation domain containing 12 | KCTD12 | 212192_at | unknown | ion channel | 4.806 |
| potassium large conductance calcium-activated channel, subfamily M, alpha member 1 | KCNMA1 | 221584 s at | Plasma Membrane | ion channel | −2.389 |
| potassium voltage-gated channel, KQT-like subfamily, member 2 | KCNQ2 | 205737_at | Plasma Membrane | ion channel | −1.246 |
| pregnancy-associated plasma protein A, pappalysin 1 | PAPPA | 201982_s_at | Extracellular Space | peptidase | −1.672 |
| prostaglandin E receptor 2 (subtype EP2), 53 kDa | PTGER2 | 206631_at | Plasma Membrane | receptor | −2.328 |
| prostaglandin F2 receptor negative regulator | PTGFRN | 224937_at | Plasma Membrane | other | 2.301 |
| proteasome (prosome, macropain) subunit, alpha type, 7 | PSMA7 | 216088_s_at | Cytoplasm | peptidase | 0.658 |
| protein kinase, cAMP-dependent, catalytic, beta | PRKACB | 235780_at | Cytoplasm | kinase | −2.17 |
| protein tyrosine phosphatase, receptor type, D | PTPRD | 214043_at | Plasma Membrane | phosphatase | -1.16 |
| protein tyrosine phosphatase, receptor type, E | PTPRE | 221840_at | Plasma Membrane | phosphatase | 3.044 |
| protein tyrosine phosphatase, receptor type, G | PTPRG | 204944_at | Plasma Membrane | phosphatase | 1.237 |
| RAB35, member RAS oncogene family | RAB35 | 205461_at | Cytoplasm | enzyme | 0.737 |
| RAB6B, member RAS oncogene family | RAB6B | 225259_at | Cytoplasm | enzyme | −1.229 |
| Rac/Cdc42 guanine nucleotide exchange factor (GEF) 6 | ARHGEF6 | 209539_at | Cytoplasm | other | 2.719 |
| RAN, member RAS oncogene family | RAN | 200750_s_at | Nucleus | enzyme | 0.59 |

TABLE 16-continued

Genes Identified using IPA Core Analysis

| Gene Name | Gene Symbol | Probe ID. No. | Location | Type | Log Ratio |
|---|---|---|---|---|---|
| RAS and EF-hand domain containing | RASEF | 1553986_at | unknown | other | 1.393 |
| ras homolog gene family, member U | RHOU | 223168_at | Cytoplasm | enzyme | −1.154 |
| regulator of G-protein signaling 5 | RGSS | 1555725_a_at | Plasma Membrane | other | 4.038 |
| regulator of G-protein signaling 5 | RGSS | 209070_s_at | Plasma Membrane | other | 3.729 |
| regulator of G-protein signaling 5 | RGSS | 209071_s_at | Plasma Membrane | other | 3.468 |
| regulator of G-protein signaling 5 | RGSS | 218353 at | Plasma Membrane | other | 3.65 |
| RELT-like 1 | RELL1 | 226430_at | unknown | other | 1.214 |
| retinoblastoma-like 1 (p107) | RBL1 | 1559307_s_at | Nucleus | other | 0.959 |
| retrotransposon gag domain containing 4 | RGAG4 | 227823_at | unknown | other | −1.775 |
| Rho GTPase activating protein 6 | ARHGAP6 | 206167_s_at | Cytoplasm | other | 2.809 |
| ribosomal L1 domain containing 1 | RSL1D1 | 213750 at | Cytoplasm | other | −0.816 |
| RIMS binding protein 2 | RIMBP2 | 238817_at | Plasma Membrane | other | 1.679 |
| ring finger protein 13 | RNF13 | 201780_s_at | Nucleus | other | −0.707 |
| ring finger protein 182 | RNF182 | 230720_at | unknown | other | 2.696 |
| ring finger protein 34 | RNF34 | 219035_s_at | Cytoplasm | enzyme | 0.85 |
| ring finger protein 41 | RNF41 | 201962_s_at | Cytoplasm | other | −0.591 |
| RNA polymerase I transcription factor homolog pseudogene 1 | LOC94431 | 216908_x_at | unknown | other | −0.674 |
| sal-like 4 | SALL4 | 229661_at | Nucleus | other | 1.586 |
| salt-inducible kinase 1 | SIK1 | 208078_s_at | Cytoplasm | kinase | −1.403 |
| seizure related 6 homolog (mouse)-like | SEZ6L | 207873_x_at | Plasma | other | 0.866 |
| seizure related 6 homolog (mouse)-like | SEZ6L | 211894_x_at | Plasma Membrane | other | 0.797 |
| sema domain, transmembrane domain (TM), and cytoplasmic domain, (semaphorin) 6A | SEMA6A | 220454_s_at | Plasma Membrane | other | 1.356 |
| serine peptidase inhibitor, Kunitz type, 2 | SPINT2 | 210715_s_at | Extracellular Space | other | −1.889 |
| SH3 domain containing, Ysc84-like 1 | SH3YL1 | 204019 s at | unknown | other | −0.859 |
| SH3-domain GRB2-like 2 | SH3GL2 | 205751_at | Plasma Membrane | enzyme | −1.605 |
| similar to hCG2031213 | LOC728052 | 1558795_at | unknown | other | 2.239 |
| similar to hCG2031213 | LOC728052 | 1558796 a at | unknown | other | 1.887 |
| single immunoglobulin and toll-interleukin 1 receptor (TIR) domain | SIGIRR | 52940_at | Plasma | receptor | −1.42 |
| single-minded homolog 1 | SIM1 | 1556300 s at | Nucleus | transcription regulator | 6.36 |
| single-minded homolog 1 | SIM1 | 206876_at | Nucleus | transcription regulator | 5.737 |
| SLIT and NTRK-like family, member 5 | SLITRKS | 214930_at | unknown | other | 4.094 |
| SMG1 homolog, phosphatidylinositol 3-kinase-related kinase pseudogene | LOC641298 | 244766_at | unknown | other | 1.065 |
| solute carrier family 12 (potassium/chloride transporters), member 7 | SLC12A7 | 218066 at | Plasma Membrane | transporter | −1.258 |
| solute carrier family 22, member 17 | SLC22A17 | 218675 at | Plasma | transporter | −0.724 |
| solute carrier family 35, member F3 | SLC35F3 | 229065_at | unknown | other | −3.048 |
| solute carrier family 44, member 5 | SLC44A5 | 1569112_at | unknown | other | 2.738 |
| solute carrier family 44, member 5 | SLC44A5 | 235763_at | unknown | other | 1.845 |
| solute carrier family 7 (cationic amino acid transporter, y+ system), member 2 | SLC7A2 | 225516_at | Plasma Membrane | transporter | 1.892 |
| solute carrier organic anion transporter family, member 3A1 | SLCO3A1 | 219229_at | Plasma Membrane | transporter | 1.622 |
| solute carrier organic anion transporter family, member 3A1 | SLCO3A1 | 227367_at | Plasma Membrane | transporter | 1.045 |

TABLE 16-continued

Genes Identified using IPA Core Analysis

| Gene Name | Gene Symbol | Probe ID. No. | Location | Type | Log Ratio |
|---|---|---|---|---|---|
| sparc/osteonectin, cwcv and kazal-like domains proteoglycan (testican) 2 | SPOCK2 | 202524_s_at | Extracellular Space | other | −0.83 |
| sperm associated antigen 6 | SPAG6 | 210032_s_at | Cytoplasm | other | 1.687 |
| sperm associated antigen 6 | SPAG6 | 210033_s_at | Cytoplasm | other | 2.774 |
| spermatogenesis associated, serine-rich 2-like | SPATS2L | 222154_s_at | unknown | other | 0.907 |
| sphingosine-1-phosphate receptor 3 | S1PR3 | 228176_at | Plasma Membrane | receptor | 1.9 |
| ST8 alpha-N-acetyl-neuraminide alpha-2,8-sialyltransferase 1 | ST8SIA1 | 210073_at | Cytoplasm | enzyme | 1.114 |
| ST8 alpha-N-acetyl-neuraminide alpha-2,8-sialyltransferase 3 | ST8SIA3 | 230262_at | Cytoplasm | enzyme | −1.039 |
| stathmin-like 3 | STMN3 | 222557 at | Nucleus | other | 0.788 |
| STEAP family member 3 | STEAP3 | 218424_s_at | Cytoplasm | transporter | −1.827 |
| steroidogenic acute regulatory protein | STAR | 204548 at | Cytoplasm | transporter | −1.093 |
| stimulated by retinoic acid gene 6 homolog | STRA6 | 1569334_at | Plasma Membrane | other | 1.359 |
| stimulated by retinoic acid gene 6 homolog | STRA6 | 1569335_a_at | Plasma Membrane | other | 1.167 |
| storkhead box 2 | STOX2 | 226822_at | unknown | other | −0.854 |
| synaptojanin 1 | SYNJ1 | 212990_at | Cytoplasm | phosphatase | −0.624 |
| synaptotagmin XIII | SYT13 | 226086_at | unknown | transporter | −4.754 |
| synuclein, alpha (non A4 component of amyloid precursor) | SNCA | 236081_at | Cytoplasm | other | −0.935 |
| taxilin beta | TXLNB | 227834_at | Cytoplasm | other | −2.226 |
| teashirt zinc finger homeobox 3 | TSHZ3 | 223392_s_at | Nucleus | transcription regulator | 1.472 |
| teashirt zinc finger homeobox 3 | TSHZ3 | 223393_s_at | Nucleus | transcription regulator | 0.962 |
| tetratricopeptide repeat domain 39C | TTC39C | 238480 at | unknown | other | −0.824 |
| TH1-like | TH1L | 220607_x_at | Nucleus | other | 1.027 |
| TH1-like | TH1L | 225006_x_at | Nucleus | other | 0.884 |
| TH1-like | TH1L | 225261_x_at | Nucleus | other | 0.883 |
| TH1-like | TH1L | 225865_x_at | Nucleus | other | 0.904 |
| thioredoxin reductase 1 | TXNRD1 | 201266_at | Cytoplasm | enzyme | 1.032 |
| THO complex 4 | THOC4 | 226319 s at | Nucleus | transcription regulator | 0.996 |
| TIMP metallopeptidase inhibitor 3 | TIMP3 | 201147_s_at | Extracellular Space | other | 5.151 |
| TIMP metallopeptidase inhibitor 3 | TIMP3 | 201148_s_at | Extracellular Space | other | 3.637 |
| TIMP metallopeptidase inhibitor 3 | TIMP3 | 201149_s_at | Extracellular Space | other | 5.037 |
| TIMP metallopeptidase inhibitor 3 | TIMP3 | 201150_s_at | Extracellular Space | other | 4.312 |
| tissue factor pathway inhibitor 2 | TFPI2 | 209277_at | Extracellular Space | other | 1.592 |
| tissue factor pathway inhibitor 2 | TFPI2 | 209278_s_at | Extracellular Space | other | 2.326 |
| TM2 domain containing 1 | TM2D1 transcription | 213882_at | Plasma Membrane | receptor | −0.769 |
| transcription factor 7-like 2 (T-cell specific, HMG-box) | TCF7L2 | 212761_at | Nucleus | transcription regulator | 1.005 |
| transcription factor 7-like 2 (T-cell specific, HMG-box) | TCF7L2 | 212762 s at | Nucleus | transcription regulator | 1.224 |
| transcription factor 7-like 2 (T-cell specific, HMG-box) | TCF7L2 | 216035_x_at | Nucleus | transcription regulator | 1.072 |
| transcription factor 7-like 2 (T-cell specific, HMG-box) | TCF7L2 | 216037_x_at | Nucleus | transcription regulator | 0.81 |
| transcription factor 7-like 2 (T-cell specific, HMG-box) | TCF7L2 | 216511_s_at | Nucleus | transcription regulator | 1.003 |
| transducin-like enhancer of split 3 | TLE3 | 212770 at | Nucleus | other | 0.976 |
| transformer 2 alpha homolog | TRA2A | 213593 s at | Nucleus | other | 1.12 |
| transmembrane inner ear | TMIE | 1553601_a_at | unknown | other | −3.334 |
| transmembrane protein 132C | TM CEM 132 C | 232313_at | unknown | other | 4.02 |
| transmembrane protein 178 | TMEM178 | 229302_at | unknown | other | 1.697 |
| transmembrane protein 184C | TMC 184 C | 219074_at | unknown | other | −0.779 |
| transmembrane protein 5 | TMEM5 | 204808_s_at | Plasma Membrane | other | −1.074 |

TABLE 16-continued

Genes Identified using IPA Core Analysis

| Gene Name | Gene Symbol | Probe ID. No. | Location | Type | Log Ratio |
|---|---|---|---|---|---|
| transmembrane protein 59-like | TMEM59L | 219005_at | Cytoplasm | other | −0.845 |
| tripartite motif-containing 29 | TRIM29 | 211002_s_at | Cytoplasm | transcription regulator | 2.005 |
| tripartite motif-containing 36 | TRIM36 | 219736_at | Cytoplasm | other | 2.221 |
| trophoblast glycoprotein | TPBG | 203476_at | Plasma Membrane | other | 2.158 |
| tumor suppressor candidate 3 | TUSC3 | 232770_at | Extracellular Space | enzyme | −1.407 |
| U2 small nuclear RNA auxiliary factor 1 | U2AF1 | 232141_at | Nucleus | other | 0.776 |
| ubiquitin-conjugating enzyme E2 variant 1 | UBE2V1 | 201003_x_at | Nucleus | transcription regulator | 0.663 |
| urocortin | UCN | 206072_at | Extracellular Space | other | −0.961 |
| vacuolar protein sorting 29 homolog | VPS29 | 223026_s_at | Cytoplasm | transporter | 0.805 |
| v-erb-a erythroblastic leukemia viral oncogene homolog 4 | ERBB4 | 206794_at | Plasma Membrane | kinase | −1.537 |
| v-erb-a erythroblastic leukemia viral oncogene homolog 4 | ERBB4 | 214053_at | Plasma Membrane | kinase | −1.708 |
| v-erb-b2 erythroblastic leukemia viral oncogene homolog 2, neuro/glioblastoma derived oncogene homolog | ERBB2 | 216836_s_at | Plasma Membrane | kinase | −0.698 |
| v-raf-1 murine leukemia viral oncogene homolog 1 | RAF1 | 1557675_at | Cytoplasm | kinase | 0.696 |
| WD repeat and FYVE domain containing 3 | WDFY3 | 212602_at | Cytoplasm | enzyme | −0.626 |
| WD repeat and FYVE domain containing 3 | WDFY3 | 212606_at | Cytoplasm | enzyme | −0.785 |
| zinc finger homeobox 4 | ZFHX4 | 219779_at | unknown | other | 1.36 |
| zinc finger homeobox 4 | ZFHX4 | 241700_at | unknown | other | 1.234 |
| zinc finger protein 217 | ZNF217 | 203739_at | Nucleus | transcription regulator | 1.096 |
| zinc finger protein 503 | ZNF503 | 227195_at | Nucleus | other | 1.373 |
| zinc finger protein 641 | ZNF641 | 226509_at | unknown | other | −1.427 |
| zinc finger protein 662 | ZNF662 | 228538_at | unknown | other | −3.352 |
| zinc finger, CCCH-type with G patch domain | ZGPAT | 221848_at | unknown | other | 0.991 |

Computer analysis was performed as in Example V, except that the list of probes reflects genes that were greater than 1.5-fold differential expressed in the H1 cell line and the BB10 cell line when compared to both the 2D6 and SiMa parental cell lines, and also a greater than 1.5-fold differential expressed in the SiMa parental cell line when compared to the 2D6 cell line. When the p-value cut off was set to 0.05, this analysis identified 94 gene probes that could be classified to 70 genes (Table 17).

TABLE 17

Genes Identified using IPA Core Analysis

| Gene Name | Gene Symbol | Probe ID. No. | Location | Type | Log Ratio |
|---|---|---|---|---|---|
| achaete-scute complex homolog 1 | ASCL1 | 209985_s_at | Nucleus | transcription regulator | 2.429 |
| achaete-scute complex homolog 1 | ASCL1 | 209988_s_at | Nucleus | transcription regulator | 1.446 |
| achaete-scute complex homolog 1 | ASCL1 | 213768_s_at | Nucleus | transcription regulator | 1.578 |
| activated leukocyte cell adhesion molecule | ALCAM | 201952_at | Plasma Membrane | other | 1.521 |
| ADP-ribosylation factor 1 | ARF1 | 1565651_at | Cytoplasm | enzyme | 1.063 |
| ADP-ribosylation factor-like 17A | ARL17A | 243899_at | unknown | other | 0.741 |
| ataxin 2-binding protein 1 | A2BP1 | 1553422_s_at | Cytoplasm | other | 1.453 |
| ataxin 2-binding protein 1 | A2BP1 | 221217_s_at | Cytoplasm | other | 1.497 |

TABLE 17-continued

Genes Identified using IPA Core Analysis

| Gene Name | Gene Symbol | Probe ID. No. | Location | Type | Log Ratio |
|---|---|---|---|---|---|
| brain abundant, membrane attached signal protein 1 | BASP1 | 202391_at | Plasma Membrane | other | 1.146 |
| CAP, adenylate cyclase-associated protein, 2 | CAP2 | 21255_at | Plasma Membrane | other | −1.974 |
| CD9 molecule | CD9 | 201005_at | Plasma Membrane | other | 1.415 |
| CUG triplet repeat, RNA binding protein 2 | CUGBP2 | 202157_s_at | Nucleus | other | 2.156 |
| cyclic nucleotide gated channel alpha 3 | CNGA3 | 207261_at | Plasma Membrane | ion channel | −3.182 |
| cyclin-dependent kinase inhibitor 2A (melanoma, p16, inhibits CDK4) | CDKN2A | 209644_x_at | Nucleus | transcription regulator | −1.277 |
| ELL associated factor 2 | EAF2 | 219551 _at | Nucleus | transcription regulator | 0.693 |
| eukaryotic translation initiation factor 3, subunit C | EIF3C | 236700_at | Cytoplasm | translation regulator | 1.378 |
| family with sequence similarity 162, member B | FAM162B | 228875_at | unknown | other | −0.743 |
| family with sequence similarity 181, member B | FAM181B | 231430_at | unknown | other | 0.794 |
| far upstream element (FUSE) binding protein 3 | FUBP3 | 239193_at | Nucleus | transcription regulator | 1.192 |
| fibroblast growth factor 13 | FGF13 | 205110_s_at | Extracellular Space | growth factor | −3.522 |
| follistatin-like 1 | FSTL1 | 208782_at | Extracellular Space | other | −1.275 |
| forkhead box O6 | FOXO6 | 239657_x_at | Nucleus | other | −1.512 |
| guanine nucleotide binding protein (G protein), alpha inhibiting activity polypeptide 1 | GNAI1 | 227692_at | Plasma Membrane | enzyme | 2.111 |
| guanine nucleotide binding protein (G protein), beta polypeptide 4 | GNB4 | 225710_at | Plasma Membrane | enzyme | 4.695 |
| guanine nucleotide binding protein (G protein), gamma 11 | GNG11 | 204115_at | Plasma Membrane | enzyme | 2.587 |
| KDEL (Lys-Asp-Glu-Leu) containing 2 | KDELC2 | 225128_at | unknown | other | 1.085 |
| kelch-like 13 | KLHL13 | 227875_at | unknown | other | 0.902 |
| KH domain containing, RNA binding, signal transduction associated 3 | KHDRBS3 | 209781_s_at | Nucleus | other | 1.082 |
| KH homology domain containing 1 | KHDC1 | 230055_at | unknown | other | −1.656 |
| leukemia inhibitory factor receptor alpha | LIFR | 225575_at | Plasma Membrane | transmembrane receptor | −0.941 |
| mab-21-like 2 | MAB21L2 | 210303_at | unknown | other | 2.204 |
| mesenchyme homeobox 2 | MEOX2 | 206201_s_at | Nucleus | transcription regulator | −4.213 |
| moesin | MSN | 200600_at | Plasma Membrane | other | 2.082 |
| monoamine oxidase A | MAOA | 204388_s_at | Cytoplasm | enzyme | 2.15 |
| monoamine oxidase A | MAOA | 204389_at | Cytoplasm | enzyme | 1.88 |
| monoamine oxidase A | MAOA | 212741_at | Cytoplasm | enzyme | 2.048 |
| multiple C2 domains, transmembrane 1 | MCTP1 | 220122_at | unknown | other | −1.597 |
| MYC induced nuclear antigen | MINA | 213188_s_at | Nucleus | other | 1.391 |
| MYC induced nuclear antigen | MINA | 213189_at | Nucleus | other | 1.641 |
| myosin VI | MYO6 | 203216_s_at | Cytoplasm | other | 1.104 |
| phosphatidic acid phosphatase type 2 domain containing 1A | PPAPDC1A | 236044_at | unknown | phosphatase | −2.621 |
| plastin 3 (T isoform) | PLS3 | 201215_at | Cytoplasm | other | 1.068 |
| pleiotrophin | PTN | 209466_x_at | Extracellular Space | growth factor | - 1.426 |
| pleiotrophin | PTN | 211737_x_at | Extracellular Space | growth factor | −2.929 |
| polo-like kinase 2 (Drosophila) | PLK2 | 201939_at | Nucleus | kinase | 3.606 |
| potassium large conductance calcium-activated channel, subfamily M, alpha member 1 | KCNMA1 | 221584_s_at | Plasma Membrane | ion channel | −2.389 |

TABLE 17-continued

Genes Identified using IPA Core Analysis

| Gene Name | Gene Symbol | Probe ID. No. | Location | Type | Log Ratio |
|---|---|---|---|---|---|
| RELT-like 1 | RELL1 | 226430_at | unknown | other | 1.214 |
| ring finger protein 182 | RNF182 | 230720_at | unknown | other | 2.696 |
| seizure related 6 homolog-like | SEZ6L | 207873_x_at | Plasma Membrane | other | 0.866 |
| seizure related 6 homolog (mouse)-like | SEZ6L | 211894_x_at | Plasma Membrane | other | 0.797 |
| similar to hCG2031213 | LOC728052 | 1558795_at | unknown | other | 2.239 |
| single-minded homolog 1 (Drosophila) | SIM1 | 1556300_s_at | Nucleus | transcription regulator | 6.36 |
| single-minded homolog 1 (Drosophila) | SIM1 | 206876_at | Nucleus | transcription regulator | 5.737 |
| SLIT and NTRK-like family, member 5 | SLITRK5 | 214930 at | unknown | other | 4.094 |
| SMG1 homolog, phosphatidylinositol 3-kinase-related kinase pseudogene | LOC641298 | 244766_at | unknown | other | 1.065 |
| solute carrier family 44, member 5 | SLC44A5 | 1569112_at | unknown | other | 2.738 |
| solute carrier family 44, member 5 | SLC44A5 | 235763_at | unknown | other | 1.845 |
| solute carrier family 7 (cationic amino acid transporter, y+system), member 2 | SLC7A2 | 225516_t | Plasma Membrane | transporter | 1.892 |
| solute carrier organic anion transporter family, member 3A1 | SLCO3A1 | 219229_at | Plasma Membrane | transporter | 1.622 |
| spermatogenesis associated, serine-rich 2-like | SPATS2L | 222154_s_at | unknown | other | 0.907 |
| synaptotagmin XIII | SYT13 | 226086_at | unknown | transporter | −4.754 |
| tissue factor pathway inhibitor 2 | TFPI2 | 209278_s_at | Extracellular Space | other | 2.326 |
| transcription factor 7-like 2 (T-cell specific, HMG-box) | TCF7L2 | 212761_at | Nucleus | transcription regulator | 1.005 |
| transformer 2 alpha homolog | TRA2A | 213593_s_at | Nucleus | other | 1.12 |
| transmembrane inner ear | TMIE | 1553601_a_at | unknown | other | −3.334 |
| transmembrane protein 178 | TMEM178 | 229302_at | unknown | other | 1.697 |
| U2 small nuclear RNA auxiliary factor 1 | U2AF1 | 232141_at | Nucleus | other | 0.776 |
| v-raf-1 murine leukemia viral oncogene homolog 1 | RAF1 | 1557675_at | Cytoplasm | kinase | 0.696 |
| zinc finger protein 217 | ZNF217 | 203739 at | Nucleus | transcription regulator | 1.096 |
| zinc finger protein 662 | ZNF662 | 228538 at | unknown | other | −3.352 |

The log ratio represent $log_2$ values where 0.585 is $log_2(1.5)$ which is a 1.5-fold difference, 1 is $log_2(2)$ which is a 2-fold difference, 1.584 is $log_2(3)$ which is a 3-fold difference, 2 is $log_2(4)$ which is a 4-fold difference, 2.321 is $log_2(5)$ which is a 5-fold difference, 2.584 is $log_2(6)$ which is a 6-fold difference, 2.807 is $log_2(7)$ which is a 7-fold difference, 3 is $log_2(8)$ which is a 8-fold difference, 3.169 is $log_2(9)$ which is a 9-fold difference, and 3.321 is $log_2(10)$ which is a 10-fold difference.

Example VI

Immuno-Based Method to Detect Picomolar Amounts of BoNT/A

The following example illustrates how to perform immuno-based methods of detecting BoNT/A activity that can detect picomolar amounts of the BoNT/A pharmaceutical product, such as, e.g., BOTOX® DYSPORT®/RELOXIN®, PURTOX®, XEOMIN®, NEURONOX®, or BTX-A.

1. Immuno-Based Method of Detecting BoNT/A Using ECL Sandwich ELISA.

To prepare a lysate from cells treated with a BoNT/A, approximately 150,000 cells from an established clonal cell line was plated into the wells of 96-well tissue culture poly-D-lysine plates containing 100 μL of a serum-free medium containing Minimum Essential Medium, 2 mM GlutaMAX™ I with Earle's salts, 1×B27 supplement, 1×N2 supplement, 0.1 mM Non-Essential Amino Acids, 10 mM HEPES and 60 μg/mL GT1b. The cell lines used were BB10, H1, and SiMa. These cells were incubated in a 37° C. incubator under 5% carbon dioxide until the cells differentiated, as assessed by standard and routine morphological criteria, such as growth arrest and neurite extension (approximately 3 days). The media from the differentiated cells was aspirated from each well and replaced with fresh media containing one of the following: 1) SiMa cell line, 0 (untreated), 0.98 U/mL, 1.9 U/mL, 3.91 U/mL, 7.81 U/mL, 15.6 U/mL, 31.3 U/mL, 62.5 U/mL, 125 U/mL, 250 U/mL, or 500 U/mL of a BoNT/A pharmaceutical product reconstituted in a sodium chloride free medium; 2) BB10, 0 (untreated), 0.49 U/mL, 0.98 U/mL, 1.9 U/mL, 3.91 U/mL, 7.81 U/mL, 15.6 U/mL, 31.3 U/mL, 62.5 U/mL, 125 U/mL, 250 U/mL; 3) H1, 0 (untreated), 0.3 U/mL, 1 U/mL, 3 U/mL, 9 U/mL, 28 U/mL, 83 U/mL, and 250 U/mL. Because the BoNT/A pharmaceutical product contains sodium chloride, its addition to the culture medium resulted in a hypertonic media that was detrimental to cell viability. To circumvent the hypertonicity issue, 200 μL of MEM media made without sodium chloride was used to reconstitute the BoNT/A pharmaceutical product giving a final concentration of 25 pM BoNT/A (500 U/mL). The matrix was kept constant for all concentrations along the dose-response curve by adding sodium chloride in the media used to make the dilutions match the amount of excipients present at the highest concentration used (25 pM or 500 U/mL). After a 24 hr treatment, the cells were washed, and incubated for an additional two days without toxin. To harvest the cells, 1×PBS was aspirated, the cells lysed by adding 75 μL of Lysis Buffer comprising 50 mM HEPES, 150 mM NaCl, 1.5 mM $MgCl_2$, 1 mM EGTA, 1% Triton X-100 to each well, and the plate incubated on a shaker rotating at 500 rpm for 30 minutes at 4° C. The plate was centrifuged at 4000 rpm for 20 minutes at 4° C. to pellet cellular debris and the supernatant was transferred to a capture antibody coated 96-well plate to perform the detection step.

To prepare the α-SNAP-25 capture antibody solution, the α-SNAP-25 monoclonal antibody contained in the ascites from hybridoma cell line 2E2A6 (Example VII) was purified using a standard Protein A purification protocol. To prepare the α-SNAP-25 detection antibody solution, α-SNAP-25 rabbit polyclonal antibody S9684 (Sigma, St. Louis, Mo.) was conjugated to Ruthenium(II)-tris-bipyridine-(4-methysulfonate) NHS ester labeling reagent (Meso Scale Discovery, Gaithersburg, Md.) according to the manufacturer's instructions (Meso Scale Discovery, Gaithersburg, Md.). The conjugation reaction was performed by adding 30 μL of distilled water reconstituted MSD SULFO-TAG™ stock solution to 200 μL of 2 mg/mL α-SNAP-25 polyclonal antibodies and incubating the reaction at room temperature for 2 hours in the dark. The labeled antibodies were purified using a standard spin column protocol and the protein concentration determined using a standard colorimetric protein assay. The absorbance of the α-SNAP-25 antibody/MSD SULFO-TAG™ conjugate was measured at 455 nm using a spectrophotometer to determine the concentration in moles per liter. The detection antibody solution was stored at 4° C. until needed.

To prepare the solid phase support comprising the capture antibody that is specific for a SNAP-25 cleaved product, approximately 1 μL of α-SNAP-25 monoclonal antibody 2E2A6 solution (45 μg/mL in 1×PBS, 750 μg/mL of BSA) was added to each well of a 96-well MSD High Bind plate (Meso Scale Discovery, Gaithersburg, Md.) and the solution is allowed to air dry in a biological safety cabinet for 2-3 hours in order to liquid evaporate the solution, and then the plates were sealed and stored at 4° C. until needed. The dried capture antibody-bound wells were then blocked by adding 150 μL of Blocking Buffer comprising 1×PBS, 0.05% Tween-20, 2% ECL Blocking reagent (GE Healthcare-Amersham), and 1% goat serum (Rockland Immunochemicals, Gilbertsville, Pa.) at room temperature for 2 hours with rotation at 600 rpm.

To detect the presence of a SNAP-25 cleavage product by ECL sandwich ELISA analysis, the Blocking Buffer from plates was aspirated, 25 μL of a lysate from cells treated with BoNT/A was added to each well and the plates were incubated at 4° C. for overnight. Plate wells were washed three times by aspirating the cell lysate and rinsing each well three times with 200 μL 1×PBS, 0.1% TWEEN-20® (polyoxyethylene (20) sorbitan monolaureate). After washing, 25 μl of 5 μg/mL α-SNAP-25 detection antibody solution comprising 2% Amersham Blocking Reagent in 1×PBS, 0.1% TWEEN-20® (polyoxyethylene (20) sorbitan monolaureate) was added to each well, the plate was sealed, and the sealed plate was incubated at room temperature for 1 hour with shaking. After α-SNAP-25 detection antibody incubation, the wells were washed three times with 250 μL 1×PBS, 0.1% TWEEN-20® (polyoxyethylene (20) sorbitan monolaureate). After washing 150 μL of 1× Read Buffer (Meso Scale Discovery, Gaithersburg, Md.) was added to each well and the plates were read using a SECTOR™ Imager 6000 Image Reader (Meso Scale Discovery, Gaithersburg, Md.). The raw data was then transferred to SigmaPlot v 10.0 and a 4-parameter logistics fit was used to define the dose-response curves. There were no constraints used for the 4-parameter logistic function when plotting the data. Graphical reports were generated using the following analysis: R2 (correlation coefficient), a (Max for data set), b (hillslope), and X0±SE ($EC_{50}$ value±standard error).

These results indicated that on average the cells comprising the BB10 and H1 clonal cell lines were more susceptible to BoNT/A intoxication as compared to cells comprising the parental SiMa cell line. Cells from a BB10 cell line exhibited an $EC_{50}$ for BoNT/A activity of 7 U/mL, cells from a H1 cell line exhibited an $EC_{50}$ for BoNT/A activity of 8 U/mL, and cells from the parental SiMa cell line exhibited an $EC_{50}$ for BoNT/A activity of 13 U/mL. This method can also be performed in a multiplex fashion as described in Ester Fernandez-Salas, et al., Immuno-Based Botulinum Toxin Serotype A Activity Assays, U.S. patent application Ser. No. 12/403,531, which is hereby incorporated by reference in its entirety.

Example VII

Transfection of BoNT/A Receptor DNA into Sensitive Clonal Cell Lines Further Improves Sensitivity of the Clonal Cell Line for BoNT/A The following example illustrates how to introduce a polynucleotide molecule encoding a BoNT/A receptor into cells from a clonal cell line to further improve susceptibility to BoNT/A intoxication or improve BoNT/A uptake capacity.

To introduce an exogenous BoNT/A receptor into cells comprising an established clonal cell line, a mammalian expression construct comprising a polynucleotide molecule of SEQ ID NO: 139 encoding the FGFR3 of SEQ ID NO: 25, was transfected into cells from a H1 clonal cell line by a cationic lipid method. A suitable density (about $5\times10^6$ cells) of cells from an established clonal cell line are plated in a 100 mm tissue culture dish containing 5 mL of complete culture media and grown in a 37° C. incubator under 5% carbon dioxide until the cells reached a density appropriate for transfection. A 3 mL transfection solution is prepared by adding 1.5 mL of OPTI-MEM® Reduced Serum Medium containing 60 μL of LIPOFECTAMINE® 2000 (Invitrogen, Carlsbad, Calif.) incubated at room temperature for 5 minutes to 1.5 mL of OPTI-MEM® Reduced Serum Medium containing 24 μg of an expression construct encoding the FGFR3 of SEQ ID NO: 25. This transfection mixture is incubated at room temperature for approximately 30 minutes. The complete media on the cells is replaced with the 3 mL transfection solution and the cells are incubated in a 37° C. incubator under 5% carbon dioxide for approximately 8 hours. Transfection media is replaced with 3 mL of fresh complete culture media and the cells are incubated in a 37° C. incubator under 5% carbon dioxide for approximately 24 hours. Media is replaced with 3 mL of fresh complete culture media containing approximately 1 mM G418 (Invitrogen, Carlsbad, Calif.) for selection of transfected cells. Cells are incubated in a 37° C. incubator under 5% carbon dioxide for approximately 1 week, the old media is replaced with fresh complete culture media containing 0.5 mM G418 and the cells are plated onto one 96-well collagen IV coated plate at a plating density of 0.5 cells per well. Cell growth and viability was monitored by microscopic examination and after about 3 weeks single clones appeared in about 20% of the wells. These clones were grown for an additional 2 weeks and then transferred to duplicate 24-well collagen IV coated plates, one to maintain the clonal cell line and the other to test for BoNT/A susceptibility.

To determine the susceptibility of the cells comprising the clonal cell lines overexpressing a BoNT/A receptor, a Western blot analysis was done to determine sensitivity and an ECL sandwich ELISA was done to determine an $EC_{50}$ value. A total of eight clones were tested for the FGFR3 stably transfected H1 cells.

To prepare a cell lysate for the Western blot analysis, cells from the clonal cell line were plated into two wells in a poly-D-lysine coated 96-well plate in serum-free medium containing Minimum Essential Medium, 2 mM GLUTAMAX™ I with Earle's salts, 1×B27 supplement, 1×N2 supplement, 0.1 mM Non-Essential Amino Acids, 10 mM HEPES and 25 μg/mL GT1b (Alexis Biochemicals, Lausen, Switzerland). These cells were incubated in a 37° C. incubator under 5% carbon dioxide until the cells differentiated, as assessed by standard and routine morphological criteria, such as growth arrest and neurite extension (approximately 3 days). The media from the differentiated cells was aspirated from each well and replaced with fresh media containing either 0 (untreated), 0.5 nM or 0.25 nM of a BoNT/A complex. After a 6 hr treatment, the cells were washed, and incubated for an additional 18 hr without toxin. After the incubation, the cells were washed by aspirating the growth media and rinsing each well with 200 μl of 1×PBS. To harvest the cells, the 1×PBS was aspirated, the cells were lysed by adding 40 μL of 2×SDS Loading Buffer and the plate was swirled for an even coating of Loading Buffer. The lysate was transferred to a new 96-well PCR plate (Axygen, Union City, Calif.) and the plate was heated to 95° C. for 5 min to complete cell lysis and denature proteins.

To detect for the presence of both uncleaved SNAP-25 substrate and cleaved SNAP-25 products, an aliquot from each harvested sample was analyzed by Western blot. In this analysis, a 12 μL aliquot of the harvested sample was separated by MOPS polyacrylamide gel electrophoresis using NUPAGE® Novex 12% Bis-Tris precast polyacrylamide gels (Invitrogen Inc., Carlsbad, Calif.) under denaturing, reducing conditions. Separated proteins were transferred from the gel onto nitrocellulose membranes (Bio-Rad Laboratories, Hercules, Calif.) by Western blotting using a "Transfer +4 cassettes & Cooler" transfer chamber (GE Healthcare, Piscataway, N.J.). Membranes were blocked by incubating at room temperature for 1 hr with gentle agitation in a solution containing Tris-Buffered Saline (TBS) (25 mM 2-amino-2-hydroxymethyl-1,3-propanediol hydrochloric acid (Tris-HCl) (pH 7.4), 137 mM sodium chloride, 2.7 mM potassium chloride), 0.1% TWEEN-20® (polyoxyethylene (20) sorbitan monolaureate), 2% Bovine Serum Albumin (BSA), 5% nonfat dry milk. Blocked membranes were incubated at 4° C. for overnight in TBS, 0.1% TWEEN-20® (polyoxyethylene (20) sorbitan monolaureate), 2% BSA, and 5% nonfat dry milk containing a 1:5,000 dilution of α-SNAP-25 rabbit polyclonal antiserum S9684 (Sigma, St. Louis, Mo.) as the primary antibody. The α-SNAP-25 rabbit polyclonal antibodies can detect both the uncleaved SNAP-25 substrate and the SNAP-25 cleavage product, allowing for the assessment of overall SNAP-25 expression in each cell line and the percent of SNAP-25 cleaved after BoNT/A treatment as a parameter to assess the amount of BoNT/A uptake. Primary antibody probed blots were washed three times for 5 minutes each time in TBS, TWEEN-20® (polyoxyethylene (20) sorbitan monolaureate). Washed membranes were incubated at room temperature for 2 hours in TBS, 0.1% TWEEN-20® (polyoxyethylene (20) sorbitan monolaureate), 2% BSA, and 5% nonfat dry milk containing a 1:10,000 dilution of goat polyclonal anti-rabbit immunoglobulin G, heavy and light chains (IgG, H+L) antibody conjugated to horseradish peroxidase (Invitrogen, Inc., Carlsbad, Calif.) as a secondary antibody. Secondary antibody-probed blots were washed five times for 5 minutes each time in TBS, 0.1% TWEEN-20® (polyoxyethylene (20) sorbitan monolaureate). Signal detection of the labeled SNAP-25 products were visualized using the ECL Plus™ Western Blot Detection System (GE Healthcare, Amersham Biosciences, Piscataway, N.J.) and the membrane was imaged and the percent of cleaved SNAP-25 products quantified with a Typhoon 9410 Variable Mode Imager and Imager Analysis software (GE Healthcare, Amersham Biosciences, Piscataway, N.J.). The choice of pixel size (100 to 200 pixels) and PMT voltage settings (350 to 600, normally 400) depended on the individual blot. The volumes of the bands corresponding to either intact and cleaved SNAP-25 product were quantified using Image Quant TL and the total amount of SNAP-25 and the percentage of SNAP-25 cleaved were calculated based on the intensity of these two SNAP-25 bands.

Clone H1 1.4 had a high percentage of SNAP-25 cleavage and high levels of total SNAP25 and was selected for further testing. The selected clone was first grown on a 10 $cm^2$ dish and then in T175 flasks to ensure that enough cells were produced for both ECL sandwich ELISA assay and for freezing stocks. Frozen stocks were made with $1\times10^6$ cells and 1 mL of Recovery Cell Culture Freezing Media (GIBCO-Invitrogen, #12648-010 Freezing media).

To prepare a cell lysate for the ECL sandwich ELISA, approximately 50,000 cells from H1 clonal cell line and from H1 1.4 clonal cell line overexpressing FGFR3 were plated and differentiated as described above. The media from the differentiated cells was aspirated from each well and replaced with fresh media containing either (untreated), 0.27 pM, 0.82 pM, 2.47 pM, 7.4 pM, 22.2 pM, 66.6 pM, or 200 pM of a BoNT/A complex of a BoNT/A complex. After a 6 hr treatment, the cells were washed, and incubated overnight without toxin. After a 24 hr treatment, the cells were washed by aspirating the BoNT/A containing media and rinsing each well with 200 μL of 1×PBS. Washed cells were harvested by lysing in freshly prepared Triton X-100 Lysis Buffer (150 mM NaCl, 20 mM Tris-HCl (pH 7.5), 1 mM EDTA, 1 mM EGTA, 1% Triton X-100 plus protease inhibitors) at 4° C. for 30 minutes with constant agitation. Lysed cells were centrifuged at 4000 rpm for 20 min at 4° C. to pellet debris.

The α-SNAP-25 capture antibody solution, the α-SNAP-25 detection antibody solution, and the solid phase support comprising the capture antibody that is specific for a SNAP-25 cleaved product were prepared as described in Example V. To detect the presence of a cleaved SNAP-25 product by ECL sandwich ELISA, the plates were processed, and the data collected and analyzed, and the $EC_{50}$ calculated as described in Example VI. The $EC_{50}$ for H1 1.4 cells was estimated to about 1.7 pM, compared to an $EC_{50}$ about 8.7 pM for H1 cells indicating that the newly generated H1 1.4 cell line is about 5 times more sensitive than the H1 cell line for BoNT/A uptake (average of two independent experiments with similar results). The maximum signal for both cell lines was identical indicating similar efficacy towards SNAP25 cleavage. The increase in sensitivity is especially prominent at lower concentrations of BoNT/A, where the H1 1.4 cells are many times more sensitive to BoNT/A compared to H1 cells producing a very robust signal over background at the 0.27 pM concentration. Over-expression of FGFR3 was verified in a Western blot using α-FGFR3 antibodies sc-123 (Santa Cruz Biotechnologies, Santa Cruz, Calif.).

Example VIII

Development of α-SNAP-25 Monoclonal Antibodies that Selectively Bind a SNAP-25 Epitope Having a Free Carboxyl-Terminus at the $P_1$ Residue of the BoNT/A Cleavage Site Scissile Bond The following example illustrates how to make α-SNAP-25 monoclonal antibodies that can selectively bind to a SNAP-25 epitope having a carboxyl-terminus at the $P_1$ residue of the BoNT/A cleavage site scissile bond.

1. Generation of α-SNAP-25 Monoclonal Antibodies.

α-SNAP-25 monoclonal antibodies with higher binding affinity for a SNAP-25 cleavage product and/or α-SNAP-25 antibodies with a higher binding specificity for a SNAP-25 cleavage product were developed. In addition, because a permanent, stable and renewable source of α-SNAP-25 antibodies is preferable for an FDA-approved assay, screens to isolate monoclonal antibodies were undertaken. To develop monoclonal α-SNAP-25 antibodies the 13-residue peptide $CDSNKTRIDEANQ_{COOH}$ (SEQ ID NO: 38) was designed as a SNAP-25 antigen having a carboxyl-terminus at the $P_1$ residue of the BoNT/A cleavage site scissile bond. This peptide comprises a flexible linker region and a N-terminal Cysteine residue for conjugation to KLH and amino acids 186-197 of human SNAP-25 (SEQ ID NO: 5) with a carboxylated C-terminal glutamine (SEQ ID NO: 38). The generation of monoclonal antibodies to well-chosen, unique peptide sequences provides control over epitope specificity, allowing the identification of a particular subpopulation of protein among a pool of closely related isoforms. Blast searches revealed that this peptide has high homology only to SNAP-25 and almost no possible cross-reactivity with other proteins in neuronal cells. The sequence was also carefully scrutinized by utilizing computer algorithms to determine hydropathy index, protein surface probability, regions of flexibility, and favorable secondary structure, followed by proper orientation and presentation of the chosen peptide sequence. The peptide was synthesized and conjugated to Keyhole Limpet Hemocyanin (KLH) to increase immunogenicity. Six Balb/c mice were immunized with this peptide, and after three immunizations in about eight weeks, the mice were bled for testing. The blood was allowed to clot by incubating at 4° C. for 60 minutes. The clotted blood was centrifuged at 10,000×g at 4° C. for 10 minutes to pellet the cellular debris. The resulting serum sample was dispensed into 50 μL aliquots and stored at −20° C. until needed.

A similar strategy based on other SNAP-25 antigens disclosed in the present specification is used to develop α-SNAP-25 monoclonal antibodies that can selectively bind to a SNAP-25 having a carboxyl-terminus at the $P_1$ residue of the BoNT/A cleavage site scissile bond. For example, the SNAP-25 antigen of SEQ ID NO: 45 can be conjugated to KLH instead of the SNAP-25 antigen of SEQ ID NO: 38. As another example, the amino acids 186-197 of human SNAP-25 from the SNAP-25 antigen of SEQ ID NO: 38 can be replaced with SEQ ID NO: 32, SEQ ID NO: 33, SEQ ID NO: 34, SEQ ID NO: 35, SEQ ID NO: 36, SEQ ID NO: 39, SEQ ID NO: 40, SEQ ID NO: 41, SEQ ID NO: 42, SEQ ID NO: 43, SEQ ID NO: 44, SEQ ID NO: 147, or SEQ ID NO: 148.

2. Screening for the Presence of α-SNAP-25 Monoclonal Antibodies.

To determine the presence of an α-SNAP-25 monoclonal antibody that can selectively bind to a SNAP-25 antigen having a carboxyl-terminus at the $P_1$ residue of the BoNT/A cleavage site scissile bond, comparative ELISA and cell-based cleavage assay were performed using the extracted mouse serum. For comparative ELISA, two fusion proteins were constructed: BIRA-HIS TAG®-SNAP-$25_{134-197}$ of SEQ ID NO: 48 and the BIRA-HIS TAG®-SNAP-$25_{134-206}$ of SEQ ID NO: 49. BIRA-HIS TAG®-SNAP-$25_{134-197}$ comprised a naturally-biotinylated 16 amino acid BirA peptide of SEQ ID NO: 50 amino-terminally linked to a SNAP-25 peptide comprising amino acids 134-197 of SEQ ID NO: 5. BIRA-HIS TAG®-SNAP-$25_{134-206}$ comprised a naturally-biotinylated 16 amino acid BirA peptide of SEQ ID NO: 50 amino-terminally linked to a SNAP-25 peptide comprising amino acids 134-206 of SEQ ID NO: 5. These two substrates were suspended in 1×PBS at a concentration of 10 μg/mL BIRA-HIS TAG®-SNAP-$25_{134-197}$ and the BIRA-HIS TAG®-SNAP-$25_{134-206}$. The BIRA-HIS TAG®-SNAP-$25_{134-197}$ and the BIRA-HIS TAG®-SNAP-$25_{134-206}$ were coated onto separate plates by adding approximately 100 μl of the appropriate Substrate Solution and incubating the plates at room temperature for one hour. Washed plates were incubated at 37° C. for one hour in 0.5% BSA in 1×TBS containing a 1:10 to 1:100 dilution of an antibody-containing serum derived from one of the six immunized mice (Mouse 1, Mouse 2, Mouse 3, Mouse 4, Mouse 5, and Mouse 6). Primary antibody probed plates were washed four times for 5 minutes each time in 200 μl TBS, 0.1% TWEEN-20® (polyoxyethylene (20) sorbitan monolaureate). Washed plates were incubated at 37° C. for 1 hour in 1×TBS containing a 1:10,000 dilution of goat polyclonal anti-mouse IgG antibody conjugated to Horseradish peroxidase (Pierce Biotechnology, Rockford, Ill.) as a secondary antibody. Secondary antibody-probed plates were washed four times in 200 μl TBS, 0.1% TWEEN-20® (polyoxyethylene (20) sorbitan monolaureate). Chromogenic detection of the labeled SNAP-25 products were visualized by chromogenic detection using ImmunoPure TMB substrate kit (Pierce Biotechnology, Rockford, Ill.). The development of a yellow color in the BIRA-HIS TAG®-SNAP-$25_{134-197}$ coated plates, but not the BIRA-HIS TAG®-SNAP-$25_{134-206}$ coated plates, indicated that the α-SNAP-25 antibody preferentially recognized the SNAP-$25_{197}$ cleavage product. The resulted indicated that of the six mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

These results were confirmed using an ELISA light chain activity assay. A 96-well Reacti-Bind Streptavidin coated plates (Pierce Biotechnology, Rockford, Ill.) were prepared by adding approximately 100 μl of the following Substrate Solution: Rows A-C were coated with 100 μL of BIRA-HIS TAG®-SNAP-$25_{134-197}$ at twelve different concentrations; Rows D-H were coated with 100 μL of BIRA-HIS TAG®-SNAP-$25_{134-206}$ at 10 μg/mL. The plates were washed by aspirating the Substrate Solution and rinsing each well three times with 200 μl TBS, 0.1% TWEEN-20® (polyoxyethylene (20) sorbitan monolaureate). Dilutions of BoNT/A were pre-reduced at 37° C. for 20 minutes in BoNT/A Incubation Buffer (50 mM HEPES, pH 7.4, 1% fetal bovine serum, 10 pM $ZnCl_2$, 10 mM dithiothrietol) and 100 μl of the pre-reduced BoNT/A was added to the substrate-coated plates and incubated at 37° C. for 90 minutes. BoNT/A treated plates were washed by aspirating the BoNT/A Incubation Buffer and rinsing each plate three times with 200 μl TBS, 0.1% TWEEN-20® (polyoxyethylene (20) sorbitan monolaureate). Washed plates were incubated at 37° C. for one hour in 0.5% BSA in 1×TBS containing a 1:10 to 1:100 dilution of the antibody-containing serum being tested. Primary antibody probed plates were washed four times for 5 minutes each time in 200 μl TBS, 0.1% TWEEN-20® (polyoxyethylene (20) sorbitan monolaureate). Washed plates were incubated at 37° C. for 1 hour in 1×TBS containing a 1:10,000 dilution of goat polyclonal anti-mouse IgG antibody conjugated to Horseradish peroxidase (Pierce Biotechnology, Rockford, Ill.) as a secondary antibody. Secondary antibody-probed plates were washed four times in 200 μl TBS, 0.1% TWEEN-20® (polyoxyethylene (20) sorbitan monolaureate). Chromogenic detection of the labeled SNAP-25 products were visualized by chromogenic detection using ImmunoPure TMB substrate kit (Pierce Biotechnology, Rockford, Ill.). The development of a yellow color, which correlated with the presence of the SNAP-$25_{197}$ cleavage product was detected in BoNT/A treated samples, but not untreated controls, using antibody-containing serum derived from all six immunized mice (Mouse 1, Mouse 2, Mouse 3, Mouse 4, Mouse 5, and Mouse 6). Thus, the comparative ELISA analysis indicated that of the mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

For cell-based cleavage assay, a suitable density of PC12 cells were plated into 60 $mm^2$ tissue culture plates containing 3 mL of an appropriate serum medium (Table 1). The cells were grown in a 37° C. incubator under 5% carbon dioxide until cells reached the appropriate density. A 500 μL transfection solution was prepared by adding 250 μL of OPTI-MEM® Reduced Serum Medium containing 15 μL of LIPOFECTAINE® 2000 (Invitrogen Inc., Carlsbad, Calif.) incubated at room temperature for 5 minutes to 250 μL of OPTI-MEM® Reduced Serum Medium containing 10 μg of a pQBI-25/GFP-BoNT/A-LC expression construct (SEQ ID NO: 51). The pQBI-25/GFP-BoNT/A-LC expression construct comprises a pQBI-25 expression vector (Qbiogene Inc., Carlsbad, Calif.) whose promoter elements are functionally linked to a polynucleotide encoding the GFP-BoNT/A light chain of SEQ ID NO: 52. This transfection mixture was incubated at room temperature for approximately 20 minutes. The media was replaced with fresh unsupplemented media and the 500 μL transfection solution was added to the cells. The cells were then incubated in a 37° C. incubator under 5% carbon dioxide for approximately 6 to 18 hours. The cells were washed and harvested as described in Example II. To detect for the presence of the cleaved SNAP-$25_{197}$ product, an aliquot from each harvested sample was analyzed by Western blot as described in Example II, except that the primary antibody used was a 1:1,000 dilution of the antibody-containing serum and the secondary antibody used was a 1:20,000 of mouse α-IgG Horseradish Peroxidase (Pierce Biotechnology, Rockford, Ill.). A single band corresponding to the SNAP-$25_{197}$ cleavage product was detected in BoNT/A treated samples, but not untreated controls, using antibody-containing serum derived from three mice (Mouse 2, Mouse 3, and Mouse 4). Thus, the cell-based cleavage assay indicated that of the mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

3. Production of Hybridomas.

To make hybridomas producing α-SNAP-25 monoclonal antibodies that can selectively bind to a SNAP-25 antigen having a carboxyl-terminus at the $P_1$ residue of the BoNT/A cleavage site scissile bond, the spleen from Mouse 2 was harvested three days subsequent to a final "booster" immunization and the spleen cells were fused with myeloma cells P3-X63 Ag8.653 using standard hybridoma protocols. These cells were plated into five 96-well plates and hybrids were selected using HAT medium. Within 8-14 days after fusion, the first screening of the approximately 480 parent clones was carried out using comparative ELISA with the BIRA-HIS TAG®-SNAP-$25_{134-197}$ and the BIRA-HIS TAG®-SNAP-$25_{134-206}$ peptides coated in two separate plates. The comparative ELISA provided a quick screen method to identify hybridomas producing antibodies specific for the cleaved SNAP-$25_{197}$. The top 18 clones were subjected to further screening using the cell-based cleavage assay described above and immunostaining of LC/A transfected cells. (Table 18).

TABLE 18

Analysis of Supernatants Containing α-SNAP-25 Monoclonal Antibody

| | Comparative ELISA | | | | Cell-Based Assay | |
|---|---|---|---|---|---|---|
| Clone | OD SNAP-$25_{197}$ | OD SNAP-$25_{206}$ | $Ratio_{197/206}$ | $Ratio_{206/197}$ | SNAP-$25_{197}$ | SNAP-$25_{206}$ |
| 1D3 | 1.805 | 0.225 | 8.02 | 0.13 | +++ | – |
| 1F12 | 0.365 | 0.093 | 3.92 | 0.25 | – | – |
| 1G10 | 0.590 | 0.137 | 4.31 | 0.23 | ++ | – |
| 1H1 | 0.335 | 0.121 | 2.77 | 0.36 | – | – |
| 1H8 | 0.310 | 0.302 | 1.03 | 0.97 | + | – |
| 2C9 | 0.139 | 0.274 | 0.51 | 1.97 | – | – |
| 2E2 | 0.892 | 0.036 | 24.78 | 0.04 | ++ | – |
| 2E4 | 0.228 | 0.069 | 3.30 | 0.30 | + | – |
| 2F11 | 1.095 | 1.781 | 0.61 | 1.63 | – | – |
| 3C1 | 1.268 | 0.053 | 23.92 | 0.04 | ++ | – |
| 3C3 | 0.809 | 0.052 | 15.56 | 0.06 | ++ | – |
| 3E1 | 0.086 | 0.155 | 0.55 | 1.80 | 0 | – |
| 3E8 | 2.048 | 0.053 | 38.64 | 0.03 | +++ | – |
| 3G2 | 0.053 | 0.158 | 0.34 | 2.98 | – | – |
| 4D1 | 0.106 | 0.218 | 0.49 | 2.06 | – | – |
| 4G6 | 0.061 | 0.159 | 0.38 | 2.61 | – | – |
| 5A5 | 0.251 | 0.106 | 2.37 | 0.42 | + | – |
| 5F11 | 0.243 | 0.061 | 3.98 | 0.25 | – | – |

Clones 1D3, 1G10, 2E2, 3C1, 3C3, and 3E8 were further cloned by limiting dilution because the conditioned media produced by these clones comprised α-SNAP-25 antibodies with a preferential binding specificity having a $ratio_{197/206}$ of at least 4:1 for the SNAP-$25_{197}$ cleavage product relative to the SNAP-$25_{206}$ uncleaved substrate and detected the SNAP-$25_{197}$-cleavage product using the cell-based cleavage assay and the immunostaining of PC12 cells transfected with GFP-LC/A. Similarly clones 2C9, 2F11, 3G2, 4D1 and 4G6 were further cloned by limiting dilution because the conditioned media produced by these clones comprised α-SNAP-25 antibodies with a preferential binding specificity having a $ratio_{206/197}$ of at least 1.5:1 for the SNAP-$25_{206}$ uncleaved substrate relative to the SNAP-$25_{197}$ cleavage product and detected the SNAP-$25_{206}$-uncleaved substrate using the cell-based cleavage assay. These single-cell derived clones were screened again using comparative ELISA, cell-based cleavage, and immunostaining to confirm their affinity and specificity, and the antibodies were isotyped using standard procedures. Ascites were produced from clones 1D3B8 (IgM.k), 1G10A12 (IgG3.k), 2C9B10 (IgG3.k), 2E2A6 (IgG3.k), 2F11B6 (IgM.k), 3C1A5 (IgG2a.k), and 3C3E2 (IgG2a.k). Clone 3E8 stopped producing antibodies during the cloning process and could not be further evaluated.

4. Evaluation of Binding Specificity of α-SNAP-25 Monoclonal Antibodies.

To evaluate binding specificity of an α-SNAP-25 monoclonal antibody that can selectively bind to a SNAP-25 antigen having a carboxyl-terminus at the $P_1$ residue of the BoNT/A cleavage site scissile bond, ascites from clones 1D3B8, 1G10A12, 2C9B10, 2E2A6, 2F11B6, 3C1A5, and 3C3E2 were used to detect SNAP-25 cleavage product using the cell-based activity assay, immunocytochemistry and immunoprecipitation.

For the cell-based activity assay, binding specificity was determined by analyzing the ability of α-SNAP-25 antibody-containing ascites to detect the uncleaved SNAP-$25_{206}$ substrate and the cleaved SNAP-$25_{197}$ product by Western blot analysis. A suitable density of PC12 cells were plated into 60 $mm^2$ tissue culture plates containing 3 mL of an appropriate serum medium, grown in a 37° C. incubator under 5% carbon dioxide until an appropriate cell density was reached, and transfected with the either a transfection solution lacking the pQBI-25/GFP-BoNT/A-LC expression construct (untransfected cells) or a transfection solution containing the pQBI-25/GFP-BoNT/A-LC expression construct (transfected cells) as described above. The cells were washed and harvested as described in Example I. To detect for the presence of both the uncleaved SNAP-$25_{206}$ substrate and the cleaved SNAP-$25_{197}$ product, an aliquot from each harvested sample was analyzed by Western blot as described in Example I, except that the primary antibody used was a 1:100 dilution of the α-SNAP-25 monoclonal antibody-containing ascites and the secondary antibody used was a 1:20,000 of α-mouse IgG conjugated to Horseradish Peroxidase (Pierce Biotechnology, Rockford, Ill.). In addition, three commercially available mouse α-SNAP-25 monoclonal antibodies were tested. SMI-81 (Sternberger Monoclonals Inc., Lutherville, Md.), an α-SNAP-25 antibody the manufacturer indicates detects both the uncleaved SNAP-$25_{206}$ substrate and the cleaved SNAP-$25_{197}$ product, was used at a 15,000 dilution according to the manufacturer's recommendations. MC-6050 (Research & Diagnostic Antibodies, Las Vegas, Nev.), an α-SNAP-25 antibody the manufacturer indicates detects both the uncleaved SNAP-$25_{206}$ substrate and the cleaved SNAP-$25_{197}$ product, was used at a 1:100 dilution according to the manufacturer's recommendations. MC-6053 (Research & Diagnostic Antibodies, Las Vegas, Nev.), an α-SNAP-25 antibody the manufacturer indicates detects only the cleaved SNAP-$25_{197}$ product, was used at a 1:100 dilution according to the manufacturer's recommendations.

Table 19 indicates the α-SNAP-25 antibody-containing ascites that detected only the SNAP-$25_{197}$ cleavage product. The cell-based cleavage assay indicated that ascites produced from clones 1D3B8, 2C9B10, 2E2A6, 3C1A5, and 3C3E2 synthesize an α-SNAP-25 monoclonal antibody having high binding specificity for the SNAP-$25_{197}$ cleavage product that allows for the selective recognition of this cleavage product relative to the SNAP-$25_{206}$ uncleaved substrate. Commercial antibody SMI-81 detected the SNAP-$25_{206}$ uncleaved substrate, but only poorly recognized the SNAP-$25_{197}$ cleavage product (Table 19). Surprisingly, commercial antibody MC-6050 only detected the SNAP-$25_{206}$ uncleaved substrate, and failed to recognize the SNAP-$25_{197}$ cleavage product (Table 19). Even more surprisingly, commercial antibody MC-6050 only detected the SNAP-$25_{206}$ uncleaved substrate, and failed to recognize the SNAP-$25_{197}$ cleavage product, even though the manufacturer advertises that this antibody selectively detects the SNAP-$25_{197}$ cleavage product (Table 19). Thus, this analysis indicates that while 1D3B8, 2C9B10, 2E2A6, 3C1A5, and 3C3E2 exhibit suitable selectivity for the SNAP-$25_{197}$ cleavage product, 1G10A12 and 2F11B6 do not. In addition, commercial antibodies SMI-81, MC-6050 and MC-6053 all are unsuitable for the immuno-based methods disclosed in the present application because all failed to selectivity detect the SNAP-$25_{197}$ cleavage product.

For immunocytochemistry analysis, binding specificity was determined by analyzing the ability of α-SNAP-25 antibody-containing ascites to detect the uncleaved SNAP-$25_{206}$ substrate and the cleaved SNAP-$25_{197}$ product by immunostaining. See e.g., Ester Fernandez-Salas et al., *Plasma Membrane Localization Signals in the Light Chain of Botulinum Neurotoxin*, Proc. Natl. Acad. Sci., U.S.A. 101(9): 3208-3213 (2004). A suitable density of PC12 cells were plated, grown, and transfected with either a transfection solution lacking the pQBI-25/GFP-BoNT/A-LC expression construct (untransfected cells) or a transfection solution containing the pQBI-25/GFP-BoNT/A-LC expression construct (transfected cells) as described above. The cells were washed in 1×PBS and fixed in 5 mL of PAF at room temperature for 30 minutes. Fixed cells were washed in phosphate buffered saline, incubated in 5 mL of 0.5% Triton® X-100 (polyethylene glycol octylphenol ether) in 1×PBS, washed in 1×PBS, and permeabilized in 5 mL of methanol at −20° C. for six minutes. Permeabilized cells were blocked in 5 mL of 100 mM glycine at room temperature for 30 minutes, washed in 1×PBS, and blocked in 5 mL of 0.5% BSA in 1×PBS at room temperature for 30 minutes. Blocked cells were washed in 1×PBS and incubated at room temperature for two hours in 0.5% BSA in 1×PBS containing a 1:10 dilution of an ascites from a clonal hybridoma cell line being tested. Primary antibody probed cells were washed three times for 5 minutes each time in 1×PBS. Washed cells were incubated at room temperature for 2 hours in 1×PBS containing a 1:200 dilution of goat polyclonal anti-mouse immunoglobulin G, heavy and light chains (IgG, H+L) antibody conjugated to ALEXA® FLUOR 568 (Invitrogen Inc., Carlsbad, Calif.) as a secondary antibody. Secondary antibody-probed cells were washed three times for 5 minutes each time in 1×PBS. Washed cells were prepared for microscopic examination by mounting in VECTASHIELD® Mounting Media (Vector Laboratories, Burlingame, Calif.) and coverslipped. Images of signal detection were obtained with a Leica confocal microscope using appropriate laser settings. Table 19 indicates that the α-SNAP-25 antibody-containing ascites that specifically detected the SNAP-$25_{197}$-cleavage product. The immunocytochemistry analysis indicated that ascites produced from clones 1D3B8, 2C9B10, 2E2A6, 3C1A5, and 3C3E2 synthesize an α-SNAP-25 monoclonal antibody having high binding specificity for the SNAP-$25_{197}$ cleavage product that allows for the preferential recognition of this cleavage product relative to the SNAP-$25_{206}$ uncleaved substrate.

For immunoprecipitation analysis, binding specificity was determined by analyzing the ability of Protein A (HiTrap™ Protein A HP Columns, GE Healthcare, Amersham, Piscataway, N.J.), purified α-SNAP-25 monoclonal antibodies to precipitate the uncleaved SNAP-$25_{206}$ substrate and the cleaved SNAP-$25_{197}$ product. See e.g., Chapter 8 *Storing and Purifying Antibodies*, pp. 309-311, Harlow & Lane, supra, 1998a. A suitable density of PC12 cells were plated, grown, and transfected with either a transfection solution containing a pQBI-25/GFP expression construct (control cells; SEQ ID NO: 53) or a transfection solution containing the pQBI-25/GFP-BoNT/A-LC expression construct (experimental cells) as described above. The pQBI-25/GFP expression construct comprises an expression vector whose promoter elements are functionally linked to a polynucleotide encoding GFP of SEQ ID NO: 54. After an overnight incubation, the cells were washed by aspirating the growth media and rinsing each well with 200 μL 1×PBS. To harvest the cells, the PBS was aspirated, the cells were lysed by adding an Immunoprecipitation Lysis Buffer comprising 50 mM HEPES, 150 mM NaCl, 1.5 mM $MgCl_2$, 1 mM EGDT, 10% glycerol, 1% Triton® X-100 (polyethylene glycol octylphenol ether) and a 1× COMPLETE™ Protease inhibitor cocktail (Roche Applied Biosciences, Indianapolis, Ind.) and incubating at 4° C. for one hour. The lysed cells were centrifuged at 3,000×g at 4° C. for 10 minutes to remove cellular debris and the supernatant transferred to a clean tube and diluted to a protein concentration of approximately 1 mg/mL. Approximately 5 μg of purified monoclonal antibody was added to 0.5 mL of diluted supernatant and incubated at 4° C. for two hours. After primary antibody incubation, approximately 50 μl of immobilized Protein G (Pierce Biotechnology, Rockford, Ill.) was added to the diluted supernatant and incubated at 4° C. for one hour. The incubated supernatant was washed three times for 30 minutes each time by adding 0.5 mL of Immunoprecipitation Lysis Buffer, centrifuging at 300×g at 4° C. for one minute to pellet the immobilized Protein G, and decanting the supernatant. After washing, the pellet was resuspended in 30 μL of 1×SDS Loading Buffer and the sample was heated to 95° C. for 5 minutes. To detect for the presence of both the uncleaved SNAP-$25_{206}$ substrate and the cleaved SNAP-$25_{197}$ product, an aliquot from each harvested sample was analyzed by Western blot as described in Example I, except that the primary antibody used was a 1:1,000 dilution of the α-SNAP-25 polyclonal antibody serum (see Example IV) and the secondary antibody used was a 1:20,000 of rabbit α-IgG Horseradish Peroxidase (Pierce Biotechnology, Rockford, Ill.). Table 19 indicates the α-SNAP-25 antibody-containing ascites that specifically pulled down the SNAP-$25_{197}$-cleavage product by immunoprecipitation analysis. The immunoprecipitation analysis indicated that ascites produced from clones 2E2A6 and 3C1A5 synthesize an α-SNAP-25 monoclonal antibody having high binding specificity for the SNAP-$25_{197}$ cleavage product that allows for the preferential recognition of this cleavage product relative to the SNAP-$25_{206}$ uncleaved substrate.

TABLE 19

Analysis of Clone Ascites Containing α-SNAP-25 Monoclonal Antibody

| Clone | Cell-Based Assay | | Immunocytochemistry | | Immunoprecipitation | |
|---|---|---|---|---|---|---|
| | SNAP-$25_{197}$ | SNAP-$25_{206}$ | SNAP-$25_{197}$ | SNAP-$25_{206}$ | SNAP-$25_{197}$ | SNAP-$25_{206}$ |
| 1D3B8 | ++ | − | ++ | − | Not Tested | Not Tested |
| 1G10A12 | ++ | ++ | Not Tested | Not Tested | Not Tested | Not Tested |
| 2C9B10 | ++ | − | ++ | − | Not Tested | Not Tested |
| 2E2A6 | ++ | − | ++ | − | ++ | − |
| 2F11B6 | + | + | + | + | Not Tested | Not Tested |
| 3C1A5 | ++ | − | ++ | − | ++ | − |
| 3C3E2 | + | − | Not Tested | Not Tested | Not Tested | Not Tested |
| MC-6050 | − | + | Not Tested | Not Tested | Not Tested | Not Tested |
| MC-6053 | − | + | Not Tested | Not Tested | Not Tested | Not Tested |
| SMI-81 | −/+ | ++ | Not Tested | Not Tested | Not Tested | Not Tested |

5. Evaluation of Binding Affinity of α-SNAP-25 Monoclonal Antibodies.

To determine the binding affinity of an α-SNAP-25 monoclonal antibody showing high binding specificity for either the SNAP-$25_{197}$ cleavage product or the SNAP-$25_{206}$ uncleaved substrate, binding affinity assays were performed on a BIACORE 3000 instrument using carboxymethyl dextran (CM5) sensor chips (BIAcore, Inc., Piscataway, N.J.). Runs were conducted at 25° C. with HBS-EP buffer comprising 10 mM HEPES (pH 7.4), 150 mM sodium chloride, 3 mM EDTA, 0.005% (v/v) surfactant P20 at a flow rate of 10 μl/min. SNAP-25 peptides comprising amino acids 134-197 of SEQ ID NO: 5 (SNAP-$25_{134-197}$) or amino acids 134-206 of SEQ ID NO: 5 (SNAP-$25_{134-206}$) were covalently attached to the surface of the CM5 sensor chips using standard amine coupling. Briefly, the CM5 chips were activated by a 7 minute injection of a mixture of 0.2 M 1-ethyl-3-(3-dimethylaminopropyl)carbodiimide and 0.05 M N-hydroxysuccimide; the SNAP-25 peptides were then injected in 10 mM sodium acetate (pH 4.0) for 20 min at a flow rate of 10 μL/min; and unreacted succimide esters were blocked by a 7-min injection of 1 M ethanolamine hydrochloride, pH 8.5. The immobilized amount of SNAP-$25_{134-197}$ or SNAP-$25_{134-206}$ on the chip was reflected by a 100-150 increase in response units (about 0.10-0.15 ng/$mm^2$). Antibody samples comprising either ascites or purified monoclonal antibodies produced from clones 1D3B8, 2C9B10, 2E2A6, 3C1A5, and 3C3E2, as well as, commercially available α-SNAP-25 antibodies were passed over the surface of the CM5 chips allowing an association time of 10 min and a dissociation time of 20 min. The surfaces were regenerated between runs by a 1 minute injection of 10 mM glycine-HCl (pH 2.5) at a flow rate of 15 μL/min. Sensorgram curves were fitted to a 1:1 kinetic binding model with the BIAevaluation 3.0 software.

The results indicate that both 2E2A6 and 3C1A5 were highly specific for cleaved SNAP-$25_{197}$ product over SNAP-25 uncleaved substrate (Table 20). When compared to the binding affinities of MC-6050 and MC-6053, 1D3B6 had an approximately 10-fold higher equilibrium disassociation constant for the SNAP-25 cleavage product relative to these commercial antibodies (Table 20). Interestingly, 2E2A6 had only a slightly lower equilibrium disassociation constant for the SNAP-25 cleavage product relative to these commercial antibodies (0.405 nM versus 0.497 and 0.508) (Table 20). As neither of these commercial α-SNAP-25 antibodies selectively recognized the SNAP-25 cleavage product (Table 19), an equilibrium disassociation constant lower than about 0.5 nM appears, in part, critical to achieve such selectivity. Similarly, when compared to the binding affinities of MC-6050 and MC-6053, 2E2A6 had an about at least one-fold slower off rate/dissociation constant ($6.74\times10^{-5}$ versus $8.82\times10^{-4}$ $s^{-1}$ and $1.18\times10^{-3}$ $s^{-1}$) (Table 20). This further suggests that an off rate/dissociation constant lower than about $8.82\times10^{-4}$ appears, in part, critical to achieve selective binding for the SNAP-25 cleavage product. This result is consistent with 1D3B8, which had an off rate/dissociation constant of $5.78\times10^{-5}$ $s^{-1}$ (Table 20).

TABLE 20

| Analysis of Binding Affinity α-SNAP-25 Monoclonal Antibodies | | | | |
|---|---|---|---|---|
| | 1D3B8 | | 2E2A6 | |
| SPR Parameter | SNAP-$25_{197}$ | SNAP-$25_{206}$[a] | SNAP-$25_{197}$ | SNAP-$25_{206}$[b] |
| Ka ($M^{-1}$ $s^{-1}$) | $1.06 \times 10^6$ | — | $1.70 \times 10^6$<br>($1.66 \times 10^5$) | —<br>(—) |
| Kd ($s^{-1}$) | $5.78 \times 10^{-5}$ | — | $1.53 \times 10^{-4}$<br>($6.74 \times 10^{-5}$) | —<br>(—) |
| KD (nM) | 0.050 | — | 0.090<br>(0.405) | —<br>(—) |
| | 3C1A5 | | 2C9B10 | |
| SPR Parameter | SNAP-$25_{197}$ | SNAP-$25_{206}$[c] | SNAP-$25_{197}$ | SNAP-$25_{206}$[d] |
| Ka ($M^{-1}$ $s^{-1}$) | $2.17 \times 10^5$ | — | $1.15 \times 10^4$ | — |
| Kd ($s^{-1}$) | $2.88 \times 10^{-4}$ | — | $3.11 \times 10^{-4}$ | — |
| KD (nM) | 1.33 | — | 27.1 | — |
| | MC-6050 | | MC-6053 | |
| SPR Parameter | SNAP-$25_{197}$ | SNAP-$25_{206}$ | SNAP-$25_{197}$ | SNAP-$25_{206}$ |
| Ka ($M^{-1}$ $s^{-1}$) | $1.78 \times 10^6$ | $3.06 \times 10^2$ | $2.32 \times 10^6$ | $1.06 \times 10^2$ |
| Kd ($s^{-1}$) | $8.82 \times 10^{-4}$ | $6.07 \times 10^{-3}$ | $1.18 \times 10^{-3}$ | $2.56 \times 10^{-5}$ |
| KD (nM) | 0.497 | 19,800 | 0.508 | 240 |

[a]No binding was observed when up to 125 nM of α-SNAP-25 monoclonal antibody 1D3B8 was passed over the surface of the CM5 sensor chip after a 10 minute association time.
[b]No binding was observed when up to 10 μM of α-SNAP-25 monoclonal antibody 2E2A6 was passed over the surface of the CM5 sensor chip after a 10 minute association time.
[c]No binding was observed when up to 100 nM of α-SNAP-25 monoclonal antibody 3C1A5 was passed over the surface of the CM5 sensor chip after a 10 minute association time.
[d]No binding was observed when up to 100 nM of α-SNAP-25 monoclonal antibody 2C9B10 was passed over the surface of the CM5 sensor chip after a 10 minute association time.

Figure 3A:
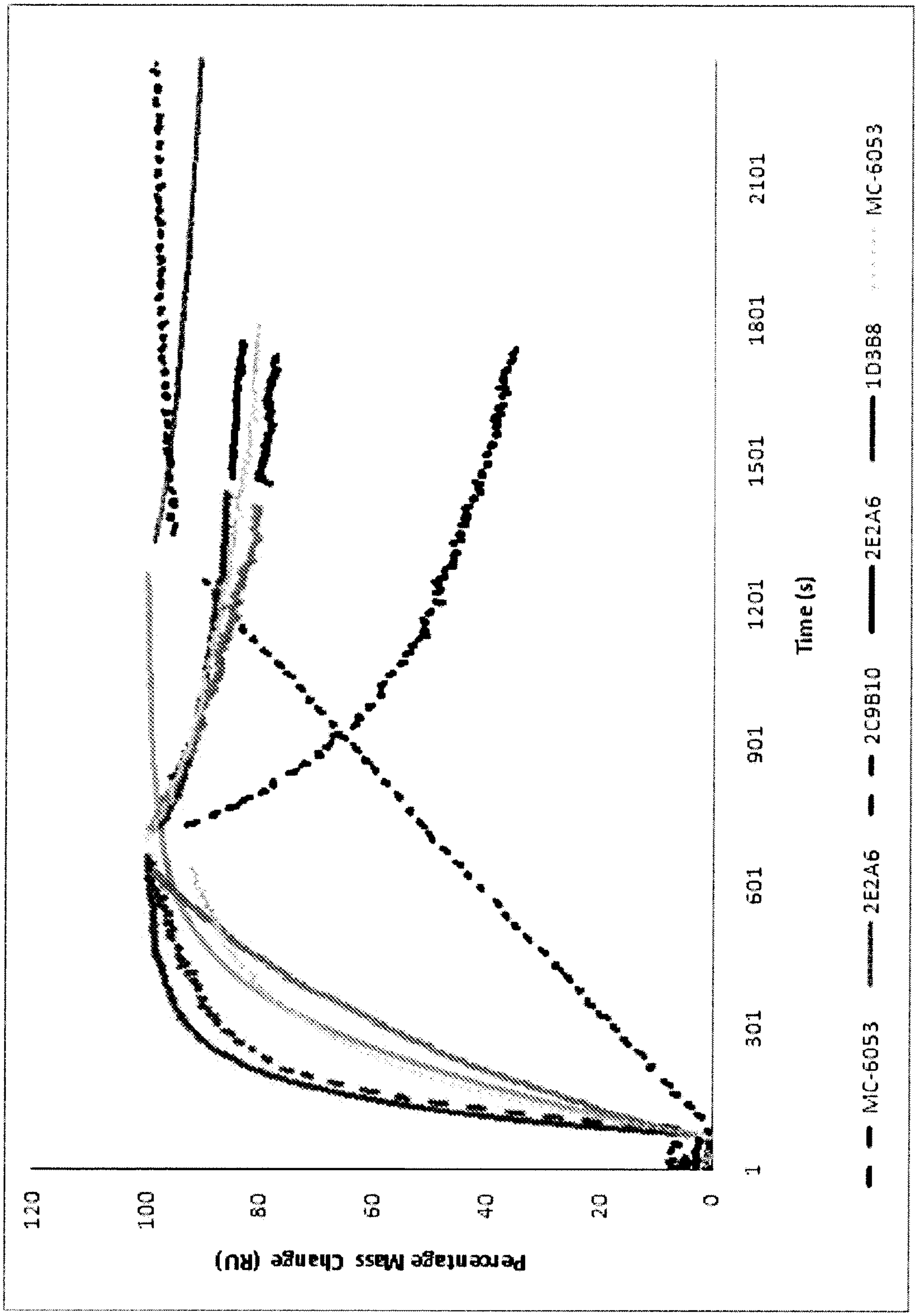
FIG. 3A shows the normalized data for the on-rate of each antibody.
Figure 3B:
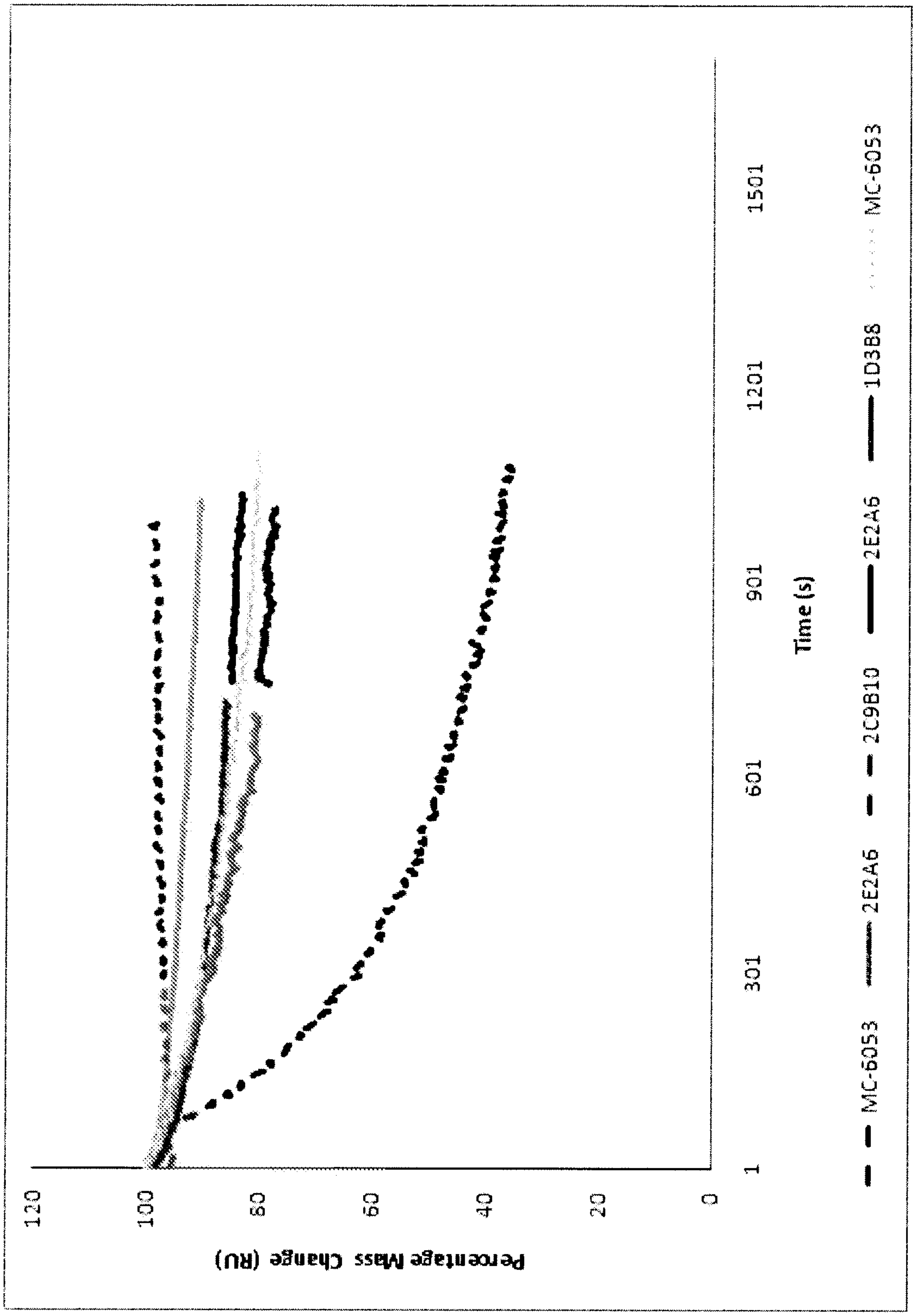
FIG. 3B shows the normalized data for the off-rate of each antibody.

To compare the six different antibodies, the on-rate (ka) and off-rate (kd) for each was normalized using a program from the BIA evaluation 4.1 software. For comparison of the on-rates, the data were first individually trimmed by deleting the re-generation portion and the injection spikes, and then normalized to a 0 to 100 scale. For comparison of the off-rate, the data were normalized to the injection stop/top point. This analysis showed that 2C9B10 had a much slower on-rate than the other antibodies (FIG. 3A), and that MC-6053 has a much faster off-rate (dissociation) that the other antibodies (FIG. 3B). The fast off-rate of MC-6053 indicates that this antibody will not perform well in the methods disclosed in the present specification because this antibody will have difficulty staying bound to the substrate antigen during the washing steps.

6. Sequencing of the Epitope from Isolated α-SNAP-25 Monoclonal Antibodies.

To determine the epitope of an isolated α-SNAP-25 monoclonal antibody that can selectively bind to a SNAP-25 antigen having a carboxyl-terminus at the $P_1$ residue of the BoNT/A cleavage site scissile bond, the polynucleotide molecule encoding the variable heavy ($V_H$) and variable light ($V_L$) chains of the α-SNAP-25 monoclonal antibody produced by hybridomas 1D3B8, 2C9B10, 2E2A6, 3C1A5 and 3C3E2 were sequenced. mRNA was extracted and purified from each hybridoma using standard protocols and reversed transcribed into cDNA using either an oligo dT anti-sense primer or a gene-specific (murine IgG1 CH and kappa CL) anti-sense primer. Specific murine and human constant domain primers were used to amplify the cDNA by PCR after cDNA production to determine the isotype of the antibody. Degenerate $V_H$ and $V_L$ primers were used to amplify the variable domains from the cDNA. For 5'RACE, a homopolymeric dCTP tail was added to the 3' end of the cDNA. The heavy and light chains were then amplified with an oligo dG sense primer and a gene specific (CH/KC) anti-sense primer. PCR products included the sequence of the signal peptide, variable domains and constant domains up to the anti-sense primer. The PCR products were gel purified to remove small fragments, and cloned into a blunt or TA vector for sequencing. Five independent clones for each chain were sequenced and alignments of $V_H$ and VL chains and consensus sequences were determined. Methods used to determine the $V_H$ and $V_L$ amino acid sequences are described in, e.g., Roger A. Sabbadini, et al., Novel Bioactive Lipid Derivatives and Methods of Making and Using Same, U.S. Patent Publication 2007/0281320; and Peter Amersdorfer, et al., *Molecular Characterization of Murine Humoral Immune Response to Botulinum Neurotoxin Type A Binding Domain as Assessed by Using Phage Antibody Libraries,* 65(9) Infect. Immun. 3743-3752, each of which is hereby incorporated by reference in its entirety. In addition, commercial services are available to sequence the variable heavy ($V_H$) and variable light ($V_L$) chains of an antibody and identify the CDR regions, see, e.g., Fusion Antibodies Ltd., Northern Ireland.

The polynucleotide sequence comprising the $V_H$ and $V_L$ chains of the α-SNAP-25 monoclonal antibody produced by the hybridomas disclosed in the present specification is as follows: 1D3B8 $V_H$ (SEQ ID NO: 71), 2C9B10 $V_H$ (SEQ ID NO: 73), 2E2A6 $V_H$ (SEQ ID NO: 75), 3C1A5 $V_H$ (SEQ ID NO: 77), 3C3E2 $V_H$ variant 1 (SEQ ID NO: 79), 3C3E2 $V_H$ variant 2 (SEQ ID NO: 81), 3C3E2 $V_H$ variant 3 (SEQ ID NO: 149), 1D3B8 $V_L$ (SEQ ID NO: 83), 2C9B10 $V_L$ (SEQ ID NO: 85), 2E2A6 $V_L$ (SEQ ID NO: 87), 3C1A5 $V_L$ (SEQ ID NO: 89), and 3C3E2 $V_L$ (SEQ ID NO: 91). The amino acid sequence comprising the $V_H$ and $V_L$ chains of the α-SNAP-25 monoclonal antibody produced by the hybridomas disclosed in the present specification is as follows: 1D3B8 $V_H$ (SEQ ID NO: 72), 2C9B10 $V_H$ (SEQ ID NO: 74), 2E2A6 $V_H$ (SEQ ID NO: 76), 3C1A5 $V_H$ (SEQ ID NO: 78), 3C3E2 $V_H$ variant 1 (SEQ ID NO: 80), 3C3E2 $V_H$ variant 2 (SEQ ID NO: 82); 3C3E2 $V_H$ variant 2 (SEQ ID NO: 150), 1D3B8 $V_L$ (SEQ ID NO: 84), 2C9B10 $V_L$ (SEQ ID NO: 86), 2E2A6 $V_L$ (SEQ ID NO: 88), 3C1A5 $V_L$ (SEQ ID NO: 90), and 3C3E2 $V_L$ (SEQ ID NO: 92). The amino acid sequences comprising the $V_H$ and $V_L$ CDR domains of the α-SNAP-25 monoclonal antibody produced by the hybridomas 1D3B8, 2C9B10, 2E2A6, 3C1A5, and 3C3E2 are given in Table 21.

TABLE 21

CDR Sequences of $V_H$ and $V_L$ domains from α-SNAP-25 Monoclonal Antibodies

| CDR | Sequence | Identified In | SEQ ID NO: |
|---|---|---|---|
| $V_H$ CDR 1 | TFTDHSIH | 2E2A6<br>2C9B10<br>3C1A5 | 93 |
| $V_H$ CDR 1 | TFTNYVIH | 3C3E2 | 94 |
| $V_H$ CDR 1 | IFTDHALH | 1D3B8 | 95 |
| $V_H$ CDR 2 | YIFPGNGNIEYNDKFKG | 2E2A6 | 96 |
| $V_H$ CDR 2 | YLFPGNGNFEYNEKFKG | 2C9B10<br>3C1A5 | 97 |
| $V_H$ CDR 2 | YINPYNDGSKYNEKFKG | 3C3E2 | 98 |
| $V_H$ CDR 2 | YIFPGNGNIEYNEKFKG | 1D3B8 | 99 |
| $V_H$ CDR 3 | KRMGY | 2E2A6<br>3C1A5 | 100 |
| $V_H$ CDR 3 | KKMDY | 2C9B10<br>1D3B8 | 101 |
| $V_H$ CDR 3 | ARMDY | 3C3E2var1 | 102 |
| $V_H$ CDR 3 | ARMGY | 3C3E2var2 | 151 |
| $V_H$ CDR 3 | ARHLANTYYYFDY | 3C3E2var3 | 152 |
| $V_L$ CDR 1 | RSSQSIVHSNGNTYLE | 1D3B8 | 103 |
| $V_L$ CDR 1 | RTTENIYSYFV | 2C9B10 | 104 |
| $V_L$ CDR 1 | KSSQSLLYTNGKTYLT | 2E2A6 | 105 |
| $V_L$ CDR 1 | KSSQSLLNTNGKTYLT | 3C1A5 | 106 |
| $V_L$ CDR 1 | RASQNIGNYLH | 3C3E2 | 107 |
| $V_L$ CDR 2 | KVSNRFS | 1D3B8 | 108 |
| $V_L$ CDR 2 | NAKSLAE | 2C9B10 | 109 |
| $V_L$ CDR 2 | LVSELDS | 2E2A6 | 110 |
| $V_L$ CDR 2 | LVSKLDS | 3C1A5 | 111 |
| $V_L$ CDR 2 | YASQSIS | 3C3E2 | 112 |
| $V_L$ CDR 3 | FQGSHVPPT | 1D3B8 | 113 |
| $V_L$ CDR 3 | QHHYGTPYT | 2C9B10 | 114 |
| $V_L$ CDR 3 | LQSAHFPFT | 2E2A6 | 115 |
| $V_L$ CDR 3 | LQSSHFPFT | 3C1A5 | 116 |
| $V_L$ CDR 3 | QQSDTWPLT | 3C3E2 | 117 |

Non-limiting examples of amino acid sequences comprising $V_H$ CDR domain variants of the α-SNAP-25 monoclonal antibody produced by the hybridomas disclosed in the present specification include $V_H$ CDR1 variant SEQ ID NO: 118 for 1D3B8; $V_H$ CDR1 variant SEQ ID NO: 119 for 2C9B10, 2E2A6 and 3C1A5 $V_H$; $V_H$ CDR1 variant SEQ ID NO: 120 for 3C1A5 $V_H$ and 3C3E2 variant 3; $V_H$ CDR2 variant SEQ ID NO: 121 for 1D3B8 and 2E2A6; $V_H$ CDR2 variant SEQ ID NO: 122 for 2C9B10 and 3C1A5 $V_H$; $V_H$ CDR2 variant SEQ ID NO: 123 for 3C1A5 $V_H$ and 3C3E2 variant 3; $V_H$ CDR3 variant MDY for 1D3B8 and 2C9B10; $V_H$ CDR3 variant MGY for 2E2A6 and 3C1A5 $V_H$; and $V_H$ CDR3 variant SEQ ID NO: 124 for 3C1A5 $V_H$ and 3C3E2 variant 3. Non-limiting examples of amino acid sequences comprising $V_L$ CDR domain variants of the α-SNAP-25 monoclonal antibody produced by the hybridomas disclosed in the present specification include $V_L$ CDR1 variant SEQ ID NO: 125 for 1D3B8; $V_L$ CDR1 variant SEQ ID NO: 126 for 2C9B10; $V_L$ CDR1 variant SEQ ID NO: 127 for 2E2A6; $V_L$ CDR1 variant SEQ ID NO: 128 for 3C1A5; $V_L$ CDR1 variant SEQ ID NO: 129 for 3C3E2; $V_L$ CDR2 variant KVS for 1D3B8; $V_L$ CDR2 variant NAK for 2C9B10; $V_L$ CDR2 variant LVS for 2E2A6; $V_L$ CDR2 variant YAT for 3C1A5; and $V_L$ CDR2 variant YAS for 3C3E2.

Example IX

Development of α-SNAP-25 Polyclonal Antibodies that Selectively Bind a SNAP-25 Epitope Having a Free Carboxyl-Terminus at the $P_1$ Residue of the BoNT/A Cleavage Site Scissile Bond The following example illustrates how to make α-SNAP-25 polyclonal antibodies that can selectively bind to a SNAP- 25 epitope having a carboxyl-terminus at the $P_1$ residue of the BoNT/A cleavage site scissile bond.

To develop α-SNAP-25 polyclonal antibodies that bind an epitope comprising a carboxyl-terminus at the P1 residue from the BoNT/A cleavage site scissile bond from a SNAP-25 cleavage product, the 10-residue peptide CGGGRIDEANQ (SEQ ID NO: 46) was designed as a SNAP-25 cleavage product antigen. This peptide comprising a N-terminal Cysteine residue for conjugation to KLH, a G-spacer flexible spacer (GGG) linked to amino acids 191-197 of human SNAP-25 (SEQ ID NO: 5) and has a carboxylated C-terminal glutamine. Blast searches revealed that this peptide has high homology only to SNAP-25 and almost no possible cross-reactivity with other proteins in neuronal cells. The sequence was also carefully scrutinized by utilizing computer algorithms to determine hydropathy index, protein surface probability, regions of flexibility, and favorable secondary structure, followed by proper orientation and presentation of the chosen peptide sequence. The peptide was synthesized and conjugated to Keyhole Limpet Hemocyanin (KLH) to increase immunogenicity. Before the animals were immunized, naïve rabbits were first screened against cell lysates from candidate cell lines in a Western blot in order to identify animals that had no immunoreactivity to the proteins present in the cell lysates. Two pre-screened rabbits were immunized with this peptide, and after three immunizations in about eight weeks, the rabbits were bled for testing. The blood was allowed to clot by incubating at 4° C. for 60 minutes. The clotted blood was centrifuged at 10,000×g at 4° C. for 10 minutes to pellet the cellular debris. The resulting serum sample was dispensed into 50 μL aliquots and stored at −20° C. until needed.

A similar strategy based on other SNAP-25 antigens disclosed in the present specification is used to develop α-SNAP-25 polyclonal antibodies that bind an epitope comprising a carboxyl-terminus at the P1 residue from the BoNT/A cleavage site scissile bond from a SNAP-25 cleavage product. For example, the SNAP-25 antigen of SEQ ID NO: 47 can be conjugated to KLH instead of the SNAP-25 antigen of SEQ ID NO: 46. As another example, the amino acids 191-197 of human SNAP-25 from the SNAP-25 antigen of SEQ ID NO: 38 can be replaced with SEQ ID NO: 33, SEQ ID NO: 34, SEQ ID NO: 35, SEQ ID NO: 36, SEQ ID NO: 37, SEQ ID NO: 39, SEQ ID NO: 40, SEQ ID NO: 41, SEQ ID NO: 42, SEQ ID NO: 43, or SEQ ID NO: 44.

2. Screening for the Presence of α-SNAP-25 Polyclonal Antibodies.

To determine the presence of α-SNAP-25 polyclonal antibodies that can selectively bind to a SNAP-25 antigen having a carboxyl-terminus at the $P_1$ residue of the BoNT/A cleavage site scissile bond, comparative ELISA and cell-based cleavage assays were performed using the extracted rabbit serum as described in Example VIII. The serum from both rabbits contained α-SNAP-25 polyclonal antibodies that can selectively bind to a SNAP-25 antigen having a carboxyl-terminus at the $P_1$ residue of the BoNT/A cleavage site scissile bond. The α-SNAP-25 rabbit polyclonal antibodies were designated as NTP 22 and NTP 23.

3. Purification of α-SNAP-25 Polyclonal Antibodies.

To purify α-SNAP-25 polyclonal antibodies that can selectively bind to a SNAP-25 antigen having a carboxyl-terminus at the $P_1$ residue of the BoNT/A cleavage site scissile bond, NTP 22 and NTP 23 antibodies from rabbit serum were purified using affinity columns containing the SNAP-25 antigen of SEQ ID NO: 46.

4. Evaluation of Binding Specificity of α-SNAP-25 Polyclonal Antibodies.

To evaluate binding specificity of an α-SNAP-25 polyclonal antibody that can selectively bind to a SNAP-25 antigen having a carboxyl-terminus at the $P_1$ residue of the BoNT/A cleavage site scissile bond, purified NTP 22 and NTP 23 α-SNAP-25 polyclonal antibodies were used to detect cleavage product using the cell-based activity assay, immunnocytochemistry and immunoprecipitation as described in Example VIII. The cell-based cleavage assay, immunocytochemistry analysis and immunoprecipitation analysis all indicated that NTP 22 and NTP 23 α-SNAP-25 polyclonal antibodies did not cross-react with uncleaved SNAP-25. Thus both NTP 22 and NTP 23 have high binding specificity for the SNAP-$25_{197}$ cleavage product that allows for the preferential recognition of this cleavage product relative to the SNAP-$25_{206}$ uncleaved substrate. Affinity for the antigens can be determined using SPR in the BiAcore as described in Example VIII.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

SEQUENCE LISTING

```
<160> NUMBER OF SEQ ID NOS: 152

<210> SEQ ID NO 1
<211> LENGTH: 1296
<212> TYPE: PRT
<213> ORGANISM: Clostridium botulinum

<400> SEQUENCE: 1

Met Pro Phe Val Asn Lys Gln Phe Asn Tyr Lys Asp Pro Val Asn Gly
```

-continued

```
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430
```

-continued

```
Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860
```

-continued

```
Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
        1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
```

1285 1290 1295

<210> SEQ ID NO 2
<211> LENGTH: 1296
<212> TYPE: PRT
<213> ORGANISM: Clostridium botulinum

<400> SEQUENCE: 2

Met Pro Phe Val Asn Lys Gln Phe Asn Tyr Lys Asp Pro Val Asn Gly
1 5 10 15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg
35 40 45

Asp Thr Phe Thr Asn Pro Glu Glu Gly Asp Leu Asn Pro Pro Pro Glu
50 55 60

Ala Lys Gln Val Pro Val Ser Tyr Tyr Asp Ser Thr Tyr Leu Ser Thr
65 70 75 80

Asp Asn Glu Lys Asp Asn Tyr Leu Lys Gly Val Thr Lys Leu Phe Glu
85 90 95

Arg Ile Tyr Ser Thr Asp Leu Gly Arg Met Leu Leu Thr Ser Ile Val
100 105 110

Arg Gly Ile Pro Phe Trp Gly Gly Ser Thr Ile Asp Thr Glu Leu Lys
115 120 125

Val Ile Asp Thr Asn Cys Ile Asn Val Ile Gln Pro Asp Gly Ser Tyr
130 135 140

Arg Ser Glu Glu Leu Asn Leu Val Ile Ile Gly Pro Ser Ala Asp Ile
145 150 155 160

Ile Gln Phe Glu Cys Lys Ser Phe Gly His Asp Val Leu Asn Leu Thr
165 170 175

Arg Asn Gly Tyr Gly Ser Thr Gln Tyr Ile Arg Phe Ser Pro Asp Phe
180 185 190

Thr Phe Gly Phe Glu Glu Ser Leu Glu Val Asp Thr Asn Pro Leu Leu
195 200 205

Gly Ala Gly Lys Phe Ala Thr Asp Pro Ala Val Thr Leu Ala His Glu
210 215 220

Leu Ile His Ala Glu His Arg Leu Tyr Gly Ile Ala Ile Asn Pro Asn
225 230 235 240

Arg Val Phe Lys Val Asn Thr Asn Ala Tyr Tyr Glu Met Ser Gly Leu
245 250 255

Glu Val Ser Phe Glu Glu Leu Arg Thr Phe Gly Gly His Asp Ala Lys
260 265 270

Phe Ile Asp Ser Leu Gln Glu Asn Glu Phe Arg Leu Tyr Tyr Tyr Asn
275 280 285

Lys Phe Lys Asp Val Ala Ser Thr Leu Asn Lys Ala Lys Ser Ile Ile
290 295 300

Gly Thr Thr Ala Ser Leu Gln Tyr Met Lys Asn Val Phe Lys Glu Lys
305 310 315 320

Tyr Leu Leu Ser Glu Asp Thr Ser Gly Lys Phe Ser Val Asp Lys Leu
325 330 335

Lys Phe Asp Lys Leu Tyr Lys Met Leu Thr Glu Ile Tyr Thr Glu Asp
340 345 350

Asn Phe Val Asn Phe Phe Lys Val Ile Asn Arg Lys Thr Tyr Leu Asn
355 360 365

Phe Asp Lys Ala Val Phe Arg Ile Asn Ile Val Pro Asp Glu Asn Tyr

-continued

```
    370                 375                 380

Thr Ile Lys Asp Gly Phe Asn Leu Lys Gly Ala Asn Leu Ser Thr Asn
385                 390                 395                 400

Phe Asn Gly Gln Asn Thr Glu Ile Asn Ser Arg Asn Phe Thr Arg Leu
                405                 410                 415

Lys Asn Phe Thr Gly Leu Phe Glu Phe Tyr Lys Leu Leu Cys Val Arg
            420                 425                 430

Gly Ile Ile Pro Phe Lys Thr Lys Ser Leu Asp Glu Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asp Lys Val Glu Glu
465                 470                 475                 480

Ile Thr Ala Asp Thr Asn Ile Glu Ala Ala Glu Glu Asn Ile Ser Leu
                485                 490                 495

Asp Leu Ile Gln Gln Tyr Tyr Leu Thr Phe Asp Phe Asp Asn Glu Pro
            500                 505                 510

Glu Asn Ile Ser Ile Glu Asn Leu Ser Ser Asp Ile Ile Gly Gln Leu
        515                 520                 525

Glu Pro Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Asp Ser Arg Ile Ile Leu Thr Asn Ser Ala Glu Glu Ala Leu
                565                 570                 575

Leu Lys Pro Asn Val Ala Tyr Thr Phe Phe Ser Ser Lys Tyr Val Lys
            580                 585                 590

Lys Ile Asn Lys Ala Val Glu Ala Phe Met Phe Leu Asn Trp Ala Glu
        595                 600                 605

Glu Leu Val Tyr Asp Phe Thr Asp Glu Thr Asn Glu Val Thr Thr Met
    610                 615                 620

Asp Lys Ile Ala Asp Ile Thr Ile Ile Val Pro Tyr Ile Gly Pro Ala
625                 630                 635                 640

Leu Asn Ile Gly Asn Met Leu Ser Lys Gly Glu Phe Val Glu Ala Ile
                645                 650                 655

Ile Phe Thr Gly Val Val Ala Met Leu Glu Phe Ile Pro Glu Tyr Ala
            660                 665                 670

Leu Pro Val Phe Gly Thr Phe Ala Ile Val Ser Tyr Ile Ala Asn Lys
        675                 680                 685

Val Leu Thr Val Gln Thr Ile Asn Asn Ala Leu Ser Lys Arg Asn Glu
    690                 695                 700

Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
    770                 775                 780

Asn Lys Phe Leu Asp Gln Cys Ser Val Ser Tyr Leu Met Asn Ser Met
785                 790                 795                 800
```

```
Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Val Leu
            820                 825                 830

Gln Val Asp Arg Leu Lys Asp Glu Val Asn Asn Thr Leu Ser Ala Asp
        835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn Ile Val Asn Thr Ser Ile Leu Ser
865                 870                 875                 880

Ile Val Tyr Lys Lys Asp Asp Leu Ile Asp Leu Ser Arg Tyr Gly Ala
                885                 890                 895

Lys Ile Asn Ile Gly Asp Arg Val Tyr Tyr Asp Ser Ile Asp Lys Asn
            900                 905                 910

Gln Ile Lys Leu Ile Asn Leu Glu Ser Ser Thr Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Lys Ile Pro Lys Tyr Phe Ser Lys Ile Asn Leu Asn Asn
945                 950                 955                 960

Glu Tyr Thr Ile Ile Asn Cys Ile Glu Asn Asn Ser Gly Trp Lys Val
                965                 970                 975

Ser Leu Asn Tyr Gly Glu Ile Ile Trp Thr Leu Gln Asp Asn Lys Gln
            980                 985                 990

Asn Ile Gln Arg Val Val Phe Lys Tyr Ser Gln Met Val Asn Ile Ser
        995                 1000                1005

Asp Tyr Ile Asn Arg Trp Ile Phe Val Thr Ile Thr Asn Asn Arg Leu
    1010                1015                1020

Thr Lys Ser Lys Ile Tyr Ile Asn Gly Arg Leu Ile Asp Gln Lys Pro
1025                1030                1035                1040

Ile Ser Asn Leu Gly Asn Ile His Ala Ser Asn Lys Ile Met Phe Lys
                1045                1050                1055

Leu Asp Gly Cys Arg Asp Pro Arg Arg Tyr Ile Met Ile Lys Tyr Phe
            1060                1065                1070

Asn Leu Phe Asp Lys Glu Leu Asn Glu Lys Glu Ile Lys Asp Leu Tyr
        1075                1080                1085

Asp Ser Gln Ser Asn Ser Gly Ile Leu Lys Asp Phe Trp Gly Asn Tyr
    1090                1095                1100

Leu Gln Tyr Asp Lys Pro Tyr Tyr Met Leu Asn Leu Phe Asp Pro Asn
1105                1110                1115                1120

Lys Tyr Val Asp Val Asn Asn Ile Gly Ile Arg Gly Tyr Met Tyr Leu
                1125                1130                1135

Lys Gly Pro Arg Gly Ser Val Val Thr Thr Asn Ile Tyr Leu Asn Ser
            1140                1145                1150

Thr Leu Tyr Glu Gly Thr Lys Phe Ile Ile Lys Lys Tyr Ala Ser Gly
        1155                1160                1165

Asn Glu Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asp Asp Gln Gly Ile Arg
            1220                1225                1230
```

```
Asn Lys Cys Lys Met Asn Leu Gln Asp Asn Asn Gly Asn Asp Ile Gly
        1235                1240                1245

Phe Ile Gly Phe His Leu Tyr Asp Asn Ile Ala Lys Leu Val Ala Ser
    1250                1255                1260

Asn Trp Tyr Asn Arg Gln Val Gly Lys Ala Ser Arg Thr Phe Gly Cys
1265                1270                1275                1280

Ser Trp Glu Phe Ile Pro Val Asp Asp Gly Trp Gly Glu Ser Ser Leu
                1285                1290                1295


<210> SEQ ID NO 3
<211> LENGTH: 1292
<212> TYPE: PRT
<213> ORGANISM: Clostridium botulinum

<400> SEQUENCE: 3

Met Pro Phe Val Asn Lys Pro Phe Asn Tyr Arg Asp Pro Gly Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Glu Gly Val Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Ile Lys Leu Phe Asp
                85                  90                  95

Arg Ile Tyr Ser Thr Gly Leu Gly Arg Met Leu Leu Ser Phe Ile Val
            100                 105                 110

Lys Gly Ile Pro Phe Trp Gly Gly Ser Thr Ile Asp Thr Glu Leu Lys
        115                 120                 125

Val Ile Asp Thr Asn Cys Ile Asn Val Ile Glu Pro Gly Gly Ser Tyr
    130                 135                 140

Arg Ser Glu Glu Leu Asn Leu Val Ile Thr Gly Pro Ser Ala Asp Ile
145                 150                 155                 160

Ile Gln Phe Glu Cys Lys Ser Phe Gly His Asp Val Phe Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Thr Phe Ala Thr Asp Pro Ala Val Thr Leu Ala His Glu
    210                 215                 220

Leu Ile His Ala Ala His Arg Leu Tyr Gly Ile Ala Ile Asn Pro Asn
225                 230                 235                 240

Arg Val Leu Lys Val Lys Thr Asn Ala Tyr Tyr Glu Met Ser Gly Leu
                245                 250                 255

Glu Val Ser Phe Glu Glu Leu Arg Thr Phe Gly Gly Asn Asp Thr Asn
            260                 265                 270

Phe Ile Asp Ser Leu Trp Gln Lys Lys Phe Ser Arg Asp Ala Tyr Asp
        275                 280                 285

Asn Leu Gln Asn Ile Ala Arg Ile Leu Asn Glu Ala Lys Thr Ile Val
    290                 295                 300

Gly Thr Thr Thr Pro Leu Gln Tyr Met Lys Asn Ile Phe Ile Arg Lys
305                 310                 315                 320
```

-continued

```
Tyr Phe Leu Ser Glu Asp Ala Ser Gly Lys Ile Ser Val Asn Lys Ala
                325                 330                 335

Ala Phe Lys Glu Phe Tyr Arg Val Leu Thr Arg Gly Phe Thr Glu Leu
            340                 345                 350

Glu Phe Val Asn Pro Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
    370                 375                 380

Thr Ile Asn Glu Gly Phe Asn Leu Glu Gly Ala Asn Ser Asn Gly Gln
385                 390                 395                 400

Asn Thr Glu Ile Asn Ser Arg Asn Phe Thr Arg Leu Lys Asn Phe Thr
                405                 410                 415

Gly Leu Phe Glu Phe Tyr Lys Leu Leu Cys Val Arg Gly Ile Ile Pro
            420                 425                 430

Phe Lys Thr Lys Ser Leu Asp Glu Gly Tyr Asn Lys Ala Leu Asn Tyr
        435                 440                 445

Leu Cys Ile Lys Val Asn Asn Trp Asp Leu Phe Phe Ser Pro Ser Glu
    450                 455                 460

Asp Asn Phe Thr Asn Asp Leu Asp Lys Val Glu Glu Ile Thr Ala Asp
465                 470                 475                 480

Thr Asn Ile Glu Ala Ala Glu Glu Asn Ile Ser Ser Asp Leu Ile Gln
                485                 490                 495

Gln Tyr Tyr Leu Thr Phe Asp Phe Asp Asn Glu Pro Glu Asn Ile Ser
            500                 505                 510

Ile Glu Asn Leu Ser Ser Asp Ile Ile Gly Gln Leu Glu Pro Met Pro
        515                 520                 525

Asn Ile Glu Arg Phe Pro Asn Gly Lys Lys Tyr Glu Leu Asp Lys Tyr
    530                 535                 540

Thr Met Phe His Tyr Leu Arg Ala Gln Glu Phe Glu His Gly Asp Ser
545                 550                 555                 560

Arg Ile Ile Leu Thr Asn Ser Ala Glu Glu Ala Leu Leu Lys Pro Asn
                565                 570                 575

Val Ala Tyr Thr Phe Phe Ser Ser Lys Tyr Val Lys Lys Ile Asn Lys
            580                 585                 590

Ala Val Glu Ala Val Ile Phe Leu Ser Trp Ala Glu Glu Leu Val Tyr
        595                 600                 605

Asp Phe Thr Asp Glu Thr Asn Glu Val Thr Thr Met Asp Lys Ile Ala
    610                 615                 620

Asp Ile Thr Ile Ile Val Pro Tyr Ile Gly Pro Ala Leu Asn Ile Gly
625                 630                 635                 640

Asn Met Val Ser Lys Gly Glu Phe Val Glu Ala Ile Leu Phe Thr Gly
                645                 650                 655

Val Val Ala Leu Leu Glu Phe Ile Pro Glu Tyr Ser Leu Pro Val Phe
            660                 665                 670

Gly Thr Phe Ala Ile Val Ser Tyr Ile Ala Asn Lys Val Leu Thr Val
        675                 680                 685

Gln Thr Ile Asn Asn Ala Leu Ser Lys Arg Asn Glu Lys Trp Asp Glu
    690                 695                 700

Val Tyr Lys Tyr Thr Val Thr Asn Trp Leu Ala Lys Val Asn Thr Gln
705                 710                 715                 720

Ile Asp Leu Ile Arg Glu Lys Met Lys Lys Ala Leu Glu Asn Gln Ala
                725                 730                 735

Glu Ala Thr Arg Ala Ile Ile Asn Tyr Gln Tyr Asn Gln Tyr Thr Glu
```

-continued

```
            740                 745                 750

Glu Glu Lys Asn Asn Ile Asn Phe Asn Ile Asp Asp Leu Ser Ser Lys
        755                 760                 765

Leu Asn Arg Ser Ile Asn Arg Ala Met Ile Asn Ile Asn Lys Phe Leu
    770                 775                 780

Asp Gln Cys Ser Val Ser Tyr Leu Met Asn Ser Met Ile Pro Tyr Ala
785                 790                 795                 800

Val Lys Arg Leu Lys Asp Phe Asp Ala Ser Val Arg Asp Val Leu Leu
                805                 810                 815

Lys Tyr Ile Tyr Asp Asn Arg Gly Thr Leu Ile Leu Gln Val Asp Arg
            820                 825                 830

Leu Lys Asp Glu Val Asn Asn Thr Leu Ser Ala Asp Ile Pro Phe Gln
        835                 840                 845

Leu Ser Lys Tyr Val Asn Asp Lys Lys Leu Leu Ser Thr Phe Thr Glu
    850                 855                 860

Tyr Ile Lys Asn Ile Val Asn Thr Ser Ile Leu Ser Ile Val Tyr Lys
865                 870                 875                 880

Lys Asp Asp Leu Ile Asp Leu Ser Arg Tyr Gly Ala Lys Ile Asn Ile
                885                 890                 895

Gly Asp Arg Val Tyr Tyr Asp Ser Ile Asp Lys Asn Gln Ile Lys Leu
            900                 905                 910

Ile Asn Leu Glu Ser Ser Thr Ile Glu Val Ile Leu Lys Asn Ala Ile
        915                 920                 925

Val Tyr Asn Ser Met Tyr Glu Asn Phe Ser Thr Ser Phe Trp Ile Lys
    930                 935                 940

Ile Pro Lys Tyr Phe Ser Lys Ile Asn Leu Asn Asn Glu Tyr Thr Ile
945                 950                 955                 960

Ile Asn Cys Ile Glu Asn Asn Ser Gly Trp Lys Val Ser Leu Asn Tyr
                965                 970                 975

Gly Glu Ile Ile Trp Thr Leu Gln Asp Asn Lys Gln Asn Ile Gln Arg
            980                 985                 990

Val Val Phe Lys Tyr Ser Gln Met Val Asn Ile Ser Asp Tyr Ile Asn
        995                 1000                1005

Arg Trp Met Phe Val Thr Ile Thr Asn Asn Arg Leu Thr Lys Ser Lys
    1010                1015                1020

Ile Tyr Ile Asn Gly Arg Leu Ile Asp Gln Lys Pro Ile Ser Asn Leu
1025                1030                1035                1040

Gly Asn Ile His Ala Ser Asn Lys Ile Met Phe Lys Leu Asp Gly Cys
                1045                1050                1055

Arg Asp Pro Arg Arg Tyr Ile Met Ile Lys Tyr Phe Asn Leu Phe Asp
            1060                1065                1070

Lys Glu Leu Asn Glu Lys Glu Ile Lys Asp Leu Tyr Asp Ser Gln Ser
        1075                1080                1085

Asn Pro Gly Ile Leu Lys Asp Phe Trp Gly Asn Tyr Leu Gln Tyr Asp
    1090                1095                1100

Lys Pro Tyr Tyr Met Leu Asn Leu Phe Asp Pro Asn Lys Tyr Val Asp
1105                1110                1115                1120

Val Asn Asn Ile Gly Ile Arg Gly Tyr Met Tyr Leu Lys Gly Pro Arg
                1125                1130                1135

Gly Ser Val Met Thr Thr Asn Ile Tyr Leu Asn Ser Thr Leu Tyr Met
            1140                1145                1150

Gly Thr Lys Phe Ile Ile Lys Lys Tyr Ala Ser Gly Asn Glu Asp Asn
        1155                1160                1165
```

-continued

```
Ile Val Arg Asn Asn Asp Arg Val Tyr Ile Asn Val Val Val Lys Asn
    1170                1175                1180

Lys Glu Tyr Arg Leu Ala Thr Asn Ala Ser Gln Ala Gly Val Glu Lys
1185                1190                1195                1200

Ile Leu Ser Ala Leu Glu Ile Pro Asp Val Gly Asn Leu Ser Gln Val
                1205                1210                1215

Val Val Met Lys Ser Lys Asp Asp Gln Gly Ile Arg Asn Lys Cys Lys
            1220                1225                1230

Met Asn Leu Gln Asp Asn Asn Gly Asn Asp Ile Gly Phe Val Gly Phe
        1235                1240                1245

His Leu Tyr Asp Asn Ile Ala Lys Leu Val Ala Ser Asn Trp Tyr Asn
    1250                1255                1260

Arg Gln Val Gly Lys Ala Ser Arg Thr Phe Gly Cys Ser Trp Glu Phe
1265                1270                1275                1280

Ile Pro Val Asp Asp Gly Trp Gly Glu Ser Ser Leu
                1285                1290


<210> SEQ ID NO 4
<211> LENGTH: 1296
<212> TYPE: PRT
<213> ORGANISM: Clostridium botulinum

<400> SEQUENCE: 4

Met Pro Leu Val Asn Gln Gln Ile Asn Tyr Tyr Asp Pro Val Asn Gly
 1               5                  10                  15

Val Asp Ile Ala Tyr Ile Lys Ile Pro Asn Ala Gly Lys Met Gln Pro
            20                  25                  30

Val Lys Ala Phe Lys Ile His Asn Lys Val Trp Val Ile Pro Glu Arg
        35                  40                  45

Asp Ile Phe Thr Asn Pro Glu Glu Val Asp Leu Asn Pro Pro Pro Glu
    50                  55                  60

Ala Lys Gln Val Pro Ile Ser Tyr Tyr Asp Ser Ala Tyr Leu Ser Thr
65                  70                  75                  80

Asp Asn Glu Lys Asp Asn Tyr Leu Lys Gly Val Ile Lys Leu Phe Glu
                85                  90                  95

Arg Ile Tyr Ser Thr Asp Leu Gly Arg Met Leu Leu Ile Ser Ile Val
            100                 105                 110

Arg Gly Ile Pro Phe Trp Gly Gly Gly Lys Ile Asp Thr Glu Leu Lys
        115                 120                 125

Val Ile Asp Thr Asn Cys Ile Asn Ile Ile Gln Leu Asp Asp Ser Tyr
    130                 135                 140

Arg Ser Glu Glu Leu Asn Leu Ala Ile Ile Gly Pro Ser Ala Asn Ile
145                 150                 155                 160

Ile Glu Ser Gln Cys Ser Ser Phe Arg Asp Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Val Gly Phe Glu Glu Ser Leu Glu Val Asp Thr Asn Pro Leu Leu
        195                 200                 205

Gly Ala Gly Lys Phe Ala Gln Asp Pro Ala Val Ala Leu Ala His Glu
    210                 215                 220

Leu Ile His Ala Glu His Arg Leu Tyr Gly Ile Ala Ile Asn Thr Asn
225                 230                 235                 240

Arg Val Phe Lys Val Asn Thr Asn Ala Tyr Tyr Glu Met Ala Gly Leu
                245                 250                 255
```

```
Glu Val Ser Leu Glu Glu Leu Ile Thr Phe Gly Gly Asn Asp Ala Lys
            260                 265                 270

Phe Ile Asp Ser Leu Gln Lys Lys Glu Phe Ser Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Ala Thr Gly Lys Phe Leu Val Asp Arg Leu
                325                 330                 335

Lys Phe Asp Glu Leu Tyr Lys Leu Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Asp Val Asn Tyr
    370                 375                 380

Thr Ile His Asp Gly Phe Asn Leu Arg Asn Thr Asn Leu Ala Ala Asn
385                 390                 395                 400

Phe Asn Gly Gln Asn Ile Glu Ile Asn Asn Lys Asn Phe Asp Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Glu Gly Tyr Asn Lys
        435                 440                 445

Ala Leu Asn Glu Leu Cys Ile Lys Val Asn Asn Trp Asp Leu Phe Phe
    450                 455                 460

Ser Pro Ser Glu Asp Asn Phe Thr Asn Asp Leu Asp Lys Val Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Asn Phe Asn Phe Asp Asn Glu Pro
            500                 505                 510

Glu Asn Thr Ser Ile Glu Asn Leu Ser Ser Asp Ile Ile Gly Gln Leu
        515                 520                 525

Glu Pro Met Pro Asn Ile Glu Arg Phe Pro Asn Gly Lys Lys Tyr Glu
    530                 535                 540

Leu Asn Lys Tyr Thr Met Phe His Tyr Leu Arg Ala Gln Glu Phe Lys
545                 550                 555                 560

His Ser Asn Ser Arg Ile Ile Leu Thr Asn Ser Ala Lys Glu Ala Leu
                565                 570                 575

Leu Lys Pro Asn Ile Val Tyr Thr Phe Phe Ser Ser Lys Tyr Ile Lys
            580                 585                 590

Ala Ile Asn Lys Ala Val Glu Ala Val Thr Phe Val Asn Trp Ile Glu
        595                 600                 605

Asn Leu Val Tyr Asp Phe Thr Asp Glu Thr Asn Glu Val Ser Thr Met
    610                 615                 620

Asp Lys Ile Ala Asp Ile Thr Ile Val Ile Pro Tyr Ile Gly Pro Ala
625                 630                 635                 640

Leu Asn Ile Gly Asn Met Ile Tyr Lys Gly Glu Phe Val Glu Ala Ile
                645                 650                 655

Ile Phe Ser Gly Ala Val Ile Leu Leu Glu Ile Val Pro Glu Ile Ala
            660                 665                 670

Leu Pro Val Leu Gly Thr Phe Ala Leu Val Ser Tyr Val Ser Asn Lys
        675                 680                 685
```

```
Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Ile
705                 710                 715                 720

Val Asn Thr Gln Ile Asn Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Ile Gly
            820                 825                 830

Gln Val Asn Arg Leu Lys Asp Lys Val Asn Asn Thr Leu Ser Ala Asp
        835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn Ile Thr Asn Ala Ser Ile Leu Ser
865                 870                 875                 880

Ile Val Tyr Lys Asp Asp Asp Leu Ile Asp Leu Ser Arg Tyr Gly Ala
                885                 890                 895

Glu Ile Tyr Asn Gly Asp Lys Val Tyr Tyr Asn Ser Ile Asp Lys Asn
            900                 905                 910

Gln Ile Arg Leu Ile Asn Leu Glu Ser Ser Thr Ile Glu Val Ile Leu
        915                 920                 925

Lys Lys Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Phe Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Ile
    1010                1015                1020

Thr Lys Ser Lys Ile Tyr Ile Asn Gly Arg Leu Ile Asp Gln Lys Pro
1025                1030                1035                1040

Ile Ser Asn Leu Gly Asn Ile His Ala Ser Asn Lys Ile Met Phe Lys
                1045                1050                1055

Leu Asp Gly Cys Arg Asp Pro His Arg Tyr Ile Val Ile Lys Tyr Phe
            1060                1065                1070

Asn Leu Phe Asp Lys Glu Leu Ser Glu Lys Glu Ile Lys Asp Leu Tyr
        1075                1080                1085

Asp Asn Gln Ser Asn Ser Gly Ile Leu Lys Asp Phe Trp Gly Asp Tyr
    1090                1095                1100

Leu Gln Tyr Asp Lys Ser Tyr Tyr Met Leu Asn Leu Tyr Asp Pro Asn
```

-continued

```
1105                1110                1115                1120

Lys Tyr Val Asp Val Asn Asn Val Gly Ile Arg Gly Tyr Met Tyr Leu
                1125                1130                1135

Lys Gly Pro Arg Asp Asn Val Met Thr Thr Asn Ile Tyr Leu Asn Ser
            1140                1145                1150

Ser Leu Tyr Met Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Arg Glu Arg Pro Leu
                1285                1290                1295


<210> SEQ ID NO 5
<211> LENGTH: 206
<212> TYPE: PRT
<213> ORGANISM: Homo sapiens

<400> SEQUENCE: 5

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
```

```
        195                 200                 205


<210> SEQ ID NO 6
<211> LENGTH: 206
<212> TYPE: PRT
<213> ORGANISM: Homo sapiens

<400> SEQUENCE: 6

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 7
<211> LENGTH: 206
<212> TYPE: PRT
<213> ORGANISM: Macaca mulatta

<400> SEQUENCE: 7

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125
```

```
Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 8
<211> LENGTH: 206
<212> TYPE: PRT
<213> ORGANISM: Rattus norvegicus

<400> SEQUENCE: 8

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 9
<211> LENGTH: 206
<212> TYPE: PRT
<213> ORGANISM: Rattus norvegicus

<400> SEQUENCE: 9

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45
```

```
Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 10
<211> LENGTH: 206
<212> TYPE: PRT
<213> ORGANISM: Mus musculus

<400> SEQUENCE: 10

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 11
<211> LENGTH: 206
```

<212> TYPE: PRT
<213> ORGANISM: Gallus gallus

<400> SEQUENCE: 11

```
Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 12
<211> LENGTH: 204
<212> TYPE: PRT
<213> ORGANISM: Carassius auratus

<400> SEQUENCE: 12

```
Met Ala Glu Asp Ala Asp Met Arg Asn Glu Leu Ser Asp Met Gln Gln
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Asp Ala Glu Lys Asn Leu Asn Asp
65                  70                  75                  80

Leu Gly Lys Phe Cys Gly Leu Cys Ser Cys Pro Cys Asn Lys Met Lys
                85                  90                  95

Ser Gly Gly Ser Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
        115                 120                 125

Gly Gly Phe Ile Arg Arg Val Thr Asp Asp Ala Arg Glu Asn Glu Met
    130                 135                 140

Asp Glu Asn Leu Glu Gln Val Gly Gly Ile Ile Gly Asn Leu Arg His
```

```
145                 150                 155                 160

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
            180                 185                 190

Ala Asn Gln Arg Ala Thr Lys Met Leu Gly Ser Gly
        195                 200


<210> SEQ ID NO 13
<211> LENGTH: 203
<212> TYPE: PRT
<213> ORGANISM: Carassius auratus

<400> SEQUENCE: 13

Met Ala Asp Glu Ala Asp Met Arg Asn Glu Leu Thr Asp Met Gln Ala
 1               5                  10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
                85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
        115                 120                 125

Gly Phe Ile Arg Arg Val Thr Asn Asp Ala Arg Glu Asn Glu Met Asp
    130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
            180                 185                 190

Asn Gln Arg Ala Thr Lys Met Leu Gly Ser Gly
        195                 200


<210> SEQ ID NO 14
<211> LENGTH: 204
<212> TYPE: PRT
<213> ORGANISM: Danio rerio

<400> SEQUENCE: 14

Met Ala Glu Asp Ser Asp Met Arg Asn Glu Leu Ala Asp Met Gln Gln
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Asp Ala Glu Lys Asn Leu Asn Asp
65                  70                  75                  80
```

```
Leu Gly Lys Phe Cys Gly Leu Cys Ser Cys Pro Cys Asn Lys Met Lys
                85                  90                  95

Ser Gly Ala Ser Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
        115                 120                 125

Gly Gly Phe Ile Arg Arg Val Thr Asp Asp Ala Arg Glu Asn Glu Met
    130                 135                 140

Asp Glu Asn Leu Glu Gln Val Gly Gly Ile Ile Gly Asn Leu Arg His
145                 150                 155                 160

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
            180                 185                 190

Ala Asn Gln Arg Ala Thr Lys Met Leu Gly Ser Gly
        195                 200


<210> SEQ ID NO 15
<211> LENGTH: 203
<212> TYPE: PRT
<213> ORGANISM: Danio rerio

<400> SEQUENCE: 15

Met Ala Asp Glu Ser Asp Met Arg Asn Glu Leu Asn Asp Met Gln Ala
 1               5                  10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
                85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
        115                 120                 125

Gly Phe Ile Arg Arg Val Thr Asn Asp Ala Arg Glu Asn Glu Met Asp
    130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
            180                 185                 190

Asn Gln Arg Ala Thr Lys Met Leu Gly Ser Gly
        195                 200


<210> SEQ ID NO 16
<211> LENGTH: 210
<212> TYPE: PRT
<213> ORGANISM: Torpedo marmorata

<400> SEQUENCE: 16
```

```
Met Glu Asn Ser Val Glu Asn Ser Met Asp Pro Arg Ser Glu Gln Glu
 1               5                  10                  15

Glu Met Gln Arg Cys Ala Asp Gln Ile Thr Asp Glu Ser Leu Glu Ser
            20                  25                  30

Thr Arg Arg Met Leu Gln Leu Val Glu Glu Ser Lys Asp Ala Gly Ile
        35                  40                  45

Arg Thr Leu Val Met Leu Asp Glu Gln Gly Glu Gln Leu Glu Arg Ile
    50                  55                  60

Glu Glu Gly Met Asp Gln Ile Asn Lys Asp Met Lys Glu Ala Glu Lys
65                  70                  75                  80

Asn Leu Ser Asp Leu Gly Lys Cys Cys Gly Leu Cys Ser Cys Pro Cys
                85                  90                  95

Asn Lys Leu Lys Asn Phe Glu Ala Gly Gly Ala Tyr Lys Lys Val Trp
            100                 105                 110

Gly Asn Asn Gln Asp Gly Val Val Ala Ser Gln Pro Ala Arg Val Met
        115                 120                 125

Asp Asp Arg Glu Gln Met Ala Met Ser Gly Gly Tyr Ile Arg Arg Ile
    130                 135                 140

Thr Asp Asp Ala Arg Glu Asn Glu Met Glu Glu Asn Leu Asp Gln Val
145                 150                 155                 160

Gly Ser Ile Ile Gly Asn Leu Arg His Met Ala Leu Asp Met Ser Asn
                165                 170                 175

Glu Ile Gly Ser Gln Asn Ala Gln Ile Asp Arg Ile Val Val Lys Gly
            180                 185                 190

Asp Met Asn Lys Ala Arg Ile Asp Glu Ala Asn Lys His Ala Thr Lys
        195                 200                 205

Met Leu
    210
```

<210> SEQ ID NO 17
<211> LENGTH: 206
<212> TYPE: PRT
<213> ORGANISM: Xenopus laevis

<400> SEQUENCE: 17

```
Met Ala Asp Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Tyr Val Glu Gly Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Gly Ala Tyr Asn Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Val Arg Arg Val Thr Asn Asp Ala Arg Glu Thr
    130                 135                 140

Glu Met Asp Glu Asn Leu Glu Gln Val Gly Gly Ile Ile Gly Asn Leu
145                 150                 155                 160
```

```
Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Ala Arg Ile
            180                 185                 190

Asp Glu Ala Asn Lys His Ala Thr Lys Met Leu Gly Ser Gly
        195                 200                 205


<210> SEQ ID NO 18
<211> LENGTH: 206
<212> TYPE: PRT
<213> ORGANISM: Xenopus laevis

<400> SEQUENCE: 18

Met Ala Asp Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Tyr Val Glu Gly Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Glu Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Val Arg Arg Val Thr Asn Asp Ala Arg Glu Thr
    130                 135                 140

Glu Met Asp Glu Asn Leu Glu Gln Val Gly Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Ala Arg Ile
            180                 185                 190

Asp Glu Ala Asn Lys His Ala Thr Lys Met Leu Gly Ser Gly
        195                 200                 205


<210> SEQ ID NO 19
<211> LENGTH: 212
<212> TYPE: PRT
<213> ORGANISM: Strongylocentrotus purpuratus

<400> SEQUENCE: 19

Met Glu Asp Gln Asn Asp Met Asn Met Arg Ser Glu Leu Glu Glu Ile
 1               5                  10                  15

Gln Met Gln Ser Asn Met Gln Thr Asp Glu Ser Leu Glu Ser Thr Arg
            20                  25                  30

Arg Met Leu Gln Met Ala Glu Glu Ser Gln Asp Met Gly Ile Lys Thr
        35                  40                  45

Leu Val Met Leu Asp Glu Gln Gly Glu Gln Leu Asp Arg Ile Glu Glu
    50                  55                  60

Gly Met Asp Gln Ile Asn Thr Asp Met Arg Glu Ala Glu Lys Asn Leu
65                  70                  75                  80

Thr Gly Leu Glu Lys Cys Cys Gly Ile Cys Val Cys Pro Trp Lys Lys
```

-continued

```
                85                  90                  95

Leu Gly Asn Phe Glu Lys Gly Asp Asp Tyr Lys Lys Thr Trp Lys Gly
            100                 105                 110

Asn Asp Asp Gly Lys Val Asn Ser His Gln Pro Met Arg Met Glu Asp
        115                 120                 125

Asp Arg Asp Gly Cys Gly Gly Asn Ala Ser Met Ile Thr Arg Ile Thr
    130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                165                 170                 175

Ile Gly Ala Gln Asn Ser Gln Val Gly Arg Ile Thr Ser Lys Ala Glu
            180                 185                 190

Ser Asn Glu Gly Arg Ile Asn Ser Ala Asp Lys Arg Ala Lys Asn Ile
        195                 200                 205

Leu Arg Asn Lys
    210


<210> SEQ ID NO 20
<211> LENGTH: 212
<212> TYPE: PRT
<213> ORGANISM: Drosophila melanogaster

<400> SEQUENCE: 20

Met Pro Ala Asp Pro Ser Glu Glu Val Ala Pro Gln Val Pro Lys Thr
 1               5                  10                  15

Glu Leu Glu Glu Leu Gln Ile Asn Ala Gln Gly Val Ala Asp Glu Ser
            20                  25                  30

Leu Glu Ser Thr Arg Arg Met Leu Ala Leu Cys Glu Glu Ser Lys Glu
        35                  40                  45

Ala Gly Ile Arg Thr Leu Val Ala Leu Asp Asp Gln Gly Glu Gln Leu
    50                  55                  60

Asp Arg Ile Glu Glu Gly Met Asp Gln Ile Asn Ala Asp Met Arg Glu
65                  70                  75                  80

Ala Glu Lys Asn Leu Ser Gly Met Glu Lys Cys Cys Gly Ile Cys Val
                85                  90                  95

Leu Pro Cys Asn Lys Ser Gln Ser Phe Lys Glu Asp Asp Gly Thr Trp
            100                 105                 110

Lys Gly Asn Asp Asp Gly Lys Val Val Asn Asn Gln Pro Gln Arg Val
        115                 120                 125

Met Asp Asp Arg Asn Gly Met Met Ala Gln Ala Gly Tyr Ile Gly Arg
    130                 135                 140

Ile Thr Asn Asp Ala Arg Glu Asp Glu Met Glu Glu Asn Met Gly Gln
145                 150                 155                 160

Val Asn Thr Met Ile Gly Asn Leu Arg Asn Met Ala Leu Asp Met Gly
                165                 170                 175

Ser Glu Leu Glu Asn Gln Asn Arg Gln Ile Asp Arg Ile Asn Arg Lys
            180                 185                 190

Gly Glu Ser Asn Glu Ala Arg Ile Ala Val Ala Asn Gln Arg Ala His
        195                 200                 205

Gln Leu Leu Lys
    210


<210> SEQ ID NO 21
<211> LENGTH: 212
<212> TYPE: PRT
```

```
<213> ORGANISM: Hirudo medicinalis

<400> SEQUENCE: 21

Met Ala Lys Asp Ile Lys Pro Lys Pro Ala Asn Gly Arg Asp Ser Pro
 1               5                  10                  15

Thr Asp Leu Gln Glu Ile Gln Leu Gln Met Asn Ala Ile Thr Asp Asp
            20                  25                  30

Ser Leu Glu Ser Thr Arg Arg Met Leu Ala Met Cys Glu Glu Ser Lys
        35                  40                  45

Asp Ala Gly Ile Arg Thr Leu Val Met Leu Asp Glu Gln Gly Glu Gln
    50                  55                  60

Leu Asp Arg Ile Glu Glu Gly Met Asp Gln Ile Asn Gln Asp Met Arg
65                  70                  75                  80

Asp Ala Glu Lys Asn Leu Glu Gly Met Glu Lys Cys Cys Gly Leu Cys
                85                  90                  95

Ile Leu Pro Trp Lys Arg Thr Lys Asn Phe Asp Lys Gly Ala Glu Trp
            100                 105                 110

Asn Lys Gly Asp Glu Gly Lys Val Asn Thr Asp Gly Pro Arg Leu Val
        115                 120                 125

Val Gly Asp Gly Asn Met Gly Pro Ser Gly Gly Phe Ile Thr Lys Ile
    130                 135                 140

Thr Asn Asp Ala Arg Glu Glu Glu Met Glu Gln Asn Met Gly Glu Val
145                 150                 155                 160

Ser Asn Met Ile Ser Asn Leu Arg Asn Met Ala Val Asp Met Gly Ser
                165                 170                 175

Glu Ile Asp Ser Gln Asn Arg Gln Val Asp Arg Ile Asn Asn Lys Met
            180                 185                 190

Thr Ser Asn Gln Leu Arg Ile Ser Asp Ala Asn Lys Arg Ala Ser Lys
        195                 200                 205

Leu Leu Lys Glu
    210


<210> SEQ ID NO 22
<211> LENGTH: 212
<212> TYPE: PRT
<213> ORGANISM: Loligo pealei

<400> SEQUENCE: 22

Met Ser Ala Asn Gly Glu Val Glu Val Pro Lys Thr Glu Leu Glu Glu
 1               5                  10                  15

Ile Gln Gln Gln Cys Asn Gln Val Thr Asp Asp Ser Leu Glu Ser Thr
            20                  25                  30

Arg Arg Met Leu Asn Met Cys Glu Glu Ser Lys Glu Ala Gly Ile Arg
        35                  40                  45

Thr Leu Val Met Leu Asp Glu Gln Gly Glu Gln Leu Asp Arg Ile Glu
    50                  55                  60

Glu Gly Leu Asp Gln Ile Asn Gln Asp Met Lys Asp Ala Glu Lys Asn
65                  70                  75                  80

Leu Glu Gly Met Glu Lys Cys Cys Gly Leu Cys Val Leu Pro Trp Lys
                85                  90                  95

Arg Gly Lys Ser Phe Glu Lys Ser Gly Asp Tyr Ala Asn Thr Trp Lys
            100                 105                 110

Lys Asp Asp Asp Gly Pro Thr Asn Thr Asn Gly Pro Arg Val Thr Val
        115                 120                 125

Gly Asp Gln Asn Gly Met Gly Pro Ser Ser Gly Tyr Val Thr Arg Ile
    130                 135                 140
```

Thr Asn Asp Ala Arg Glu Asp Asp Met Glu Asn Asn Met Lys Glu Val
145 150 155 160

Ser Ser Met Ile Gly Asn Leu Arg Asn Met Ala Ile Asp Met Gly Asn
165 170 175

Glu Ile Gly Ser Gln Asn Arg Gln Val Asp Arg Ile Gln Gln Lys Ala
180 185 190

Glu Ser Asn Glu Ser Arg Ile Asp Glu Ala Asn Lys Lys Ala Thr Lys
195 200 205

Leu Leu Lys Asn
210

<210> SEQ ID NO 23
<211> LENGTH: 220
<212> TYPE: PRT
<213> ORGANISM: Lymnaea stagnalis

<400> SEQUENCE: 23

Met Thr Thr Asn Gly Glu Ile Leu Pro Val Gly Glu Glu Glu Glu Glu
1 5 10 15

Glu Leu Gly Glu Asp Ala Leu Leu Arg Lys Gln Ile Asp Cys Asn Thr
20 25 30

Asn Glu Ser Leu Glu Ser Thr Arg Arg Met Leu Ser Leu Cys Glu Glu
35 40 45

Ser Lys Glu Ala Gly Ile Lys Thr Leu Val Met Leu Asp Glu Gln Gly
50 55 60

Glu Gln Leu Asp Arg Ile Glu Glu Gly Met Gly Gln Ile Asn Gln Asp
65 70 75 80

Met Arg Asp Ala Glu Lys Asn Leu Glu Gly Leu Glu Lys Cys Cys Gly
85 90 95

Leu Cys Val Leu Pro Trp Lys Arg Ser Lys Asn Phe Glu Lys Gly Ser
100 105 110

Asp Tyr Asn Lys Thr Trp Lys Ala Ser Glu Asp Gly Lys Ile Asn Thr
115 120 125

Asn Gly Pro Arg Leu Val Val Asp Gln Gly Asn Gly Ser Gly Pro Thr
130 135 140

Gly Gly Tyr Ile Thr Arg Ile Thr Asn Asp Ala Arg Glu Asp Glu Met
145 150 155 160

Glu Gln Asn Ile Gly Glu Val Ala Gly Met Val Ser Asn Leu Arg Asn
165 170 175

Met Ala Val Asp Met Gly Asn Glu Ile Glu Ser Gln Asn Lys Gln Leu
180 185 190

Asp Arg Ile Asn Gln Lys Gly Gly Ser Leu Asn Val Arg Val Asp Glu
195 200 205

Ala Asn Lys Arg Ala Asn Arg Ile Leu Arg Lys Gln
210 215 220

<210> SEQ ID NO 24
<211> LENGTH: 207
<212> TYPE: PRT
<213> ORGANISM: Caenorhabditis elegans

<400> SEQUENCE: 24

Met Ser Gly Asp Asp Asp Ile Pro Glu Gly Leu Glu Ala Ile Asn Leu
1 5 10 15

Lys Met Asn Ala Thr Thr Asp Asp Ser Leu Glu Ser Thr Arg Arg Met
20 25 30

```
Leu Ala Leu Cys Glu Glu Ser Lys Glu Ala Gly Ile Lys Thr Leu Val
        35                  40                  45

Met Leu Asp Asp Gln Gly Glu Gln Leu Glu Arg Cys Glu Gly Ala Leu
    50                  55                  60

Asp Thr Ile Asn Gln Asp Met Lys Glu Ala Glu Asp His Leu Lys Gly
65                  70                  75                  80

Met Glu Lys Cys Cys Gly Leu Cys Val Leu Pro Trp Asn Lys Thr Asp
                85                  90                  95

Asp Phe Glu Lys Thr Glu Phe Ala Lys Ala Trp Lys Lys Asp Asp Asp
            100                 105                 110

Gly Gly Val Ile Ser Asp Gln Pro Arg Ile Thr Val Gly Asp Ser Ser
        115                 120                 125

Met Gly Pro Gln Gly Gly Tyr Ile Thr Lys Ile Thr Asn Asp Ala Arg
    130                 135                 140

Glu Asp Glu Met Asp Glu Asn Val Gln Gln Val Ser Thr Met Val Gly
145                 150                 155                 160

Asn Leu Arg Asn Met Ala Ile Asp Met Ser Thr Glu Val Ser Asn Gln
                165                 170                 175

Asn Arg Gln Leu Asp Arg Ile His Asp Lys Ala Gln Ser Asn Glu Val
            180                 185                 190

Arg Val Glu Ser Ala Asn Lys Arg Ala Lys Asn Leu Ile Thr Lys
        195                 200                 205


<210> SEQ ID NO 25
<211> LENGTH: 808
<212> TYPE: PRT
<213> ORGANISM: Homo sapiens

<400> SEQUENCE: 25

Met Gly Ala Pro Ala Cys Ala Leu Ala Leu Cys Val Ala Val Ala Ile
 1               5                  10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205
```

-continued

```
Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Glu Leu Val Glu Ala
        355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
        515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
    610                 615                 620

Val Leu Val Thr Glu Asp Asn Val Met Lys Ile Ala Asp Phe Gly Leu
625                 630                 635                 640
```

```
Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Ile Pro Val Glu Glu
    690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
        755                 760                 765

Phe Glu Gln Tyr Ser Pro Gly Gly Gln Asp Thr Pro Ser Ser Ser Ser
    770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805


<210> SEQ ID NO 26
<211> LENGTH: 806
<212> TYPE: PRT
<213> ORGANISM: Homo sapiens

<400> SEQUENCE: 26

Met Gly Ala Pro Ala Cys Ala Leu Ala Leu Cys Val Ala Val Ala Ile
 1               5                  10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205
```

-continued

```
Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
```

625 630 635 640

Asp Val His Asn Leu Asp Tyr Tyr Lys Lys Thr Thr Asn Gly Arg Leu
645 650 655

Pro Val Lys Trp Met Ala Pro Glu Ala Leu Phe Asp Arg Val Tyr Thr
660 665 670

His Gln Ser Asp Val Trp Ser Phe Gly Val Leu Leu Trp Glu Ile Phe
675 680 685

Thr Leu Gly Gly Ser Pro Tyr Pro Gly Ile Pro Val Glu Glu Leu Phe
690 695 700

Lys Leu Leu Lys Glu Gly His Arg Met Asp Lys Pro Ala Asn Cys Thr
705 710 715 720

His Asp Leu Tyr Met Ile Met Arg Glu Cys Trp His Ala Ala Pro Ser
725 730 735

Gln Arg Pro Thr Phe Lys Gln Leu Val Glu Asp Leu Asp Arg Val Leu
740 745 750

Thr Val Thr Ser Thr Asp Glu Tyr Leu Asp Leu Ser Ala Pro Phe Glu
755 760 765

Gln Tyr Ser Pro Gly Gly Gln Asp Thr Pro Ser Ser Ser Ser Ser Gly
770 775 780

Asp Asp Ser Val Phe Ala His Asp Leu Leu Pro Pro Ala Pro Pro Ser
785 790 795 800

Ser Gly Gly Ser Arg Thr
805

<210> SEQ ID NO 27
<211> LENGTH: 694
<212> TYPE: PRT
<213> ORGANISM: Homo sapiens

<400> SEQUENCE: 27

Met Gly Ala Pro Ala Cys Ala Leu Ala Leu Cys Val Ala Val Ala Ile
1 5 10 15

Val Ala Gly Ala Ser Ser Glu Ser Leu Gly Thr Glu Gln Arg Val Val
20 25 30

Gly Arg Ala Ala Glu Val Pro Gly Pro Glu Pro Gly Gln Gln Glu Gln
35 40 45

Leu Val Phe Gly Ser Gly Asp Ala Val Glu Leu Ser Cys Pro Pro Pro
50 55 60

Gly Gly Gly Pro Met Gly Pro Thr Val Trp Val Lys Asp Gly Thr Gly
65 70 75 80

Leu Val Pro Ser Glu Arg Val Leu Val Gly Pro Gln Arg Leu Gln Val
85 90 95

Leu Asn Ala Ser His Glu Asp Ser Gly Ala Tyr Ser Cys Arg Gln Arg
100 105 110

Leu Thr Gln Arg Val Leu Cys His Phe Ser Val Arg Val Thr Asp Ala
115 120 125

Pro Ser Ser Gly Asp Asp Glu Asp Gly Glu Asp Glu Ala Glu Asp Thr
130 135 140

Gly Val Asp Thr Gly Ala Pro Tyr Trp Thr Arg Pro Glu Arg Met Asp
145 150 155 160

Lys Lys Leu Leu Ala Val Pro Ala Ala Asn Thr Val Arg Phe Arg Cys
165 170 175

Pro Ala Ala Gly Asn Pro Thr Pro Ser Ile Ser Trp Leu Lys Asn Gly
180 185 190

Arg Glu Phe Arg Gly Glu His Arg Ile Gly Gly Ile Lys Leu Arg His

-continued

```
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Val Ser Leu Glu Ser Asn Ala Ser Met Ser
305                 310                 315                 320

Ser Asn Thr Pro Leu Val Arg Ile Ala Arg Leu Ser Ser Gly Glu Gly
                325                 330                 335

Pro Thr Leu Ala Asn Val Ser Glu Leu Glu Leu Pro Ala Asp Pro Lys
            340                 345                 350

Trp Glu Leu Ser Arg Ala Arg Leu Thr Leu Gly Lys Pro Leu Gly Glu
        355                 360                 365

Gly Cys Phe Gly Gln Val Val Met Ala Glu Ala Ile Gly Ile Asp Lys
    370                 375                 380

Asp Arg Ala Ala Lys Pro Val Thr Val Ala Val Lys Met Leu Lys Asp
385                 390                 395                 400

Asp Ala Thr Asp Lys Asp Leu Ser Asp Leu Val Ser Glu Met Glu Met
                405                 410                 415

Met Lys Met Ile Gly Lys His Lys Asn Ile Ile Asn Leu Leu Gly Ala
            420                 425                 430

Cys Thr Gln Gly Gly Pro Leu Tyr Val Leu Val Glu Tyr Ala Ala Lys
        435                 440                 445

Gly Asn Leu Arg Glu Phe Leu Arg Ala Arg Arg Pro Pro Gly Leu Asp
    450                 455                 460

Tyr Ser Phe Asp Thr Cys Lys Pro Pro Glu Glu Gln Leu Thr Phe Lys
465                 470                 475                 480

Asp Leu Val Ser Cys Ala Tyr Gln Val Ala Arg Gly Met Glu Tyr Leu
                485                 490                 495

Ala Ser Gln Lys Cys Ile His Arg Asp Leu Ala Ala Arg Asn Val Leu
            500                 505                 510

Val Thr Glu Asp Asn Val Met Lys Ile Ala Asp Phe Gly Leu Ala Arg
        515                 520                 525

Asp Val His Asn Leu Asp Tyr Tyr Lys Lys Thr Thr Asn Gly Arg Leu
    530                 535                 540

Pro Val Lys Trp Met Ala Pro Glu Ala Leu Phe Asp Arg Val Tyr Thr
545                 550                 555                 560

His Gln Ser Asp Val Trp Ser Phe Gly Val Leu Leu Trp Glu Ile Phe
                565                 570                 575

Thr Leu Gly Gly Ser Pro Tyr Pro Gly Ile Pro Val Glu Glu Leu Phe
            580                 585                 590

Lys Leu Leu Lys Glu Gly His Arg Met Asp Lys Pro Ala Asn Cys Thr
        595                 600                 605

His Asp Leu Tyr Met Ile Met Arg Glu Cys Trp His Ala Ala Pro Ser
    610                 615                 620
```

```
Gln Arg Pro Thr Phe Lys Gln Leu Val Glu Asp Leu Asp Arg Val Leu
625                 630                 635                 640

Thr Val Thr Ser Thr Asp Glu Tyr Leu Asp Leu Ser Ala Pro Phe Glu
                645                 650                 655

Gln Tyr Ser Pro Gly Gly Gln Asp Thr Pro Ser Ser Ser Ser Ser Gly
            660                 665                 670

Asp Asp Ser Val Phe Ala His Asp Leu Leu Pro Pro Ala Pro Pro Ser
        675                 680                 685

Ser Gly Gly Ser Arg Thr
    690


<210> SEQ ID NO 28
<211> LENGTH: 604
<212> TYPE: PRT
<213> ORGANISM: Homo sapiens

<400> SEQUENCE: 28

Ala Gln Arg Arg Lys Glu Arg Glu Glu Leu Ala Gln Gln Tyr Glu Ala
 1               5                  10                  15

Ile Leu Arg Glu Cys Gly His Gly Arg Phe Gln Trp Thr Leu Tyr Phe
            20                  25                  30

Val Leu Gly Leu Ala Leu Met Ala Asp Gly Val Glu Val Phe Val Val
        35                  40                  45

Gly Phe Val Leu Pro Ser Ala Glu Lys Asp Met Cys Leu Ser Asp Ser
    50                  55                  60

Asn Lys Gly Met Leu Gly Leu Ile Val Tyr Leu Gly Met Met Val Gly
65                  70                  75                  80

Ala Phe Leu Trp Gly Gly Leu Ala Asp Arg Leu Gly Arg Arg Gln Cys
                85                  90                  95

Leu Leu Ile Ser Leu Ser Val Asn Ser Val Phe Ala Phe Phe Ser Ser
            100                 105                 110

Phe Val Gln Gly Tyr Gly Thr Phe Leu Phe Cys Arg Leu Leu Ser Gly
        115                 120                 125

Val Gly Ile Gly Gly Ser Ile Pro Ile Val Phe Ser Tyr Phe Ser Glu
    130                 135                 140

Phe Leu Ala Gln Glu Lys Arg Gly Glu His Leu Ser Trp Leu Cys Met
145                 150                 155                 160

Phe Trp Met Ile Gly Gly Val Tyr Ala Ala Ala Met Ala Trp Ala Ile
                165                 170                 175

Ile Pro His Tyr Gly Trp Ser Phe Gln Met Gly Ser Ala Tyr Gln Phe
            180                 185                 190

His Ser Trp Arg Val Phe Val Leu Val Cys Ala Phe Pro Ser Val Phe
        195                 200                 205

Ala Ile Gly Ala Leu Thr Thr Gln Pro Glu Ser Pro Arg Phe Phe Leu
    210                 215                 220

Glu Asn Gly Lys His Asp Glu Ala Trp Met Val Leu Lys Gln Val His
225                 230                 235                 240

Asp Thr Asn Met Arg Ala Lys Gly His Pro Glu Arg Val Phe Ser Val
                245                 250                 255

Thr His Ile Lys Thr Ile His Gln Glu Asp Glu Leu Ile Glu Ile Gln
            260                 265                 270

Ser Asp Thr Gly Thr Trp Tyr Gln Arg Trp Gly Val Arg Ala Leu Ser
        275                 280                 285

Leu Gly Gly Gln Val Trp Gly Asn Phe Leu Ser Cys Phe Gly Pro Glu
    290                 295                 300
```

```
Tyr Arg Arg Ile Thr Leu Met Met Met Gly Val Trp Phe Thr Met Ser
305                 310                 315                 320

Phe Ser Tyr Tyr Gly Leu Thr Val Trp Phe Pro Asp Met Ile Arg His
                325                 330                 335

Leu Gln Ala Val Asp Tyr Ala Ser Arg Thr Lys Val Phe Pro Gly Glu
            340                 345                 350

Arg Val Glu His Val Thr Phe Asn Phe Thr Leu Glu Asn Gln Ile His
        355                 360                 365

Arg Gly Gly Gln Tyr Phe Asn Asp Lys Phe Ile Gly Leu Arg Leu Lys
    370                 375                 380

Ser Val Ser Phe Glu Asp Ser Leu Phe Glu Glu Cys Tyr Phe Glu Asp
385                 390                 395                 400

Val Thr Ser Ser Asn Thr Phe Phe Arg Asn Cys Thr Phe Ile Asn Thr
                405                 410                 415

Val Phe Tyr Asn Thr Asp Leu Phe Glu Tyr Lys Phe Val Asn Ser Arg
            420                 425                 430

Leu Ile Asn Ser Thr Phe Leu His Asn Lys Glu Gly Cys Pro Leu Asp
        435                 440                 445

Val Thr Gly Thr Gly Glu Gly Ala Tyr Met Val Tyr Phe Val Ser Phe
    450                 455                 460

Leu Gly Thr Leu Ala Val Leu Pro Gly Asn Ile Val Ser Ala Leu Leu
465                 470                 475                 480

Met Asp Lys Ile Gly Arg Leu Arg Met Leu Ala Gly Ser Ser Val Met
                485                 490                 495

Ser Cys Val Ser Cys Phe Phe Leu Ser Phe Gly Asn Ser Glu Ser Ala
            500                 505                 510

Met Ile Ala Leu Leu Cys Leu Phe Gly Gly Val Ser Ile Ala Ser Trp
        515                 520                 525

Asn Ala Leu Asp Val Leu Thr Val Glu Leu Tyr Pro Ser Asp Lys Arg
    530                 535                 540

Thr Thr Ala Phe Gly Phe Leu Asn Ala Leu Cys Lys Leu Ala Ala Val
545                 550                 555                 560

Leu Gly Ile Ser Ile Phe Thr Ser Phe Val Gly Ile Thr Lys Ala Ala
                565                 570                 575

Pro Ile Leu Phe Ala Ser Ala Ala Leu Ala Leu Gly Ser Ser Leu Ala
            580                 585                 590

Leu Lys Leu Pro Glu Thr Arg Gly Gln Val Leu Gln
        595                 600


<210> SEQ ID NO 29
<211> LENGTH: 683
<212> TYPE: PRT
<213> ORGANISM: Homo sapiens

<400> SEQUENCE: 29

Met Asp Asp Tyr Lys Tyr Gln Asp Asn Tyr Gly Gly Tyr Ala Pro Ser
 1               5                  10                  15

Asp Gly Tyr Tyr Arg Gly Asn Glu Ser Asn Pro Glu Glu Asp Ala Gln
            20                  25                  30

Ser Asp Val Thr Glu Gly His Asp Glu Glu Asp Glu Ile Tyr Glu Gly
        35                  40                  45

Glu Tyr Gln Gly Ile Pro His Pro Asp Asp Val Lys Ala Lys Gln Ala
    50                  55                  60

Lys Met Ala Pro Ser Arg Met Asp Ser Leu Arg Gly Gln Thr Asp Leu
65                  70                  75                  80
```

-continued

Met Ala Glu Arg Leu Glu Asp Glu Glu Gln Leu Ala His Gln Tyr Glu
85 90 95

Thr Ile Met Asp Glu Cys Gly His Gly Arg Phe Gln Trp Ile Leu Phe
100 105 110

Phe Val Leu Gly Leu Ala Leu Met Ala Asp Gly Val Glu Val Phe Val
115 120 125

Val Ser Phe Ala Leu Pro Ser Ala Glu Lys Asp Met Cys Leu Ser Ser
130 135 140

Ser Lys Lys Gly Met Leu Gly Met Ile Val Tyr Leu Gly Met Met Ala
145 150 155 160

Gly Ala Phe Ile Leu Gly Gly Leu Ala Asp Lys Leu Gly Arg Lys Arg
165 170 175

Val Leu Ser Met Ser Leu Ala Val Asn Ala Ser Phe Ala Ser Leu Ser
180 185 190

Ser Phe Val Gln Gly Tyr Gly Ala Phe Leu Phe Cys Arg Leu Ile Ser
195 200 205

Gly Ile Gly Ile Gly Gly Ala Leu Pro Ile Val Phe Ala Tyr Phe Ser
210 215 220

Glu Phe Leu Ser Arg Glu Lys Arg Gly Glu His Leu Ser Trp Leu Gly
225 230 235 240

Ile Phe Trp Met Thr Gly Gly Leu Tyr Ala Ser Ala Met Ala Trp Ser
245 250 255

Ile Ile Pro His Tyr Gly Trp Gly Phe Ser Met Gly Thr Asn Tyr His
260 265 270

Phe His Ser Trp Arg Val Phe Val Ile Val Cys Ala Leu Pro Cys Thr
275 280 285

Val Ser Met Val Ala Leu Lys Phe Met Pro Glu Ser Pro Arg Phe Leu
290 295 300

Leu Glu Met Gly Lys His Asp Glu Ala Trp Met Ile Leu Lys Gln Val
305 310 315 320

His Asp Thr Asn Met Arg Ala Lys Gly Thr Pro Glu Lys Val Phe Thr
325 330 335

Val Ser Asn Ile Lys Thr Pro Lys Gln Met Asp Glu Phe Ile Glu Ile
340 345 350

Gln Ser Ser Thr Gly Thr Trp Tyr Gln Arg Trp Leu Val Arg Phe Lys
355 360 365

Thr Ile Phe Lys Gln Val Trp Asp Asn Ala Leu Tyr Cys Val Met Gly
370 375 380

Pro Tyr Arg Met Asn Thr Leu Ile Leu Ala Val Val Trp Phe Ala Met
385 390 395 400

Ala Phe Ser Tyr Tyr Gly Leu Thr Val Trp Phe Pro Asp Met Ile Arg
405 410 415

Tyr Phe Gln Asp Glu Glu Tyr Lys Ser Lys Met Lys Val Phe Phe Gly
420 425 430

Glu His Val Tyr Gly Ala Thr Ile Asn Phe Thr Met Glu Asn Gln Ile
435 440 445

His Gln His Gly Lys Leu Val Asn Asp Lys Phe Thr Arg Met Tyr Phe
450 455 460

Lys His Val Leu Phe Glu Asp Thr Phe Phe Asp Glu Cys Tyr Phe Glu
465 470 475 480

Asp Val Thr Ser Thr Asp Thr Tyr Phe Lys Asn Cys Thr Ile Glu Ser
485 490 495

Thr Ile Phe Tyr Asn Thr Asp Leu Tyr Glu His Lys Phe Ile Asn Cys
500 505 510

```
Arg Phe Ile Asn Ser Thr Phe Leu Glu Gln Lys Glu Gly Cys His Met
        515                 520                 525

Asp Leu Glu Gln Asp Asn Asp Phe Leu Ile Tyr Leu Val Ser Phe Leu
    530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Gly Ser Met Leu Ile Ser
                565                 570                 575

Ala Val Cys Cys Phe Phe Leu Phe Phe Gly Asn Ser Glu Ser Ala Met
            580                 585                 590

Ile Gly Trp Gln Cys Leu Phe Cys Gly Thr Ser Ile Ala Ala Trp Asn
        595                 600                 605

Ala Leu Asp Val Ile Thr Val Glu Leu Tyr Pro Thr Asn Gln Arg Ala
    610                 615                 620

Thr Ala Phe Gly Ile Leu Asn Gly Leu Cys Lys Phe Gly Ala Ile Leu
625                 630                 635                 640

Gly Asn Thr Ile Phe Ala Ser Phe Val Gly Ile Thr Lys Val Val Pro
                645                 650                 655

Ile Leu Leu Ala Ala Ala Ser Leu Val Gly Gly Gly Leu Ile Ala Leu
            660                 665                 670

Arg Leu Pro Glu Thr Arg Glu Gln Val Leu Ile
        675                 680


<210> SEQ ID NO 30
<211> LENGTH: 727
<212> TYPE: PRT
<213> ORGANISM: Homo sapiens

<400> SEQUENCE: 30

Met Glu Asp Ser Tyr Lys Asp Arg Thr Ser Leu Met Lys Gly Ala Lys
 1               5                  10                  15

Asp Ile Ala Arg Glu Val Lys Lys Gln Thr Val Lys Lys Val Asn Gln
            20                  25                  30

Ala Val Asp Arg Ala Gln Asp Glu Tyr Thr Gln Arg Ser Tyr Ser Arg
        35                  40                  45

Phe Gln Asp Glu Glu Asp Asp Asp Asp Tyr Tyr Pro Ala Gly Glu Thr
    50                  55                  60

Tyr Asn Gly Glu Ala Asn Asp Asp Glu Gly Ser Ser Glu Ala Thr Glu
65                  70                  75                  80

Gly His Asp Glu Asp Asp Glu Ile Tyr Glu Gly Glu Tyr Gln Gly Ile
                85                  90                  95

Pro Ser Met Asn Gln Ala Lys Asp Ser Ile Val Ser Val Gly Gln Pro
            100                 105                 110

Lys Gly Asp Glu Tyr Lys Asp Arg Arg Glu Leu Glu Ser Glu Arg Arg
        115                 120                 125

Ala Asp Glu Glu Glu Leu Ala Gln Gln Tyr Glu Leu Ile Ile Gln Glu
    130                 135                 140

Cys Gly His Gly Arg Phe Gln Trp Ala Leu Phe Phe Val Leu Gly Met
145                 150                 155                 160

Ala Leu Met Ala Asp Gly Val Glu Val Phe Val Val Gly Phe Val Leu
                165                 170                 175

Pro Ser Ala Glu Thr Asp Leu Cys Ile Pro Asn Ser Gly Ser Gly Trp
            180                 185                 190

Leu Gly Ser Ile Val Tyr Leu Gly Met Met Val Gly Ala Phe Phe Trp
        195                 200                 205
```

-continued

```
Gly Gly Leu Ala Asp Lys Val Gly Arg Lys Gln Ser Leu Leu Ile Cys
    210                 215                 220

Met Ser Val Asn Gly Phe Phe Ala Phe Leu Ser Ser Phe Val Gln Gly
225                 230                 235                 240

Tyr Gly Phe Phe Leu Phe Cys Arg Leu Leu Ser Gly Phe Gly Ile Gly
                245                 250                 255

Gly Ala Ile Pro Thr Val Phe Ser Tyr Phe Ala Glu Val Leu Ala Arg
            260                 265                 270

Glu Lys Arg Gly Glu His Leu Ser Trp Leu Cys Met Phe Trp Met Ile
        275                 280                 285

Gly Gly Ile Tyr Ala Ser Ala Met Ala Trp Ala Ile Ile Pro His Tyr
    290                 295                 300

Gly Trp Ser Phe Ser Met Gly Ser Ala Tyr Gln Phe His Ser Trp Arg
305                 310                 315                 320

Val Phe Val Ile Val Cys Ala Leu Pro Cys Val Ser Ser Val Val Ala
                325                 330                 335

Leu Thr Phe Met Pro Glu Ser Pro Arg Phe Leu Leu Glu Val Gly Lys
            340                 345                 350

His Asp Glu Ala Trp Met Ile Leu Lys Leu Ile His Asp Thr Asn Met
        355                 360                 365

Arg Ala Arg Gly Gln Pro Glu Lys Val Phe Thr Val Asn Lys Ile Lys
    370                 375                 380

Thr Pro Lys Gln Ile Asp Glu Leu Ile Glu Ile Glu Ser Asp Thr Gly
385                 390                 395                 400

Thr Trp Tyr Arg Arg Cys Phe Val Arg Ile Arg Thr Glu Leu Tyr Gly
                405                 410                 415

Ile Trp Leu Thr Phe Met Arg Cys Phe Asn Tyr Pro Val Arg Asp Asn
            420                 425                 430

Thr Ile Lys Leu Thr Ile Val Trp Phe Thr Leu Ser Phe Gly Tyr Tyr
        435                 440                 445

Gly Leu Ser Val Trp Phe Pro Asp Val Ile Lys Pro Leu Gln Ser Asp
    450                 455                 460

Glu Tyr Ala Leu Leu Thr Arg Asn Val Glu Arg Asp Lys Tyr Ala Asn
465                 470                 475                 480

Phe Thr Ile Asn Phe Thr Met Glu Asn Gln Ile His Thr Gly Met Glu
                485                 490                 495

Tyr Asp Asn Gly Arg Phe Ile Gly Val Lys Phe Lys Ser Val Thr Phe
            500                 505                 510

Lys Asp Ser Val Phe Lys Ser Cys Thr Phe Glu Asp Val Thr Ser Val
        515                 520                 525

Asn Thr Tyr Phe Lys Asn Cys Thr Phe Ile Asp Thr Val Phe Asp Asn
    530                 535                 540

Thr Asp Phe Glu Pro Tyr Lys Phe Ile Asp Ser Glu Phe Lys Asn Cys
545                 550                 555                 560

Ser Phe Phe His Asn Lys Thr Gly Cys Gln Ile Thr Phe Asp Asp Asp
                565                 570                 575

Tyr Ser Ala Tyr Trp Ile Tyr Phe Val Asn Phe Leu Gly Thr Leu Ala
            580                 585                 590

Val Leu Pro Gly Asn Ile Val Ser Ala Leu Leu Met Asp Arg Ile Gly
        595                 600                 605

Arg Leu Thr Met Leu Gly Gly Ser Met Val Leu Ser Gly Ile Ser Cys
    610                 615                 620

Phe Phe Leu Trp Phe Gly Thr Ser Glu Ser Met Met Ile Gly Met Leu
```

```
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
            660                 665                 670

Phe Leu Asn Ala Leu Cys Lys Ala Ala Ala Val Leu Gly Asn Leu Ile
        675                 680                 685

Phe Gly Ser Leu Val Ser Ile Thr Lys Ser Ile Pro Ile Leu Leu Ala
    690                 695                 700

Ser Thr Val Leu Val Cys Gly Gly Leu Val Gly Leu Cys Leu Pro Asp
705                 710                 715                 720

Thr Arg Thr Gln Val Leu Met
                725


<210> SEQ ID NO 31
<211> LENGTH: 742
<212> TYPE: PRT
<213> ORGANISM: Homo sapiens

<400> SEQUENCE: 31

Met Glu Glu Gly Phe Arg Asp Arg Ala Ala Phe Ile Arg Gly Ala Lys
 1               5                  10                  15

Asp Ile Ala Lys Glu Val Lys Lys His Ala Ala Lys Lys Val Val Lys
            20                  25                  30

Gly Leu Asp Arg Val Gln Asp Glu Tyr Ser Arg Arg Ser Tyr Ser Arg
        35                  40                  45

Phe Glu Glu Glu Asp Asp Asp Asp Asp Phe Pro Ala Pro Ser Asp Gly
    50                  55                  60

Tyr Tyr Arg Gly Glu Gly Thr Gln Asp Glu Glu Glu Gly Gly Ala Ser
65                  70                  75                  80

Ser Asp Ala Thr Glu Gly His Asp Glu Asp Asp Glu Ile Tyr Glu Gly
                85                  90                  95

Glu Tyr Gln Asp Ile Pro Arg Ala Glu Ser Gly Gly Lys Gly Glu Arg
            100                 105                 110

Met Ala Asp Gly Ala Pro Leu Ala Gly Val Arg Gly Gly Leu Ser Asp
        115                 120                 125

Gly Glu Gly Pro Pro Gly Gly Arg Gly Glu Ala Gln Arg Arg Lys Glu
    130                 135                 140

Arg Glu Glu Leu Ala Gln Gln Tyr Glu Ala Ile Leu Arg Glu Cys Gly
145                 150                 155                 160

His Gly Arg Phe Gln Trp Thr Leu Tyr Phe Val Leu Gly Leu Ala Leu
                165                 170                 175

Met Ala Asp Gly Val Glu Val Phe Val Val Gly Phe Val Leu Pro Ser
            180                 185                 190

Ala Glu Lys Asp Met Cys Leu Ser Asp Ser Asn Lys Gly Met Leu Gly
        195                 200                 205

Leu Ile Val Tyr Leu Gly Met Met Val Gly Ala Phe Leu Trp Gly Gly
    210                 215                 220

Leu Ala Asp Arg Leu Gly Arg Arg Gln Cys Leu Leu Ile Ser Leu Ser
225                 230                 235                 240

Val Asn Ser Val Phe Ala Phe Phe Ser Ser Phe Val Gln Gly Tyr Gly
                245                 250                 255

Thr Phe Leu Phe Cys Arg Leu Leu Ser Gly Val Gly Ile Gly Gly Ser
            260                 265                 270

Ile Pro Ile Val Phe Ser Tyr Phe Ser Glu Phe Leu Ala Gln Glu Lys
```

-continued

```
        275                 280                 285

Arg Gly Glu His Leu Ser Trp Leu Cys Met Phe Trp Met Ile Gly Gly
    290                 295                 300

Val Tyr Ala Ala Ala Met Ala Trp Ala Ile Ile Pro His Tyr Gly Trp
305                 310                 315                 320

Ser Phe Gln Met Gly Ser Ala Tyr Gln Phe His Ser Trp Arg Val Phe
                325                 330                 335

Val Leu Val Cys Ala Phe Pro Ser Val Phe Ala Ile Gly Ala Leu Thr
            340                 345                 350

Thr Gln Pro Glu Ser Pro Arg Phe Phe Leu Glu Asn Gly Lys His Asp
        355                 360                 365

Glu Ala Trp Met Val Leu Lys Gln Val His Asp Thr Asn Met Arg Ala
    370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
                405                 410                 415

Tyr Gln Arg Trp Gly Val Arg Ala Leu Ser Leu Gly Gly Gln Val Trp
            420                 425                 430

Gly Asn Phe Leu Ser Cys Phe Gly Pro Glu Tyr Arg Arg Ile Thr Leu
        435                 440                 445

Met Met Met Gly Val Trp Phe Thr Met Ser Phe Ser Tyr Tyr Gly Leu
    450                 455                 460

Thr Val Trp Phe Pro Asp Met Ile Arg His Leu Gln Ala Val Asp Tyr
465                 470                 475                 480

Ala Ser Arg Thr Lys Val Phe Pro Gly Glu Arg Val Gly His Val Thr
                485                 490                 495

Phe Asn Phe Thr Leu Glu Asn Gln Ile His Arg Gly Gly Gln Tyr Phe
            500                 505                 510

Asn Asp Lys Phe Ile Gly Leu Arg Leu Lys Ser Val Ser Phe Glu Asp
        515                 520                 525

Ser Leu Phe Glu Glu Cys Tyr Phe Glu Asp Val Thr Ser Ser Asn Thr
    530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Ile Asn Ser Thr Phe
                565                 570                 575

Leu His Asn Lys Glu Gly Cys Pro Leu Asp Val Thr Gly Thr Gly Glu
            580                 585                 590

Gly Ala Tyr Met Val Tyr Phe Val Ser Phe Leu Gly Thr Leu Ala Val
        595                 600                 605

Leu Pro Gly Asn Ile Val Ser Ala Leu Leu Met Asp Lys Ile Gly Arg
    610                 615                 620

Leu Arg Met Leu Ala Gly Ser Ser Val Met Ser Cys Val Ser Cys Phe
625                 630                 635                 640

Phe Leu Ser Phe Gly Asn Ser Glu Ser Ala Met Ile Ala Leu Leu Cys
                645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
        675                 680                 685

Leu Asn Ala Leu Cys Lys Leu Ala Ala Val Leu Gly Ile Ser Ile Phe
    690                 695                 700
```

-continued

Thr Ser Phe Val Gly Ile Thr Lys Ala Ala Pro Ile Leu Phe Ala Ser
705 710 715 720

Ala Ala Leu Ala Leu Gly Ser Ser Leu Ala Leu Lys Leu Pro Glu Thr
725 730 735

Arg Gly Gln Val Leu Gln
740

<210> SEQ ID NO 32
<211> LENGTH: 7
<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 32

Arg Ile Asp Glu Ala Asn Gln
1 5

<210> SEQ ID NO 33
<211> LENGTH: 8
<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 33

Thr Arg Ile Asp Glu Ala Asn Gln
1 5

<210> SEQ ID NO 34
<211> LENGTH: 9
<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 34

Lys Thr Arg Ile Asp Glu Ala Asn Gln
1 5

<210> SEQ ID NO 35
<211> LENGTH: 10
<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 35

Asn Lys Thr Arg Ile Asp Glu Ala Asn Gln
1 5 10

<210> SEQ ID NO 36
<211> LENGTH: 11
<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 36

```
Ser Asn Lys Thr Arg Ile Asp Glu Ala Asn Gln
 1               5                  10


<210> SEQ ID NO 37
<211> LENGTH: 12
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 37

Asp Ser Asn Lys Thr Arg Ile Asp Glu Ala Asn Gln
 1               5                  10


<210> SEQ ID NO 38
<211> LENGTH: 13
<212> TYPE: PRT
<213> ORGANISM: Artificial Sequence
<220> FEATURE:
<223> OTHER INFORMATION: SNAP-25 antigen having a free carboxylated
      carboxyl-terminus at the P1 residue of the
      scissile bond of the BoNT/A cleavage site
<221> NAME/KEY: SITE
<222> LOCATION: (13)...(13)
<223> OTHER INFORMATION: carboxylated glutamine

<400> SEQUENCE: 38

Cys Asp Ser Asn Lys Thr Arg Ile Asp Glu Ala Asn Gln
 1               5                  10


<210> SEQ ID NO 39
<211> LENGTH: 7
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 39

Arg Ile Asp Glu Ala Asn Lys
 1               5


<210> SEQ ID NO 40
<211> LENGTH: 8
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 40

Ala Arg Ile Asp Glu Ala Asn Lys
 1               5


<210> SEQ ID NO 41
<211> LENGTH: 9
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 41

Lys Ala Arg Ile Asp Glu Ala Asn Lys
```

```
 1               5


<210> SEQ ID NO 42
<211> LENGTH: 10
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 42

Asn Lys Ala Arg Ile Asp Glu Ala Asn Lys
 1               5                   10


<210> SEQ ID NO 43
<211> LENGTH: 11
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 43

Met Asn Lys Ala Arg Ile Asp Glu Ala Asn Lys
 1               5                   10


<210> SEQ ID NO 44
<211> LENGTH: 12
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 44

Asp Met Asn Lys Ala Arg Ile Asp Glu Ala Asn Lys
 1               5                   10


<210> SEQ ID NO 45
<211> LENGTH: 13
<212> TYPE: PRT
<213> ORGANISM: Artificial Sequence
<220> FEATURE:
<223> OTHER INFORMATION: SNAP-25 antigen having a free carboxylated
      carboxyl-terminus at the P1 residue of the
      scissile bond of the BoNT/A cleavage site
<221> NAME/KEY: SITE
<222> LOCATION: (13)...(13)
<223> OTHER INFORMATION: Carboxylated lysine

<400> SEQUENCE: 45

Cys Asp Met Asn Lys Ala Arg Ile Asp Glu Ala Asn Lys
 1               5                   10


<210> SEQ ID NO 46
<211> LENGTH: 11
<212> TYPE: PRT
<213> ORGANISM: Artificial Sequence
<220> FEATURE:
<223> OTHER INFORMATION: SNAP-25 antigen

<400> SEQUENCE: 46

Cys Gly Gly Gly Arg Ile Asp Glu Ala Asn Gln
 1               5                   10


<210> SEQ ID NO 47
```

<211> LENGTH: 11
<212> TYPE: PRT
<213> ORGANISM: Artificial Sequence
<220> FEATURE:
<223> OTHER INFORMATION: SNAP-25 antigen

<400> SEQUENCE: 47

Cys Gly Gly Gly Arg Ile Asp Glu Ala Asn Lys
1 5 10

<210> SEQ ID NO 48
<211> LENGTH: 88
<212> TYPE: PRT
<213> ORGANISM: Artificial Sequence
<220> FEATURE:
<223> OTHER INFORMATION: BirA-HisTag?-SNAP-25-134-197

<400> SEQUENCE: 48

Met Gly Gly Gly Leu Asn Asp Ile Phe Glu Ala Gln Lys Ile Glu Trp
1 5 10 15

His His His His His His His His Ile Arg Arg Val Thr Asn Asp Ala
20 25 30

Arg Glu Asn Glu Met Asp Glu Asn Leu Glu Gln Val Ser Gly Ile Ile
35 40 45

Gly Asn Leu Arg His Met Ala Leu Asp Met Gly Asn Glu Ile Asp Thr
50 55 60

Gln Asn Arg Gln Ile Asp Arg Ile Met Glu Lys Ala Asp Ser Asn Lys
65 70 75 80

Thr Arg Ile Asp Glu Ala Asn Gln
85

<210> SEQ ID NO 49
<211> LENGTH: 97
<212> TYPE: PRT
<213> ORGANISM: Artificial Sequence
<220> FEATURE:
<223> OTHER INFORMATION: BirA-HisTag?-SNAP-25-134-206

<400> SEQUENCE: 49

Met Gly Gly Gly Leu Asn Asp Ile Phe Glu Ala Gln Lys Ile Glu Trp
1 5 10 15

His His His His His His His His Ile Arg Arg Val Thr Asn Asp Ala
20 25 30

Arg Glu Asn Glu Met Asp Glu Asn Leu Glu Gln Val Ser Gly Ile Ile
35 40 45

Gly Asn Leu Arg His Met Ala Leu Asp Met Gly Asn Glu Ile Asp Thr
50 55 60

Gln Asn Arg Gln Ile Asp Arg Ile Met Glu Lys Ala Asp Ser Asn Lys
65 70 75 80

Thr Arg Ile Asp Glu Ala Asn Gln Arg Ala Thr Lys Met Leu Gly Ser
85 90 95

Gly

<210> SEQ ID NO 50
<211> LENGTH: 16
<212> TYPE: PRT
<213> ORGANISM: Artificial Sequence
<220> FEATURE:
<223> OTHER INFORMATION: BirA peptide

<400> SEQUENCE: 50

Gly Gly Gly Leu Asn Asp Ile Phe Glu Ala Gln Lys Ile Glu Trp His 1 5 10 15

<210> SEQ ID NO 51
<211> LENGTH: 7570
<212> TYPE: DNA
<213> ORGANISM: Artificial Sequence
<220> FEATURE:
<223> OTHER INFORMATION: pQBI-25/GFP-BoNT/A-LC expression construct.

<400> SEQUENCE: 51
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcc tcgaggcctg gccattgcat acgttgtatc 240
catatcataa tatgtacatt tatattggct catgtccaac attaccgcca tgttgacatt 300
gattattgac tagttattaa tagtaatcaa ttacggggtc attagttcat agcccatata 360
tggagttccg cgttacataa cttacggtaa atggcccgcc tggctgaccg cccaacgacc 420
cccgcccatt gacgtcaata atgacgtatg ttcccatagt aacgccaata gggactttcc 480
attgacgtca atgggtggag tatttacggt aaactgccca cttggcagta catcaagtgt 540
atcatatgcc aagtacgccc cctattgacg tcaatgacgg taaatggccc gcctggcatt 600
atgcccagta catgacctta tgggactttc ctacttggca gtacatctac gtattagtca 660
tcgctattac catggtgatg cggttttggc agtacatcaa tgggcgtgga tagcggtttg 720
actcacgggg atttccaagt ctccacccca ttgacgtcaa tgggagtttg ttttggcacc 780
aaaatcaacg ggactttcca aaatgtcgta acaactccgc cccattgacg caaatgggcg 840
gtaggcgtgt acggtgggag gtctatataa gcagagctcg tttagtgaac cgtcagatcg 900
cctggagacg ccatccacgc tgttttgacc tccatagaag acaccgggac cgatccagcc 960
tccgcgggcc accatggagg gcccggttac cggtaccgga tccagatatc tgggcggccg 1020
ctcagcaagc ttcgcgaatt cgggaggcgg aggtggagct agcaaaggag aagaactctt 1080
cactggagtt gtcccaattc ttgttgaatt agatggtgat gttaacggcc acaagttctc 1140
tgtcagtgga gagggtgaag gtgatgcaac atacggaaaa cttaccctga agttcatctg 1200
cactactggc aaactgcctg ttccatggcc aacactagtc actactctgt gctatggtgt 1260
tcaatgcttt tcaagatacc cggatcatat gaaacggcat gactttttca agagtgccat 1320
gcccgaaggt tatgtacagg aaaggaccat cttcttcaaa gatgacggca actacaagac 1380
acgtgctgaa gtcaagtttg aaggtgatac ccttgttaat agaatcgagt taaaaggtat 1440
tgacttcaag gaagatggca acattctggg acacaaattg gaatacaact ataactcaca 1500
caatgtatac atcatggcag acaaacaaaa gaatggaatc aaagtgaact tcaagacccg 1560
ccacaacatt gaagatggaa gcgttcaact agcagaccat tatcaacaaa atactccaat 1620
tggcgatggc cctgtccttt taccagacaa ccattacctg tccacacaat ctgccctttc 1680
gaaagatccc aacgaaaaga gagaccacat ggtccttctt gagtttgtaa cagctgctgg 1740
gattacacat ggcatggatg aactgtacaa catcgatgga ggcggaggtg gacctttttgt 1800 taataaacaa tttaattata aagatcctgt aaatggtgtt gatattgctt atataaaaat 1860
tccaaatgca ggacaaatgc aaccagtaaa agcttttaaa attcataata aaatatgggt 1920
tattccagaa agagatacat ttacaaatcc tgaagaagga gatttaaatc caccaccaga 1980
agcaaaacaa gttccagttt catattatga ttcaacatat ttaagtacag ataatgaaaa 2040

-continued

```
agataattat ttaaagggag ttacaaaatt atttgagaga atttattcaa ctgatcttgg   2100
aagaatgttg ttaacatcaa tagtaagggg aataccattt tggggtggaa gtacaataga   2160
tacagaatta aaagttattg atactaattg tattaatgtg atacaaccag atggtagtta   2220
tagatcagaa gaacttaatc tagtaataat aggaccctca gctgatatta tacagtttga   2280
atgtaaaagc tttggacatg aagttttgaa tcttacgcga aatggttatg gctctactca   2340
atacattaga tttagcccag attttacatt tggttttgag gagtcacttg aagttgatac   2400
aaatcctctt ttaggtgcag gcaaatttgc tacagatcca gcagtaacat tagcacatga   2460
acttatacat gctggacata gattatatgg aatagcaatt aatccaaata gggtttttaa   2520
agtaaatact aatgcctatt atgaaatgag tgggttagaa gtaagctttg aggaacttag   2580
aacatttggg ggacatgatg caaagtttat agatagttta caggaaaacg aatttcgtct   2640
atattattat aataagttta aagatatagc aagtacactt aataaagcta aatcaatagt   2700
aggtactact gcttcattac agtatatgaa aaatgttttt aaagagaaat atctcctatc   2760
tgaagataca tctggaaaat tttcggtaga taaattaaaa tttgataagt tatacaaaat   2820
gttaacagag atttacacag aggataattt tgttaagttt tttaaagtac ttaacagaaa   2880
aacatatttg aattttgata aagccgtatt taagataaat atagtaccta aggtaaatta   2940
cacaatatat gatggattta atttaagaaa tacaaattta gcagcaaact ttaatggtca   3000
aaatacagaa attaataata tgaattttac taaactaaaa aattttactg gattgtttga   3060
attttataag ttgctatgtg taagagggat aatcacttcg aaatgaacgc gttggcccta   3120
ttctatagtg tcacctaaat gctagagctc gctgatcagc ctcgactgtg ccttctagtt   3180
gccagccatc tgttgtttgc ccctcccccg tgccttcctt gaccctggaa ggtgccactc   3240
ccactgtcct ttcctaataa aatgaggaaa ttgcatcgca ttgtctgagt aggtgtcatt   3300
ctattctggg gggtggggtg gggcaggaca gcaaggggga ggattgggaa gacaatagca   3360
ggcatgctgg ggatgcggtg ggctctatgg cttctgaggc ggaaagaacc agctggggct   3420
ctagggggta tccccacgcg ccctgtagcg gcgcattaag cgcggcgggt gtggtggtta   3480
cgcgcagcgt gaccgctaca cttgccagcg ccctagcgcc cgctcctttc gctttcttcc   3540
cttcctttct cgccacgttc gccggctttc cccgtcaagc tctaaatcgg ggcatccctt   3600
tagggttccg atttagtgct ttacggcacc tcgaccccaa aaaacttgat tagggtgatg   3660
gttcacgtag tgggccatcg ccctgataga cggtttttcg ccctttgacg ttggagtcca   3720
cgttctttaa tagtggactc ttgttccaaa ctggaacaac actcaaccct atctcggtct   3780
attcttttga tttataaggg attttgggga tttcggccta ttggttaaaa aatgagctga   3840
tttaacaaaa atttaacgcg aattaattct gtggaatgtg tgtcagttag ggtgtggaaa   3900
gtccccaggc tccccaggca ggcagaagta tgcaaagcat gcatctcaat tagtcagcaa   3960
ccaggtgtgg aaagtcccca ggctccccag caggcagaag tatgcaaagc atgcatctca   4020
attagtcagc aaccatagtc ccgcccctaa ctccgcccat cccgccccta actccgccca   4080
gttccgccca ttctccgccc catggctgac taattttttt tatttatgca gaggccgagg   4140
ccgcctctgc ctctgagcta ttccagaagt agtgaggagg cttttttgga ggcctaggct   4200
tttgcaaaaa gctcccggga gcttgtatat ccattttcgg atctgatcaa gagacaggat   4260
gaggatcgtt tcgcatgatt gaacaagatg gattgcacgc aggttctccg gccgcttggg   4320
tggagaggct attcggctat gactgggcac aacagacaat cggctgctct gatgccgccg   4380
tgttccggct gtcagcgcag gggcgcccgg ttctttttgt caagaccgac ctgtccggtg   4440
```

ccctgaatga actgcaggac gaggcagcgc ggctatcgtg gctggccacg acgggcgttc 4500
cttgcgcagc tgtgctcgac gttgtcactg aagcgggaag ggactggctg ctattgggcg 4560
aagtgccggg gcaggatctc ctgtcatctc accttgctcc tgccgagaaa gtatccatca 4620
tggctgatgc aatgcggcgg ctgcatacgc ttgatccggc tacctgccca ttcgaccacc 4680
aagcgaaaca tcgcatcgag cgagcacgta ctcggatgga agccggtctt gtcgatcagg 4740
atgatctgga cgaagagcat caggggctcg cgccagccga actgttcgcc aggctcaagg 4800
cgcgcatgcc cgacggcgag gatctcgtcg tgacccatgg cgatgcctgc ttgccgaata 4860
tcatggtgga aaatggccgc ttttctggat tcatcgactg tggccggctg ggtgtggcgg 4920
accgctatca ggacatagcg ttggctaccc gtgatattgc tgaagagctt ggcggcgaat 4980
gggctgaccg cttcctcgtg ctttacggta tcgccgctcc cgattcgcag cgcatcgcct 5040
tctatcgcct tcttgacgag ttcttctgag cgggactctg gggttcgaaa tgaccgacca 5100
agcgacgccc aacctgccat cacgagattt cgattccacc gccgccttct atgaaaggtt 5160
gggcttcgga atcgttttcc gggacgccgg ctggatgatc ctccagcgcg gggatctcat 5220
gctggagttc ttcgcccacc ccaacttgtt tattgcagct tataatggtt acaaataaag 5280
caatagcatc acaaatttca caaataaagc atttttttca ctgcattcta gttgtggttt 5340
gtccaaactc atcaatgtat cttatcatgt ctgtataccg tcgacctcta gctagagctt 5400
ggcgtaatca tggtcatagc tgtttcctgt gtgaaattgt tatccgctca caattccaca 5460
caacatacga gccggaagca taaagtgtaa agcctggggt gcctaatgag tgagctaact 5520
cacattaatt gcgttgcgct cactgcccgc tttccagtcg ggaaacctgt cgtgccagct 5580
gcattaatga atcggccaac gcgcggggag aggcggtttg cgtattgggc gctcttccgc 5640
ttcctcgctc actgactcgc tgcgctcggt cgttcggctg cggcgagcgg tatcagctca 5700
ctcaaaggcg gtaatacggt tatccacaga atcaggggat aacgcaggaa agaacatgtg 5760
agcaaaaggc cagcaaaagg ccaggaaccg taaaaaggcc gcgttgctgg cgtttttcca 5820
taggctccgc ccccctgacg agcatcacaa aaatcgacgc tcaagtcaga ggtggcgaaa 5880
cccgacagga ctataaagat accaggcgtt tccccctgga agctccctcg tgcgctctcc 5940
tgttccgacc ctgccgctta ccggatacct gtccgccttt ctcccttcgg gaagcgtggc 6000
gctttctcaa tgctcacgct gtaggtatct cagttcggtg taggtcgttc gctccaagct 6060
gggctgtgtg cacgaacccc ccgttcagcc cgaccgctgc gccttatccg gtaactatcg 6120
tcttgagtcc aacccggtaa gacacgactt atcgccactg gcagcagcca ctggtaacag 6180
gattagcaga gcgaggtatg taggcggtgc tacagagttc ttgaagtggt ggcctaacta 6240
cggctacact agaaggacag tatttggtat ctgcgctctg ctgaagccag ttaccttcgg 6300
aaaaagagtt ggtagctctt gatccggcaa acaaaccacc gctggtagcg gtggtttttt 6360
tgtttgcaag cagcagatta cgcgcagaaa aaaaggatct caagaagatc ctttgatctt 6420
ttctacgggg tctgacgctc agtggaacga aaactcacgt taagggattt tggtcatgag 6480
attatcaaaa aggatcttca cctagatcct tttaaattaa aaatgaagtt ttaaatcaat 6540
ctaaagtata tatgagtaaa cttggtctga cagttaccaa tgcttaatca gtgaggcacc 6600
tatctcagcg atctgtctat ttcgttcatc catagttgcc tgactccccg tcgtgtagat 6660
aactacgata cgggagggct taccatctgg ccccagtgct gcaatgatac cgcgagaccc 6720
acgctcaccg gctccagatt tatcagcaat aaaccagcca gccggaaggg ccgagcgcag 6780
aagtggtcct gcaactttat ccgcctccat ccagtctatt aattgttgcc gggaagctag 6840

```
agtaagtagt tcgccagtta atagtttgcg caacgttgtt gccattgcta caggcatcgt   6900

ggtgtcacgc tcgtcgtttg gtatggcttc attcagctcc ggttcccaac gatcaaggcg   6960

agttacatga tcccccatgt tgtgcaaaaa agcggttagc tccttcggtc ctccgatcgt   7020

tgtcagaagt aagttggccg cagtgttatc actcatggtt atggcagcac tgcataattc   7080

tcttactgtc atgccatccg taagatgctt ttctgtgact ggtgagtact caaccaagtc   7140

attctgagaa tagtgtatgc ggcgaccgag ttgctcttgc ccggcgtcaa tacgggataa   7200

taccgcgcca catagcagaa ctttaaaagt gctcatcatt ggaaaacgtt cttcggggcg   7260

aaaactctca aggatcttac cgctgttgag atccagttcg atgtaaccca ctcgtgcacc   7320

caactgatct tcagcatctt ttactttcac cagcgtttct gggtgagcaa aaacaggaag   7380

gcaaaatgcc gcaaaaaagg gaataagggc gacacggaaa tgttgaatac tcatactctt   7440

cctttttcaa tattattgaa gcatttatca gggttattgt ctcatgagcg gatacatatt   7500

tgaatgtatt tagaaaaata aacaaatagg ggttccgcgc acatttcccc gaaaagtgcc   7560

acctgacgtc                                                          7570
```

<210> SEQ ID NO 52
<211> LENGTH: 682
<212> TYPE: PRT
<213> ORGANISM: Artificial Sequence
<220> FEATURE:
<223> OTHER INFORMATION: GFP-BoNT/A light chain amino acid sequence.

<400> SEQUENCE: 52

```
Ala Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Cys Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Thr Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Asn Ile Asp
225                 230                 235                 240
```

-continued

```
Gly Gly Gly Gly Gly Pro Phe Val Asn Lys Gln Phe Asn Tyr Lys Asp
                245                 250                 255

Pro Val Asn Gly Val Asp Ile Ala Tyr Ile Lys Ile Pro Asn Ala Gly
            260                 265                 270

Gln Met Gln Pro Val Lys Ala Phe Lys Ile His Asn Lys Ile Trp Val
        275                 280                 285

Ile Pro Glu Arg Asp Thr Phe Thr Asn Pro Glu Glu Gly Asp Leu Asn
    290                 295                 300

Pro Pro Pro Glu Ala Lys Gln Val Pro Val Ser Tyr Tyr Asp Ser Thr
305                 310                 315                 320

Tyr Leu Ser Thr Asp Asn Glu Lys Asp Asn Tyr Leu Lys Gly Val Thr
                325                 330                 335

Lys Leu Phe Glu Arg Ile Tyr Ser Thr Asp Leu Gly Arg Met Leu Leu
            340                 345                 350

Thr Ser Ile Val Arg Gly Ile Pro Phe Trp Gly Gly Ser Thr Ile Asp
        355                 360                 365

Thr Glu Leu Lys Val Ile Asp Thr Asn Cys Ile Asn Val Ile Gln Pro
    370                 375                 380

Asp Gly Ser Tyr Arg Ser Glu Glu Leu Asn Leu Val Ile Ile Gly Pro
385                 390                 395                 400

Ser Ala Asp Ile Ile Gln Phe Glu Cys Lys Ser Phe Gly His Glu Val
                405                 410                 415

Leu Asn Leu Thr Arg Asn Gly Tyr Gly Ser Thr Gln Tyr Ile Arg Phe
            420                 425                 430

Ser Pro Asp Phe Thr Phe Gly Phe Glu Glu Ser Leu Glu Val Asp Thr
        435                 440                 445

Asn Pro Leu Leu Gly Ala Gly Lys Phe Ala Thr Asp Pro Ala Val Thr
    450                 455                 460

Leu Ala His Glu Leu Ile His Ala Gly His Arg Leu Tyr Gly Ile Ala
465                 470                 475                 480

Ile Asn Pro Asn Arg Val Phe Lys Val Asn Thr Asn Ala Tyr Tyr Glu
                485                 490                 495

Met Ser Gly Leu Glu Val Ser Phe Glu Glu Leu Arg Thr Phe Gly Gly
            500                 505                 510

His Asp Ala Lys Phe Ile Asp Ser Leu Gln Glu Asn Glu Phe Arg Leu
        515                 520                 525

Tyr Tyr Tyr Asn Lys Phe Lys Asp Ile Ala Ser Thr Leu Asn Lys Ala
    530                 535                 540

Lys Ser Ile Val Gly Thr Thr Ala Ser Leu Gln Tyr Met Lys Asn Val
545                 550                 555                 560

Phe Lys Glu Lys Tyr Leu Leu Ser Glu Asp Thr Ser Gly Lys Phe Ser
                565                 570                 575

Val Asp Lys Leu Lys Phe Asp Lys Leu Tyr Lys Met Leu Thr Glu Ile
            580                 585                 590

Tyr Thr Glu Asp Asn Phe Val Lys Phe Phe Lys Val Leu Asn Arg Lys
        595                 600                 605

Thr Tyr Leu Asn Phe Asp Lys Ala Val Phe Lys Ile Asn Ile Val Pro
    610                 615                 620

Lys Val Asn Tyr Thr Ile Tyr Asp Gly Phe Asn Leu Arg Asn Thr Asn
625                 630                 635                 640

Leu Ala Ala Asn Phe Asn Gly Gln Asn Thr Glu Ile Asn Asn Met Asn
                645                 650                 655

Phe Thr Lys Leu Lys Asn Phe Thr Gly Leu Phe Glu Phe Tyr Lys Leu
```

-continued

```
            660                 665                 670

Leu Cys Val Arg Gly Ile Ile Thr Ser Lys
        675                 680


<210> SEQ ID NO 53
<211> LENGTH: 6259
<212> TYPE: DNA
<213> ORGANISM: Artificial Sequence
<220> FEATURE:
<223> OTHER INFORMATION: pQBI-25/GFP expression construct.

<400> SEQUENCE: 53

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcc tcgaggcctg gccattgcat acgttgtatc    240

catatcataa tatgtacatt tatattggct catgtccaac attaccgcca tgttgacatt    300

gattattgac tagttattaa tagtaatcaa ttacggggtc attagttcat agcccatata    360

tggagttccg cgttacataa cttacggtaa atggcccgcc tggctgaccg cccaacgacc    420

cccgcccatt gacgtcaata atgacgtatg ttcccatagt aacgccaata gggactttcc    480

attgacgtca atgggtggag tatttacggt aaactgccca cttggcagta catcaagtgt    540

atcatatgcc aagtacgccc cctattgacg tcaatgacgg taaatggccc gcctggcatt    600

atgcccagta catgacctta tgggactttc ctacttggca gtacatctac gtattagtca    660

tcgctattac catggtgatg cggttttggc agtacatcaa tgggcgtgga tagcggtttg    720

actcacgggg atttccaagt ctccacccca ttgacgtcaa tgggagtttg ttttggcacc    780

aaaatcaacg ggactttcca aaatgtcgta acaactccgc cccattgacg caaatgggcg    840

gtaggcgtgt acggtgggag gtctatataa gcagagctcg tttagtgaac cgtcagatcg    900

cctggagacg ccatccacgc tgttttgacc tccatagaag acaccgggac cgatccagcc    960

tccgcgggcc accatggagg gcccggttac cggtaccgga tccagatatc tgggcggccg   1020

ctcagcaagc ttcgcgaatt cgggaggcgg aggtggagct agcaaaggag aagaactctt   1080

cactggagtt gtcccaattc ttgttgaatt agatggtgat gttaacggcc acaagttctc   1140

tgtcagtgga gagggtgaag gtgatgcaac atacggaaaa cttaccctga agttcatctg   1200

cactactggc aaactgcctg ttccatggcc aacactagtc actactctgt gctatggtgt   1260

tcaatgcttt tcaagatacc cggatcatat gaaacggcat gactttttca agagtgccat   1320

gcccgaaggt tatgtacagg aaaggaccat cttcttcaaa gatgacggca actacaagac   1380

acgtgctgaa gtcaagtttg aaggtgatac ccttgttaat agaatcgagt taaaaggtat   1440

tgacttcaag gaagatggca acattctggg acacaaattg gaatacaact ataactcaca   1500

caatgtatac atcatggcag acaaacaaaa gaatggaatc aaagtgaact tcaagacccg   1560

ccacaacatt gaagatggaa gcgttcaact agcagaccat tatcaacaaa atactccaat   1620

tggcgatggc cctgtccttt taccagacaa ccattacctg tccacacaat ctgccctttc   1680

gaaagatccc aacgaaaaga gagaccacat ggtccttctt gagtttgtaa cagctgctgg   1740

gattacacat ggcatggatg aactgtacaa catcgatgga ggcggaggtg gatgaacgcg   1800

ttggccctat tctatagtgt cacctaaatg ctagagctcg ctgatcagcc tcgactgtgc   1860

cttctagttg ccagccatct gttgtttgcc cctcccccgt gccttccttg accctggaag   1920

gtgccactcc cactgtcctt tcctaataaa atgaggaaat tgcatcgcat tgtctgagta   1980
```

-continued

```
ggtgtcattc tattctgggg ggtggggtgg ggcaggacag caaggggggag gattgggaag   2040
acaatagcag gcatgctggg gatgcggtgg gctctatggc ttctgaggcg gaaagaacca   2100
gctggggctc taggggggtat ccccacgcgc cctgtagcgg cgcattaagc gcggcgggtg   2160
tggtggttac gcgcagcgtg accgctacac ttgccagcgc cctagcgccc gctcctttcg   2220
ctttcttccc ttcctttctc gccacgttcg ccggctttcc ccgtcaagct ctaaatcggg   2280
gcatcccttt agggttccga tttagtgctt tacggcacct cgaccccaaa aaacttgatt   2340
agggtgatgg ttcacgtagt gggccatcgc cctgatagac ggtttttcgc cctttgacgt   2400
tggagtccac gttctttaat agtggactct tgttccaaac tggaacaaca ctcaacccta   2460
tctcggtcta ttcttttgat ttataaggga ttttggggat ttcggcctat tggttaaaaa   2520
atgagctgat ttaacaaaaa tttaacgcga attaattctg tggaatgtgt gtcagttagg   2580
gtgtggaaag tccccaggct ccccaggcag gcagaagtat gcaaagcatg catctcaatt   2640
agtcagcaac caggtgtgga aagtccccag gctccccagc aggcagaagt atgcaaagca   2700
tgcatctcaa ttagtcagca accatagtcc cgcccctaac tccgcccatc ccgcccctaa   2760
ctccgcccag ttccgcccat tctccgcccc atggctgact aatttttttt atttatgcag   2820
aggccgaggc cgcctctgcc tctgagctat tccagaagta gtgaggaggc ttttttggag   2880
gcctaggctt ttgcaaaaag ctcccgggag cttgtatatc cattttcgga tctgatcaag   2940
agacaggatg aggatcgttt cgcatgattg aacaagatgg attgcacgca ggttctccgg   3000
ccgcttgggt ggagaggcta ttcggctatg actgggcaca acagacaatc ggctgctctg   3060
atgccgccgt gttccggctg tcagcgcagg ggcgcccggt tctttttgtc aagaccgacc   3120
tgtccggtgc cctgaatgaa ctgcaggacg aggcagcgcg gctatcgtgg ctggccacga   3180
cgggcgttcc ttgcgcagct gtgctcgacg ttgtcactga agcgggaagg gactggctgc   3240
tattgggcga agtgccgggg caggatctcc tgtcatctca ccttgctcct gccgagaaag   3300
tatccatcat ggctgatgca atgcggcggc tgcatacgct tgatccggct acctgcccat   3360
tcgaccacca agcgaaacat cgcatcgagc gagcacgtac tcggatggaa gccggtcttg   3420
tcgatcagga tgatctggac gaagagcatc aggggctcgc gccagccgaa ctgttcgcca   3480
ggctcaaggc gcgcatgccc gacggcgagg atctcgtcgt gacccatggc gatgcctgct   3540
tgccgaatat catggtggaa aatggccgct tttctggatt catcgactgt ggccggctgg   3600
gtgtggcgga ccgctatcag gacatagcgt tggctacccg tgatattgct gaagagcttg   3660
gcggcgaatg ggctgaccgc ttcctcgtgc tttacggtat cgccgctccc gattcgcagc   3720
gcatcgcctt ctatcgcctt cttgacgagt tcttctgagc gggactctgg ggttcgaaat   3780
gaccgaccaa gcgacgccca acctgccatc acgagatttc gattccaccg ccgccttcta   3840
tgaaaggttg ggcttcggaa tcgttttccg ggacgccggc tggatgatcc tccagcgcgg   3900
ggatctcatg ctggagttct tcgcccaccc caacttgttt attgcagctt ataatggtta   3960
caaataaagc aatagcatca caaatttcac aaataaagca tttttttcac tgcattctag   4020
ttgtggtttg tccaaactca tcaatgtatc ttatcatgtc tgtataccgt cgacctctag   4080
ctagagcttg gcgtaatcat ggtcatagct gtttcctgtg tgaaattgtt atccgctcac   4140
aattccacac aacatacgag ccggaagcat aaagtgtaaa gcctggggtg cctaatgagt   4200
gagctaactc acattaattg cgttgcgctc actgcccgct ttccagtcgg gaaacctgtc   4260
gtgccagctg cattaatgaa tcggccaacg cgcggggaga ggcggtttgc gtattgggcg   4320
ctcttccgct tcctcgctca ctgactcgct gcgctcggtc gttcggctgc ggcgagcggt   4380
```

```
atcagctcac tcaaaggcgg taatacggtt atccacagaa tcaggggata acgcaggaaa   4440

gaacatgtga gcaaaaggcc agcaaaaggc caggaaccgt aaaaaggccg cgttgctggc   4500

gtttttccat aggctccgcc cccctgacga gcatcacaaa aatcgacgct caagtcagag   4560

gtggcgaaac ccgacaggac tataaagata ccaggcgttt ccccctggaa gctccctcgt   4620

gcgctctcct gttccgaccc tgccgcttac cggatacctg tccgcctttc tcccttcggg   4680

aagcgtggcg ctttctcaat gctcacgctg taggtatctc agttcggtgt aggtcgttcg   4740

ctccaagctg ggctgtgtgc acgaaccccc cgttcagccc gaccgctgcg ccttatccgg   4800

taactatcgt cttgagtcca acccggtaag acacgactta tcgccactgg cagcagccac   4860

tggtaacagg attagcagag cgaggtatgt aggcggtgct acagagttct tgaagtggtg   4920

gcctaactac ggctacacta gaaggacagt atttggtatc tgcgctctgc tgaagccagt   4980

taccttcgga aaaagagttg gtagctcttg atccggcaaa caaaccaccg ctggtagcgg   5040

tggttttttt gtttgcaagc agcagattac gcgcagaaaa aaaggatctc aagaagatcc   5100

tttgatcttt tctacggggt ctgacgctca gtggaacgaa aactcacgtt aagggatttt   5160

ggtcatgaga ttatcaaaaa ggatcttcac ctagatcctt ttaaattaaa aatgaagttt   5220

taaatcaatc taaagtatat atgagtaaac ttggtctgac agttaccaat gcttaatcag   5280

tgaggcacct atctcagcga tctgtctatt tcgttcatcc atagttgcct gactccccgt   5340

cgtgtagata actacgatac gggagggctt accatctggc cccagtgctg caatgatacc   5400

gcgagaccca cgctcaccgg ctccagattt atcagcaata aaccagccag ccggaagggc   5460

cgagcgcaga agtggtcctg caactttatc cgcctccatc cagtctatta attgttgccg   5520

ggaagctaga gtaagtagtt cgccagttaa tagtttgcgc aacgttgttg ccattgctac   5580

aggcatcgtg gtgtcacgct cgtcgtttgg tatggcttca ttcagctccg gttcccaacg   5640

atcaaggcga gttacatgat cccccatgtt gtgcaaaaaa gcggttagct ccttcggtcc   5700

tccgatcgtt gtcagaagta agttggccgc agtgttatca ctcatggtta tggcagcact   5760

gcataattct cttactgtca tgccatccgt aagatgcttt tctgtgactg gtgagtactc   5820

aaccaagtca ttctgagaat agtgtatgcg gcgaccgagt tgctcttgcc cggcgtcaat   5880

acgggataat accgcgccac atagcagaac tttaaaagtg ctcatcattg gaaaacgttc   5940

ttcggggcga aaactctcaa ggatcttacc gctgttgaga tccagttcga tgtaacccac   6000

tcgtgcaccc aactgatctt cagcatcttt tactttcacc agcgtttctg ggtgagcaaa   6060

aacaggaagg caaaatgccg caaaaaaggg aataagggcg acacggaaat gttgaatact   6120

catactcttc ctttttcaat attattgaag catttatcag ggttattgtc tcatgagcgg   6180

atacatattt gaatgtattt agaaaaataa acaaataggg gttccgcgca catttccccg   6240

aaaagtgcca cctgacgtc                                                6259
```

<210> SEQ ID NO 54
<211> LENGTH: 245
<212> TYPE: PRT
<213> ORGANISM: Artificial Sequence
<220> FEATURE:
<223> OTHER INFORMATION: GFP amino acid sequence.

<400> SEQUENCE: 54

```
Ala Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30
```

-continued

```
Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Cys Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Thr Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Asn Ile Asp
225                 230                 235                 240

Gly Gly Gly Gly Gly
                245


<210> SEQ ID NO 55
<211> LENGTH: 4
<212> TYPE: PRT
<213> ORGANISM: Artificial Sequence
<220> FEATURE:
<223> OTHER INFORMATION: G-spacer flexible spacer

<400> SEQUENCE: 55

Gly Gly Gly Gly
 1


<210> SEQ ID NO 56
<211> LENGTH: 5
<212> TYPE: PRT
<213> ORGANISM: Artificial Sequence
<220> FEATURE:
<223> OTHER INFORMATION: G-spacer flexible spacer

<400> SEQUENCE: 56

Gly Gly Gly Gly Ser
 1               5


<210> SEQ ID NO 57
<211> LENGTH: 4
<212> TYPE: PRT
<213> ORGANISM: Artificial Sequence
<220> FEATURE:
<223> OTHER INFORMATION: A-spacer flexible spacer

<400> SEQUENCE: 57

Ala Ala Ala Ala
```

-continued

1

<210> SEQ ID NO 58
<211> LENGTH: 5
<212> TYPE: PRT
<213> ORGANISM: Artificial Sequence
<220> FEATURE:
<223> OTHER INFORMATION: A-spacer flexible spacer

<400> SEQUENCE: 58

Ala Ala Ala Ala Val
1 5

<210> SEQ ID NO 59
<211> LENGTH: 821
<212> TYPE: PRT
<213> ORGANISM: Homo sapiens

<400> SEQUENCE: 59

Met Val Ser Trp Gly Arg Phe Ile Cys Leu Val Val Val Thr Met Ala
1 5 10 15

Thr Leu Ser Leu Ala Arg Pro Ser Phe Ser Leu Val Glu Asp Thr Thr
20 25 30

Leu Glu Pro Glu Glu Pro Pro Thr Lys Tyr Gln Ile Ser Gln Pro Glu
35 40 45

Val Tyr Val Ala Ala Pro Gly Glu Ser Leu Glu Val Arg Cys Leu Leu
50 55 60

Lys Asp Ala Ala Val Ile Ser Trp Thr Lys Asp Gly Val His Leu Gly
65 70 75 80

Pro Asn Asn Arg Thr Val Leu Ile Gly Glu Tyr Leu Gln Ile Lys Gly
85 90 95

Ala Thr Pro Arg Asp Ser Gly Leu Tyr Ala Cys Thr Ala Ser Arg Thr
100 105 110

Val Asp Ser Glu Thr Trp Tyr Phe Met Val Asn Val Thr Asp Ala Ile
115 120 125

Ser Ser Gly Asp Asp Glu Asp Asp Thr Asp Gly Ala Glu Asp Phe Val
130 135 140

Ser Glu Asn Ser Asn Asn Lys Arg Ala Pro Tyr Trp Thr Asn Thr Glu
145 150 155 160

Lys Met Glu Lys Arg Leu His Ala Val Pro Ala Ala Asn Thr Val Lys
165 170 175

Phe Arg Cys Pro Ala Gly Gly Asn Pro Met Pro Thr Met Arg Trp Leu
180 185 190

Lys Asn Gly Lys Glu Phe Lys Gln Glu His Arg Ile Gly Gly Tyr Lys
195 200 205

Val Arg Asn Gln His Trp Ser Leu Ile Met Glu Ser Val Val Pro Ser
210 215 220

Asp Lys Gly Asn Tyr Thr Cys Val Val Glu Asn Glu Tyr Gly Ser Ile
225 230 235 240

Asn His Thr Tyr His Leu Asp Val Val Glu Arg Ser Pro His Arg Pro
245 250 255

Ile Leu Gln Ala Gly Leu Pro Ala Asn Ala Ser Thr Val Val Gly Gly
260 265 270

Asp Val Glu Phe Val Cys Lys Val Tyr Ser Asp Ala Gln Pro His Ile
275 280 285

Gln Trp Ile Lys His Val Glu Lys Asn Gly Ser Lys Tyr Gly Pro Asp
290 295 300

-continued

```
Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
        355                 360                 365

Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
        435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
        515                 520                 525

Ser Asp Leu Val Ser Glu Met Glu Met Met Lys Met Ile Gly Lys His
    530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
        595                 600                 605

Gln Leu Ala Arg Gly Met Glu Tyr Leu Ala Ser Gln Lys Cys Ile His
    610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
    690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735
```

```
Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
    770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820
```

<210> SEQ ID NO 60
<211> LENGTH: 822
<212> TYPE: PRT
<213> ORGANISM: Homo sapiens

<400> SEQUENCE: 60

```
Met Val Ser Trp Gly Arg Phe Ile Cys Leu Val Val Val Thr Met Ala
 1               5                  10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285
```

```
Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
```

```
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Glu Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
            820


<210> SEQ ID NO 61
<211> LENGTH: 769
<212> TYPE: PRT
<213> ORGANISM: Homo sapiens

<400> SEQUENCE: 61

Met Val Ser Trp Gly Arg Phe Ile Cys Leu Val Val Val Thr Met Ala
 1               5                  10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
```

```
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685
```

```
Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Ile


<210> SEQ ID NO 62
<211> LENGTH: 709
<212> TYPE: PRT
<213> ORGANISM: Homo sapiens

<400> SEQUENCE: 62

Met Val Ser Trp Gly Arg Phe Ile Cys Leu Val Val Val Thr Met Ala
 1               5                  10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Ala Pro Gly Arg Glu Lys Glu
                245                 250                 255

Ile Thr Ala Ser Pro Asp Tyr Leu Glu Ile Ala Ile Tyr Cys Ile Gly
            260                 265                 270

Val Phe Leu Ile Ala Cys Met Val Val Thr Val Ile Leu Cys Arg Met
        275                 280                 285

Lys Asn Thr Thr Lys Lys Pro Asp Phe Ser Ser Gln Pro Ala Val His
```

-continued

```
    290                 295                 300

Lys Leu Thr Lys Arg Ile Pro Leu Arg Arg Gln Val Thr Val Ser Ala
305                 310                 315                 320

Glu Ser Ser Ser Ser Met Asn Ser Asn Thr Pro Leu Val Arg Ile Thr
                325                 330                 335

Thr Arg Leu Ser Ser Thr Ala Asp Thr Pro Met Leu Ala Gly Val Ser
            340                 345                 350

Glu Tyr Glu Leu Pro Glu Asp Pro Lys Trp Glu Phe Pro Arg Asp Lys
        355                 360                 365

Leu Thr Leu Gly Lys Pro Leu Gly Glu Gly Cys Phe Gly Gln Val Val
    370                 375                 380

Met Ala Glu Ala Val Gly Ile Asp Lys Asp Lys Pro Lys Glu Ala Val
385                 390                 395                 400

Thr Val Ala Val Lys Met Leu Lys Asp Asp Ala Thr Glu Lys Asp Leu
                405                 410                 415

Ser Asp Leu Val Ser Glu Met Glu Met Met Lys Met Ile Gly Lys His
            420                 425                 430

Lys Asn Ile Ile Asn Leu Leu Gly Ala Cys Thr Gln Asp Gly Pro Leu
        435                 440                 445

Tyr Val Ile Val Glu Tyr Ala Ser Lys Gly Asn Leu Arg Glu Tyr Leu
    450                 455                 460

Arg Ala Arg Arg Pro Pro Gly Met Glu Tyr Ser Tyr Asp Ile Asn Arg
465                 470                 475                 480

Val Pro Glu Glu Gln Met Thr Phe Lys Asp Leu Val Ser Cys Thr Tyr
                485                 490                 495

Gln Leu Ala Arg Gly Met Glu Tyr Leu Ala Ser Gln Lys Cys Ile His
            500                 505                 510

Arg Asp Leu Ala Ala Arg Asn Val Leu Val Thr Glu Asn Asn Val Met
        515                 520                 525

Lys Ile Ala Asp Phe Gly Leu Ala Arg Asp Ile Asn Asn Ile Asp Tyr
    530                 535                 540

Tyr Lys Lys Thr Thr Asn Gly Arg Leu Pro Val Lys Trp Met Ala Pro
545                 550                 555                 560

Glu Ala Leu Phe Asp Arg Val Tyr Thr His Gln Ser Asp Val Trp Ser
                565                 570                 575

Phe Gly Val Leu Met Trp Glu Ile Phe Thr Leu Gly Gly Ser Pro Tyr
            580                 585                 590

Pro Gly Ile Pro Val Glu Glu Leu Phe Lys Leu Leu Lys Glu Gly His
        595                 600                 605

Arg Met Asp Lys Pro Ala Asn Cys Thr Asn Glu Leu Tyr Met Met Met
    610                 615                 620

Arg Asp Cys Trp His Ala Val Pro Ser Gln Arg Pro Thr Phe Lys Gln
625                 630                 635                 640

Leu Val Glu Asp Leu Asp Arg Ile Leu Thr Leu Thr Thr Asn Glu Glu
                645                 650                 655

Tyr Leu Asp Leu Ser Gln Pro Leu Glu Gln Tyr Ser Pro Ser Tyr Pro
            660                 665                 670

Asp Thr Arg Ser Ser Cys Ser Ser Gly Asp Asp Ser Val Phe Ser Pro
        675                 680                 685

Asp Pro Met Pro Tyr Glu Pro Cys Leu Pro Gln Tyr Pro His Ile Asn
    690                 695                 700

Gly Ser Val Lys Thr
705
```

<210> SEQ ID NO 63
<211> LENGTH: 707
<212> TYPE: PRT
<213> ORGANISM: Homo sapiens

<400> SEQUENCE: 63

Met Val Ser Trp Gly Arg Phe Ile Cys Leu Val Val Val Thr Met Ala
1 5 10 15

Thr Leu Ser Leu Ala Arg Pro Ser Phe Ser Leu Val Glu Asp Thr Thr
20 25 30

Leu Glu Pro Glu Asp Ala Ile Ser Ser Gly Asp Asp Glu Asp Asp Thr
35 40 45

Asp Gly Ala Glu Asp Phe Val Ser Glu Asn Ser Asn Asn Lys Arg Ala
50 55 60

Pro Tyr Trp Thr Asn Thr Glu Lys Met Glu Lys Arg Leu His Ala Val
65 70 75 80

Pro Ala Ala Asn Thr Val Lys Phe Arg Cys Pro Ala Gly Gly Asn Pro
85 90 95

Met Pro Thr Met Arg Trp Leu Lys Asn Gly Lys Glu Phe Lys Gln Glu
100 105 110

His Arg Ile Gly Gly Tyr Lys Val Arg Asn Gln His Trp Ser Leu Ile
115 120 125

Met Glu Ser Val Val Pro Ser Asp Lys Gly Asn Tyr Thr Cys Val Val
130 135 140

Glu Asn Glu Tyr Gly Ser Ile Asn His Thr Tyr His Leu Asp Val Val
145 150 155 160

Glu Arg Ser Pro His Arg Pro Ile Leu Gln Ala Gly Leu Pro Ala Asn
165 170 175

Ala Ser Thr Val Val Gly Gly Asp Val Glu Phe Val Cys Lys Val Tyr
180 185 190

Ser Asp Ala Gln Pro His Ile Gln Trp Ile Lys His Val Glu Lys Asn
195 200 205

Gly Ser Lys Tyr Gly Pro Asp Gly Leu Pro Tyr Leu Lys Val Leu Lys
210 215 220

Ala Ala Gly Val Asn Thr Thr Asp Lys Glu Ile Glu Val Leu Tyr Ile
225 230 235 240

Arg Asn Val Thr Phe Glu Asp Ala Gly Glu Tyr Thr Cys Leu Ala Gly
245 250 255

Asn Ser Ile Gly Ile Ser Phe His Ser Ala Trp Leu Thr Val Leu Pro
260 265 270

Ala Pro Gly Arg Glu Lys Glu Ile Thr Ala Ser Pro Asp Tyr Leu Glu
275 280 285

Ile Ala Ile Tyr Cys Ile Gly Val Phe Leu Ile Ala Cys Met Val Val
290 295 300

Thr Val Ile Leu Cys Arg Met Lys Asn Thr Thr Lys Lys Pro Asp Phe
305 310 315 320

Ser Ser Gln Pro Ala Val His Lys Leu Thr Lys Arg Ile Pro Leu Arg
325 330 335

Arg Gln Val Thr Val Ser Ala Glu Ser Ser Ser Ser Met Asn Ser Asn
340 345 350

Thr Pro Leu Val Arg Ile Thr Thr Arg Leu Ser Ser Thr Ala Asp Thr
355 360 365

Pro Met Leu Ala Gly Val Ser Glu Tyr Glu Leu Pro Glu Asp Pro Lys
370 375 380

-continued

```
Trp Glu Phe Pro Arg Asp Lys Leu Thr Leu Gly Lys Pro Leu Gly Glu
385                 390                 395                 400

Gly Cys Phe Gly Gln Val Val Met Ala Glu Ala Val Gly Ile Asp Lys
                405                 410                 415

Asp Lys Pro Lys Glu Ala Val Thr Val Ala Val Lys Met Leu Lys Asp
            420                 425                 430

Asp Ala Thr Glu Lys Asp Leu Ser Asp Leu Val Ser Glu Met Glu Met
        435                 440                 445

Met Lys Met Ile Gly Lys His Lys Asn Ile Ile Asn Leu Leu Gly Ala
    450                 455                 460

Cys Thr Gln Asp Gly Pro Leu Tyr Val Ile Val Glu Tyr Ala Ser Lys
465                 470                 475                 480

Gly Asn Leu Arg Glu Tyr Leu Arg Ala Arg Arg Pro Pro Gly Met Glu
                485                 490                 495

Tyr Ser Tyr Asp Ile Asn Arg Val Pro Glu Glu Gln Met Thr Phe Lys
            500                 505                 510

Asp Leu Val Ser Cys Thr Tyr Gln Leu Ala Arg Gly Met Glu Tyr Leu
        515                 520                 525

Ala Ser Gln Lys Cys Ile His Arg Asp Leu Ala Ala Arg Asn Val Leu
    530                 535                 540

Val Thr Glu Asn Asn Val Met Lys Ile Ala Asp Phe Gly Leu Ala Arg
545                 550                 555                 560

Asp Ile Asn Asn Ile Asp Tyr Tyr Lys Lys Thr Thr Asn Gly Arg Leu
                565                 570                 575

Pro Val Lys Trp Met Ala Pro Glu Ala Leu Phe Asp Arg Val Tyr Thr
            580                 585                 590

His Gln Ser Asp Val Trp Ser Phe Gly Val Leu Met Trp Glu Ile Phe
        595                 600                 605

Thr Leu Gly Gly Ser Pro Tyr Pro Gly Ile Pro Val Glu Glu Leu Phe
    610                 615                 620

Lys Leu Leu Lys Glu Gly His Arg Met Asp Lys Pro Ala Asn Cys Thr
625                 630                 635                 640

Asn Glu Leu Tyr Met Met Met Arg Asp Cys Trp His Ala Val Pro Ser
                645                 650                 655

Gln Arg Pro Thr Phe Lys Gln Leu Val Glu Asp Leu Asp Arg Ile Leu
            660                 665                 670

Thr Leu Thr Thr Asn Glu Glu Glu Lys Lys Val Ser Gly Ala Val Asp
        675                 680                 685

Cys His Lys Pro Pro Cys Asn Pro Ser His Leu Pro Cys Val Leu Ala
    690                 695                 700

Val Asp Gln
705


<210> SEQ ID NO 64
<211> LENGTH: 706
<212> TYPE: PRT
<213> ORGANISM: Homo sapiens

<400> SEQUENCE: 64

Met Val Ser Trp Gly Arg Phe Ile Cys Leu Val Val Val Thr Met Ala
 1               5                  10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
        35                  40                  45
```

```
Lys Arg Leu His Ala Val Pro Ala Ala Asn Thr Val Lys Phe Arg Cys
    50                  55                  60

Pro Ala Gly Gly Asn Pro Met Pro Thr Met Arg Trp Leu Lys Asn Gly
65                  70                  75                  80

Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
            100                 105                 110

Asn Tyr Thr Cys Val Val Glu Asn Glu Tyr Gly Ser Ile Asn His Thr
        115                 120                 125

Tyr His Leu Asp Val Val Glu Arg Ser Pro His Arg Pro Ile Leu Gln
    130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys Ala Ala Gly Val Asn Thr Thr Asp Lys Glu
        195                 200                 205

Ile Glu Val Leu Tyr Ile Arg Asn Val Thr Phe Glu Asp Ala Gly Glu
    210                 215                 220

Tyr Thr Cys Leu Ala Gly Asn Ser Ile Gly Ile Ser Phe His Ser Ala
225                 230                 235                 240

Trp Leu Thr Val Leu Pro Ala Pro Gly Arg Glu Lys Glu Ile Thr Ala
                245                 250                 255

Ser Pro Asp Tyr Leu Glu Ile Ala Ile Tyr Cys Ile Gly Val Phe Leu
            260                 265                 270

Ile Ala Cys Met Val Val Thr Val Ile Leu Cys Arg Met Lys Asn Thr
        275                 280                 285

Thr Lys Lys Pro Asp Phe Ser Ser Gln Pro Ala Val His Lys Leu Thr
    290                 295                 300

Lys Arg Ile Pro Leu Arg Arg Gln Val Thr Val Ser Ala Glu Ser Ser
305                 310                 315                 320

Ser Ser Met Asn Ser Asn Thr Pro Leu Val Arg Ile Thr Thr Arg Leu
                325                 330                 335

Ser Ser Thr Ala Asp Thr Pro Met Leu Ala Gly Val Ser Glu Tyr Glu
            340                 345                 350

Leu Pro Glu Asp Pro Lys Trp Glu Phe Pro Arg Asp Lys Leu Thr Leu
        355                 360                 365

Gly Lys Pro Leu Gly Glu Gly Cys Phe Gly Gln Val Val Met Ala Glu
    370                 375                 380

Ala Val Gly Ile Asp Lys Asp Lys Pro Lys Glu Ala Val Thr Val Ala
385                 390                 395                 400

Val Lys Met Leu Lys Asp Asp Ala Thr Glu Lys Asp Leu Ser Asp Leu
                405                 410                 415

Val Ser Glu Met Glu Met Met Lys Met Ile Gly Lys His Lys Asn Ile
            420                 425                 430

Ile Asn Leu Leu Gly Ala Cys Thr Gln Asp Gly Pro Leu Tyr Val Ile
        435                 440                 445

Val Glu Tyr Ala Ser Lys Gly Asn Leu Arg Glu Tyr Leu Arg Ala Arg
    450                 455                 460

Arg Pro Pro Gly Met Glu Tyr Ser Tyr Asp Ile Asn Arg Val Pro Glu
465                 470                 475                 480
```

```
Glu Gln Met Thr Phe Lys Asp Leu Val Ser Cys Thr Tyr Gln Leu Ala
                485                 490                 495

Arg Gly Met Glu Tyr Leu Ala Ser Gln Lys Cys Ile His Arg Asp Leu
            500                 505                 510

Ala Ala Arg Asn Val Leu Val Thr Glu Asn Asn Val Met Lys Ile Ala
        515                 520                 525

Asp Phe Gly Leu Ala Arg Asp Ile Asn Asn Ile Asp Tyr Tyr Lys Lys
    530                 535                 540

Thr Thr Asn Gly Arg Leu Pro Val Lys Trp Met Ala Pro Glu Ala Leu
545                 550                 555                 560

Phe Asp Arg Val Tyr Thr His Gln Ser Asp Val Trp Ser Phe Gly Val
                565                 570                 575

Leu Met Trp Glu Ile Phe Thr Leu Gly Gly Ser Pro Tyr Pro Gly Ile
            580                 585                 590

Pro Val Glu Glu Leu Phe Lys Leu Leu Lys Glu Gly His Arg Met Asp
        595                 600                 605

Lys Pro Ala Asn Cys Thr Asn Glu Leu Tyr Met Met Met Arg Asp Cys
    610                 615                 620

Trp His Ala Val Pro Ser Gln Arg Pro Thr Phe Lys Gln Leu Val Glu
625                 630                 635                 640

Asp Leu Asp Arg Ile Leu Thr Leu Thr Thr Asn Glu Glu Tyr Leu Asp
                645                 650                 655

Leu Ser Gln Pro Leu Glu Gln Tyr Ser Pro Ser Tyr Pro Asp Thr Arg
            660                 665                 670

Ser Ser Cys Ser Ser Gly Asp Asp Ser Val Phe Ser Pro Asp Pro Met
        675                 680                 685

Pro Tyr Glu Pro Cys Leu Pro Gln Tyr Pro His Ile Asn Gly Ser Val
    690                 695                 700

Lys Thr
705


<210> SEQ ID NO 65
<211> LENGTH: 705
<212> TYPE: PRT
<213> ORGANISM: Homo sapiens

<400> SEQUENCE: 65

Met Val Ser Trp Gly Arg Phe Ile Cys Leu Val Val Val Thr Met Ala
 1               5                  10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140
```

```
Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Val Ser Ala Glu Ser Ser Ser
305                 310                 315                 320

Ser Met Asn Ser Asn Thr Pro Leu Val Arg Ile Thr Thr Arg Leu Ser
                325                 330                 335

Ser Thr Ala Asp Thr Pro Met Leu Ala Gly Val Ser Glu Tyr Glu Leu
            340                 345                 350

Pro Glu Asp Pro Lys Trp Glu Phe Pro Arg Asp Lys Leu Thr Leu Gly
        355                 360                 365

Lys Pro Leu Gly Glu Gly Cys Phe Gly Gln Val Val Met Ala Glu Ala
    370                 375                 380

Val Gly Ile Asp Lys Asp Lys Pro Lys Glu Ala Val Thr Val Ala Val
385                 390                 395                 400

Lys Met Leu Lys Asp Asp Ala Thr Glu Lys Asp Leu Ser Asp Leu Val
                405                 410                 415

Ser Glu Met Glu Met Met Lys Met Ile Gly Lys His Lys Asn Ile Ile
            420                 425                 430

Asn Leu Leu Gly Ala Cys Thr Gln Asp Gly Pro Leu Tyr Val Ile Val
        435                 440                 445

Glu Tyr Ala Ser Lys Gly Asn Leu Arg Glu Tyr Leu Arg Ala Arg Arg
    450                 455                 460

Pro Pro Gly Met Glu Tyr Ser Tyr Asp Ile Asn Arg Val Pro Glu Glu
465                 470                 475                 480

Gln Met Thr Phe Lys Asp Leu Val Ser Cys Thr Tyr Gln Leu Ala Arg
                485                 490                 495

Gly Met Glu Tyr Leu Ala Ser Gln Lys Cys Ile His Arg Asp Leu Ala
            500                 505                 510

Ala Arg Asn Val Leu Val Thr Glu Asn Asn Val Met Lys Ile Ala Asp
        515                 520                 525

Phe Gly Leu Ala Arg Asp Ile Asn Asn Ile Asp Tyr Tyr Lys Lys Thr
    530                 535                 540

Thr Asn Gly Arg Leu Pro Val Lys Trp Met Ala Pro Glu Ala Leu Phe
545                 550                 555                 560

Asp Arg Val Tyr Thr His Gln Ser Asp Val Trp Ser Phe Gly Val Leu
```

```
                565                 570                 575

Met Trp Glu Ile Phe Thr Leu Gly Gly Ser Pro Tyr Pro Gly Ile Pro
            580                 585                 590

Val Glu Glu Leu Phe Lys Leu Leu Lys Glu Gly His Arg Met Asp Lys
        595                 600                 605

Pro Ala Asn Cys Thr Asn Glu Leu Tyr Met Met Met Arg Asp Cys Trp
    610                 615                 620

His Ala Val Pro Ser Gln Arg Pro Thr Phe Lys Gln Leu Val Glu Asp
625                 630                 635                 640

Leu Asp Arg Ile Leu Thr Leu Thr Thr Asn Glu Glu Tyr Leu Asp Leu
                645                 650                 655

Ser Gln Pro Leu Glu Gln Tyr Ser Pro Ser Tyr Pro Asp Thr Arg Ser
            660                 665                 670

Ser Cys Ser Ser Gly Asp Asp Ser Val Phe Ser Pro Asp Pro Met Pro
        675                 680                 685

Tyr Glu Pro Cys Leu Pro Gln Tyr Pro His Ile Asn Gly Ser Val Lys
    690                 695                 700

Thr
705
```

<210> SEQ ID NO 66
<211> LENGTH: 704
<212> TYPE: PRT
<213> ORGANISM: Homo sapiens

<400> SEQUENCE: 66

```
Met Val Ser Trp Gly Arg Phe Ile Cys Leu Val Val Val Thr Met Ala
 1               5                  10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
        35                  40                  45

Lys Arg Leu His Ala Val Pro Ala Ala Asn Thr Val Lys Phe Arg Cys
    50                  55                  60

Pro Ala Gly Gly Asn Pro Met Pro Thr Met Arg Trp Leu Lys Asn Gly
65                  70                  75                  80

Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
            100                 105                 110

Asn Tyr Thr Cys Val Val Glu Asn Glu Tyr Gly Ser Ile Asn His Thr
        115                 120                 125

Tyr His Leu Asp Val Val Glu Arg Ser Pro His Arg Pro Ile Leu Gln
    130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys Ala Ala Gly Val Asn Thr Thr Asp Lys Glu
        195                 200                 205

Ile Glu Val Leu Tyr Ile Arg Asn Val Thr Phe Glu Asp Ala Gly Glu
    210                 215                 220

Tyr Thr Cys Leu Ala Gly Asn Ser Ile Gly Ile Ser Phe His Ser Ala
```

```
225                 230                 235                 240

Trp Leu Thr Val Leu Pro Ala Pro Gly Arg Glu Lys Glu Ile Thr Ala
                245                 250                 255

Ser Pro Asp Tyr Leu Glu Ile Ala Ile Tyr Cys Ile Gly Val Phe Leu
            260                 265                 270

Ile Ala Cys Met Val Val Thr Val Ile Leu Cys Arg Met Lys Asn Thr
        275                 280                 285

Thr Lys Lys Pro Asp Phe Ser Ser Gln Pro Ala Val His Lys Leu Thr
    290                 295                 300

Lys Arg Ile Pro Leu Arg Arg Gln Val Ser Ala Glu Ser Ser Ser Ser
305                 310                 315                 320

Met Asn Ser Asn Thr Pro Leu Val Arg Ile Thr Thr Arg Leu Ser Ser
                325                 330                 335

Thr Ala Asp Thr Pro Met Leu Ala Gly Val Ser Glu Tyr Glu Leu Pro
            340                 345                 350

Glu Asp Pro Lys Trp Glu Phe Pro Arg Asp Lys Leu Thr Leu Gly Lys
        355                 360                 365

Pro Leu Gly Glu Gly Cys Phe Gly Gln Val Val Met Ala Glu Ala Val
    370                 375                 380

Gly Ile Asp Lys Asp Lys Pro Lys Glu Ala Val Thr Val Ala Val Lys
385                 390                 395                 400

Met Leu Lys Asp Asp Ala Thr Glu Lys Asp Leu Ser Asp Leu Val Ser
                405                 410                 415

Glu Met Glu Met Met Lys Met Ile Gly Lys His Lys Asn Ile Ile Asn
            420                 425                 430

Leu Leu Gly Ala Cys Thr Gln Asp Gly Pro Leu Tyr Val Ile Val Glu
        435                 440                 445

Tyr Ala Ser Lys Gly Asn Leu Arg Glu Tyr Leu Arg Ala Arg Arg Pro
    450                 455                 460

Pro Gly Met Glu Tyr Ser Tyr Asp Ile Asn Arg Val Pro Glu Glu Gln
465                 470                 475                 480

Met Thr Phe Lys Asp Leu Val Ser Cys Thr Tyr Gln Leu Ala Arg Gly
                485                 490                 495

Met Glu Tyr Leu Ala Ser Gln Lys Cys Ile His Arg Asp Leu Ala Ala
            500                 505                 510

Arg Asn Val Leu Val Thr Glu Asn Asn Val Met Lys Ile Ala Asp Phe
        515                 520                 525

Gly Leu Ala Arg Asp Ile Asn Asn Ile Asp Tyr Tyr Lys Lys Thr Thr
    530                 535                 540

Asn Gly Arg Leu Pro Val Lys Trp Met Ala Pro Glu Ala Leu Phe Asp
545                 550                 555                 560

Arg Val Tyr Thr His Gln Ser Asp Val Trp Ser Phe Gly Val Leu Met
                565                 570                 575

Trp Glu Ile Phe Thr Leu Gly Gly Ser Pro Tyr Pro Gly Ile Pro Val
            580                 585                 590

Glu Glu Leu Phe Lys Leu Leu Lys Glu Gly His Arg Met Asp Lys Pro
        595                 600                 605

Ala Asn Cys Thr Asn Glu Leu Tyr Met Met Met Arg Asp Cys Trp His
    610                 615                 620

Ala Val Pro Ser Gln Arg Pro Thr Phe Lys Gln Leu Val Glu Asp Leu
625                 630                 635                 640

Asp Arg Ile Leu Thr Leu Thr Thr Asn Glu Glu Tyr Leu Asp Leu Ser
                645                 650                 655
```

Gln Pro Leu Glu Gln Tyr Ser Pro Ser Tyr Pro Asp Thr Arg Ser Ser
660 665 670

Cys Ser Ser Gly Asp Asp Ser Val Phe Ser Pro Asp Pro Met Pro Tyr
675 680 685

Glu Pro Cys Leu Pro Gln Tyr Pro His Ile Asn Gly Ser Val Lys Thr
690 695 700

<210> SEQ ID NO 67
<211> LENGTH: 680
<212> TYPE: PRT
<213> ORGANISM: Homo sapiens

<400> SEQUENCE: 67

Met Val Ser Trp Gly Arg Phe Ile Cys Leu Val Val Val Thr Met Ala
1 5 10 15

Thr Leu Ser Leu Ala Arg Pro Ser Phe Ser Leu Val Glu Asp Thr Thr
20 25 30

Leu Glu Pro Glu Asp Ala Ile Ser Ser Gly Asp Asp Glu Asp Asp Thr
35 40 45

Asp Gly Ala Glu Asp Phe Val Ser Glu Asn Ser Asn Asn Lys Arg Ala
50 55 60

Pro Tyr Trp Thr Asn Thr Glu Lys Met Glu Lys Arg Leu His Ala Val
65 70 75 80

Pro Ala Ala Asn Thr Val Lys Phe Arg Cys Pro Ala Gly Gly Asn Pro
85 90 95

Met Pro Thr Met Arg Trp Leu Lys Asn Gly Lys Glu Phe Lys Gln Glu
100 105 110

His Arg Ile Gly Gly Tyr Lys Val Arg Asn Gln His Trp Ser Leu Ile
115 120 125

Met Glu Ser Val Val Pro Ser Asp Lys Gly Asn Tyr Thr Cys Val Val
130 135 140

Glu Asn Glu Tyr Gly Ser Ile Asn His Thr Tyr His Leu Asp Val Val
145 150 155 160

Glu Arg Ser Pro His Arg Pro Ile Leu Gln Ala Gly Leu Pro Ala Asn
165 170 175

Ala Ser Thr Val Val Gly Gly Asp Val Glu Phe Val Cys Lys Val Tyr
180 185 190

Ser Asp Ala Gln Pro His Ile Gln Trp Ile Lys His Val Glu Lys Asn
195 200 205

Gly Ser Lys Tyr Gly Pro Asp Gly Leu Pro Tyr Leu Lys Val Leu Lys
210 215 220

His Ser Gly Ile Asn Ser Ser Asn Ala Glu Val Leu Ala Leu Phe Asn
225 230 235 240

Val Thr Glu Ala Asp Ala Gly Glu Tyr Ile Cys Lys Val Ser Asn Tyr
245 250 255

Ile Gly Gln Ala Asn Gln Ser Ala Trp Leu Thr Val Leu Pro Lys Gln
260 265 270

Gln Ala Pro Gly Arg Glu Lys Glu Ile Thr Ala Ser Pro Asp Tyr Leu
275 280 285

Glu Ile Ala Ile Tyr Cys Ile Gly Val Phe Leu Ile Ala Cys Met Val
290 295 300

Val Thr Val Ile Leu Cys Arg Met Lys Asn Thr Thr Lys Lys Pro Asp
305 310 315 320

Phe Ser Ser Gln Pro Ala Val His Lys Leu Thr Lys Arg Ile Pro Leu
325 330 335

```
Arg Arg Gln Val Thr Val Ser Ala Glu Ser Ser Ser Ser Met Asn Ser
            340                 345                 350

Asn Thr Pro Leu Val Arg Ile Thr Thr Arg Leu Ser Ser Thr Ala Asp
        355                 360                 365

Thr Pro Met Leu Ala Gly Val Ser Glu Tyr Glu Leu Pro Glu Asp Pro
    370                 375                 380

Lys Trp Glu Phe Pro Arg Asp Lys Leu Thr Leu Gly Lys Pro Leu Gly
385                 390                 395                 400

Glu Gly Cys Phe Gly Gln Val Val Met Ala Glu Ala Val Gly Ile Asp
                405                 410                 415

Lys Asp Lys Pro Lys Glu Ala Val Thr Val Ala Val Lys Met Leu Lys
            420                 425                 430

Asp Asp Ala Thr Glu Lys Asp Leu Ser Asp Leu Val Ser Glu Met Glu
        435                 440                 445

Met Met Lys Met Ile Gly Lys His Lys Asn Ile Ile Asn Leu Leu Gly
    450                 455                 460

Ala Cys Thr Gln Asp Gly Pro Leu Tyr Val Ile Val Glu Tyr Ala Ser
465                 470                 475                 480

Lys Gly Asn Leu Arg Glu Tyr Leu Arg Ala Arg Arg Pro Pro Gly Met
                485                 490                 495

Glu Tyr Ser Tyr Asp Ile Asn Arg Val Pro Glu Glu Gln Met Thr Phe
            500                 505                 510

Lys Asp Leu Val Ser Cys Thr Tyr Gln Leu Ala Arg Gly Met Glu Tyr
        515                 520                 525

Leu Ala Ser Gln Lys Cys Ile His Arg Asp Leu Ala Ala Arg Asn Val
    530                 535                 540

Leu Val Thr Glu Asn Asn Val Met Lys Ile Ala Asp Phe Gly Leu Ala
545                 550                 555                 560

Arg Asp Ile Asn Asn Ile Asp Tyr Tyr Lys Lys Thr Thr Asn Gly Arg
                565                 570                 575

Leu Pro Val Lys Trp Met Ala Pro Glu Ala Leu Phe Asp Arg Val Tyr
            580                 585                 590

Thr His Gln Ser Asp Val Trp Ser Phe Gly Val Leu Met Trp Glu Ile
        595                 600                 605

Phe Thr Leu Gly Gly Ser Pro Tyr Pro Gly Ile Pro Val Glu Glu Leu
    610                 615                 620

Phe Lys Leu Leu Lys Glu Gly His Arg Met Asp Lys Pro Ala Asn Cys
625                 630                 635                 640

Thr Asn Glu Leu Tyr Met Met Met Arg Asp Cys Trp His Ala Val Pro
                645                 650                 655

Ser Gln Arg Pro Thr Phe Lys Gln Leu Val Glu Asp Leu Asp Arg Ile
            660                 665                 670

Leu Thr Leu Thr Thr Asn Glu Ile
        675                 680
```

<210> SEQ ID NO 68
<211> LENGTH: 396
<212> TYPE: PRT
<213> ORGANISM: Homo sapiens

<400> SEQUENCE: 68

```
Met Val Ser Trp Gly Arg Phe Ile Cys Leu Val Val Val Thr Met Ala
 1               5                  10                  15

Thr Leu Ser Leu Ala Arg Pro Ser Phe Ser Leu Val Glu Asp Thr Thr
            20                  25                  30
```

```
Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Thr Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Gly Ile Tyr Cys Ser Phe Ser
        355                 360                 365

Leu Gly Phe Phe Pro Phe Ser Trp Leu Thr Ala Ile Lys Leu Thr Gln
    370                 375                 380

Leu Leu Leu Ser Glu Met Ala Pro Phe Ile Leu Ala
385                 390                 395


<210> SEQ ID NO 69
<211> LENGTH: 317
<212> TYPE: PRT
<213> ORGANISM: Homo sapiens

<400> SEQUENCE: 69

Met Val Ser Trp Gly Arg Phe Ile Cys Leu Val Val Val Thr Met Ala
 1               5                  10                  15
```

```
Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Val Arg Thr Phe
305                 310                 315


<210> SEQ ID NO 70
<211> LENGTH: 266
<212> TYPE: PRT
<213> ORGANISM: Homo sapiens

<400> SEQUENCE: 70

Met Val Ser Trp Gly Arg Phe Ile Cys Leu Val Val Val Thr Met Ala
 1               5                  10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80
```

```
Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Gly Glu Ser Ala Ser Pro Arg
                245                 250                 255

Val Ala Ala Ala Tyr Gln Pro Ile Leu Ala
            260                 265
```

<210> SEQ ID NO 71
<211> LENGTH: 336
<212> TYPE: DNA
<213> ORGANISM: Mus musculus

<400> SEQUENCE: 71

```
caggtgaagc tgcaggagtc tggcgctgag ttggtgaaac ctggggcttc agtgaagata      60

tcctgcaagg cttctggcta catcttcact gaccatgctc ttcactgggt gaggcagaag     120

cctgaacagg gcctggaatg gattggtat atttttcccg gaaatggtaa tattgagtac     180

aatgagaagt tcaagggcaa ggccacactg actgcagaca aatcctccag tactgcctac     240

atgcagctca acagcctgac atctggagat tctgcaatgt atttctgtaa aaagatggac     300

tactggggcc aagggaccac ggtcaccgtc tcctca                               336
```

<210> SEQ ID NO 72
<211> LENGTH: 112
<212> TYPE: PRT
<213> ORGANISM: Mus musculus

<400> SEQUENCE: 72

```
Gln Val Lys Leu Gln Glu Ser Gly Ala Glu Leu Val Lys Pro Gly Ala
 1               5                  10                  15

Ser Val Lys Ile Ser Cys Lys Ala Ser Gly Tyr Ile Phe Thr Asp His
            20                  25                  30

Ala Leu His Trp Val Arg Gln Lys Pro Glu Gln Gly Leu Glu Trp Ile
        35                  40                  45

Gly Tyr Ile Phe Pro Gly Asn Gly Asn Ile Glu Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Gly Asp Ser Ala Met Tyr Phe Cys
```

```
                85                  90                  95

Lys Lys Met Asp Tyr Trp Gly Gln Gly Thr Thr Val Thr Val Ser Ser
            100                 105                 110


<210> SEQ ID NO 73
<211> LENGTH: 336
<212> TYPE: DNA
<213> ORGANISM: Mus musculus

<400> SEQUENCE: 73

caggtgaagc tgcaggagtc tggcgctgag ttggtgaaac ctggggcttc agtgaagatc      60

tcctgcaagg cttctggtta caccttcact gaccattcta ttcactgggt gaagcagaag     120

cctggacagg gcctagaatg gattggatat ctttttcccg gaaatggtaa ttttgaatat     180

aatgagaaat tcaagggcaa ggccacactg actgcagaca aatcctccag cactgcctac     240

atgcacctca acagcctgac atctgaggat tctgcagtgt atttctgtaa aaagatggac     300

tactggggcc aagggaccac ggtcaccgtc tcctca                               336


<210> SEQ ID NO 74
<211> LENGTH: 112
<212> TYPE: PRT
<213> ORGANISM: Mus musculus

<400> SEQUENCE: 74

Gln Val Lys Leu Gln Glu Ser Gly Ala Glu Leu Val Lys Pro Gly Ala
 1               5                  10                  15

Ser Val Lys Ile Ser Cys Lys Ala Ser Gly Tyr Thr Phe Thr Asp His
            20                  25                  30

Ser Ile His Trp Val Lys Gln Lys Pro Gly Gln Gly Leu Glu Trp Ile
        35                  40                  45

Gly Tyr Leu Phe Pro Gly Asn Gly Asn Phe Glu Tyr Asn Glu Lys Phe
    50                  55                  60

Lys Gly Lys Ala Thr Leu Thr Ala Asp Lys Ser Ser Ser Thr Ala Tyr
65                  70                  75                  80

Met His Leu Asn Ser Leu Thr Ser Glu Asp Ser Ala Val Tyr Phe Cys
                85                  90                  95

Lys Lys Met Asp Tyr Trp Gly Gln Gly Thr Thr Val Thr Val Ser Ser
            100                 105                 110


<210> SEQ ID NO 75
<211> LENGTH: 336
<212> TYPE: DNA
<213> ORGANISM: Mus musculus

<400> SEQUENCE: 75

caggttcagc tgcagcagtc cgacgctgag ttggtgaaac ctggggcttc agtgaagata      60

tcctgcaggg cttctggcta caccttcact gaccattcta ttcactgggt gaagcagcag     120

cctggccagg gcctggaatg gatcggatat atttttcccg gaaatggaaa tattgaatac     180

aatgacaaat tcaagggcaa ggccacactg actgcagaca aatcctccgg cactgcctac     240

atgcagctca acagcctgac atctgaggat tctgcagtgt atttctgtaa aaggatgggg     300

tactggggtc aaggaacctc agtcaccgtc tcctca                               336


<210> SEQ ID NO 76
<211> LENGTH: 112
<212> TYPE: PRT
<213> ORGANISM: Mus musculus
```

<400> SEQUENCE: 76

Gln Val Gln Leu Gln Gln Ser Asp Ala Glu Leu Val Lys Pro Gly Ala
 1               5                  10                  15

Ser Val Lys Ile Ser Cys Arg Ala Ser Gly Tyr Thr Phe Thr Asp His
            20                  25                  30

Ser Ile His Trp Val Lys Gln Gln Pro Gly Gln Gly Leu Glu Trp Ile
        35                  40                  45

Gly Tyr Ile Phe Pro Gly Asn Gly Asn Ile Glu Tyr Asn Asp Lys Phe
    50                  55                  60

Lys Gly Lys Ala Thr Leu Thr Ala Asp Lys Ser Ser Gly Thr Ala Tyr
65                  70                  75                  80

Met Gln Leu Asn Ser Leu Thr Ser Glu Asp Ser Ala Val Tyr Phe Cys
                85                  90                  95

Lys Arg Met Gly Tyr Trp Gly Gln Gly Thr Ser Val Thr Val Ser Ser
            100                 105                 110

<210> SEQ ID NO 77
<211> LENGTH: 336
<212> TYPE: DNA
<213> ORGANISM: Mus musculus

<400> SEQUENCE: 77
caggtcaagc tgcaggagtc tggcgctgag ttggtgaaac ctggggcttc agtgaagatc 60
tcctgcaagg cttctggcta caccttcact gaccattcta ttcactgggt gaagcagaag 120
cctggacagg gcctagaatg gattggatat ctttttcccg gaaatggtaa ttttgagtac 180
aatgaaaaat tcaagggcaa ggccacactg actgcagaca aatcctccag cactgtctac 240
atgtacctca acagcctgac atctgaggat tctgcagtgt atttctgtaa aaggatgggg 300
tactggggcc aagggaccac ggtcaccgtc tcctca 336

<210> SEQ ID NO 78
<211> LENGTH: 112
<212> TYPE: PRT
<213> ORGANISM: Mus musculus

<400> SEQUENCE: 78

Gln Val Lys Leu Gln Glu Ser Gly Ala Glu Leu Val Lys Pro Gly Ala
 1               5                  10                  15

Ser Val Lys Ile Ser Cys Lys Ala Ser Gly Tyr Thr Phe Thr Asp His
            20                  25                  30

Ser Ile His Trp Val Lys Gln Lys Pro Gly Gln Gly Leu Glu Trp Ile
        35                  40                  45

Gly Tyr Leu Phe Pro Gly Asn Gly Asn Phe Glu Tyr Asn Glu Lys Phe
    50                  55                  60

Lys Gly Lys Ala Thr Leu Thr Ala Asp Lys Ser Ser Ser Thr Val Tyr
65                  70                  75                  80

Met Tyr Leu Asn Ser Leu Thr Ser Glu Asp Ser Ala Val Tyr Phe Cys
                85                  90                  95

Lys Arg Met Gly Tyr Trp Gly Gln Gly Thr Thr Val Thr Val Ser Ser
            100                 105                 110

<210> SEQ ID NO 79
<211> LENGTH: 336
<212> TYPE: DNA
<213> ORGANISM: Mus musculus

<400> SEQUENCE: 79
caggtcaagc tgcaggagtc tggacctgaa ctggtaaagc ctggggcttc agtgaagatg 60
tcctgcaagg cttctggata cacattcact aactatgtta tacactgggt gaagcaaaag 120
cctgggcagg gccttgagtg gattggatat attaatcctt acaatgatgg ctctaagtac 180
aatgagaagt tcaaaggcaa ggcctcactg acttcagaca aatcctccag cacagcctac 240
atggagctca gcagcctgac ctctgaggac tctgcggtct attactgtgc aagaatggac 300
tactggggcc aagggaccac ggtcaccgtc tcctca 336

<210> SEQ ID NO 80
<211> LENGTH: 112
<212> TYPE: PRT
<213> ORGANISM: Mus musculus

<400> SEQUENCE: 80

Gln Val Gln Leu Gln Glu Ser Gly Pro Glu Leu Val Lys Pro Gly Ala
1 5 10 15

Ser Val Lys Met Ser Cys Lys Ala Ser Gly Tyr Thr Phe Thr Asn Tyr
20 25 30

Val Ile His Trp Val Lys Gln Lys Pro Gly Gln Gly Leu Glu Trp Ile
35 40 45

Gly Tyr Ile Asn Pro Tyr Asn Asp Gly Ser Lys Tyr Asn Glu Lys Phe
50 55 60

Lys Gly Lys Ala Ser Leu Thr Ser Asp Lys Ser Ser Ser Thr Ala Tyr
65 70 75 80

Met Glu Leu Ser Ser Leu Thr Ser Glu Asp Ser Ala Val Tyr Tyr Cys
85 90 95

Ala Arg Met Asp Tyr Trp Gly Gln Gly Thr Thr Leu Thr Val Ser Ser
100 105 110

<210> SEQ ID NO 81
<211> LENGTH: 336
<212> TYPE: DNA
<213> ORGANISM: Mus musculus

<400> SEQUENCE: 81
caggtcaagc tgcaggagtc tggacctgaa ctggtaaagc ctggggcttc agtgaagatg 60
tcctgcaagg cttctggata cacattcact aactatgtta tacactgggt gaagcaaaag 120
cctgggcagg gccttgagtg gattggatat attaatcctt acaatgatgg ctctaagtac 180
aatgagaagt tcaaaggcaa ggcctcactg acttcagaca aatcctccag cacagcctac 240
atggagctca gcagcctgac ctctgaggac tctgcggtct attactgtgc aagaatgggg 300
tactggggcc aagggaccac ggtcaccgtc tcctca 336

<210> SEQ ID NO 82
<211> LENGTH: 112
<212> TYPE: PRT
<213> ORGANISM: Mus musculus

<400> SEQUENCE: 82

Gln Val Gln Leu Gln Glu Ser Gly Pro Glu Leu Val Lys Pro Gly Ala
1 5 10 15

Ser Val Lys Met Ser Cys Lys Ala Ser Gly Tyr Thr Phe Thr Asn Tyr
20 25 30

Val Ile His Trp Val Lys Gln Lys Pro Gly Gln Gly Leu Glu Trp Ile
35 40 45

Gly Tyr Ile Asn Pro Tyr Asn Asp Gly Ser Lys Tyr Asn Glu Lys Phe
50 55 60

```
Lys Gly Lys Ala Ser Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Met Gly Tyr Trp Gly Gln Gly Thr Thr Leu Thr Val Ser Ser
            100                 105                 110


<210> SEQ ID NO 83
<211> LENGTH: 342
<212> TYPE: DNA
<213> ORGANISM: Mus musculus

<400> SEQUENCE: 83

gatgttttga tgacccaaac tccactctcc ctgcctgtca gtcttggaga tcaagcctcc      60

atctcttgca gatctagtca gagcattgta catagtaatg gaaacaccta tttagaatgg     120

tacctgcaga aaccaggcca gtctccaaag ctcctgatct acaaagtttc caaccgattt     180

tctggggtcc cagacaggtt cagtggcagt ggatcaggga cagatttcac actcaagatc     240

agcagagtgg aggctgagga tctgggagtt tattactgct ttcaaggttc acatgttcct     300

cctacgttcg gtgctgggac caagctggag ctgaaacggg ct                        342


<210> SEQ ID NO 84
<211> LENGTH: 113
<212> TYPE: PRT
<213> ORGANISM: Mus musculus

<400> SEQUENCE: 84

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Ala Gly Thr Lys Leu Glu Leu Lys
            100                 105                 110

Arg


<210> SEQ ID NO 85
<211> LENGTH: 324
<212> TYPE: DNA
<213> ORGANISM: Mus musculus

<400> SEQUENCE: 85

gacatccaga tgactcagtc tccagcctcc ctatctgcat ctgtgggaga aactgtcacc      60

atcacatgtc gaacaactga aaatatttac agttattttg tatggtctca gcagagacag     120

ggaaaatctc ctcagctccg ggtctataat gcaaaatcct tagcagaagg tgtgccatca     180

agtttcaatg tcagtgtatc aggcacacag ttttctctga agatcaatag cctgcagcct     240

gaagattttg ggacttatca ctgtcaacac cattatggta ctccgtacac gttcggaggg     300

gggaccaggc tggaaataag acgg                                            324
```

<210> SEQ ID NO 86
<211> LENGTH: 108
<212> TYPE: PRT
<213> ORGANISM: Mus musculus

<400> SEQUENCE: 86

```
Asp Ile Gln Met Thr Gln Ser Pro Ala Ser Leu Ser Ala Ser Val Gly
 1               5                  10                  15

Glu Thr Val Thr Ile Thr Cys Arg Thr Thr Glu Asn Ile Tyr Ser Tyr
            20                  25                  30

Phe Val Trp Ser Gln Gln Arg Gln Gly Lys Ser Pro Gln Leu Arg Val
        35                  40                  45

Tyr Asn Ala Lys Ser Leu Ala Glu Gly Val Pro Ser Ser Phe Asn Val
    50                  55                  60

Ser Val Ser Gly Thr Gln Phe Ser Leu Lys Ile Asn Ser Leu Gln Pro
65                  70                  75                  80

Glu Asp Phe Gly Thr Tyr His Cys Gln His His Tyr Gly Thr Pro Tyr
                85                  90                  95

Thr Phe Gly Gly Gly Thr Arg Leu Glu Ile Arg Arg
            100                 105
```

<210> SEQ ID NO 87
<211> LENGTH: 339
<212> TYPE: DNA
<213> ORGANISM: Mus musculus

<400> SEQUENCE: 87

```
gatgttttg atgacccaaac tccactcact ttgtcggtta ccattggaca accagcttcc     60

atctcttgc aagtccagtca gagcctctta tatactaatg gaaaaaccta tttgacttgg    120

ttattccag aggccaggcca gtctccaaaa cgcctaatct atctggtgtc tgaattggac    180

tctggagtc cctgacaggtt cagtggcagt ggttcaggga cagatttcac actggaaatc    240

accagagtg gaggctgagga tttgggagtt tattactgct tgcagagtgc acattttcca    300

ttcacgttc ggctcgggcac caagctggaa atcaaacgg                           339
```

<210> SEQ ID NO 88
<211> LENGTH: 113
<212> TYPE: PRT
<213> ORGANISM: Mus musculus

<400> SEQUENCE: 88

```
Asp Val Leu Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Tyr Thr
            20                  25                  30

Asn Gly Lys Thr Tyr Leu Thr Trp Leu Phe Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Glu Ile
65                  70                  75                  80

Thr Arg Val Glu Ala Glu Asp Leu Gly Val Tyr Tyr Cys Leu Gln Ser
                85                  90                  95

Ala His Phe Pro Phe Thr Phe Gly Ser Gly Thr Lys Leu Glu Ile Lys
            100                 105                 110

Arg
```

<210> SEQ ID NO 89
<211> LENGTH: 339
<212> TYPE: DNA
<213> ORGANISM: Mus musculus

<400> SEQUENCE: 89
gatgttgtga tgacccaaac tccactcact ctgtcggtga ccattggaca accagcgttc 60
atctcttgca agtccagtca gagcctcttt aacactaatg gcaaaaccta tttgacttgg 120
ttaattcaga ggccaggcca gtctccacag cgcctgatct atctggtgtc caaattggac 180
tctggcgtcc cggacaggtt cagtggcagt ggctcaggga cagatttcac actgaaaatc 240
agcagagtgg aggctgagga tctgggagtt tattactgcc tgcagagtag ccattttccg 300
tttacgttcg gctcgggcac caagctggaa atcaaacgg 339

<210> SEQ ID NO 90
<211> LENGTH: 113
<212> TYPE: PRT
<213> ORGANISM: Mus musculus

<400> SEQUENCE: 90

Asp Val Val Met Thr Gln Thr Pro Leu Thr Leu Ser Val Thr Ile Gly
1 5 10 15

Gln Pro Ala Ser Ile Ser Cys Lys Ser Ser Gln Ser Leu Leu Asn Thr
20 25 30

Asn Gly Lys Thr Tyr Leu Thr Trp Leu Ile Gln Arg Pro Gly Gln Ser
35 40 45

Pro Gln Arg Leu Ile Tyr Leu Val Ser Lys Leu Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Leu Gln Ser
85 90 95

Ser His Phe Pro Phe Thr Phe Gly Ser Gly Thr Lys Leu Glu Ile Lys
100 105 110

Arg

<210> SEQ ID NO 91
<211> LENGTH: 327
<212> TYPE: DNA
<213> ORGANISM: Mus musculus

<400> SEQUENCE: 91
gatgttgtgc taactcagtc tcctgccacc ctgtctgtga ctccaggaga tagagtcagt 60
ctttcctgca gggccagcca aaatattggc aactacctac actggtatca acagaaatca 120
catgagtctc caaggcttct catcaagtat gcttcccagt ccatctctgg gatcccctcc 180
aggttcagtg gcagtggatc agtcacagat ttcactctca atatcaacag tgtggagact 240
gaagattttg gaatgtattt ctgtcaacag agtgacacct ggcctctcac gttcggtgct 300
gggaccaagc tggagctgaa acgggct 327

<210> SEQ ID NO 92
<211> LENGTH: 108
<212> TYPE: PRT
<213> ORGANISM: Mus musculus

<400> SEQUENCE: 92

```
Asp Val Val Leu Thr Gln Ser Pro Ala Thr Leu Ser Val Thr Pro Gly
 1               5                  10                  15

Asp Arg Val Ser Leu Ser Cys Arg Ala Ser Gln Asn Ile Gly Asn Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Val Thr Asp Phe Thr Leu Asn Ile Asn Ser Val Glu Thr
65                  70                  75                  80

Glu Asp Phe Gly Met Tyr Phe Cys Gln Gln Ser Asp Thr Trp Pro Leu
                85                  90                  95

Thr Phe Gly Ala Gly Thr Lys Leu Glu Leu Lys Arg
            100                 105


<210> SEQ ID NO 93
<211> LENGTH: 8
<212> TYPE: PRT
<213> ORGANISM: Mus musculus

<400> SEQUENCE: 93

Thr Phe Thr Asp His Ser Ile His
 1               5


<210> SEQ ID NO 94
<211> LENGTH: 8
<212> TYPE: PRT
<213> ORGANISM: Mus musculus

<400> SEQUENCE: 94

Thr Phe Thr Asn Tyr Val Ile His
 1               5


<210> SEQ ID NO 95
<211> LENGTH: 8
<212> TYPE: PRT
<213> ORGANISM: Mus musculus

<400> SEQUENCE: 95

Ile Phe Thr Asp His Ala Leu His
 1               5


<210> SEQ ID NO 96
<211> LENGTH: 17
<212> TYPE: PRT
<213> ORGANISM: Mus musculus

<400> SEQUENCE: 96

Tyr Ile Phe Pro Gly Asn Gly Asn Ile Glu Tyr Asn Asp Lys Phe Lys
 1               5                  10                  15

Gly


<210> SEQ ID NO 97
<211> LENGTH: 17
<212> TYPE: PRT
<213> ORGANISM: Mus musculus

<400> SEQUENCE: 97

Tyr Leu Phe Pro Gly Asn Gly Asn Phe Glu Tyr Asn Glu Lys Phe Lys
 1               5                  10                  15

Gly
```

<210> SEQ ID NO 98
<211> LENGTH: 17
<212> TYPE: PRT
<213> ORGANISM: Mus musculus

<400> SEQUENCE: 98

Tyr Ile Asn Pro Tyr Asn Asp Gly Ser Lys Tyr Asn Glu Lys Phe Lys
1 5 10 15

Gly

<210> SEQ ID NO 99
<211> LENGTH: 17
<212> TYPE: PRT
<213> ORGANISM: Mus musculus

<400> SEQUENCE: 99

Tyr Ile Phe Pro Gly Asn Gly Asn Ile Glu Tyr Asn Glu Lys Phe Lys
1 5 10 15

Gly

<210> SEQ ID NO 100
<211> LENGTH: 5
<212> TYPE: PRT
<213> ORGANISM: Mus musculus

<400> SEQUENCE: 100

Lys Arg Met Gly Tyr
1 5

<210> SEQ ID NO 101
<211> LENGTH: 5
<212> TYPE: PRT
<213> ORGANISM: Mus musculus

<400> SEQUENCE: 101

Lys Lys Met Asp Tyr
1 5

<210> SEQ ID NO 102
<211> LENGTH: 5
<212> TYPE: PRT
<213> ORGANISM: Mus musculus

<400> SEQUENCE: 102

Ala Arg Met Asp Tyr
1 5

<210> SEQ ID NO 103
<211> LENGTH: 16
<212> TYPE: PRT
<213> ORGANISM: Mus musculus

<400> SEQUENCE: 103

Arg Ser Ser Gln Ser Ile Val His Ser Asn Gly Asn Thr Tyr Leu Glu
1 5 10 15

<210> SEQ ID NO 104
<211> LENGTH: 11
<212> TYPE: PRT
<213> ORGANISM: Mus musculus

<400> SEQUENCE: 104

Arg Thr Thr Glu Asn Ile Tyr Ser Tyr Phe Val
1 5 10

<210> SEQ ID NO 105
<211> LENGTH: 16
<212> TYPE: PRT
<213> ORGANISM: Mus musculus

<400> SEQUENCE: 105

Lys Ser Ser Gln Ser Leu Leu Tyr Thr Asn Gly Lys Thr Tyr Leu Thr
1 5 10 15

<210> SEQ ID NO 106
<211> LENGTH: 16
<212> TYPE: PRT
<213> ORGANISM: Mus musculus

<400> SEQUENCE: 106

Lys Ser Ser Gln Ser Leu Leu Asn Thr Asn Gly Lys Thr Tyr Leu Thr
1 5 10 15

<210> SEQ ID NO 107
<211> LENGTH: 11
<212> TYPE: PRT
<213> ORGANISM: Mus musculus

<400> SEQUENCE: 107

Arg Ala Ser Gln Asn Ile Gly Asn Tyr Leu His
1 5 10

<210> SEQ ID NO 108
<211> LENGTH: 7
<212> TYPE: PRT
<213> ORGANISM: Mus musculus

<400> SEQUENCE: 108

Lys Val Ser Asn Arg Phe Ser
1 5

<210> SEQ ID NO 109
<211> LENGTH: 7
<212> TYPE: PRT
<213> ORGANISM: Mus musculus

<400> SEQUENCE: 109

Asn Ala Lys Ser Leu Ala Glu
1 5

<210> SEQ ID NO 110
<211> LENGTH: 7
<212> TYPE: PRT
<213> ORGANISM: Mus musculus

<400> SEQUENCE: 110

Leu Val Ser Glu Leu Asp Ser
1 5

<210> SEQ ID NO 111
<211> LENGTH: 7
<212> TYPE: PRT
<213> ORGANISM: Mus musculus

<400> SEQUENCE: 111

Leu Val Ser Lys Leu Asp Ser
1 5

<210> SEQ ID NO 112

<211> LENGTH: 7
<212> TYPE: PRT
<213> ORGANISM: Mus musculus

<400> SEQUENCE: 112

Tyr Ala Ser Gln Ser Ile Ser
1 5

<210> SEQ ID NO 113
<211> LENGTH: 9
<212> TYPE: PRT
<213> ORGANISM: Mus musculus

<400> SEQUENCE: 113

Phe Gln Gly Ser His Val Pro Pro Thr
1 5

<210> SEQ ID NO 114
<211> LENGTH: 9
<212> TYPE: PRT
<213> ORGANISM: Mus musculus

<400> SEQUENCE: 114

Gln His His Tyr Gly Thr Pro Tyr Thr
1 5

<210> SEQ ID NO 115
<211> LENGTH: 9
<212> TYPE: PRT
<213> ORGANISM: Mus musculus

<400> SEQUENCE: 115

Leu Gln Ser Ala His Phe Pro Phe Thr
1 5

<210> SEQ ID NO 116
<211> LENGTH: 9
<212> TYPE: PRT
<213> ORGANISM: Mus musculus

<400> SEQUENCE: 116

Leu Gln Ser Ser His Phe Pro Phe Thr
1 5

<210> SEQ ID NO 117
<211> LENGTH: 9
<212> TYPE: PRT
<213> ORGANISM: Mus musculus

<400> SEQUENCE: 117

Gln Gln Ser Asp Thr Trp Pro Leu Thr
1 5

<210> SEQ ID NO 118
<211> LENGTH: 5
<212> TYPE: PRT
<213> ORGANISM: Mus musculus

<400> SEQUENCE: 118

Asp His Ala Leu His
1 5

<210> SEQ ID NO 119
<211> LENGTH: 5
<212> TYPE: PRT
<213> ORGANISM: Mus musculus

<400> SEQUENCE: 119

Asp His Ser Ile His
 1              5

<210> SEQ ID NO 120
<211> LENGTH: 5
<212> TYPE: PRT
<213> ORGANISM: Mus musculus

<400> SEQUENCE: 120

Asn Tyr Val Ile His
 1              5

<210> SEQ ID NO 121
<211> LENGTH: 9
<212> TYPE: PRT
<213> ORGANISM: Mus musculus

<400> SEQUENCE: 121

Ile Phe Pro Gly Asn Gly Asn Ile Glu
 1              5

<210> SEQ ID NO 122
<211> LENGTH: 9
<212> TYPE: PRT
<213> ORGANISM: Mus musculus

<400> SEQUENCE: 122

Leu Phe Pro Gly Asn Gly Asn Phe Glu
 1              5

<210> SEQ ID NO 123
<211> LENGTH: 9
<212> TYPE: PRT
<213> ORGANISM: Mus musculus

<400> SEQUENCE: 123

Ile Asn Pro Tyr Asn Asp Gly Ser Lys
 1              5

<210> SEQ ID NO 124
<211> LENGTH: 11
<212> TYPE: PRT
<213> ORGANISM: Mus musculus

<400> SEQUENCE: 124

His Leu Ala Asn Thr Tyr Tyr Tyr Phe Asp Tyr
 1              5                   10

<210> SEQ ID NO 125
<211> LENGTH: 5
<212> TYPE: PRT
<213> ORGANISM: Mus musculus

<400> SEQUENCE: 125

Ser Asn Gly Asn Thr
 1              5

<210> SEQ ID NO 126
<211> LENGTH: 5
<212> TYPE: PRT
<213> ORGANISM: Mus musculus

<400> SEQUENCE: 126

Glu Asn Ile Tyr Ser
1 5

<210> SEQ ID NO 127
<211> LENGTH: 5
<212> TYPE: PRT
<213> ORGANISM: Mus musculus

<400> SEQUENCE: 127

Thr Ser Gly Tyr Ser
1 5

<210> SEQ ID NO 128
<211> LENGTH: 5
<212> TYPE: PRT
<213> ORGANISM: Mus musculus

<400> SEQUENCE: 128

Gln Asp Ile Lys Ser
1 5

<210> SEQ ID NO 129
<211> LENGTH: 5
<212> TYPE: PRT
<213> ORGANISM: Mus musculus

<400> SEQUENCE: 129

Gln Asn Ile Gly Asn
1 5

<210> SEQ ID NO 130
<211> LENGTH: 4654
<212> TYPE: DNA
<213> ORGANISM: Homo sapiens

<400> SEQUENCE: 130
ggcggcggct ggaggagagc gcggtggaga gccgagcggg cgggcggcgg gtgcggagcg 60
ggcgagggag cgcgcgcggc cgccacaaag ctcgggcgcc gcggggctgc atgcggcgta 120
cctggcccgg cgcggcgact gctctccggg ctggcggggg ccggccgcga gccccggggg 180
ccccgaggcc gcagcttgcc tgcgcgctct gagccttcgc aactcgcgag caaagtttgg 240
tggaggcaac gccaagcctg agtcctttct tcctctcgtt ccccaaatcc gagggcagcc 300
cgcgggcgtc atgcccgcgc tcctccgcag cctggggtac gcgtgaagcc cgggaggctt 360
ggcgccggcg aagacccaag gaccactctt ctgcgtttgg agttgctccc cgcaaccccg 420
ggctcgtcgc tttctccatc ccgacccacg cggggcgcgg ggacaacaca ggtcgcggag 480
gagcgttgcc attcaagtga ctgcagcagc agcggcagcg cctcggttcc tgagcccacc 540
gcaggctgaa ggcattgcgc gtagtccatg cccgtagagg aagtgtgcag atgggattaa 600
cgtccacatg gagatatgga agaggaccgg ggattggtac cgtaaccatg gtcagctggg 660
gtcgtttcat ctgcctggtc gtggtcacca tggcaacctt gtccctggcc cggccctcct 720
tcagtttagt tgaggatacc acattagagc cagaagagcc accaaccaaa taccaaatct 780
ctcaaccaga agtgtacgtg gctgcgccag gggagtcgct agaggtgcgc tgcctgttga 840
aagatgccgc cgtgatcagt tggactaagg atggggtgca cttggggccc aacaatagga 900
cagtgcttat tggggagtac ttgcagataa agggcgccac gcctagagac tccggcctct 960
atgcttgtac tgccagtagg actgtagaca gtgaaacttg gtacttcatg gtgaatgtca 1020
cagatgccat ctcatccgga gatgatgagg atgacaccga tggtgcggaa gattttgtca 1080

-continued

```
gtgagaacag taacaacaag agagcaccat actggaccaa cacagaaaag atggaaaagc   1140
ggctccatgc tgtgcctgcg gccaacactg tcaagtttcg ctgcccagcc ggggggaacc   1200
caatgccaac catgcggtgg ctgaaaaacg ggaaggagtt taagcaggag catcgcattg   1260
gaggctacaa ggtacgaaac cagcactgga gcctcattat ggaaagtgtg gtcccatctg   1320
acaagggaaa ttatacctgt gtagtggaga atgaatacgg gtccatcaat cacacgtacc   1380
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
agccccacat ccagtggatc aagcacgtgg aaaagaacgg cagtaaatac gggcccgacg   1560
ggctgcccta cctcaaggtt ctcaaggccg ccggtgttaa caccacggac aaagagattg   1620
aggttctcta tattcggaat gtaacttttg aggacgctgg ggaatatacg tgcttggcgg   1680
gtaattctat tgggatatcc tttcactctg catggttgac agttctgcca gcgcctggaa   1740
gagaaaagga gattacagct tccccagact acctggagat agccatttac tgcatagggg   1800
tcttcttaat cgcctgtatg gtggtaacag tcatcctgtg ccgaatgaag aacacgacca   1860
agaagccaga cttcagcagc cagccggctg tgcacaagct gaccaaacgt atcccccctgc   1920
ggagacaggt aacagtttcg gctgagtcca gctcctccat gaactccaac accccgctgg   1980
tgaggataac aacacgcctc tcttcaacgg cagacacccc catgctggca ggggtctccg   2040
agtatgaact tccagaggac ccaaaatggg agtttccaag agataagctg acactgggca   2100
agcccctggg agaaggttgc tttgggcaag tggtcatggc ggaagcagtg ggaattgaca   2160
aagacaagcc caaggaggcg gtcaccgtgg ccgtgaagat gttgaaagat gatgccacag   2220
agaaagacct ttctgatctg gtgtcagaga tggagatgat gaagatgatt gggaaacaca   2280
agaatatcat aaatcttctt ggagcctgca cacaggatgg gcctctctat gtcatagttg   2340
agtatgcctc taaaggcaac ctccgagaat acctccgagc ccggaggcca cccgggatgg   2400
agtactccta tgacattaac cgtgttcctg aggagcagat gaccttcaag gacttggtgt   2460
catgcaccta ccagctggcc agaggcatgg agtacttggc ttcccaaaaa tgtattcatc   2520
gagatttagc agccagaaat gttttggtaa cagaaaacaa tgtgatgaaa atagcagact   2580
ttggactcgc cagagatatc aacaatatag actattacaa aaagaccacc aatgggcggc   2640
ttccagtcaa gtggatggct ccagaagccc tgtttgatag agtatacact catcagagtg   2700
atgtctggtc cttcggggtg ttaatgtggg agatcttcac tttagggggc tcgccctacc   2760
cagggattcc cgtggaggaa ctttttaagc tgctgaagga aggacacaga atggataagc   2820
cagccaactg caccaacgaa ctgtacatga tgatgaggga ctgttggcat gcagtgccct   2880
cccagagacc aacgttcaag cagttggtag aagacttgga tcgaattctc actctcacaa   2940
ccaatgagga atacttggac ctcagccaac ctctcgaaca gtattcacct agttaccctg   3000
acacaagaag ttcttgttct tcaggagatg attctgtttt ttctccagac cccatgcctt   3060
acgaaccatg ccttcctcag tatccacaca taaacggcag tgttaaaaca tgaatgactg   3120
tgtctgcctg tccccaaaca ggacagcact gggaacctag ctacactgag cagggagacc   3180
atgcctccca gagcttgttg tctccacttg tatatatgga tcagaggagt aaataattgg   3240
aaaagtaatc agcatatgtg taaagattta tacagttgaa aacttgtaat cttccccagg   3300
aggagaagaa ggtttctgga gcagtggact gccacaagcc accatgtaac ccctctcacc   3360
tgccgtgcgt actggctgtg gaccagtagg actcaaggtg gacgtgcgtt ctgccttcct   3420
tgttaatttt gtaataattg gagaagattt atgtcagcac acacttacag agcacaaatg   3480
```

-continued

```
cagtatatag gtgctggatg tatgtaaata tattcaaatt atgtataaat atatattata   3540

tatttacaag gagttatttt ttgtattgat tttaaatgga tgtcccaatg cacctagaaa   3600

attggtctct cttttttttaa tagctatttg ctaaatgctg ttcttacaca taatttctta   3660

attttcaccg agcagaggtg gaaaaatact tttgctttca gggaaaatgg tataacgtta   3720

atttattaat aaattggtaa tatacaaaac aattaatcat ttatagtttt ttttgtaatt   3780

taagtggcat ttctatgcag gcagcacagc agactagtta atctattgct tggacttaac   3840

tagttatcag atcctttgaa aagagaatat ttacaatata tgactaattt ggggaaaatg   3900

aagttttgat ttatttgtgt ttaaatgctg ctgtcagacg attgttctta gacctcctaa   3960

atgccccata ttaaaagaac tcattcatag gaaggtgttt cattttggtg tgcaaccctg   4020

tcattacgtc aacgcaacgt ctaactggac ttcccaagat aaatggtacc agcgtcctct   4080

taaaagatgc cttaatccat tccttgagga cagaccttag ttgaaatgat agcagaatgt   4140

gcttctctct ggcagctggc cttctgcttc tgagttgcac attaatcaga ttagcctgta   4200

ttctcttcag tgaattttga taatggcttc cagactcttt ggcgttggag acgcctgtta   4260

ggatcttcaa gtcccatcat agaaaattga aacacagagt tgttctgctg atagttttgg   4320

ggatacgtcc atctttttaa gggattgctt tcatctaatt ctggcaggac ctcaccaaaa   4380

gatccagcct catacctaca tcagacaaaa tatcgccgtt gttccttctg tactaaagta   4440

ttgtgttttg ctttggaaac acccactcac tttgcaatag ccgtgcaaga tgaatgcaga   4500

ttacactgat cttatgtgtt acaaaattgg agaaagtatt taataaaacc tgttaatttt   4560

tatactgaca ataaaaatgt ttctacagat attaatgtta acaagacaaa ataaatgtca   4620

cgcaacttat ttttttaata aaaaaaaaaa aaaa                                4654


<210> SEQ ID NO 131
<211> LENGTH: 4657
<212> TYPE: DNA
<213> ORGANISM: Homo sapiens

<400> SEQUENCE: 131

ggcggcggct ggaggagagc gcggtggaga gccgagcggg cgggcggcgg gtgcggagcg     60

ggcgagggag cgcgcgcggc cgccacaaag ctcgggcgcc gcggggctgc atgcggcgta    120

cctggcccgg cgcggcgact gctctccggg ctggcggggg ccggccgcga gccccggggg    180

ccccgaggcc gcagcttgcc tgcgcgctct gagccttcgc aactcgcgag caaagtttgg    240

tggaggcaac gccaagcctg agtcctttct tcctctcgtt ccccaaatcc gagggcagcc    300

cgcgggcgtc atgcccgcgc tcctccgcag cctggggtac gcgtgaagcc cgggaggctt    360

ggcgccggcg aagacccaag gaccactctt ctgcgtttgg agttgctccc cgcaaccccg    420

ggctcgtcgc tttctccatc ccgacccacg cggggcgcgg ggacaacaca ggtcgcggag    480

gagcgttgcc attcaagtga ctgcagcagc agcggcagcg cctcggttcc tgagcccacc    540

gcaggctgaa ggcattgcgc gtagtccatg cccgtagagg aagtgtgcag atgggattaa    600

cgtccacatg gagatatgga agaggaccgg ggattggtac cgtaaccatg gtcagctggg    660

gtcgtttcat ctgcctggtc gtggtcacca tggcaacctt gtccctggcc cggccctcct    720

tcagtttagt tgaggatacc acattagagc cagaagagcc accaaccaaa taccaaatct    780

ctcaaccaga agtgtacgtg gctgcgccag gggagtcgct agaggtgcgc tgcctgttga    840

aagatgccgc cgtgatcagt tggactaagg atggggtgca cttggggccc aacaatagga    900

cagtgcttat tggggagtac ttgcagataa agggcgccac gcctagagac tccggcctct    960
```

-continued

```
atgcttgtac tgccagtagg actgtagaca gtgaaacttg gtacttcatg gtgaatgtca   1020
cagatgccat ctcatccgga gatgatgagg atgacaccga tggtgcggaa gattttgtca   1080
gtgagaacag taacaacaag agagcaccat actggaccaa cacagaaaag atggaaaagc   1140
ggctccatgc tgtgcctgcg gccaacactg tcaagtttcg ctgcccagcc gggggggaacc   1200
caatgccaac catgcggtgg ctgaaaaacg ggaaggagtt taagcaggag catcgcattg   1260
gaggctacaa ggtacgaaac cagcactgga gcctcattat ggaaagtgtg gtcccatctg   1320
acaagggaaa ttatacctgt gtagtggaga atgaatacgg gtccatcaat cacacgtacc   1380
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
agccccacat ccagtggatc aagcacgtgg aaaagaacgg cagtaaatac gggcccgacg   1560
ggctgcccta cctcaaggtt ctcaagcact cggggataaa tagttccaat gcagaagtgc   1620
tggctctgtt caatgtgacc gaggcggatg ctggggaata tatatgtaag gtctccaatt   1680
atatagggca ggccaaccag tctgcctggc tcactgtcct gccaaaacag caagcgcctg   1740
gaagagaaaa ggagattaca gcttccccag actacctgga gatagccatt tactgcatag   1800
gggtcttctt aatcgcctgt atggtggtaa cagtcatcct gtgccgaatg aagaacacga   1860
ccaagaagcc agacttcagc agccagccgg ctgtgcacaa gctgaccaaa cgtatccccc   1920
tgcggagaca ggtaacagtt tcggctgagt ccagctcctc catgaactcc aacaccccgc   1980
tggtgaggat aacaacacgc ctctcttcaa cggcagacac ccccatgctg gcaggggtct   2040
ccgagtatga acttccagag gacccaaaat gggagtttcc aagagataag ctgacactgg   2100
gcaagcccct gggagaaggt tgctttgggc aagtggtcat ggcggaagca gtgggaattg   2160
acaaagacaa gcccaaggag gcggtcaccg tggccgtgaa gatgttgaaa gatgatgcca   2220
cagagaaaga cctttctgat ctggtgtcag agatggagat gatgaagatg attgggaaac   2280
acaagaatat cataaatctt cttggagcct gcacacagga tgggcctctc tatgtcatag   2340
ttgagtatgc ctctaaaggc aacctccgag aatacctccg agcccggagg ccacccggga   2400
tggagtactc ctatgacatt aaccgtgttc ctgaggagca gatgaccttc aaggacttgg   2460
tgtcatgcac ctaccagctg gccagaggca tggagtactt ggcttcccaa aaatgtattc   2520
atcgagattt agcagccaga aatgttttgg taacagaaaa caatgtgatg aaaatagcag   2580
actttggact cgccagagat atcaacaata tagactatta caaaaagacc accaatgggc   2640
ggcttccagt caagtggatg gctccagaag ccctgtttga tagagtatac actcatcaga   2700
gtgatgtctg gtccttcggg gtgttaatgt gggagatctt cactttaggg ggctcgccct   2760
acccagggat tcccgtggag gaacttttta agctgctgaa ggaaggacac agaatggata   2820
agccagccaa ctgcaccaac gaactgtaca tgatgatgag ggactgttgg catgcagtgc   2880
cctcccagag accaacgttc aagcagttgg tagaagactt ggatcgaatt ctcactctca   2940
caaccaatga ggaatacttg gacctcagcc aacctctcga acagtattca cctagttacc   3000
ctgacacaag aagttcttgt tcttcaggag atgattctgt tttttctcca gaccccatgc   3060
cttacgaacc atgccttcct cagtatccac acataaacgg cagtgttaaa acatgaatga   3120
ctgtgtctgc ctgtccccaa acaggacagc actgggaacc tagctacact gagcagggag   3180
accatgcctc ccagagcttg ttgtctccac ttgtatatat ggatcagagg agtaaataat   3240
tggaaaagta atcagcatat gtgtaaagat ttatacagtt gaaaacttgt aatcttcccc   3300
aggaggagaa gaaggtttct ggagcagtgg actgccacaa gccaccatgt aacccctctc   3360
```

-continued acctgccgtg cgtactggct gtggaccagt aggactcaag gtggacgtgc gttctgcctt 3420
ccttgttaat tttgtaataa ttggagaaga tttatgtcag cacacactta cagagcacaa 3480
atgcagtata taggtgctgg atgtatgtaa atatattcaa attatgtata aatatatatt 3540
atatatttac aaggagttat tttttgtatt gattttaaat ggatgtccca atgcacctag 3600
aaaattggtc tctctttttt taatagctat ttgctaaatg ctgttcttac acataatttc 3660
ttaattttca ccgagcagag gtggaaaaat acttttgctt tcagggaaaa tggtataacg 3720
ttaatttatt aataaattgg taatatacaa aacaattaat catttatagt tttttttgta 3780
atttaagtgg catttctatg caggcagcac agcagactag ttaatctatt gcttggactt 3840
aactagttat cagatccttt gaaaagagaa tatttacaat atatgactaa tttggggaaa 3900
atgaagtttt gatttatttg tgtttaaatg ctgctgtcag acgattgttc ttagacctcc 3960
taaatgcccc atattaaaag aactcattca taggaaggtg tttcattttg gtgtgcaacc 4020
ctgtcattac gtcaacgcaa cgtctaactg gacttcccaa gataaatggt accagcgtcc 4080
tcttaaaaga tgccttaatc cattccttga ggacagacct tagttgaaat gatagcagaa 4140
tgtgcttctc tctggcagct ggccttctgc ttctgagttg cacattaatc agattagcct 4200
gtattctctt cagtgaattt tgataatggc ttccagactc tttggcgttg gagacgcctg 4260
ttaggatctt caagtcccat catagaaaat tgaaacacag agttgttctg ctgatagttt 4320
tggggatacg tccatctttt taagggattg ctttcatcta attctggcag gacctcacca 4380
aaagatccag cctcatacct acatcagaca aaatatcgcc gttgttcctt ctgtactaaa 4440
gtattgtgtt ttgctttgga aacacccact cactttgcaa tagccgtgca agatgaatgc 4500
agattacact gatcttatgt gttacaaaat tggagaaagt atttaataaa acctgttaat 4560
ttttatactg acaataaaaa tgtttctaca gatattaatg ttaacaagac aaaataaatg 4620
tcacgcaact tatttttta ataaaaaaaa aaaaaaa 4657

<210> SEQ ID NO 132
<211> LENGTH: 2781
<212> TYPE: DNA
<213> ORGANISM: Homo sapiens

<400> SEQUENCE: 132
tgactgcagc agcagcggca gcgcctcggt tcctgagccc accgcaggct gaaggcattg 60
cgcgtagtcc atgcccgtag aggaagtgtg cagatgggat taacgtccac atggagatat 120
ggaagaggac cggggattgg taccgtaacc atggtcagct ggggtcgttt catctgcctg 180
gtcgtggtca ccatggcaac cttgtccctg gcccggccct ccttcagttt agttgaggat 240
accacattag agccagaaga gccaccaacc aaataccaaa tctctcaacc agaagtgtac 300
gtggctgcgc caggggagtc gctagaggtg cgctgcctgt tgaaagatgc cgccgtgatc 360
agttggacta aggatggggt gcacttgggg cccaacaata ggacagtgct tattggggag 420
tacttgcaga taaagggcgc cacgcctaga gactccggcc tctatgcttg tactgccagt 480
aggactgtag acagtgaaac ttggtacttc atggtgaatg tcacagatgc catctcatcc 540
ggagatgatg aggatgacac cgatggtgcg gaagattttg tcagtgagaa cagtaacaac 600
aagagagcac catactggac caacacagaa aagatggaaa agcggctcca tgctgtgcct 660
gcggccaaca ctgtcaagtt tcgctgccca gccgggggga acccaatgcc aaccatgcgg 720
tggctgaaaa acgggaagga gtttaagcag gagcatcgca ttggaggcta caaggtacga 780
aaccagcact ggagcctcat tatggaaagt gtggtcccat ctgacaaggg aaattatacc 840

```
tgtgtagtgg agaatgaata cgggtccatc aatcacacgt accacctgga tgttgtggag    900
cgatcgcctc accggcccat cctccaagcc ggactgccgg caaatgcctc cacagtggtc    960
ggaggagacg tagagtttgt ctgcaaggtt tacagtgatg cccagcccca catccagtgg   1020
atcaagcacg tggaaaagaa cggcagtaaa tacgggcccg acgggctgcc ctacctcaag   1080
gttctcaagc actcggggat aaatagttcc aatgcagaag tgctggctct gttcaatgtg   1140
accgaggcgg atgctgggga atatatatgt aaggtctcca attatatagg gcaggccaac   1200
cagtctgcct ggctcactgt cctgccaaaa cagcaagcgc ctggaagaga aaaggagatt   1260
acagcttccc cagactacct ggagatagcc atttactgca taggggtctt cttaatcgcc   1320
tgtatggtgg taacagtcat cctgtgccga atgaagaaca cgaccaagaa gccagacttc   1380
agcagccagc cggctgtgca caagctgacc aaacgtatcc ccctgcggag acaggtaaca   1440
gtttcggctg agtccagctc ctccatgaac tccaacaccc cgctggtgag gataacaaca   1500
cgcctctctt caacggcaga cacccccatg ctggcagggg tctccgagta tgaacttcca   1560
gaggacccaa aatgggagtt tccaagagat aagctgacac tgggcaagcc cctgggagaa   1620
ggttgctttg ggcaagtggt catggcggaa gcagtgggaa ttgacaaaga caagcccaag   1680
gaggcggtca ccgtggccgt gaagatgttg aaagatgatg ccacagagaa agacctttct   1740
gatctggtgt cagagatgga gatgatgaag atgattggga aacacaagaa tatcataaat   1800
cttcttggag cctgcacaca ggatgggcct ctctatgtca tagttgagta tgcctctaaa   1860
ggcaacctcc gagaatacct ccgagcccgg aggccacccg ggatggagta ctcctatgac   1920
attaaccgtg ttcctgagga gcagatgacc ttcaaggact tggtgtcatg cacctaccag   1980
ctggccagag gcatggagta cttggcttcc caaaaatgta ttcatcgaga tttagcagcc   2040
agaaatgttt tggtaacaga aaacaatgtg atgaaaatag cagactttgg actcgccaga   2100
gatatcaaca atatagacta ttacaaaaag accaccaatg ggcggcttcc agtcaagtgg   2160
atggctccag aagccctgtt tgatagagta tacactcatc agagtgatgt ctggtccttc   2220
ggggtgttaa tgtgggagat cttcacttta gggggctcgc cctacccagg gattcccgtg   2280
gaggaacttt ttaagctgct gaaggaagga cacagaatgg ataagccagc caactgcacc   2340
aacgaactgt acatgatgat gagggactgt tggcatgcag tgccctccca gagaccaacg   2400
ttcaagcagt tggtagaaga cttggatcga attctcactc tcacaaccaa tgagatctga   2460
aagtttatgg cttcattgag aaactgggaa aagttggtca ggcgcagtgg ctcatgcctg   2520
taatcccagc actttgggag gccgaggcag gcggatcatg aggtcaggag ttccagacca   2580
gcctggccaa catggtgaaa ccctgtctct actaaagata caaaaaatta gccgggcgtg   2640
ttggtgtgca cctgtaatcc cagctactcc gggaggctga ggcaggagag tcacttgaac   2700
cggggaggcg gaggttgcag tgagccgaga tcatgccatt gcattccagc cttggcgaca   2760
gagcgagact ccgtctcaaa a                                             2781
```

<210> SEQ ID NO 133
<211> LENGTH: 3821
<212> TYPE: DNA
<213> ORGANISM: Homo sapiens

<400> SEQUENCE: 133

```
tgactgcagc agcagcggca gcgcctcggt tcctgagccc accgcaggct gaaggcattg     60
cgcgtagtcc atgcccgtag aggaagtgtg cagatgggat taacgtccac atggagatat    120
ggaagaggac cggggattgg taccgtaacc atggtcagct ggggtcgttt catctgcctg    180
```

-continued

```
gtcgtggtca ccatggcaac cttgtccctg gcccggccct ccttcagttt agttgaggat    240
accacattag agccagaaga gccaccaacc aaataccaaa tctctcaacc agaagtgtac    300
gtggctgcgc caggggagtc gctagaggtg cgctgcctgt tgaaagatgc cgccgtgatc    360
agttggacta aggatggggt gcacttgggg cccaacaata ggacagtgct tattggggag    420
tacttgcaga taaagggcgc cacgcctaga gactccggcc tctatgcttg tactgccagt    480
aggactgtag acagtgaaac ttggtacttc atggtgaatg tcacagatgc catctcatcc    540
ggagatgatg aggatgacac cgatggtgcg gaagattttg tcagtgagaa cagtaacaac    600
aagagagcac catactggac caacacagaa aagatggaaa agcggctcca tgctgtgcct    660
gcggccaaca ctgtcaagtt tcgctgccca gccgggggga acccaatgcc aaccatgcgg    720
tggctgaaaa acgggaagga gtttaagcag gagcatcgca ttggaggcta caaggtacga    780
aaccagcact ggagcctcat tatggaaagt gtggtcccat ctgacaaggg aaattatacc    840
tgtgtagtgg agaatgaata cgggtccatc aatcacacgt accacctgga tgttgtggcg    900
cctggaagag aaaaggagat tacagcttcc ccagactacc tggagatagc catttactgc    960
ataggggtct tcttaatcgc ctgtatggtg gtaacagtca tcctgtgccg aatgaagaac   1020
acgaccaaga agccagactt cagcagccag ccggctgtgc acaagctgac caaacgtatc   1080
cccctgcgga gacaggtaac agtttcggct gagtccagct cctccatgaa ctccaacacc   1140
ccgctggtga ggataacaac acgcctctct tcaacggcag acacccccat gctggcaggg   1200
gtctccgagt atgaacttcc agaggaccca aaatgggagt ttccaagaga taagctgaca   1260
ctgggcaagc ccctgggaga aggttgcttt gggcaagtgg tcatggcgga agcagtggga   1320
attgacaaag acaagcccaa ggaggcggtc accgtggccg tgaagatgtt gaaagatgat   1380
gccacagaga aagacctttc tgatctggtg tcagagatgg agatgatgaa gatgattggg   1440
aaacacaaga atatcataaa tcttcttgga gcctgcacac aggatgggcc tctctatgtc   1500
atagttgagt atgcctctaa aggcaacctc cgagaatacc tccgagcccg gaggccaccc   1560
gggatggagt actcctatga cattaaccgt gttcctgagg agcagatgac cttcaaggac   1620
ttggtgtcat gcacctacca gctggccaga ggcatggagt acttggcttc ccaaaaatgt   1680
attcatcgag atttagcagc cagaaatgtt ttggtaacag aaaacaatgt gatgaaaata   1740
gcagactttg gactcgccag agatatcaac aatatagact attacaaaaa gaccaccaat   1800
gggcggcttc cagtcaagtg gatggctcca gaagccctgt ttgatagagt atacactcat   1860
cagagtgatg tctggtcctt cggggtgtta atgtgggaga tcttcacttt agggggctcg   1920
ccctacccag ggattcccgt ggaggaactt tttaagctgc tgaaggaagg acacagaatg   1980
gataagccag ccaactgcac caacgaactg tacatgatga tgagggactg ttggcatgca   2040
gtgccctccc agagaccaac gttcaagcag ttggtagaag acttggatcg aattctcact   2100
ctcacaacca atgaggaata cttggacctc agccaacctc tcgaacagta ttcacctagt   2160
taccctgaca caagaagttc ttgttcttca ggagatgatt ctgttttttc tccagacccc   2220
atgccttacg aaccatgcct tcctcagtat ccacacataa acggcagtgt taaaacatga   2280
atgactgtgt ctgcctgtcc ccaaacagga cagcactggg aacctagcta cactgagcag   2340
ggagaccatg cctcccagag cttgttgtct ccacttgtat atatggatca gaggagtaaa   2400
taattggaaa agtaatcagc atatgtgtaa agatttatac agttgaaaac ttgtaatctt   2460
ccccaggagg agaagaaggt ttctggagca gtggactgcc acaagccacc atgtaacccc   2520
tctcacctgc cgtgcgtact ggctgtggac cagtaggact caaggtggac gtgcgttctg   2580
```

ccttccttgt taattttgta ataattggag aagatttatg tcagcacaca cttacagagc 2640
acaaatgcag tatataggtg ctggatgtat gtaaatatat tcaaattatg tataaatata 2700
tattatatat ttacaaggag ttattttttg tattgatttt aaatggatgt cccaatgcac 2760
ctagaaaatt ggtctctctt tttttaatag ctatttgcta aatgctgttc ttacacataa 2820
tttcttaatt ttcaccgagc agaggtggaa aaatactttt gctttcaggg aaaatggtat 2880
aacgttaatt tattaataaa ttggtaatat acaaaacaat taatcattta tagttttttt 2940
tgtaatttaa gtggcatttc tatgcaggca gcacagcaga ctagttaatc tattgcttgg 3000
acttaactag ttatcagatc ctttgaaaag agaatattta caatatatga ctaatttggg 3060
gaaaatgaag ttttgattta tttgtgttta aatgctgctg tcagacgatt gttcttagac 3120
ctcctaaatg ccccatatta aaagaactca ttcataggaa ggtgtttcat tttggtgtgc 3180
aaccctgtca ttacgtcaac gcaacgtcta actggacttc ccaagataaa tggtaccagc 3240
gtcctcttaa aagatgcctt aatccattcc ttgaggacag accttagttg aaatgatagc 3300
agaatgtgct tctctctggc agctggcctt ctgcttctga gttgcacatt aatcagatta 3360
gcctgtattc tcttcagtga attttgataa tggcttccag actctttggc gttggagacg 3420
cctgttagga tcttcaagtc ccatcataga aaattgaaac acagagttgt tctgctgata 3480
gttttgggga tacgtccatc tttttaaggg attgctttca tctaattctg gcaggacctc 3540
accaaaagat ccagcctcat acctacatca gacaaaatat cgccgttgtt ccttctgtac 3600
taaagtattg tgttttgctt tggaaacacc cactcacttt gcaatagccg tgcaagatga 3660
atgcagatta cactgatctt atgtgttaca aaattggaga aagtatttaa taaaacctgt 3720
taatttttat actgacaata aaaatgtttc tacagatatt aatgttaaca agacaaaata 3780
aatgtcacgc aacttatttt tttaataaaa aaaaaaaaaa a 3821

<210> SEQ ID NO 134
<211> LENGTH: 3708
<212> TYPE: DNA
<213> ORGANISM: Homo sapiens

<400> SEQUENCE: 134
aatttgttga ggaatttccc cctagccttg accccttgac agctcccgct cctactcagt 60
gctggggaga agtagggagg ccttaagcga agagatgggt ctgcactttg gaggagccgg 120
acactgttga ctttcctgat gtgaaatcta cccaggaaca aaacaccagt gactgcagca 180
gcagcggcag cgcctcggtt cctgagccca ccgcaggctg aaggcattgc gcgtagtcca 240
tgcccgtaga ggaagtgtgc agatgggatt aacgtccaca tggagatatg gaagaggacc 300
ggggattggt accgtaacca tggtcagctg gggtcgtttc atctgcctgg tcgtggtcac 360
catggcaacc ttgtccctgg cccggccctc cttcagttta gttgaggata ccacattaga 420
gccagaagat gccatctcat ccggagatga tgaggatgac accgatggtg cggaagattt 480
tgtcagtgag aacagtaaca acaagagagc accatactgg accaacacag aaaagatgga 540
aaagcggctc catgctgtgc ctgcggccaa cactgtcaag tttcgctgcc cagccggggg 600
gaacccaatg ccaaccatgc ggtggctgaa aaacgggaag gagtttaagc aggagcatcg 660
cattggaggc tacaaggtac gaaaccagca ctggagcctc attatggaaa gtgtggtccc 720
atctgacaag ggaaattata cctgtgtagt ggagaatgaa tacgggtcca tcaatcacac 780
gtaccacctg gatgttgtgg agcgatcgcc tcaccggccc atcctccaag ccggactgcc 840
ggcaaatgcc tccacagtgg tcggaggaga cgtagagttt gtctgcaagg tttacagtga 900

-continued

```
tgcccagccc cacatccagt ggatcaagca cgtggaaaag aacggcagta aatacgggcc    960
cgacgggctg ccctacctca aggttctcaa ggccgccggt gttaacacca cggacaaaga   1020
gattgaggtt ctctatattc ggaatgtaac ttttgaggac gctggggaat atacgtgctt   1080
ggcgggtaat tctattggga tatcctttca ctctgcatgg ttgacagttc tgccagcgcc   1140
tggaagagaa aaggagatta cagcttcccc agactacctg gagatagcca tttactgcat   1200
aggggtcttc ttaatcgcct gtatggtggt aacagtcatc ctgtgccgaa tgaagaacac   1260
gaccaagaag ccagacttca gcagccagcc ggctgtgcac aagctgacca aacgtatccc   1320
cctgcggaga caggtaacag tttcggctga gtccagctcc tccatgaact ccaacacccc   1380
gctggtgagg ataacaacac gcctctcttc aacggcagac acccccatgc tggcaggggt   1440
ctccgagtat gaacttccag aggacccaaa atgggagttt ccaagagata agctgacact   1500
gggcaagccc ctgggagaag gttgctttgg gcaagtggtc atggcggaag cagtgggaat   1560
tgacaaagac aagcccaagg aggcggtcac cgtggccgtg aagatgttga aagatgatgc   1620
cacagagaaa gacctttctg atctggtgtc agagatggag atgatgaaga tgattgggaa   1680
acacaagaat atcataaatc ttcttggagc ctgcacacag gatgggcctc tctatgtcat   1740
agttgagtat gcctctaaag gcaacctccg agaatacctc cgagcccgga ggccacccgg   1800
gatggagtac tcctatgaca ttaaccgtgt tcctgaggag cagatgacct tcaaggactt   1860
ggtgtcatgc acctaccagc tggccagagg catggagtac ttggcttccc aaaaatgtat   1920
tcatcgagat ttagcagcca gaaatgtttt ggtaacagaa aacaatgtga tgaaaatagc   1980
agactttgga ctcgccagag atatcaacaa tatagactat tacaaaaaga ccaccaatgg   2040
gcggcttcca gtcaagtgga tggctccaga agccctgttt gatagagtat acactcatca   2100
gagtgatgtc tggtccttcg gggtgttaat gtgggagatc ttcactttag gggctcgcc   2160
ctacccaggg attcccgtgg aggaactttt taagctgctg aaggaaggac acagaatgga   2220
taagccagcc aactgcacca acgaactgta catgatgatg agggactgtt ggcatgcagt   2280
gccctcccag agaccaacgt tcaagcagtt ggtagaagac ttggatcgaa ttctcactct   2340
cacaaccaat gaggaggaga agaaggtttc tggagcagtg gactgccaca agccaccatg   2400
taacccctct cacctgccgt gcgtactggc tgtggaccag taggactcaa ggtggacgtg   2460
cgttctgcct tccttgttaa ttttgtaata attggagaag atttatgtca gcacacactt   2520
acagagcaca aatgcagtat ataggtgctg gatgtatgta aatatattca aattatgtat   2580
aaatatatat tatatattta caaggagtta tttttttgtat tgattttaaa tggatgtccc   2640
aatgcaccta gaaaattggt ctctcttttt ttaatagcta tttgctaaat gctgttctta   2700
cacataattt cttaattttc accgagcaga ggtggaaaaa tacttttgct ttcagggaaa   2760
atggtataac gttaatttat taataaattg gtaatataca aaacaattaa tcatttatag   2820
tttttttttgt aatttaagtg gcatttctat gcaggcagca cagcagacta gttaatctat   2880
tgcttggact taactagtta tcagatcctt tgaaaagaga atatttacaa tatatgacta   2940
atttggggaa aatgaagttt tgatttattt gtgtttaaat gctgctgtca gacgattgtt   3000
cttagacctc ctaaatgccc catattaaaa gaactcattc ataggaaggt gtttcatttt   3060
ggtgtgcaac cctgtcatta cgtcaacgca acgtctaact ggacttccca agataaatgg   3120
taccagcgtc ctcttaaaag atgccttaat ccattccttg aggacagacc ttagttgaaa   3180
tgatagcaga atgtgcttct ctctggcagc tggccttctg cttctgagtt gcacattaat   3240
cagattagcc tgtattctct tcagtgaatt ttgataatgg cttccagact ctttggcgtt   3300
```

```
ggagacgcct gttaggatct tcaagtccca tcatagaaaa ttgaaacaca gagttgttct   3360

gctgatagtt ttggggatac gtccatcttt ttaagggatt gctttcatct aattctggca   3420

ggacctcacc aaaagatcca gcctcatacc tacatcagac aaaatatcgc cgttgttcct   3480

tctgtactaa agtattgtgt tttgctttgg aaacacccac tcactttgca atagccgtgc   3540

aagatgaatg cagattacac tgatcttatg tgttacaaaa ttggagaaag tatttaataa   3600

aacctgttaa tttttatact gacaataaaa atgtttctac agatattaat gttaacaaga   3660

caaaataaat gtcacgcaac ttattttttt aataaaaaaa aaaaaaaa                 3708
```

<210> SEQ ID NO 135
<211> LENGTH: 4103
<212> TYPE: DNA
<213> ORGANISM: Homo sapiens

<400> SEQUENCE: 135

```
gagcacacat tgcctcactg aagtggctgc acgtatctga gtcctgtagc tactgtttta     60

tctctgtttc ttaaaagtat gcttttaaaa agattagcct cacacatttc tgtggaccgg    120

tctggtggta tcacctggga ctctgaggtg aggatggaag gatttagcag ataatgaaaa    180

agaactctgt ttgcgcacat ttgagaggct gaaaaatggt tttatcccac ttgggctgga    240

gtgatttggc attggggaag attccctgac tcgccaatct ctttccttta gtgactgcag    300

cagcagcggc agcgcctcgg ttcctgagcc caccgcaggc tgaaggcatt gcgcgtagtc    360

catgcccgta gaggaagtgt gcagatggga ttaacgtcca catggagata tggaagagga    420

ccggggattg gtaccgtaac catggtcagc tggggtcgtt tcatctgcct ggtcgtggtc    480

accatggcaa ccttgtccct ggcccggccc tccttcagtt tagttgagga taccacatta    540

gagccagaag gagcaccata ctggaccaac acagaaaaga tggaaaagcg gctccatgct    600

gtgcctgcgg ccaacactgt caagtttcgc tgcccagccg gggggaaccc aatgccaacc    660

atgcggtggc tgaaaaacgg gaaggagttt aagcaggagc atcgcattgg aggctacaag    720

gtacgaaacc agcactggag cctcattatg gaaagtgtgg tcccatctga caagggaaat    780

tatacctgtg tagtggagaa tgaatacggg tccatcaatc acacgtacca cctggatgtt    840

gtggagcgat cgcctcaccg gcccatcctc caagccggac tgccggcaaa tgcctccaca    900

gtggtcggag gagacgtaga gtttgtctgc aaggtttaca gtgatgccca gccccacatc    960

cagtggatca agcacgtgga aaagaacggc agtaaatacg ggcccgacgg gctgccctac   1020

ctcaaggttc tcaaggccgc cggtgttaac accacggaca aagagattga ggttctctat   1080

attcggaatg taacttttga ggacgctggg gaatatacgt gcttggcggg taattctatt   1140

gggatatcct ttcactctgc atggttgaca gttctgccag cgcctggaag agaaaaggag   1200

attacagctt ccccagacta cctggagata gccatttact gcataggggt cttcttaatc   1260

gcctgtatgg tggtaacagt catcctgtgc cgaatgaaga acacgaccaa gaagccagac   1320

ttcagcagcc agccggctgt gcacaagctg accaaacgta tcccccctgcg gagacaggta   1380

acagtttcgg ctgagtccag ctcctccatg aactccaaca ccccgctggt gaggataaca   1440

acacgcctct cttcaacggc agacaccccc atgctggcag gggtctccga gtatgaactt   1500

ccagaggacc caaaatggga gtttccaaga gataagctga cactgggcaa gcccctggga   1560

gaaggttgct ttgggcaagt ggtcatggcg gaagcagtgg gaattgacaa agacaagccc   1620

aaggaggcgg tcaccgtggc cgtgaagatg ttgaaagatg atgccacaga gaaagacctt   1680

tctgatctgg tgtcagagat ggagatgatg aagatgattg ggaaacacaa gaatatcata   1740
```

-continued

```
aatcttcttg gagcctgcac acaggatggg cctctctatg tcatagttga gtatgcctct   1800
aaaggcaacc tccgagaata cctccgagcc cggaggccac ccgggatgga gtactcctat   1860
gacattaacc gtgttcctga ggagcagatg accttcaagg acttggtgtc atgcacctac   1920
cagctggcca gaggcatgga gtacttggct tcccaaaaat gtattcatcg agatttagca   1980
gccagaaatg ttttggtaac agaaaacaat gtgatgaaaa tagcagactt tggactcgcc   2040
agagatatca acaatataga ctattacaaa aagaccacca atgggcggct tccagtcaag   2100
tggatggctc cagaagccct gtttgataga gtatacactc atcagagtga tgtctggtcc   2160
ttcggggtgt taatgtggga gatcttcact ttagggggct cgccctaccc agggattccc   2220
gtggaggaac tttttaagct gctgaaggaa ggacacagaa tggataagcc agccaactgc   2280
accaacgaac tgtacatgat gatgagggac tgttggcatg cagtgccctc ccagagacca   2340
acgttcaagc agttggtaga agacttggat cgaattctca ctctcacaac caatgaggaa   2400
tacttggacc tcagccaacc tctcgaacag tattcaccta gttaccctga cacaagaagt   2460
tcttgttctt caggagatga ttctgttttt tctccagacc ccatgcctta cgaaccatgc   2520
cttcctcagt atccacacat aaacggcagt gttaaaacat gaatgactgt gtctgcctgt   2580
ccccaaacag gacagcactg ggaacctagc tacactgagc agggagacca tgcctcccag   2640
agcttgttgt ctccacttgt atatatggat cagaggagta aataattgga aaagtaatca   2700
gcatatgtgt aaagatttat acagttgaaa acttgtaatc ttccccagga ggagaagaag   2760
gtttctggag cagtggactg ccacaagcca ccatgtaacc cctctcacct gccgtgcgta   2820
ctggctgtgg accagtagga ctcaaggtgg acgtgcgttc tgccttcctt gttaattttg   2880
taataattgg agaagattta tgtcagcaca cacttacaga gcacaaatgc agtatatagg   2940
tgctggatgt atgtaaatat attcaaatta tgtataaata tatattatat atttacaagg   3000
agttattttt tgtattgatt ttaaatggat gtcccaatgc acctagaaaa ttggtctctc   3060
ttttttaat agctatttgc taaatgctgt tcttacacat aatttcttaa ttttcaccga   3120
gcagaggtgg aaaaatactt ttgctttcag ggaaaatggt ataacgttaa tttattaata   3180
aattggtaat atacaaaaca attaatcatt tatagttttt tttgtaattt aagtggcatt   3240
tctatgcagg cagcacagca gactagttaa tctattgctt ggacttaact agttatcaga   3300
tcctttgaaa agagaatatt tacaatatat gactaatttg gggaaaatga agttttgatt   3360
tatttgtgtt taaatgctgc tgtcagacga ttgttcttag acctcctaaa tgccccatat   3420
taaaagaact cattcatagg aaggtgtttc attttggtgt gcaaccctgt cattacgtca   3480
acgcaacgtc taactggact tcccaagata aatggtacca gcgtcctctt aaaagatgcc   3540
ttaatccatt ccttgaggac agaccttagt tgaaatgata gcagaatgtg cttctctctg   3600
gcagctggcc ttctgcttct gagttgcaca ttaatcagat tagcctgtat tctcttcagt   3660
gaattttgat aatggcttcc agactctttg gcgttggaga cgcctgttag gatcttcaag   3720
tcccatcata gaaaattgaa acacagagtt gttctgctga tagttttggg gatacgtcca   3780
tctttttaag ggattgcttt catctaattc tggcaggacc tcaccaaaag atccagcctc   3840
atacctacat cagacaaaat atcgccgttg ttccttctgt actaaagtat tgtgttttgc   3900
tttggaaaca cccactcact ttgcaatagc cgtgcaagat gaatgcagat tacactgatc   3960
ttatgtgtta caaaattgga gaaagtattt aataaaacct gttaattttt atactgacaa   4020
taaaaatgtt tctacagata ttaatgttaa caagacaaaa taaatgtcac gcaacttatt   4080
tttttaataa aaaaaaaaaa aaa                                           4103
```

<210> SEQ ID NO 136
<211> LENGTH: 4306
<212> TYPE: DNA
<213> ORGANISM: Homo sapiens

<400> SEQUENCE: 136

```
ggcggcggct ggaggagagc gcggtggaga gccgagcggg cgggcggcgg gtgcggagcg     60
ggcgagggag cgcgcgcggc cgccacaaag ctcgggcgcc gcggggctgc atgcggcgta    120
cctggcccgg cgcggcgact gctctccggg ctggcggggg ccggccgcga gccccggggg    180
ccccgaggcc gcagcttgcc tgcgcgctct gagccttcgc aactcgcgag caaagtttgg    240
tggaggcaac gccaagcctg agtcctttct tcctctcgtt ccccaaatcc gagggcagcc    300
cgcgggcgtc atgcccgcgc tcctccgcag cctggggtac gcgtgaagcc cgggaggctt    360
ggcgccggcg aagacccaag gaccactctt ctgcgtttgg agttgctccc cgcaaccccg    420
ggctcgtcgc tttctccatc ccgacccacg cggggcgcgg ggacaacaca ggtcgcggag    480
gagcgttgcc attcaagtga ctgcagcagc agcggcagcg cctcggttcc tgagcccacc    540
gcaggctgaa ggcattgcgc gtagtccatg cccgtagagg aagtgtgcag atgggattaa    600
cgtccacatg gagatatgga agaggaccgg ggattggtac cgtaaccatg gtcagctggg    660
gtcgtttcat ctgcctggtc gtggtcacca tggcaacctt gtccctggcc cggccctcct    720
tcagtttagt tgaggatacc acattagagc cagaagagcc accaaccaaa taccaaatct    780
ctcaaccaga agtgtacgtg gctgcgccag gggagtcgct agaggtgcgc tgcctgttga    840
aagatgccgc cgtgatcagt tggactaagg atggggtgca cttggggccc aacaatagga    900
cagtgcttat tggggagtac ttgcagataa agggcgccac gcctagagac tccggcctct    960
atgcttgtac tgccagtagg actgtagaca gtgaaacttg gtacttcatg gtgaatgtca   1020
cagatgccat ctcatccgga gatgatgagg atgacaccga tggtgcggaa gattttgtca   1080
gtgagaacag taacaacaag agagcaccat actggaccaa cacagaaaag atggaaaagc   1140
ggctccatgc tgtgcctgcg gccaacactg tcaagtttcg ctgcccagcc ggggggaacc   1200
caatgccaac catgcggtgg ctgaaaaacg ggaaggagtt taagcaggag catcgcattg   1260
gaggctacaa ggtacgaaac cagcactgga gcctcattat ggaaagtgtg gtcccatctg   1320
acaagggaaa ttatacctgt gtagtggaga atgaatacgg gtccatcaat cacacgtacc   1380
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
agccccacat ccagtggatc aagcacgtgg aaaagaacgg cagtaaatac gggcccgacg   1560
ggctgcccta cctcaaggtt ctcaaggttt cggctgagtc cagctcctcc atgaactcca   1620
acaccccgct ggtgaggata acaacacgcc tctcttcaac ggcagacacc cccatgctgg   1680
caggggtctc cgagtatgaa cttccagagg acccaaaatg ggagtttcca agagataagc   1740
tgacactggg caagcccctg ggagaaggtt gctttgggca agtggtcatg gcggaagcag   1800
tgggaattga caaagacaag cccaaggagg cggtcaccgt ggccgtgaag atgttgaaag   1860
atgatgccac agagaaagac ctttctgatc tggtgtcaga gatggagatg atgaagatga   1920
ttgggaaaca caagaatatc ataaatcttc ttggagcctg cacacaggat gggcctctct   1980
atgtcatagt tgagtatgcc tctaaaggca acctccgaga atacctccga gcccggaggc   2040
cacccgggat ggagtactcc tatgacatta accgtgttcc tgaggagcag atgaccttca   2100
aggacttggt gtcatgcacc taccagctgg ccagaggcat ggagtacttg gcttcccaaa   2160
```

aatgtattca tcgagattta gcagccagaa atgttttggt aacagaaaac aatgtgatga 2220
aaatagcaga ctttggactc gccagagata tcaacaatat agactattac aaaaagacca 2280
ccaatgggcg gcttccagtc aagtggatgg ctccagaagc cctgtttgat agagtataca 2340
ctcatcagag tgatgtctgg tccttcgggg tgttaatgtg ggagatcttc actttagggg 2400
gctcgcccta cccagggatt cccgtggagg aactttttaa gctgctgaag gaaggacaca 2460
gaatggataa gccagccaac tgcaccaacg aactgtacat gatgatgagg gactgttggc 2520
atgcagtgcc ctcccagaga ccaacgttca agcagttggt agaagacttg gatcgaattc 2580
tcactctcac aaccaatgag gaatacttgg acctcagcca acctctcgaa cagtattcac 2640
ctagttaccc tgacacaaga agttcttgtt cttcaggaga tgattctgtt ttttctccag 2700
accccatgcc ttacgaacca tgccttcctc agtatccaca cataaacggc agtgttaaaa 2760
catgaatgac tgtgtctgcc tgtccccaaa caggacagca ctgggaacct agctacactg 2820
agcagggaga ccatgcctcc cagagcttgt tgtctccact tgtatatatg gatcagagga 2880
gtaaataatt ggaaaagtaa tcagcatatg tgtaaagatt tatacagttg aaaacttgta 2940
atcttcccca ggaggagaag aaggtttctg gagcagtgga ctgccacaag ccaccatgta 3000
acccctctca cctgccgtgc gtactggctg tggaccagta ggactcaagg tggacgtgcg 3060
ttctgccttc cttgttaatt ttgtaataat tggagaagat ttatgtcagc acacacttac 3120
agagcacaaa tgcagtatat aggtgctgga tgtatgtaaa tatattcaaa ttatgtataa 3180
atatatatta tatatttaca aggagttatt ttttgtattg attttaaatg gatgtcccaa 3240
tgcacctaga aaattggtct ctcttttttt aatagctatt tgctaaatgc tgttcttaca 3300
cataatttct taattttcac cgagcagagg tggaaaaata cttttgcttt cagggaaaat 3360
ggtataacgt taatttatta ataaattggt aatatacaaa acaattaatc atttatagtt 3420
ttttttgtaa tttaagtggc atttctatgc aggcagcaca gcagactagt taatctattg 3480
cttggactta actagttatc agatcctttg aaaagagaat atttacaata tatgactaat 3540
ttggggaaaa tgaagttttg atttatttgt gtttaaatgc tgctgtcaga cgattgttct 3600
tagacctcct aaatgcccca tattaaaaga actcattcat aggaaggtgt ttcattttgg 3660
tgtgcaaccc tgtcattacg tcaacgcaac gtctaactgg acttcccaag ataaatggta 3720
ccagcgtcct cttaaaagat gccttaatcc attccttgag gacagacctt agttgaaatg 3780
atagcagaat gtgcttctct ctggcagctg gccttctgct tctgagttgc acattaatca 3840
gattagcctg tattctcttc agtgaatttt gataatggct tccagactct ttggcgttgg 3900
agacgcctgt taggatcttc aagtcccatc atagaaaatt gaaacacaga gttgttctgc 3960
tgatagtttt ggggatacgt ccatcttttt aagggattgc tttcatctaa ttctggcagg 4020
acctcaccaa aagatccagc ctcataccta catcagacaa aatatcgccg ttgttccttc 4080
tgtactaaag tattgtgttt tgctttggaa acacccactc actttgcaat agccgtgcaa 4140
gatgaatgca gattacactg atcttatgtg ttacaaaatt ggagaaagta tttaataaaa 4200
cctgttaatt tttatactga caataaaaat gtttctacag atattaatgt taacaagaca 4260
aaataaatgt cacgcaactt atttttttaa taaaaaaaaa aaaaaa 4306

<210> SEQ ID NO 137
<211> LENGTH: 4303
<212> TYPE: DNA
<213> ORGANISM: Homo sapiens

<400> SEQUENCE: 137

-continued

```
ggcggcggct ggaggagagc gcggtggaga gccgagcggg cgggcggcgg gtgcggagcg      60
ggcgagggag cgcgcgcggc cgccacaaag ctcgggcgcc gcggggctgc atgcggcgta     120
cctggcccgg cgcggcgact gctctccggg ctggcggggg ccggccgcga gccccggggg     180
ccccgaggcc gcagcttgcc tgcgcgctct gagccttcgc aactcgcgag caaagtttgg     240
tggaggcaac gccaagcctg agtcctttct tcctctcgtt ccccaaatcc gagggcagcc     300
cgcgggcgtc atgcccgcgc tcctccgcag cctggggtac gcgtgaagcc cgggaggctt     360
ggcgccggcg aagacccaag gaccactctt ctgcgtttgg agttgctccc cgcaaccccg     420
ggctcgtcgc tttctccatc ccgacccacg cggggcgcgg ggacaacaca ggtcgcggag     480
gagcgttgcc attcaagtga ctgcagcagc agcggcagcg cctcggttcc tgagcccacc     540
gcaggctgaa ggcattgcgc gtagtccatg cccgtagagg aagtgtgcag atgggattaa     600
cgtccacatg gagatatgga agaggaccgg ggattggtac cgtaaccatg gtcagctggg     660
gtcgtttcat ctgcctggtc gtggtcacca tggcaacctt gtccctggcc cggccctcct     720
tcagtttagt tgaggatacc acattagagc cagaaggagc accatactgg accaacacag     780
aaaagatgga aaagcggctc catgctgtgc ctgcggccaa cactgtcaag tttcgctgcc     840
cagccggggg gaacccaatg ccaaccatgc ggtggctgaa aaacgggaag gagtttaagc     900
aggagcatcg cattggaggc tacaaggtac gaaaccagca ctggagcctc attatggaaa     960
gtgtggtccc atctgacaag ggaaattata cctgtgtagt ggagaatgaa tacgggtcca    1020
tcaatcacac gtaccacctg gatgttgtgg agcgatcgcc tcaccggccc atcctccaag    1080
ccggactgcc ggcaaatgcc tccacagtgg tcggaggaga cgtagagttt gtctgcaagg    1140
tttacagtga tgcccagccc cacatccagt ggatcaagca cgtggaaaag aacggcagta    1200
aatacgggcc cgacgggctg ccctacctca aggttctcaa ggccgccggt gttaacacca    1260
cggacaaaga gattgaggtt ctctatattc ggaatgtaac ttttgaggac gctggggaat    1320
atacgtgctt ggcgggtaat tctattggga tatcctttca ctctgcatgg ttgacagttc    1380
tgccagcgcc tggaagagaa aaggagatta cagcttcccc agactacctg gagatagcca    1440
tttactgcat aggggtcttc ttaatcgcct gtatggtggt aacagtcatc ctgtgccgaa    1500
tgaagaacac gaccaagaag ccagacttca gcagccagcc ggctgtgcac aagctgacca    1560
aacgtatccc cctgcggaga caggtttcgg ctgagtccag ctcctccatg aactccaaca    1620
ccccgctggt gaggataaca acacgcctct cttcaacggc agacaccccc atgctggcag    1680
gggtctccga gtatgaactt ccagaggacc caaaatggga gtttccaaga gataagctga    1740
cactgggcaa gcccctggga gaaggttgct ttgggcaagt ggtcatggcg gaagcagtgg    1800
gaattgacaa agacaagccc aaggaggcgg tcaccgtggc cgtgaagatg ttgaaagatg    1860
atgccacaga gaaagacctt tctgatctgg tgtcagagat ggagatgatg aagatgattg    1920
ggaaacacaa gaatatcata aatcttcttg gagcctgcac acaggatggg cctctctatg    1980
tcatagttga gtatgcctct aaaggcaacc tccgagaata cctccgagcc cggaggccac    2040
ccgggatgga gtactcctat gacattaacc gtgttcctga ggagcagatg accttcaagg    2100
acttggtgtc atgcacctac cagctggcca gaggcatgga gtacttggct tcccaaaaat    2160
gtattcatcg agatttagca gccagaaatg ttttggtaac agaaaacaat gtgatgaaaa    2220
tagcagactt tggactcgcc agagatatca acaatataga ctattacaaa aagaccacca    2280
atgggcggct tccagtcaag tggatggctc cagaagccct gtttgataga gtatacactc    2340
atcagagtga tgtctggtcc ttcggggtgt taatgtggga gatcttcact ttagggggct    2400
```

-continued

```
cgccctaccc agggattccc gtggaggaac tttttaagct gctgaaggaa ggacacagaa   2460
tggataagcc agccaactgc accaacgaac tgtacatgat gatgagggac tgttggcatg   2520
cagtgccctc ccagagacca acgttcaagc agttggtaga agacttggat cgaattctca   2580
ctctcacaac caatgaggaa tacttggacc tcagccaacc tctcgaacag tattcaccta   2640
gttaccctga cacaagaagt tcttgttctt caggagatga ttctgttttt tctccagacc   2700
ccatgcctta cgaaccatgc cttcctcagt atccacacat aaacggcagt gttaaaacat   2760
gaatgactgt gtctgcctgt ccccaaacag gacagcactg ggaacctagc tacactgagc   2820
agggagacca tgcctcccag agcttgttgt ctccacttgt atatatggat cagaggagta   2880
aataattgga aaagtaatca gcatatgtgt aaagatttat acagttgaaa acttgtaatc   2940
ttccccagga ggagaagaag gtttctggag cagtggactg ccacaagcca ccatgtaacc   3000
cctctcacct gccgtgcgta ctggctgtgg accagtagga ctcaaggtgg acgtgcgttc   3060
tgccttcctt gttaattttg taataattgg agaagattta tgtcagcaca cacttacaga   3120
gcacaaatgc agtatatagg tgctggatgt atgtaaatat attcaaatta tgtataaata   3180
tatattatat atttacaagg agttattttt tgtattgatt ttaaatggat gtcccaatgc   3240
acctagaaaa ttggtctctc ttttttttaat agctatttgc taaatgctgt tcttacacat   3300
aatttcttaa ttttcaccga gcagaggtgg aaaaatactt ttgctttcag ggaaaatggt   3360
ataacgttaa tttattaata aattggtaat atacaaaaca attaatcatt tatagttttt   3420
tttgtaattt aagtggcatt tctatgcagg cagcacagca gactagttaa tctattgctt   3480
ggacttaact agttatcaga tcctttgaaa agagaatatt tacaatatat gactaatttg   3540
gggaaaatga agttttgatt tatttgtgtt taaatgctgc tgtcagacga ttgttcttag   3600
acctcctaaa tgccccatat taaaagaact cattcatagg aaggtgtttc attttggtgt   3660
gcaaccctgt cattacgtca acgcaacgtc taactggact tcccaagata aatggtacca   3720
gcgtcctctt aaaagatgcc ttaatccatt ccttgaggac agaccttagt tgaaatgata   3780
gcagaatgtg cttctctctg gcagctggcc ttctgcttct gagttgcaca ttaatcagat   3840
tagcctgtat tctcttcagt gaattttgat aatggcttcc agactctttg gcgttggaga   3900
cgcctgttag gatcttcaag tcccatcata gaaaattgaa acacagagtt gttctgctga   3960
tagttttggg gatacgtcca tctttttaag ggattgcttt catctaattc tggcaggacc   4020
tcaccaaaag atccagcctc atacctacat cagacaaaat atcgccgttg ttccttctgt   4080
actaaagtat tgtgttttgc tttggaaaca cccactcact ttgcaatagc cgtgcaagat   4140
gaatgcagat tacactgatc ttatgtgtta caaaattgga gaaagtattt aataaaacct   4200
gttaattttt atactgacaa taaaaatgtt tctacagata ttaatgttaa caagacaaaa   4260
taaatgtcac gcaacttatt tttttaataa aaaaaaaaaa aaa                     4303
```

<210> SEQ ID NO 138
<211> LENGTH: 3011
<212> TYPE: DNA
<213> ORGANISM: Homo sapiens

<400> SEQUENCE: 138

```
ggcggcggct ggaggagagc gcggtggaga gccgagcggg cgggcggcgg gtgcggagcg     60
ggcgagggag cgcgcgcggc cgccacaaag ctcgggcgcc gcggggctgc atgcggcgta    120
cctggcccgg cgcggcgact gctctccggg ctggcggggg ccggccgcga gccccggggg    180
ccccgaggcc gcagcttgcc tgcgcgctct gagccttcgc aactcgcgag caaagtttgg    240
```

-continued

```
tggaggcaac gccaagcctg agtcctttct tcctctcgtt ccccaaatcc gagggcagcc    300
cgcgggcgtc atgcccgcgc tcctccgcag cctggggtac gcgtgaagcc cgggaggctt    360
ggcgccggcg aagacccaag gaccactctt ctgcgtttgg agttgctccc cgcaaccccg    420
ggctcgtcgc tttctccatc ccgacccacg cggggcgcgg ggacaacaca ggtcgcggag    480
gagcgttgcc attcaagtga ctgcagcagc agcggcagcg cctcggttcc tgagcccacc    540
gcaggctgaa ggcattgcgc gtagtccatg cccgtagagg aagtgtgcag atgggattaa    600
cgtccacatg gagatatgga agaggaccgg ggattggtac cgtaaccatg gtcagctggg    660
gtcgtttcat ctgcctggtc gtggtcacca tggcaacctt gtccctggcc cggccctcct    720
tcagtttagt tgaggatacc acattagagc cagaagatgc catctcatcc ggagatgatg    780
aggatgacac cgatggtgcg gaagattttg tcagtgagaa cagtaacaac aagagagcac    840
catactggac caacacagaa aagatggaaa agcggctcca tgctgtgcct gcggccaaca    900
ctgtcaagtt tcgctgccca gccgggggga acccaatgcc aaccatgcgg tggctgaaaa    960
acgggaagga gtttaagcag gagcatcgca ttggaggcta caaggtacga aaccagcact   1020
ggagcctcat tatggaaagt gtggtcccat ctgacaaggg aaattatacc tgtgtagtgg   1080
agaatgaata cgggtccatc aatcacacgt accacctgga tgttgtggag cgatcgcctc   1140
accggcccat cctccaagcc ggactgccgg caaatgcctc cacagtggtc ggaggagacg   1200
tagagtttgt ctgcaaggtt tacagtgatg cccagcccca catccagtgg atcaagcacg   1260
tggaaaagaa cggcagtaaa tacgggcccg acgggctgcc ctacctcaag gttctcaagc   1320
actcggggat aaatagttcc aatgcagaag tgctggctct gttcaatgtg accgaggcgg   1380
atgctgggga atatatatgt aaggtctcca attatatagg gcaggccaac cagtctgcct   1440
ggctcactgt cctgccaaaa cagcaagcgc ctggaagaga aaaggagatt acagcttccc   1500
cagactacct ggagatagcc atttactgca taggggtctt cttaatcgcc tgtatggtgg   1560
taacagtcat cctgtgccga atgaagaaca cgaccaagaa gccagacttc agcagccagc   1620
cggctgtgca caagctgacc aaacgtatcc ccctgcggag acaggtaaca gtttcggctg   1680
agtccagctc ctccatgaac tccaacaccc cgctggtgag gataacaaca cgcctctctt   1740
caacggcaga cacccccatg ctggcagggg tctccgagta tgaacttcca gaggacccaa   1800
aatgggagtt tccaagagat aagctgacac tgggcaagcc cctgggagaa ggttgctttg   1860
ggcaagtggt catggcggaa gcagtgggaa ttgacaaaga caagcccaag gaggcggtca   1920
ccgtggccgt gaagatgttg aaagatgatg ccacagagaa agacctttct gatctggtgt   1980
cagagatgga gatgatgaag atgattggga aacacaagaa tatcataaat cttcttggag   2040
cctgcacaca ggatgggcct ctctatgtca tagttgagta tgcctctaaa ggcaacctcc   2100
gagaatacct ccgagcccgg aggccacccg ggatggagta ctcctatgac attaaccgtg   2160
ttcctgagga gcagatgacc ttcaaggact tggtgtcatg cacctaccag ctggccagag   2220
gcatggagta cttggcttcc caaaaatgta ttcatcgaga tttagcagcc agaaatgttt   2280
tggtaacaga aaacaatgtg atgaaaatag cagactttgg actcgccaga gatatcaaca   2340
atatagacta ttacaaaaag accaccaatg ggcggcttcc agtcaagtgg atggctccag   2400
aagccctgtt tgatagagta tacactcatc agagtgatgt ctggtccttc ggggtgttaa   2460
tgtgggagat cttcacttta gggggctcgc cctacccagg gattcccgtg gaggaacttt   2520
ttaagctgct gaaggaagga cacagaatgg ataagccagc caactgcacc aacgaactgt   2580
acatgatgat gagggactgt tggcatgcag tgccctccca gagaccaacg ttcaagcagt   2640
```

-continued

```
tggtagaaga cttggatcga attctcactc tcacaaccaa tgagatctga aagtttatgg   2700

cttcattgag aaactgggaa aagttggtca ggcgcagtgg ctcatgcctg taatcccagc   2760

actttgggag gccgaggcag gcggatcatg aggtcaggag ttccagacca gcctggccaa   2820

catggtgaaa ccctgtctct actaaagata caaaaaatta gccgggcgtg ttggtgtgca   2880

cctgtaatcc cagctactcc gggaggctga ggcaggagag tcacttgaac cggggaggcg   2940

gaggttgcag tgagccgaga tcatgccatt gcattccagc cttggcgaca gagcgagact   3000

ccgtctcaaa a                                                        3011
```

<210> SEQ ID NO 139
<211> LENGTH: 4286
<212> TYPE: DNA
<213> ORGANISM: Homo sapiens

<400> SEQUENCE: 139

```
gtcgcgggca gctggcgccg cgcggtcctg ctctgccggt cgcacggacg caccggcggg     60

ccgccggccg gagggacggg gcgggagctg ggcccgcgga cagcgagccg gagcgggagc    120

cgcgcgtagc gagccgggct ccggcgctcg ccagtctccc gagcggcgcc cgcctcccgc    180

cggtgcccgc gccgggccgt ggggggcagc atgcccgcgc gcgctgcctg aggacgccgc    240

ggcccccgcc cccgccatgg gcgcccctgc ctgcgccctc gcgctctgcg tggccgtggc    300

catcgtggcc ggcgcctcct cggagtcctt ggggacggag cagcgcgtcg tggggcgagc    360

ggcagaagtc ccgggcccag agcccggcca gcaggagcag ttggtcttcg gcagcgggga    420

tgctgtggag ctgagctgtc ccccgcccgg gggtggtccc atggggccca ctgtctgggt    480

caaggatggc acagggctgg tgccctcgga gcgtgtcctg gtggggcccc agcggctgca    540

ggtgctgaat gcctcccacg aggactccgg ggcctacagc tgccggcagc ggctcacgca    600

gcgcgtactg tgccacttca gtgtgcgggt gacagacgct ccatcctcgg gagatgacga    660

agacggggag gacgaggctg aggacacagg tgtggacaca ggggcccctt actggacacg    720

gcccgagcgg atggacaaga agctgctggc cgtgccggcc gccaacaccg tccgcttccg    780

ctgcccagcc gctggcaacc ccactccctc catctcctgg ctgaagaacg gcagggagtt    840

ccgcggcgag caccgcattg gaggcatcaa gctgcggcat cagcagtgga gcctggtcat    900

ggaaagcgtg gtgccctcgg accgcggcaa ctacacctgc gtcgtggaga acaagtttgg    960

cagcatccgg cagacgtaca cgctggacgt gctggagcgc tccccgcacc ggcccatcct   1020

gcaggcgggg ctgccggcca accagacggc ggtgctgggc agcgacgtgg agttccactg   1080

caaggtgtac agtgacgcac agccccacat ccagtggctc aagcacgtgg aggtgaatgg   1140

cagcaaggtg ggcccggacg gcacacccta cgttaccgtg ctcaagacgg cgggcgctaa   1200

caccaccgac aaggagctag aggttctctc cttgcacaac gtcacctttg aggacgccgg   1260

ggagtacacc tgcctggcgg gcaattctat tgggttttct catcactctg cgtggctggt   1320

ggtgctgcca gccgaggagg agctggtgga ggctgacgag gcgggcagtg tgtatgcagg   1380

catcctcagc tacggggtgg gcttcttcct gttcatcctg gtggtggcgg ctgtgacgct   1440

ctgccgcctg cgcagccccc ccaagaaagg cctgggctcc ccccaccgtgc acaagatctc   1500

ccgcttcccg ctcaagcgac aggtgtccct ggagtccaac gcgtccatga gctccaacac   1560

accactggtg cgcatcgcaa ggctgtcctc aggggagggc cccacgctgg ccaatgtctc   1620

cgagctcgag ctgcctgccg accccaaatg ggagctgtct cgggcccggc tgaccctggg   1680

caagcccctt ggggagggct gcttcggcca ggtggtcatg gcggaggcca tcggcattga   1740
```

-continued

```
caaggaccgg gccgccaagc ctgtcaccgt agccgtgaag atgctgaaag acgatgccac   1800
tgacaaggac ctgtcggacc tggtgtctga gatggagatg atgaagatga tcgggaaaca   1860
caaaaacatc atcaacctgc tgggcgcctg cacgcagggc gggcccctgt acgtgctggt   1920
ggagtacgcg gccaagggta acctgcggga gtttctgcgg gcgcggcggc ccccgggcct   1980
ggactactcc ttcgacacct gcaagccgcc cgaggagcag ctcaccttca aggacctggt   2040
gtcctgtgcc taccaggtgg cccggggcat ggagtacttg gcctcccaga agtgcatcca   2100
cagggacctg gctgcccgca atgtgctggt gaccgaggac aacgtgatga agatcgcaga   2160
cttcgggctg gcccgggacg tgcacaacct cgactactac aagaagacga ccaacggccg   2220
gctgcccgtg aagtggatgg cgcctgaggc cttgtttgac cgagtctaca ctcaccagag   2280
tgacgtctgg tcctttgggg tcctgctctg ggagatcttc acgctggggg gctccccgta   2340
ccccggcatc cctgtggagg agctcttcaa gctgctgaag gagggccacc gcatggacaa   2400
gcccgccaac tgcacacacg acctgtacat gatcatgcgg gagtgctggc atgccgcgcc   2460
ctcccagagg cccaccttca agcagctggt ggaggacctg gaccgtgtcc ttaccgtgac   2520
gtccaccgac gagtacctgg acctgtcggc gcctttcgag cagtactccc cgggtggcca   2580
ggacaccccc agctccagct cctcagggga cgactccgtg tttgcccacg acctgctgcc   2640
cccggcccca cccagcagtg gggctcgcg gacgtgaagg gccactggtc cccaacaatg   2700
tgaggggtcc ctagcagccc accctgctgc tggtgcacag ccactccccg gcatgagact   2760
cagtgcagat ggagagacag ctacacagag ctttggtctg tgtgtgtgtg tgtgcgtgtg   2820
tgtgtgtgtg tgtgcacatc cgcgtgtgcc tgtgtgcgtg cgcatcttgc ctccaggtgc   2880
agaggtaccc tgggtgtccc cgctgctgtg caacggtctc ctgactggtg ctgcagcacc   2940
gaggggcctt tgttctgggg ggacccagtg cagaatgtaa gtgggcccac ccggtgggac   3000
ccccgtgggg cagggagctg ggcccgacat ggctccggcc tctgcctttg caccacggga   3060
catcacaggg tgggcctcgg cccctcccac acccaaagct gagcctgcag ggaagcccca   3120
catgtccagc accttgtgcc tggggtgtta gtggcaccgc ctccccacct ccaggctttc   3180
ccacttccca ccctgcccct cagagactga aattacgggt acctgaagat gggagccttt   3240
accttttatg caaaaggttt attccggaaa ctagtgtaca tttctataaa tagatgctgt   3300
gtatatggta tatatacata tatatatata acatatatgg aagaggaaaa ggctggtaca   3360
acggaggcct gcgaccctgg gggcacagga ggcaggcatg gccctgggcg gggcgtgggg   3420
gggcgtggag ggaggcccca gggggtctca cccatgcaag cagaggacca gggccttttc   3480
tggcaccgca gttttgtttt aaaactggac ctgtatattt gtaaagctat ttatgggccc   3540
ctggcactct tgttcccaca ccccaacact tccagcattt agctggccac atggcggaga   3600
gttttaattt ttaacttatt gacaaccgag aaggtttatc ccgccgatag agggacggcc   3660
aagaatgtac gtccagcctg ccccggagct ggaggatccc ctccaagcct aaaaggttgt   3720
taatagttgg aggtgattcc agtgaagata ttttatttcc tttgtccttt ttcaggagaa   3780
ttagatttct ataggatttt tctttaggag atttattttt tggacttcaa agcaagctgg   3840
tattttcata caaattcttc taattgctgt gtgtcccagg cagggagacg gtttccaggg   3900
aggggccggc cctgtgtgca ggttccgatg ttattagatg ttacaagttt atatatatct   3960
atatatataa tttattgagt ttttacaaga tgtatttgtt gtagacttaa cacttcttac   4020
gcaatgcttc tagagtttta tagcctggac tgctaccttt caaagcttgg agggaagccg   4080
tgaattcagt tggttcgttc tgtactgtta ctgggccctg agtctgggca gctgtccctt   4140
```

```
gcttgcctgc agggccatgg ctcagggtgg tctcttcttg gggcccagtg catggtggcc   4200

agaggtgtca cccaaaccgg caggtgcgat tttgttaacc cagcgacgaa ctttccgaaa   4260

aataaagaca cctggttgct aacctg                                        4286


<210> SEQ ID NO 140
<211> LENGTH: 3950
<212> TYPE: DNA
<213> ORGANISM: Homo sapiens

<400> SEQUENCE: 140

gtcgcgggca gctggcgccg cgcggtcctg ctctgccggt cgcacggacg caccggcggg     60

ccgccggccg gagggacggg gcgggagctg ggcccgcgga cagcgagccg gagcgggagc    120

cgcgcgtagc gagccgggct ccggcgctcg ccagtctccc gagcggcgcc cgcctcccgc    180

cggtgcccgc gccgggccgt ggggggcagc atgcccgcgc gcgctgcctg aggacgccgc    240

ggcccccgcc cccgccatgg gcgcccctgc ctgcgccctc gcgctctgcg tggccgtggc    300

catcgtggcc ggcgcctcct cggagtcctt ggggacggag cagcgcgtcg tggggcgagc    360

ggcagaagtc ccgggcccag agcccggcca gcaggagcag ttggtcttcg gcagcgggga    420

tgctgtggag ctgagctgtc ccccgcccgg gggtggtccc atggggccca ctgtctgggt    480

caaggatggc acagggctgg tgccctcgga gcgtgtcctg gtggggcccc agcggctgca    540

ggtgctgaat gcctcccacg aggactccgg ggcctacagc tgccggcagc ggctcacgca    600

gcgcgtactg tgccacttca gtgtgcgggt gacagacgct ccatcctcgg gagatgacga    660

agacggggag gacgaggctg aggacacagg tgtggacaca ggggcccctt actggacacg    720

gcccgagcgg atggacaaga agctgctggc cgtgccggcc gccaacaccg tccgcttccg    780

ctgcccagcc gctggcaacc ccactccctc catctcctgg ctgaagaacg gcagggagtt    840

ccgcggcgag caccgcattg gaggcatcaa gctgcggcat cagcagtgga gcctggtcat    900

ggaaagcgtg gtgccctcgg accgcggcaa ctacacctgc gtcgtggaga acaagtttgg    960

cagcatccgg cagacgtaca cgctggacgt gctggagcgc tccccgcacc ggcccatcct   1020

gcaggcgggg ctgccggcca accagacggc ggtgctgggc agcgacgtgg agttccactg   1080

caaggtgtac agtgacgcac agccccacat ccagtggctc aagcacgtgg aggtgaatgg   1140

cagcaaggtg ggcccggacg gcacacccta cgttaccgtg ctcaaggtgt ccctggagtc   1200

caacgcgtcc atgagctcca acacaccact ggtgcgcatc gcaaggctgt cctcagggga   1260

gggccccacg ctggccaatg tctccgagct cgagctgcct gccgacccca aatgggagct   1320

gtctcgggcc cggctgaccc tgggcaagcc ccttggggag ggctgcttcg gccaggtggt   1380

catggcggag gccatcggca ttgacaagga ccgggccgcc aagcctgtca ccgtagccgt   1440

gaagatgctg aaagacgatg ccactgacaa ggacctgtcg gacctggtgt ctgagatgga   1500

gatgatgaag atgatcggga aacacaaaaa catcatcaac ctgctgggcg cctgcacgca   1560

gggcgggccc ctgtacgtgc tggtggagta cgcggccaag ggtaacctgc gggagtttct   1620

gcgggcgcgg cggcccccgg gcctggacta ctccttcgac acctgcaagc cgcccgagga   1680

gcagctcacc ttcaaggacc tggtgtcctg tgcctaccag gtggcccggg gcatggagta   1740

cttggcctcc cagaagtgca tccacaggga cctggctgcc cgcaatgtgc tggtgaccga   1800

ggacaacgtg atgaagatcg cagacttcgg gctggcccgg gacgtgcaca acctcgacta   1860

ctacaagaag acgaccaacg gccggctgcc cgtgaagtgg atggcgcctg aggccttgtt   1920

tgaccgagtc tacactcacc agagtgacgt ctggtccttt ggggtcctgc tctgggagat   1980
```

```
cttcacgctg gggggctccc cgtaccccgg catccctgtg gaggagctct tcaagctgct   2040
gaaggagggc caccgcatgg acaagcccgc caactgcaca cacgacctgt acatgatcat   2100
gcgggagtgc tggcatgccg cgccctccca gaggcccacc ttcaagcagc tggtggagga   2160
cctggaccgt gtccttaccg tgacgtccac cgacgagtac ctggacctgt cggcgccttt   2220
cgagcagtac tccccgggtg gccaggacac ccccagctcc agctcctcag gggacgactc   2280
cgtgtttgcc cacgacctgc tgcccccggc cccacccagc agtgggggct cgcggacgtg   2340
aagggccact ggtccccaac aatgtgaggg gtccctagca gcccaccctg ctgctggtgc   2400
acagccactc cccggcatga gactcagtgc agatggagag acagctacac agagctttgg   2460
tctgtgtgtg tgtgtgtgcg tgtgtgtgtg tgtgtgtgca catccgcgtg tgcctgtgtg   2520
cgtgcgcatc ttgcctccag gtgcagaggt accctgggtg tccccgctgc tgtgcaacgg   2580
tctcctgact ggtgctgcag caccgagggg cctttgttct gggggggaccc agtgcagaat  2640
gtaagtgggc ccacccggtg ggacccccgt ggggcaggga gctgggcccg acatggctcc   2700
ggcctctgcc tttgcaccac gggacatcac agggtgggcc tcggcccctc ccacacccaa   2760
agctgagcct gcagggaagc cccacatgtc cagcaccttg tgcctggggt gttagtggca   2820
ccgcctcccc acctccaggc tttcccactt cccaccctgc ccctcagaga ctgaaattac   2880
gggtacctga agatgggagc ctttaccttt tatgcaaaag gtttattccg gaaactagtg   2940
tacatttcta taaatagatg ctgtgtatat ggtatatata catatatata tataacatat   3000
atggaagagg aaaaggctgg tacaacggag gcctgcgacc ctgggggcac aggaggcagg   3060
catggccctg ggcggggcgt gggggggcgt ggagggaggc cccagggggt ctcacccatg   3120
caagcagagg accagggcct tttctggcac cgcagttttg ttttaaaact ggacctgtat   3180
atttgtaaag ctatttatgg gcccctggca ctcttgttcc cacaccccaa cacttccagc   3240
atttagctgg ccacatggcg gagagtttta atttttaact tattgacaac cgagaaggtt   3300
tatcccgccg atagagggac ggccaagaat gtacgtccag cctgccccgg agctggagga   3360
tcccctccaa gcctaaaagg ttgttaatag ttggaggtga ttccagtgaa gatattttat   3420
ttcctttgtc ctttttcagg agaattagat ttctatagga tttttcttta ggagatttat   3480
tttttggact tcaaagcaag ctggtatttt catacaaatt cttctaattg ctgtgtgtcc   3540
caggcaggga gacggtttcc agggaggggc cggccctgtg tgcaggttcc gatgttatta   3600
gatgttacaa gtttatatat atctatatat ataatttatt gagtttttac aagatgtatt   3660
tgttgtagac ttaacacttc ttacgcaatg cttctagagt tttatagcct ggactgctac   3720
ctttcaaagc ttggagggaa gccgtgaatt cagttggttc gttctgtact gttactgggc   3780
cctgagtctg ggcagctgtc ccttgcttgc ctgcagggcc atggctcagg gtggtctctt   3840
cttggggccc agtgcatggt ggccagaggt gtcacccaaa ccggcaggtg cgattttgtt   3900
aacccagcga cgaactttcc gaaaaataaa gacacctggt tgctaacctg              3950
```

<210> SEQ ID NO 141
<211> LENGTH: 2085
<212> TYPE: DNA
<213> ORGANISM: Homo sapiens

<400> SEQUENCE: 141

```
atgggcgccc ctgcctgcgc cctcgcgctc tgcgtggccg tggccatcgt ggccggcgcc     60
tcctcggagt ccttggggac ggagcagcgc gtcgtggggc gagcggcaga agtcccgggc    120
ccagagcccg gccagcagga gcagttggtc ttcggcagcg gggatgctgt ggagctgagc    180
```

-continued

```
tgtcccccgc ccgggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga acggcagcaa ggtgggcccg    900
gacggcacac cctacgttac cgtgctcaag gtgtccctgg agtccaacgc gtccatgagc    960
tccaacacac cactggtgcg catcgcaagg ctgtcctcag gggagggccc cacgctggcc   1020
aatgtctccg agctcgagct gcctgccgac cccaaatggg agctgtctcg ggcccggctg   1080
accctgggca agccccttgg ggagggctgc ttcggccagg tggtcatggc ggaggccatc   1140
ggcattgaca aggaccgggc cgccaagcct gtcaccgtag ccgtgaagat gctgaaagac   1200
gatgccactg acaaggacct gtcggacctg gtgtctgaga tggagatgat gaagatgatc   1260
gggaaacaca aaaacatcat caacctgctg ggcgcctgca cgcagggcgg gcccctgtac   1320
gtgctggtgg agtacgcggc caagggtaac ctgcgggagt ttctgcgggc gcggcggccc   1380
ccgggcctgg actactcctt cgacacctgc aagccgcccg aggagcagct caccttcaag   1440
gacctggtgt cctgtgccta ccaggtggcc cggggcatgg agtacttggc ctcccagaag   1500
tgcatccaca gggacctggc tgcccgcaat gtgctggtga ccgaggacaa cgtgatgaag   1560
atcgcagact tcgggctggc ccgggacgtg cacaacctcg actactacaa gaagacaacc   1620
aacggccggc tgcccgtgaa gtggatggcg cctgaggcct tgtttgaccg agtctacact   1680
caccagagtg acgtctggtc ctttggggtc ctgctctggg agatcttcac gctgggggggc  1740
tccccgtacc ccggcatccc tgtggaggag ctcttcaagc tgctgaagga gggccaccgc   1800
atggacaagc ccgccaactg cacacacgac ctgtacatga tcatgcggga gtgctggcat   1860
gccgcgccct cccagaggcc caccttcaag cagctggtgg aggacctgga ccgtgtcctt   1920
accgtgacgt ccaccgacga gtacctggac ctgtcggcgc ctttcgagca gtactccccg   1980
ggtggccagg acacccccag ctccagctcc tcaggggacg actccgtgtt tgcccacgac   2040
ctgctgcccc cggccccacc cagcagtggg ggctcgcgga cgtga                   2085
```

<210> SEQ ID NO 142
<211> LENGTH: 4431
<212> TYPE: DNA
<213> ORGANISM: Homo sapiens

<400> SEQUENCE: 142

```
aggcggggct ggagtggtgg aagggggggtg gcaggtctgc attgccgctt ccctggtgcc     60
gggagcagtc gccgctgccg cctccgcccg cggccgggac ccccgtcctc gcccgggact    120
ccttacccgg ggaacctaga ccaggtctcc agaggcttgt ggaagagaag caggcgaccc    180
ttcctgagtt atcctggctt agcctcccaa tctggctccc cttccccttc ccattcccct    240
```

```
gctccccctg tcccttcccc atccacccaa ctgaactggg tataggtcaa agctcctctc    300
tttccttttc cttcctaggc actcattggc taggacctgt ttgctctttt ttttgtgccc    360
agagatactg gaacacgctt catctaagta actgtgggga ggggtctttt tgactctaca    420
agtccttgag caaaaagctg aaaaagaagc aggaggtgga gaagacccag tgaagtgccc    480
caagccccat catggaagag ggcttccgag accgggcagc tttcatccgt ggggccaaag    540
acattgctaa ggaagtcaaa aagcatgcgg ccaagaaggt ggtgaagggc ctggacagag    600
tccaggacga atattcccga agatcgtact cccgctttga ggaggaggat gatgatgatg    660
acttccctgc tcccagtgat ggttattacc gaggagaagg gacccaggat gaggaggaag    720
gtggtgcatc cagtgatgct actgagggcc atgacgagga tgatgagatc tatgaagggg    780
aatatcaggg cattccccgg gcagagtctg gggggcaaagg cgagcggatg gcagatgggg    840
cgcccctggc tggagtaagg gggggcttga gtgatgggga gggtcccccct gggggccggg    900
gggaggcaca acgacggaaa gaacgagaag aactggccca acagtatgaa gccatcctac    960
gggagtgtgg ccacggccgc ttccagtgga cactgtattt tgtgcttggt ctggcgctga   1020
tggctgacgg tgtggaggtc tttgtggtgg gcttcgtgct gcccagcgct gagaaagaca   1080
tgtgcctgtc cgactccaac aaaggcatgc taggcctcat cgtctacctg ggcatgatgg   1140
tgggagcctt cctctgggga ggtctggctg accggctggg tcggaggcag tgtctgctca   1200
tctcgctctc agtcaacagc gtcttcgcct tcttctcatc ttttgtccag ggttacggca   1260
ctttcctctt ctgccgccta ctttctgggg ttgggattgg agggtccatc cccattgtct   1320
tctcctattt ctccgagttt ctggcccagg agaaacgagg ggagcatttg agctggctct   1380
gcatgttttg gatgattggt ggcgtgtacg cagctgctat ggcctgggcc atcatccccc   1440
actatgggtg gagttttcag atgggttctg cctaccagtt ccacagctgg agggtcttcg   1500
tcctcgtctg cgcctttcct tctgtgtttg ccattggggc tctgaccacg cagcctgaga   1560
gcccccgttt cttcctagag aatggaaagc atgatgaggc ctggatggtg ctgaagcagg   1620
tccatgatac caacatgcga gccaaaggac atcctgagcg agtgttctca gtaacccaca   1680
ttaagacgat tcatcaggag gatgaattga ttgagatcca gtcggacaca gggacctggt   1740
accagcgctg gggggtccgg gccttgagcc tagggggggca ggtttggggg aattttctct   1800
cctgttttgg tcccgaatat cggcgcatca ctctgatgat gatgggtgtg tggttcacca   1860
tgtcattcag ctactatggc ctgaccgtct ggtttcctga catgatccgc catctccagg   1920
cagtggacta cgcatcccgc accaaagtgt tccccgggga gcgcgtagag catgtaactt   1980
ttaacttcac gttggagaat cagatccacc gaggcgggca gtacttcaat gacaagttca   2040
ttgggctgcg gctcaagtca gtgtcctttg aggattccct gtttgaagag tgttattttg   2100
aggatgtcac atccagcaac acgtttttcc gcaactgcac attcatcaac actgtgttct   2160
ataacactga cctgttcgag tacaagtttg tgaacagccg tctgataaac agtacattcc   2220
tgcacaacaa ggagggctgc ccgctagacg tgacagggac gggcgaaggt gcctacatgg   2280
tatactttgt gagcttcctg ggacactgg cagtgcttcc tgggaatatc gtgtctgccc    2340
tgctcatgga caagatcggc aggctcagaa tgcttgctgg ctccagcgtg atgtcctgtg   2400
tctcctgctt cttcctgtct tttgggaaca gtgagtcggc catgatcgct ctgctctgcc   2460
tttttggcgg ggtcagcatt gcatcctgga atgcgctgga cgtgttgact gttgaactct   2520
acccctcaga caagaggacc acagcttttg gcttcctgaa tgccctgtgt aagctggcag   2580
ctgtgctggg gatcagcatc ttcacatcct tcgtgggaat caccaaggct gcacccatcc   2640
```

```
tctttgcctc agctgccctt gcccttggca gctctctggc cctgaagctg cctgagaccc   2700
gggggcaggt gctgcagtga aggggtctct agggctttgg gattggcagg cacactgtga   2760
gaccaacaac tccttccttc ccctccctgc cctgccatcc tgacctccag agccctcact   2820
ccccactccc cgtgtttggt gtcttagctg tgtgtgcgtg tgcgtgtgca tgtgtgtaaa   2880
ccccgtgggc agggactaca gggaaggctc cttcatccca gttttgagat gaagctgtac   2940
tccccatttc ccactgccct tgactttgca caagagaagg ctgagcccca tccttctccc   3000
cctgttagag aggggccctt gcttccctgt tccaggggtt ccagaatagg cttcctgcct   3060
tccccatcat tccctctgcc taggccctgg tgaaaccaca ggtatgcaat tatgctaggg   3120
gctggggctc tggtgtagac catggaccaa aagaacttct tagagtctga agagtgggcc   3180
tcgggtgccc tctcacatct cctgttggat gctgggggag aagcaataaa cctcagccct   3240
ctggcctcca ctttcctctc aatttgggct gcaaatatga agcctgaatt ttatgaaatt   3300
agctttctga ttcttattta ttaatagatt aagttctgag gcagctccgc aggactgtgt   3360
gtgaatgtgt atgtatactt acatatgtgt gtgcatgtgc catggggcgg ggggtatcac   3420
tatactgtcc tcaaatataa gccaagggta atttcagcgg atgcacacac aaccctgcct   3480
cccacagttc ctcccctaat ctggtttctg tgttgagcct gggatggagg agccctaggc   3540
cagcctggga taagagtccc acagtctagg gagatctgag ggcatccgac aaggcccatc   3600
tccttccctc ctcaagaagc agaggcctcc tctggagtga gaggctccac ccactacagc   3660
acaggcggga atagcacagc tgccctccca tgctccctac ctgtcccctc acagggaggg   3720
gagcagggga gggaaagaaa ccaggcatct ggtcaaacca gcagatcaaa aagcacaaag   3780
agctggggca gaggcaggaa gcaggggccc tcctggcagc tcctctgagt ggggagaggt   3840
tgggcagtga gtgagggacc cctaatgcag ggactagaag cctcagtttc cccattttac   3900
ccttccacac aatagcctct gtaggttagg ctgccccatc ccaccctact ctgtgtggct   3960
gctttctttg gtgccctccc ctcaccccac tgtagctgtg acgtgttgta gtttttagat   4020
gtttgtaaaa tgtttaaaaa aatgttaaaa ggaaaaaagt gaaaataaca aaaaagaaaa   4080
tcaaaattca ccttcgtcat gctgcgtcca gtgccccaac cctgtggtca ctctccccat   4140
tttgtaacac tgtaccaggt ggtgactgtt taactctttg gtgtctgtgc tcaaaagact   4200
gccttctcca gtgcccagtg tatgagtgtg tgccctgtgc ccttgtccct cactccccac   4260
atgctggacg tagccctctt cctcgcaccc ctgggaggga cccatccatc tcccttgctc   4320
tcctggggaa ccctaaaccc aactctgttg atgtgaaaaa tgcagtgaaa aatattgacg   4380
aaaaataaaa cggaaacaaa tcctcaaaat acaaaaaaaa aaaaaaaaaa a            4431
```

<210> SEQ ID NO 143
<211> LENGTH: 5311
<212> TYPE: DNA
<213> ORGANISM: Homo sapiens

<400> SEQUENCE: 143

```
agcataacct tcggtggcag gacaaatcag gccagcacgc agtctgccaa gtcctgctcg     60
ctccctgtca agaaaaacag ctggatccat ttctaatcaa cacttcccaa cgcaacactt    120
ctgagtctct gaaggagacc agagcttgaa actttccaga cttccaacag acatcgagtg    180
caaaaggata tttaggttgt ctttgcacaa atctggttga tttgagagat aaaggggggg    240
ggaaccagtg tgactttcac ctaagaagtc acatgaacat atttcacatt tgaactacat    300
aatgaatgat ggttattgaa atagcccaaa cctctaccac agagcgaggg atatagctca    360
```

-continued

```
aggggcaacc aggcagtcgc agaaccaagg aatggatgac tacaagtatc aggacaatta    420
tgggggctat gctcccagtg atggctatta ccgcggcaat gagtccaacc cagaagaaga    480
tgcacagagt gatgtcaccg aaggccatga tgaggaagac gagatctatg agggcgagta    540
ccagggtatc cctcacccag atgatgtcaa ggccaagcag gccaagatgg cgccctccag    600
aatggacagc cttcggggcc agacagacct gatggctgag aggctggaag atgaggagca    660
gttggcccac cagtacgaga ccatcatgga tgagtgtggc catggccgct tccagtggat    720
cctctttttc gtcttgggtt tggccctgat ggccgatggg gtggaagtgt tcgtggtgag    780
ttttgccctg cccagtgcag agaaggacat gtgtctgtcc agttccaaaa aaggaatgct    840
agggatgata gtctacttgg gaatgatggc gggcgccttc atcctgggag gcctggctga    900
taagctggga aggaagcgag tcctcagcat gtctctggcc gtcaatgcct ccttcgcctc    960
cctctcttcc ttcgtgcagg gatatggagc cttcctcttc tgccgactca tctcaggcat   1020
cggtattggg ggtgctctac cgattgtttt tgcctatttt tctgaattct tgtctcggga   1080
gaagcgagga gaacacctca gttggctggg catcttctgg atgactgggg gcctgtacgc   1140
atctgccatg gcctggagca tcatcccaca ctatggctgg ggcttcagca tggggaccaa   1200
ttaccacttc catagctgga gagtgtttgt catcgtctgt gctctgccct gcaccgtgtc   1260
catggtggcc ctgaagttca tgccagagag cccaaggttt ctgctagaga tgggcaaaca   1320
tgatgaagcc tggatgattc tcaagcaagt ccatgacacc aacatgagag ctaaggggac   1380
cccagagaaa gtgttcacgg tttccaacat caaaactccc aagcaaatgg atgaattcat   1440
tgagatccaa agttcaacag gaacctggta ccagcgctgg ctggtcagat tcaagaccat   1500
tttcaagcag gtctgggata atgccctgta ctgtgtgatg gggccctaca gaatgaatac   1560
actgattctg gccgtggttt ggtttgccat ggcattcagt tactatggac tgacagtttg   1620
gtttcctgat atgatccgct attttcaaga tgaagaatac aagtctaaaa tgaaggtgtt   1680
ttttggtgag catgtgtacg gcgccacaat caacttcacg atggaaaatc agatccacca   1740
acatgggaaa cttgtgaatg ataagttcac aagaatgtac tttaaacatg tactctttga   1800
ggacacattc tttgacgagt gctattttga agacgtaaca tcaacagata cctacttcaa   1860
aaattgtacc attgaatcaa ccatctttta caacacagac ctctacgagc acaagttcat   1920
caactgtcgg tttatcaact ccaccttcct ggagcagaag gagggctgcc acatggactt   1980
ggagcaagat aatgacttcc tgatttacct cgtcagcttc ctgggcagcc tgtctgtctt   2040
acccgggaac atcatttctg ccctgctcat ggatagaatt ggaaggctca agatgattgg   2100
tggctccatg ctaatctctg cagtctgctg cttcttcctg ttttttggca acagtgagtc   2160
tgcaatgatc ggctggcagt gcctgttctg tgggacaagc attgcagcct ggaatgctct   2220
ggatgtgatc acagtggagc tgtatcccac caaccagaga gcaacagcct tcggcattct   2280
caatggatta tgcaaatttg gcgccatcct gggaaacacc atctttgctt cttttgttgg   2340
gataaccaaa gtggtcccca tccttctggc tgctgcttct ctggttgggg gtggcctgat   2400
tgcccttcga ctgccagaga ctcgagaaca ggtcctgatg tgaacaacct atgggaaaag   2460
gaaaggtcga gagaatcttg tccaggacac tgaaatgcat ccacacttcc tgcctatcac   2520
ggtccggagg acaccttgga tagcacggga ggagaagttg actttgtgac ccctagttta   2580
ggacccactt cagctgtcaa tatgtttgta actcaggtga ctgatttggg ggtgccctga   2640
gccaccctta gaatcacaga gctgcgtgtt taacttcaag tcttcccagt ccaaggcagg   2700
gagaggattc tccagtgagt gcacacacta tgcgaggagc aagcatttct ctaagtcaag   2760
```

-continued

```
tgcaaggact taacttgcgt ttgaaaagga attagagggt cagaaacacc caggttcctc   2820
cagaaagctc cttggagccc aacaacttaa caaatcaact tggctggaag ttagagtcat   2880
tatatgaaga ttgggcttga agtatatatt tttgcattta aaagtatcac ctatcatatt   2940
ttccactcga aaattgacat agtagcattg aggatactct gatctagaaa gccaagtatt   3000
tgagcaacat ctatagagat ctacttttct cctatgtctc ctaggctttc catgataatt   3060
aggtaataca tttaagaagg atatttattt ctgttttgct ctattcaaag aaacggaatg   3120
ggatagttat tctgtaaact aagtttgtat ataactttat ttgggtttaa tttccacaac   3180
tggtatctgc aaatattgcc agcattttag ccatattttg ggagaacttg gtgtttgagg   3240
tcccaggaaa tgaggtctga tcaaatgaaa tgcaagcaca atttcttaca gccatttaac   3300
tttctgttgg gaggatgaat taacaaactc acattgtgca gtctgcttaa tccaggcact   3360
tttctttgtg caggtgtagt gagtagttac ttctctccct tacacagatg acttgtgaaa   3420
ctcaagctca ccatcttcag tgctggcatt ttactttgcc actacccaaa aacaatgtga   3480
gatgtgttca gtggcctctg gtactctttg caggcaagaa tcaaacaaca tggggactga   3540
gggaaggatg gggaagtgta gccacagttc ttccaaatgt aaatactttt tgtttgttct   3600
agtggtaaaa tgcaaatgca atccatattt gttaggatgg tcaggtctca tgagaaatct   3660
atgctatgtg tccagagctt ttgaaacaga gtccattgga gtgggagtta gggagtgtag   3720
tggatgccaa atatgttttt cttcagtgct taagagaact gtttcctgaa gtccagcttt   3780
gaacataaac aggggtgtgg gttgggggag gagcttagga caaacctctc tgatgaaggt   3840
cagcaataga ctgaagtctt gactgcatgg aagaggaaaa acatcagaac tgtctgacaa   3900
tggaggggac agtgagctac gcacaactgc cagcggaggt gaacttgcac ctgcccaggc   3960
cggatgaaca tcagcctgca agaactagtt gtttgagttg atttgcagtg ctctcaatgg   4020
gcaagtgcca cattttccct ggcagagatc tccaaaaatt taaaacagaa taataatggc   4080
tatatcgagt gttttctcag tattggagaa atgcttaggt cctatgatag cttcgggaca   4140
tctttctgta attttcctca attaacgggt tggtaggggt aaatcttatg acacctttcc   4200
accgtcgatt tgagatcagt tttaatggtt aaaatgttta ctctccttct gtcaaccctc   4260
acctttttat ttacacccct cccttttttt ctgtacaggg agagaagaca tattgactct   4320
gactggacac cctgattcct ccaaatatat ataccactgt gtattaatct ttctctcagt   4380
gttttatagg agtactaaca tttattgctc tgtcaataat gaaaggctcg atgtaatata   4440
gctgtaattt actttccata tgaatacagt ggctaggttc ataaaagaga attgtgtgag   4500
tctgggatta ccacatctaa aacattattc tttaatggga taatacaatt cattgagcag   4560
ctaccactta aaaaacttgc aggacagtta gagcctgcat ttctagttaa gatggatctt   4620
gtaaatttaa aattggatta acattggagt gctggggtgg ctgcaataat ttgggggcta   4680
actccatttg gtttccaaga tctcacttct gcattatctt tatggctctt taaaccagcc   4740
acctagccaa tcaagggcaa ttcccatctc atccatcact caggtctttg taaagggtgc   4800
agccaagctc tgcagacttt tgcaggattg tctagcctga gtaccgggct acttcttaaa   4860
tgccgtcact cctgctgaga taaatgcgtc tttaaaaata gtctctgtgg caggtcactg   4920
ggggacaatg tacagcattc tggccatcca cttctttttc acttcatgtt ctaccccaag   4980
agactcccga tgtcggctgt ggagggttaa agggatgagg ctttcctttg tttagcaaat   5040
ctgttcacag ttcttgatga tgtattttat gatgcccagc ttggaaatag ttgctttcca   5100
tagtctcaac tgtattgtgt catctcctga tgctgatttt tgatcttttg ttttattaaa   5160
```

-continued

```
aataattagt gaaagaggtg tgcctatctg tgaagtttgt agtacatcat cctgaggtca   5220

tgtaacaagt aaaccccaac ccagcgttcc ctcctacgtt gtgttagttc attaaaacta   5280

aataataaaa ataactgtaa gaaaacctta a                                  5311
```

<210> SEQ ID NO 144
<211> LENGTH: 2362
<212> TYPE: DNA
<213> ORGANISM: Homo sapiens

<400> SEQUENCE: 144

```
cactcagggc aagggtgtcc gacggctgga gcgttctgtt ttgaacccaa agtggatgat     60

gctgtcagag ctgaactact gaaaggaggc tgtgaaaatt tcccatcttc tcattggcca    120

tcagttgaga taagatggaa gactcttaca aggataggac ttcactgatg aagggtgcca    180

aggacattgc cagagaggtg aagaaacaaa cagtaaagaa ggtgaatcaa gctgtggacc    240

gagcccagga tgaatacacc cagaggtcct acagtcggtt ccaagatgaa gaagatgatg    300

atgactacta cccggctgga gaaacctata atggtgaggc caacgatgac gaaggctcaa    360

gtgaagccac tgaggggcat gatgaagatg atgagatcta tgagggggag tatcagggca    420

tccccagtat gaaccaagcg aaggacagca tcgtgtcagt ggggcagccc aagggcgatg    480

agtacaagga ccgacgggag ctggaatcag aaaggagagc tgacgaggaa gagttagccc    540

agcagtatga gctgataatc caagaatgcg gtcatggtcg ttttcagtgg gcccttttct    600

tcgtcctggg catggctctt atggcagacg gtgtagaggt gtttgtcgtt ggcttcgtgt    660

tacccagtgc tgagacagac ctctgcatcc caaattcagg atctggatgg ctaggcagca    720

tagtgtacct cgggatgatg gtgggggcgt tcttctgggg aggactggca gacaaagtgg    780

gaaggaaaca gtctcttctg atttgcatgt ctgtcaacgg attctttgcc ttcctttctt    840

catttgtcca aggttatggc ttctttctct tctgtcgctt actttctgga ttcgggattg    900

gaggagccat acccactgtg ttctcgtact ttgctgaagt cctggcccgg gaaaagcggg    960

gcgaacactt gagctggctc tgcatgttct ggatgatcgg tggcatctac gcctctgcca   1020

tggcctgggc catcatcccg cactacgggt ggagcttcag catgggatcg gcctaccagt   1080

ttcacagttg gcgtgtgttt gtcatcgtct gtgcactccc ctgtgtctcc tccgtggtgg   1140

ccctcacatt catgcctgaa agcccacgat tcttgttgga ggttggaaaa catgatgaag   1200

cttggatgat tctgaagtta attcatgaca ccaacatgag agcccggggt cagcctgaga   1260

aggtcttcac ggtaaacaaa ataaaaactc ctaaacaaat agatgagctg attgaaattg   1320

agagtgacac aggaacatgg tataggaggt gttttgttcg gatccgcacc gagctgtacg   1380

gaatttggtt gacttttatg agatgtttca actacccagt cagggataat acaataaagc   1440

ttacaattgt ttggttcacc ctgtcctttg ggtactatgg attatccgtt tggttccctg   1500

atgtcattaa acctctgcag tccgatgaat atgcattgct aaccagaaat gtggagagag   1560

ataaatatgc aaatttcact attaacttta caatggaaaa tcagattcat actggaatgg   1620

aatacgacaa tggcagattc ataggggtca agttcaaatc tgtaactttc aaagactctg   1680

tttttaagtc ctgcaccttt gaggatgtaa cttcagtgaa cacctacttc aagaactgca   1740

catttattga cactgttttt gacaacacag attttgagcc atataaattc attgacagtg   1800

aatttaaaaa ctgctcgttt tttcacaaca agacgggatg tcagattacc tttgatgatg   1860

actatagtgc ctactggatt tattttgtca actttctggg gacattggca gtattgccag   1920

ggaacattgt gtctgctctg ctgatggaca gaattgggcg cttaacaatg ctaggtggct   1980
```

```
ctatggtgct ttcggggatc agctgtttct tcctttggtt cggcaccagt gaatccatga   2040

tgataggcat gctgtgtctg tacaatggat tgaccatctc agcctggaac tctcttgacg   2100

tggtcactgt ggaactgtac cccacagacc ggagggcaac aggctttggc ttcttaaatg   2160

cgctatgcaa ggcagcagcc gtcctgggaa acttaatatt tggctctctg gtcagcatca   2220

ccaaatcaat ccccatcctg ctggcttcta ctgtgctcgt gtgtggagga ctcgttgggc   2280

tgtgcctgcc tgacacacga acccaggttc tgatgtaatg ggaaaaaaag ccatccttcc   2340

tgcgtttctt cctcctgccc tg                                            2362
```

<210> SEQ ID NO 145
<211> LENGTH: 2053
<212> TYPE: DNA
<213> ORGANISM: Homo sapiens

<400> SEQUENCE: 145

```
catctttgat gagggcagag ctcacgttgc attgaagacg aaacctcggg gaggtcaggc     60

gctgtctttc cttccctccc tgctcggcgg ctccaccaca gttgcaacct gcagaggccc    120

ggagaacaca accctcccga gaagcccagg tccagagcca aacccgtcac tgacccccca    180

gcccaggcgc ccagccactc ccaccgcta ccatggccga agacgcagac atgcgcaatg    240

agctggagga gatgcagcga agggctgacc agttggctga tgagtcgctg gaaagcaccc    300

gtcgtatgct gcaactggtt gaagagagta aagatgctgg tatcaggact ttggttatgt    360

tggatgaaca aggagaacaa ctcgatcgtg tcgaagaagg catgaaccat atcaaccaag    420

acatgaagga ggctgagaaa aatttaaaag atttagggaa atgctgtggc cttttcatat    480

gtccttgtaa caagcttaaa tcaagtgatg cttacaaaaa agcctggggc aataatcagg    540

acggagtggt ggccagccag cctgctcgtg tagtggacga acgggagcag atggccatca    600

gtggcggctt catccgcagg gtaacaaatg atgcccgaga aaatgaaatg gatgaaaacc    660

tagagcaggt gagcggcatc atcgggaacc tccgtcacat ggccctggat atgggcaatg    720

agatcgatac acagaatcgc cagatcgaca ggatcatgga gaaggctgat tccaacaaaa    780

ccagaattga tgaggccaac caacgtgcaa caaagatgct gggaagtggt taagtgtgcc    840

cacccgtgtt ctcctccaaa tgctgtcggg caagatagct ccttcatgct tttctcatgg    900

tattatctag taggtctgca cacataacac acatcagtcc acccccattg tgaatgttgt    960

cctgtgtcat ctgtcagctt cccaacaata ctttgtgtct tttgttctct cttggtctct   1020

ttctttccaa aggttgtaca tagtggtcat ttggtggctc taactccttg atgtcttgag   1080

tttcattttt cattttctct cctcggtggc atttgctgaa taacaacaat ttaggaatgc   1140

tcaatgtgct gttgattctt tcaatccaca gtattgttct tgtaaaactg tgacattcca   1200

cagagttact gccacggtcc tttgagtgtc aggctctgaa tctctcaaaa tgtgccgtct   1260

ttggttcctc atggctgtta tctgtcttta tgatttcatg attagacaat gtggaattac   1320

ataacaggca ttgcactaaa agtgatgtga tttatgcatt tatgcatgag aactaaatag   1380

atttttagat tcctacttaa acaaaaactt tccatgacag tagcatactg atgagacaac   1440

acacacacac acaaaacaac agcaacaaca acagaacaac aacaaagcat gctcagtatt   1500

gagacactgt caagattaag ttataccagc aaaagtgcag tagtgtcact tttttcctgt   1560

caatatatag agacttctaa atcataatca tcctttttta aaaaaaagaa ttttaaaaaa   1620

gatggatttg acacactcac catttaatca tttccagcaa aatatatgtt tggctgaaat   1680

tatgtcaaat ggatgtaata tagggtttgt ttgctgcttt tgatggctac gttttggaga   1740
```

gagcaatctt gctgtgaaac agtgtggatg taaattttat aaggctgact cttactaacc 1800
accatttccc ctgtggtttg ttatcagtac aattctttgt tgcttaatct agagctatgc 1860
acaccaaatt gctgagatgt ttagtagctg ataaagaaac cttttaaaaa aataatataa 1920
atgaatgaaa tataaactgt gagataaata tcattatagc atgtaatatt aaattcctcc 1980
tgtctcctct gtcagtttgt gaagtgattg acattttgta gctagtttaa aattattaaa 2040
aattatagac tcc 2053

<210> SEQ ID NO 146
<211> LENGTH: 2053
<212> TYPE: DNA
<213> ORGANISM: Homo sapiens

<400> SEQUENCE: 146
catctttgat gagggcagag ctcacgttgc attgaagacg aaacctcggg gaggtcaggc 60
gctgtctttc cttccctccc tgctcggcgg ctccaccaca gttgcaacct gcagaggccc 120
ggagaacaca accctcccga gaagcccagg tccagagcca aacccgtcac tgacccccca 180
gcccaggcgc ccagccactc cccaccgcta ccatggccga agacgcagac atgcgcaatg 240
agctggagga gatgcagcga agggctgacc agttggctga tgagtcgctg gaaagcaccc 300
gtcgtatgct gcaactggtt gaagagagta aagatgctgg tatcaggact ttggttatgt 360
tggatgaaca aggagaacaa ctggaacgca ttgaggaagg gatggaccaa atcaataagg 420
acatgaaaga agcagaaaag aatttgacgg acctaggaaa attctgcggg ctttgtgtgt 480
gtccctgtaa caagcttaaa tcaagtgatg cttacaaaaa agcctggggc aataatcagg 540
acggagtggt ggccagccag cctgctcgtg tagtggacga acgggagcag atggccatca 600
gtggcggctt catccgcagg gtaacaaatg atgcccgaga aaatgaaatg gatgaaaacc 660
tagagcaggt gagcggcatc atcgggaacc tccgtcacat ggccctggat atgggcaatg 720
agatcgatac acagaatcgc cagatcgaca ggatcatgga gaaggctgat tccaacaaaa 780
ccagaattga tgaggccaac caacgtgcaa caaagatgct gggaagtggt taagtgtgcc 840
cacccgtgtt ctcctccaaa tgctgtcggg caagatagct ccttcatgct tttctcatgg 900
tattatctag taggtctgca cacataacac acatcagtcc acccccattg tgaatgttgt 960
cctgtgtcat ctgtcagctt cccaacaata ctttgtgtct tttgttctct cttggtctct 1020
ttctttccaa aggttgtaca tagtggtcat ttggtggctc taactccttg atgtcttgag 1080
tttcattttt cattttctct cctcggtggc atttgctgaa taacaacaat ttaggaatgc 1140
tcaatgtgct gttgattctt tcaatccaca gtattgttct tgtaaaactg tgacattcca 1200
cagagttact gccacggtcc tttgagtgtc aggctctgaa tctctcaaaa tgtgccgtct 1260
ttggttcctc atggctgtta tctgtcttta tgatttcatg attagacaat gtggaattac 1320
ataacaggca ttgcactaaa agtgatgtga tttatgcatt tatgcatgag aactaaatag 1380
atttttagat tcctacttaa acaaaaactt tccatgacag tagcatactg atgagacaac 1440
acacacacac acaaaacaac agcaacaaca acagaacaac aacaaagcat gctcagtatt 1500
gagacactgt caagattaag ttataccagc aaaagtgcag tagtgtcact tttttcctgt 1560
caatatatag agacttctaa atcataatca tcctttttta aaaaaaagaa ttttaaaaaa 1620
gatggatttg acacactcac catttaatca tttccagcaa aatatatgtt tggctgaaat 1680
tatgtcaaat ggatgtaata tagggtttgt ttgctgcttt tgatggctac gttttggaga 1740
gagcaatctt gctgtgaaac agtgtggatg taaattttat aaggctgact cttactaacc 1800

-continued accatttccc ctgtggtttg ttatcagtac aattctttgt tgcttaatct agagctatgc 1860
acaccaaatt gctgagatgt ttagtagctg ataaagaaac cttttaaaaa aataatataa 1920
atgaatgaaa tataaactgt gagataaata tcattatagc atgtaatatt aaattcctcc 1980
tgtctcctct gtcagtttgt gaagtgattg acattttgta gctagtttaa aattattaaa 2040
aattatagac tcc 2053

<210> SEQ ID NO 147
<211> LENGTH: 5
<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 147

Asp Glu Ala Asn Gln
1 5

<210> SEQ ID NO 148
<211> LENGTH: 6
<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 148

Ile Asp Glu Ala Asn Gln
1 5

<210> SEQ ID NO 149
<211> LENGTH: 360
<212> TYPE: DNA
<213> ORGANISM: Mus musculus

<400> SEQUENCE: 149
caggtgaagc tgcaggagtc tggacctgaa ctggtaaagc ctggggcttc agtgaagatg 60
tcctgcaagg cttctggata cacattcact aactatgtta tacactgggt gaagcaaaag 120
cctgggcagg gccttgagtg gattggatat attaatcctt acaatgatgg ctctaagtac 180
aatgagaagt tcaaaggcaa ggcctcactg acttcagaca aatcctccag cacagcctac 240
atggagctca gcagcctgac ctctgaggac tctgcggtct attactgtgc aagacatctc 300
gctaatacct actactactt tgactactgg ggccaaggca ccactctcac agtctcctca 360

<210> SEQ ID NO 150
<211> LENGTH: 120
<212> TYPE: PRT
<213> ORGANISM: Mus musculus

<400> SEQUENCE: 150

Gln Val Gln Leu Gln Glu Ser Gly Pro Glu Leu Val Lys Pro Gly Ala
1 5 10 15

Ser Val Lys Met Ser Cys Lys Ala Ser Gly Tyr Thr Phe Thr Asn Tyr
20 25 30

Val Ile His Trp Val Lys Gln Lys Pro Gly Gln Gly Leu Glu Trp Ile
35 40 45

Gly Tyr Ile Asn Pro Tyr Asn Asp Gly Ser Lys Tyr Asn Glu Lys Phe
50 55 60

-continued

```
Lys Gly Lys Ala Ser Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg His Leu Ala Asn Thr Tyr Tyr Tyr Phe Asp Tyr Trp Gly Gln
            100                 105                 110

Gly Thr Thr Leu Thr Val Ser Ser
        115                 120


<210> SEQ ID NO 151
<211> LENGTH: 5
<212> TYPE: PRT
<213> ORGANISM: Mus musculus

<400> SEQUENCE: 151

Ala Arg Met Gly Tyr
 1               5


<210> SEQ ID NO 152
<211> LENGTH: 13
<212> TYPE: PRT
<213> ORGANISM: Mus musculus

<400> SEQUENCE: 152

Ala Arg His Leu Ala Asn Thr Tyr Tyr Tyr Phe Asp Tyr
 1               5                  10
```

What is claimed:

1. An established single cell derived clonal cell line from a parental SiMa cell line DSMZ ACC 164 comprising cells susceptible to intoxication by botulinum toxin type A (BoNT/A), wherein the cells exhibit at least a 1.5-fold increase in mRNA expression levels before differentiation in the genes NR3C1, SMC6, SNCAIP and TCF7L2 relative to the mRNA expression levels of each of these genes in cells from the 2D6 derived from the parental SiMa cell line DSMZ ACC 164; and, wherein the cells exhibit at least a 1.5-fold decrease in mRNA expression levels before differentiation in the genes CAP2, CNA, PHLDA2 and PKC(s) as compared to the mRNA expression levels of each of these genes in cells from the 2D6 cell line; and, wherein the clonal cell line comprises cells susceptible to BoNT/A intoxication by about 100 pM or less of a BoNT/A.

2. The established clonal cell line of claim 1, wherein the cells exhibit at least a 2.0-fold difference in gene expression levels of at least one gene as compared to the expression levels of the gene in cells from the 2D6 cell line.

3. The established clonal cell line of claim 1, wherein the cells exhibit at least a 3.0-fold difference in gene expression levels of at least one gene as compared to the expression levels of the gene in cells from the 2D6 cell line.

4. The established clonal cell line of claim 1, wherein the cells exhibit at least a 4.0-fold difference in gene expression levels of at least one gene as compared to the expression levels of the gene in cells from the 2D6 cell line.

5. The established clonal cell line of claim 1, wherein the cell from an established clonal cell line exhibits about 100 pM or less of a BoNT/A intoxication for at least 5 or more cell passages.

* * * * *